US007880007B2

(12) United States Patent  
Hurley et al.

(10) Patent No.: US 7,880,007 B2  
(45) Date of Patent: Feb. 1, 2011

(54) BICYCLIC SUBSTITUTED PHENYL PIPERIDINE MODULATORS OF MUSCARINIC RECEPTORS

(75) Inventors: Dennis J. Hurley, San Marcos, CA (US); Daniele M. Bergeron, La Mesa, CA (US); Ioana Drutu, La Jolla, CA (US); Miguel Garcia-Guzman Blanco, San Diego, CA (US); Lewis R. Makings, Encintas, CA (US); Akiko Nakatani, San Diego, CA (US); Gabriel Raffai, Perris, CA (US); Alina Silina, San Diego, CA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 902 days.

(21) Appl. No.: 11/288,938

(22) Filed: Nov. 29, 2005

(65) Prior Publication Data

US 2006/0287303 A1  Dec. 21, 2006

Related U.S. Application Data

(60) Provisional application No. 60/631,560, filed on Nov. 29, 2004.

(51) Int. Cl.  
*C07D 211/06* (2006.01)  
*A61K 31/445* (2006.01)

(52) U.S. Cl. .................................... 546/205; 514/319

(58) Field of Classification Search ................. 546/195  
See application file for complete search history.

(56) References Cited

U.S. PATENT DOCUMENTS

| | | | |
|---|---|---|---|
| 4,198,417 A | 4/1980 | Ong et al. | |
| 5,153,228 A * | 10/1992 | Schlecker et al. | ........... 514/647 |
| 6,245,773 B1 | 6/2001 | Wong et al. | |
| 6,268,369 B1 | 7/2001 | Nagarathnam et al. | |
| 6,514,993 B1 | 2/2003 | Perregaard et al. | |
| 6,956,042 B2 | 10/2005 | Bhatti et al. | |
| 2002/0037886 A1 | 3/2002 | Andersson et al. | |
| 2002/0049195 A1 | 4/2002 | Mammen et al. | |
| 2003/0199549 A1 | 10/2003 | Burnett et al. | |
| 2004/0029919 A1 | 2/2004 | Mammen et al. | |
| 2004/0038855 A1 | 2/2004 | Salon et al. | |
| 2004/0106623 A1 | 6/2004 | Konkel et al. | |
| 2004/0122014 A1 | 6/2004 | Mammen et al. | |
| 2004/0132710 A1 | 7/2004 | Middleton et al. | |
| 2004/0142956 A1 | 7/2004 | Chen et al. | |
| 2004/0142974 A1 | 7/2004 | Hoemann | |
| 2004/0167166 A1 | 8/2004 | Alberati-Giani et al. | |
| 2005/0063909 A1 | 3/2005 | Wright, IV et al. | |
| 2005/0113413 A1 | 5/2005 | Wilson et al. | |
| 2009/0253908 A1 | 10/2009 | Budzik et al. | |

FOREIGN PATENT DOCUMENTS

| | | | |
|---|---|---|---|
| WO | WO0142212 A1 | 6/2001 | |
| WO | WO0142213 A1 | 6/2001 | |
| WO | WO0190101 A1 | 11/2001 | |

OTHER PUBLICATIONS

Sato, Susumu, et al., "New Mu-Opioid Receptor Agonists with Phenoxyacetic Acid Moiety,", *Chemical and Pharmaceutical Bulletin*, vol. 50, No. 2, pp. 292-297, (2002).

Thurkauf, Andrew, et al., "1-Phenyl-3-(aminomethyl)pyrroles as Potential Antipsychotic Agents. Synthesis and Dopamine Receptor Binding," *Journal of Medicinal Chemistry*, vol. 38, No. 25, pp. 4950-4952, (1995).

International Search Report and Written Opinion of the International Searching Authority for International Application No. PCT/US2005/042931, filed Nov. 29, 2005. Forms PCT/ISA/210 & PCT/ISA/237.

Bando, Kazunori, et al.; "Piperazine analog of vesamicol: in vitro and in vivo characterization for vesicular acetylcholine transporter," *Synapse* (New York) (2000), 38(1), 27-37.

Chambers, Mark S., et al.; "Spiropiperidines As High-Affinity, Selective σ Ligands," *Journal of Medicinal Chemistry* (1992), 35(11), 2033-9.

Dauben W. G., et al., "Organic Reactions at High Pressure, Cycloadditions with Furans," *J. Am. Chem. Soc.* 1976, 98, 1992-1993.

Dhar, T.G. Murali, et al.; "Design and Synthesis of Novel $\alpha_{1a}$ Adrenoceptor-Selective Antagonists. 2. Approaches To Eliminate Opioid Agonist Metabolities via Modification of Linker and 4-Methoxycarbonyl-4-phenylpiperidine Moiety," *Journal of Medicinal Chemistry* (1999), 42(23), 4778-4793.

Eastwood, P. R., "A versatile synthesis of 4-aryl tetrahydropyridines via palladium mediated Suzuki cross-coupling with cyclic vinyl boronates," *Tetrahedron Letters*, 2000, 41, 3705.

Efange, Simon M.N., et al.; "Comparative Tissue Distribution of Conformationally Restricted Radioiodinated Vesamicol Receptor Ligands," *Nuclear Medicine and Biology* (1995), 22(4), 437-44.

Evans, Ben E., et al.; "Orally Active, Nonpeptide Oxytocin Antagonists," *Journal of Medicinal Chemistry* (1992), 35(21), 3919-27.

Harriman, Geraldine, et al., "Synthesis of 4-substituted 4-arylpiperidines," *Tetrahedron Letters*, 2000, 41, 8853.

Laszlo, Pierre et al., "Easy Formation of Diels-Alder Cycloadducts Between Furans and α,β-Unsaturated Aldehydes and Ketones at Normal Pressure," *Tetrahedron Letters*, 1984, 25, 4387-4388.

Minardi G., et al., "3-Aminometil-2-Bornanoni N-Sostituiti," *II Farmaco Ed. Sc.* vol. 25 fasc 7 pp. 519-536.

Moore, J. A., et al., "Catalylzed Addition of Furan with Acrylic Monomers," *J. Org. Chem.* 1983, 48, 1105-1106.

Mouithys-Mickalad, Ange, et al.; "Synthesis And Pharmacological Evaluation of 6-Piperidino- and 6-Piperazinoalkyl-2(3H)-Benzothiazolones as Mixed σ/5-HT1A Ligands," *Bioorganic & Medicinal Chemistry Letters* (2002), 12(8), 1149-1152.

Nelson, W. L., et al., "Muscarinic Receptors. Derivatives of 7-Oxabicyclo[2.2.1]heptane," *J. Med. Chem.* 1971, 14, 698-702.

Simpson, Merrill M., et al.; "Dopamine D4/D2 Receptor Selectivity Is Determined By A Divergent Aromatic Microdomain Contained Within The Second, Third, And Seventh Membrane-Spanning Segments," *Molecular Pharmacology* (1999), 56(6), 1116-1126.

Wang, Shaomeng, et al., " Pharmacophore-Based Discovery, Synthesis, and Biological Evaluation of 4-Phenyl-1-arylalkyl Piperidines as Dopamine Transporter Inhibitors," *Bioorganic & Medicinal Chemistry Letters*, 2001, 11, 495.

(Continued)

*Primary Examiner*—Rita J Desai  
*Assistant Examiner*—John Mabry  
(74) *Attorney, Agent, or Firm*—Honigman Miller Schwartz and Cohn LLP; Jonathan P. O'Brien; Christopher C. Forbes

(57) ABSTRACT

The present invention relates to modulators of muscarinic receptors. The present invention also provides compositions comprising such modulators, and methods therewith for treating muscarinic receptor mediated diseases.

7 Claims, No Drawings

OTHER PUBLICATIONS

Wustrow, et al., "Coupling of Arylboronic Acids with Partially Reduced Pyridine Derivative," L. D., Synthesis, 1991, 11, 993.

Bagley, James R., et al., "New 4-(heteroanilido)piperidines, Structurally Related to the Pure Opiod Agonist Fentanyl with Agonist and/or Antagonist Properties", J. Med. Chem., (1989) 32(3), 663-671.

Caufield, M.P., "International Union of Pharmacology. XVII. Classification of Muscarinic Acetylcholine Receptors", Pharmacol. Rev., 50 (1998), pp. 279-290.

Caufield, M.P., "Muscarinic Receptors-Characterization, Coupling and function", Pharmac. Ther., vol. 58 (1993), pp. 319-379.

Diouf, O., et al., "A New Series of M3 Muscarinic Antagonists Based on the 4-Aminopiperidine Scaffold", Bioorganic and Medicinal Chemistry Letters, (2002) 12, 2535-2539.

Felder, C., "Therapeutic Opportunities for Muscarinic Receptors in the Central Nevous System", J. Med. Chem., 43 (23) (2000), pp. 4333-4353.

Freireich, et al., "Quantitative Comparison of Toxicity of Anticancer Agents in Mouse, Rat, Hamster, Dog, Monkey and Man," Cancer Chemother. Rep., 50: 219 (1966).

Hooper, Mark W., et al., "Scope and Mechanism of Palladium Catalyzed Amination of Five Membered Heterocyclic Halides", J. Org. Chem., (2003) 68(7), 2861-2873.

Hulme, E.C., "Muscarinic Receptor Subtypes", Annu. Rev. Pharmacol. Toxicol., 30 (1990), pp. 633-673.

Poulain, Rebecca, et al., "From Hit to Lead. Analyzing Structure—Profile Relationships", J. Med. Chem., (2001) 44 (21), 3391-3401.

* cited by examiner

BICYCLIC SUBSTITUTED PHENYL PIPERIDINE MODULATORS OF MUSCARINIC RECEPTORS

CLAIM OF PRIORITY

This application claims the benefit of U.S. provisional application No. 60/631,560, filed on Nov. 29, 2004, which is hereby incorporated by reference.

TECHNICAL FIELD OF THE INVENTION

The present invention relates to modulators of muscarinic receptors. The present invention also provides compositions comprising such modulators, and methods therewith for treating muscarinic receptor mediated diseases.

BACKGROUND OF THE INVENTION

The neurotransmitter acetylcholine binds to two types of cholinergic receptors: the ionotropic family of nicotinic receptors and the metabotropic family of muscarinic receptors. Muscarinic receptors belong to the large superfamily of plasma membrane-bound G protein coupled receptors (GPCRs). To date, five subtypes of muscarinic receptors ($M_1$-$M_5$) have been cloned and sequenced from a variety of species, and show a remarkably high degree of homology across species and receptor subtype. These $M_1$-$M_5$ muscarinic receptors are predominantly expressed within the parasympathetic nervous system which exerts excitatory and inhibitory control over the central and peripheral tissues and participate in a number of physiologic functions, including heart rate, arousal, cognition, sensory processing, and motor control.

Muscarinic agonists such as muscarine and pilocarpine, and antagonists, such as atropine have been known for over a century, but little progress has been made in the discovery of receptor subtype-selective compounds, thereby making it difficult to assign specific functions to the individual receptors. See, e.g., DeLapp, N. et al., "Therapeutic Opportunities for Muscarinic Receptors in the Central Nervous System," *J. Med. Chem.*, 43(23), pp. 4333-4353 (2000); Hulme, E. C. et al., "Muscarinic Receptor Subtypes," *Ann. Rev. Pharmacol. Toxicol.*, 30, pp. 633-673 (1990); Caulfield, M. P. et al., "Muscarinic Receptors—Characterization, Coupling, and Function," *Pharmacol. Ther.*, 58, pp. 319-379 (1993); Caulfield, M. P. et al., International Union of Pharmacology. XVII. Classification of Muscarinic Acetylcholine Receptors," *Pharmacol. Rev.*, 50, pp. 279-290 (1998), the disclosures of which are incorporated herein by reference.

The Muscarinic family of receptors is the target of a large number of pharmacological agents used for various diseases, including leading drugs for COPD, asthma, urinary incontinence, glaucoma, Alzheimer's (AchE inhibitors). Despite the large therapeutic value of this family, cholinergic drugs are limited by the lack of selectivity of these agents, with significant activation of the parasympathetic autonomous system and elevated incidence of adverse effects. The molecular cloning of the muscarinic receptors and the identification of the physiological role of specific isoforms using knock-out mice, has recently delineated novel opportunities for selective muscarinic ligands, and has helped to define the selectivity profile that is required for enhanced efficacy and reduced side effects.

There is a need for modulators of muscarinic receptors $M_1$-$M_5$. There is also a need for methods for treating muscarinic receptor-mediated diseases.

There is also a need for modulators of muscarinic receptors that are selective as to subtypes $M_1$-$M_5$.

SUMMARY OF THE INVENTION

The present invention provides methods of modulating activity of a muscarinic receptor (e.g., $M_1$, $M_2$, $M_3$, $M_4$, $M_5$, or combinations thereof) using compounds of formula I:

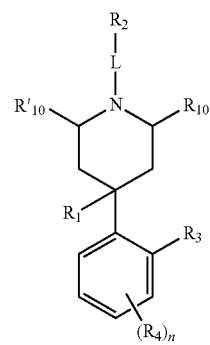

or a pharmaceutically acceptable salt thereof, wherein $R_1$, $R_2$, $R_3$, $R_4$, $R_{10}$ $R'_{10}$, L, and n are described below.

DETAILED DESCRIPTION

I. Definitions

For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

The term "muscarinic receptor," without a prefix specifying the receptor subtype, refers to one or more of the five receptor subtypes $M_1$-$M_5$.

The term "modulating" as used herein means increasing or decreasing, e.g. activity, by a measurable amount. Compounds that modulate muscarinic activity by increasing the activity of the muscarinic receptors are called agonists. Compounds that modulate muscarinic activity by decreasing the activity of the muscarinic receptors are called antagonists. An agonist interacts with a muscarinic receptor to increase the ability of the receptor to transduce an intracellular signal in response to endogenous ligand binding. An antagonist interacts with a muscarinic receptor and competes with the endogenous ligand(s) or substrate(s) for binding site(s) on the receptor to decrease the ability of the receptor to transduce an intracellular signal in response to endogenous ligand binding.

The phrase "treating or reducing the severity of a muscarinic receptor mediated disease" refers both to treatments for diseases that are directly caused by muscarinic activities and alleviation of symptoms of diseases not directly caused by muscarinic activities. Examples of diseases whose symptoms may be affected by muscarinic activity include, but are not limited to, CNS derived pathologies including cognitive disorders, Attention Deficit Hyperactivity Disorder (ADHD), obesity, Alzheimer's disease, various dementias such as vascular dementia, psychosis including schizophrenia, mania, bipolar disorders, pain conditions including acute and chronic syndromes, Huntington's Chorea, Friederich's ataxia, Gilles de la Tourette's Syndrome, Downs Syndrome, Pick disease, clinical depression, Parkinson's disease, peripheral disorders such as reduction of intra ocular pressure in Glaucoma and treatment of dry eyes and dry mouth including Sjögren's Syndrome, bradhycardia, gastric acid secretion, asthma, GI disturbances and wound healing.

As described herein, compounds of the invention may optionally be substituted with one or more substituents, such as are illustrated generally above, or as exemplified by particular classes, subclasses, and species of the invention.

As used herein the term "aliphatic" encompasses the terms alkyl, alkenyl, alkynyl.

As used herein, an "alkyl" group refers to a saturated aliphatic hydrocarbon group containing 1-8 (e.g., 1-6 or 1-4) carbon atoms. An alkyl group can be straight or branched. Examples of alkyl groups include, but are not limited to, methyl, ethyl, propyl, isopropyl, butyl, isobutyl, sec-butyl, isobutyl, n-pentyl, n-heptyl, or 2-ethylhexyl. An alkyl group can be optionally substituted with one or more substituents at any chemically feasibly position.

As used herein, an "alkenyl" group refers to an aliphatic carbon group that contains 2-10 (e.g., 2, 3, 4, 5, 6, 7, 8, 9 or 10) carbon atoms and at least one double bond. Like an alkyl group, an alkenyl group can be straight or branched. Examples of an alkenyl group include, but are not limited to, allyl, isoprenyl, 2-butenyl, and 2-hexenyl. An alkenyl group can be optionally substituted with one or more substituents.

As used herein, an "alkynyl" group refers to an aliphatic carbon group that contains 2-8 (e.g., 2-6 or 2-4) carbon atoms and at least one triple bond. Like an alkyl group, an alkynyl group can be straight or branched. An alkynyl group can be optionally substituted with one or more substituents.

As used herein, an "amino" group refers to —$NR^XR^Y$ wherein each of $R^X$ and $R^Y$ is independently hydrogen, alkyl, cycloalkyl, sulfonyl, (cycloalkyl)alkyl, aryl, aralkyl, heterocycloalkyl, (heterocycloalkyl)alkyl, heteroaryl, or heteroaralkyl each of which are defined herein and are optionally substituted. When the term "amino" is not the terminal group (e.g., alkylcarbonylamino), it is represented by —$NR^X$—. $R^X$ has the same meaning as defined above.

As used herein, an "aryl" group used alone or as part of a larger moiety as in "aralkyl", "aralkoxy", or "aryloxyalkyl" refers to monocyclic (e.g., phenyl); bicyclic (e.g., indenyl, naphthalenyl, tetrahydronaphthyl, tetrahydroindenyl); tricyclic (e.g., fluorenyl, tetrahydrofluorenyl, anthracenyl, or tetrahydroanthracenyl); or a benzofused group having 3 rings. For example, a benzofused group includes phenyl fused with two or more $C_{4-8}$ carbocyclic moieties. An aryl can be optionally substituted with one or more substituents.

As used herein, an "araliphatic" group refers to an aliphatic group (e.g., a $C_{1-4}$ alkyl group, a $C_{1-4}$ alkenyl group, or a $C_{1-4}$ alkynyl group) that is substituted with an aryl group. Both "aliphatic" and "aryl" have been defined above.

As used herein, an "aralkyl" group refers to an alkyl group (e.g., a $C_{1-4}$ alkyl group) that is substituted with an aryl group. Both "alkyl" and "aryl" are defined herein. An example of an aralkyl group is benzyl.

As used herein, a "bicyclic ring system" includes 5-12 (e.g., 7, 8, 9, 10, or 11) membered structures that form two rings, wherein the two rings have at least one atom in common (e.g., 2 atoms in common). Bicyclic ring structures include bicycloaliphatics (e.g., bicycloalkyl or bicycloalkenyl), bicycloheteroaliphatics (e.g., bicycloheteroalkyl or bicycloheteroalkenyl), bicyclic aryls, and bicyclic heteroaryls. Bicyclic ring systems also includes bridged bicyclic rings and fused bicyclic rings (e.g., benzo fused or cycloaliphatic fused).

The term "cycloaliphatic" means a saturated or partially unsaturated monocyclic, bicyclic, or tricyclic hydrocarbon ring that has a single point of attachment to the rest of the molecule. Cycloaliphatic rings are 3-8 membered monocyclic rings (e.g., 3-6 membered rings). Cycloaliphatic rings also include 8-12 membered bicyclic rings, (e.g., 10 membered bicyclic (fused or bridged) hydrocarbon rings). A cycloaliphatic group encompasses a "cycloalkyl" group and a "cycloalkenyl" group.

As used herein, a "cycloalkyl" group refers to a saturated carbocyclic mono-, bi-, or tri-, or multicyclic (fused or bridged) ring of 3-10 (e.g., 5-10) carbon atoms. Without limitation, examples of monocyclic cycloalkyl groups include cyclopropyl, cyclobutyl, cyclopentyl, cyclohexyl, cycloheptyl, or the like. Without limitation, examples of bicyclic cycloalkyl groups include octahydro-indenyl, decahydro-naphthyl, bicyclo[3.2.1]octyl, bicyclo[2.2.2]octyl, bicyclo[3.3.1]nonyl, bicyclo[3.3.2.]decyl, bicyclo[2.2.2]octyl, bicycle[2.2.1]heptanyl, bicycle[3.1.1]heptanyl, or the like. Without limitation, multicyclic groups include adamantyl, cubyl, norbomyl, or the like. Cycloalkyl rings can be optionally substituted at any chemically viable ring position.

As used herein, the term "heterocycloaliphatic" and "heterocyclic" encompasses a heterocycloalkyl group and a heterocycloalkenyl group.

As used herein, a "heterocycloalkyl" group refers to a 3-10 membered mono or bicyclic (fused or bridged) (e.g., 5 to 10 membered mono or bicyclic such as fused or bridged) saturated ring structure, in which one or more of the ring atoms is a heteroatom (e.g., N, O, S, or combinations thereof). Examples of a heterocycloalkyl group include optionally substituted piperidineyl, piperazineyl, tetrahydropyranyl, tetrahydrofuranyl, 1,4-dioxolanyl, 1,4-dithianyl, 1,3-dioxolanyl, oxazolidyl, isoxazolidyl, morpholinyl, thiomorpholinyl, octahydro-benzofuranyl, octahydro-chromenyl, octahydrothiochromenyl, octahydro-indolyl, octahydro-pyrindinyl, decahydro-quinolinyl, octahydro-benzo[b]thiophenyl, 2-oxa-bicyclo[2.2.2]octyl, 1-aza-bicyclo[2.2.2]octyl, 3-azabicyclo[3.2.1]octanyl, 2,6-dioxa-tricyclo[3.3.1.0$^{3,7}$]nonyl, tropane. A monocyclic heterocycloalkyl group may be fused with a phenyl moiety such as tetrahydroisoquinoline. Heterocycloalkyl ring structures can be optionally substituted at any chemically viable position on the ring or rings.

A "heterocycloalkenyl" group, as used herein, refers to a mono- or bicyclic (e.g., 5- to 10-membered mono- or bicyclic such as fused or bridged) non-aromatic ring structure having one or more double bonds, and wherein one or more of the ring atoms is a heteroatom (e.g., N, O, or S). Examples of heterocycloalkenyls include 2-pyrrolyl, 3-pyrrolyl, 2-imidazolyl, or 2-pyrazolyl. Monocyclic heterocycloaliphatics are numbered according to standard chemical nomenclature.

A "heteroaryl" group, as used herein, refers to a monocyclic, bicyclic, or tricyclic ring systems having 4 to 15 ring atoms wherein one or more of the ring atoms is a heteroatom (e.g., N, O, S, or combinations thereof) and wherein one or more rings of the bicyclic or tricyclic ring structure is aromatic. A heteroaryl group includes a benzofused ring system having 2 to 3 rings. For example, a benzofused group includes benzo fused with one or two $C_{4-8}$ heterocyclic moieties (e.g., indolizyl, indolyl, isoindolyl, 3H-indolyl, indolinyl, benzo[b]furyl, benzo[b]thiophenyl, quinolinyl, or isoquinolinyl). Some examples of heteroaryl are pyridinyl, 1H-indazolyl, furyl, pyrrolyl, thienyl, thiazolyl, oxazolyl, imidazolyl, tetrazolyl, benzofuryl, isoquinolinyl, benzthiazolyl, xanthene, thioxanthene, phenothiazine, dihydroindole, benzo[1,3]dioxole, benzo[b]furyl, benzo[b]thiopheneyl, indazolyl, benzimidazolyl, benzthiazolyl, puryl, cinnolineyl, quinolineyl, quinazolineyl, cinnolineyl, phthalazyl, quinazolyl, quinoxalyl, isoquinolyl, 4H-quinolizyl, benzo-1,2,5-thiadiazolyl, or 1,8-naphthyridyl. A heteroaryl can be optionally substituted at any chemically feasible position.

Without limitation, monocyclic heteroaryls include furyl, thiophenyl, 2H-pyrrolyl, pyrrolyl, oxazolyl, thiazolyl, imidazolyl, pyrazolyl, isoxazolyl, isothiazolyl, 1,3,4-thiadiazolyl, 2H-pyranyl, 4-H-pyranyl, pyridineyl, pyridazineyl, pyrimideyl, pyrazineyl, pyrazolyl, or 1,3,5-triazolineyl.

Without limitation, bicyclic heteroaryls include indolizinyl, indolyl, isoindolyl, 3H-indolyl, indolinyl, benzo[b]furyl, benzo[b]thiophenyl, quinolinyl, isoquinolinyl, indolizyl, isoindolyl, indazolyl, benzimidazyl, benzthiazolyl, purinyl, 4H-quinolizyl, quinolyl, isoquinolyl, cinnolyl, phthalazyl, quinazolyl, quinoxalyl, 1,8-naphthyridyl, or pteridyl.

A "heteroaraliphatic" group, as used herein, refers to an aliphatic group (e.g., $C_{1-4}$ alkyl group, $C_{1-4}$ alkenyl group, or $C_{1-4}$ alkynyl group) that is substituted with a heteroaryl group. Both "aliphatic" and "heteroaryl" have been defined above.

A "heteroaralkyl" group, as used herein, refers to an alkyl group (e.g., a $C_{1-4}$ alkyl group) that is substituted with a heteroaryl group. Both "alkyl" and "heteroaryl" have been defined above.

As used herein, "cyclic group" includes mono-, bi-, and tri-cyclic structures including cycloaliphatic, heterocycloaliphatic, aryl, or heteroaryl, each of which has been previously defined.

As used herein, an "acyl" group refers to a formyl group or alkyl-C(O)— (also referred to as "alkylcarbonyl") where "alkyl" has been defined previously. Acetyl and pivaloyl are examples of acyl groups.

As used herein, a "carbonyl" group, when used alone or as part of another structure refers to the structure —C(O)—.

As used herein, a "carbamoyl" group refers to a group having the structure —O—CO—$NR^XR^Y$ or —$NR^X$—CO—O—$R^Z$ wherein $R^X$ and $R^Y$ have been defined above and $R^Z$ can be alkyl, aryl, aralkyl, heterocycloalkyl, heteroaryl, or heteroaralkyl.

As used herein, a "carboxy" and a "sulfo" group refer to —C(O)OH or —C(O)$OR^X$ and —$SO_3H$ or —$SO_3R^X$, respectively.

As used herein, an "alkoxy" group refers to an alkyl-O— group where "alkyl" has been defined previously. Moreover an alkoxy group includes structures comprising two alkoxy groups on the same atom or adjacent atoms that form a ring together with the atom(s) to which they are bound.

As used herein, a "nitro" group refers to —$N^+(O)O^-$.

As used herein, a "sulfoxy" group refers to —O—SO—$R^X$ or —SO—O—$R^X$, where $R^X$ has been defined above.

As used herein, a "mercapto" group refers to —SH.

As used herein, a "sulfonyl" group refers to —$S(O)_2$—.

As used herein a "sulfinyl" group refers to —S(O)—.

As used herein a "sulfanyl" group refers to —S—.

As used herein, a "halogen" or "halo" group refers to fluorine, chlorine, bromine or iodine.

As used herein, a "haloaliphatic" group refers to an aliphatic group substituted with 1-3 halogen. For instance, the term haloalkyl includes the group —$CF_3$.

As used herein, a "sulfamoyl" group refers to the structure —$S(O)_2$—$NR^XR^Y$ or —$NR^X$—$S(O)_2$—$R^Z$ wherein $R^X$, $R^Y$, and $R^Z$ have been defined above.

As used herein, a "sulfamide" group refers to the structure —$NR^X$—$S(O)_2$—$NR^YR^Z$ wherein $R^X$, $R^Y$, and $R^Z$ have been defined above.

As used herein, a "carbonylamino" group used alone or in connection with another group refers to an amido group such as $R^X$—C(O)—$NR^X$—. For instance an alkylcarbonylamino includes alkyl-C(O)—$NR^X$—, wherein $R^X$ has been defined above.

As used herein, a "aminocarbonyl" group used alone or in connection with another group refers to an amido group such as $N(R^X)_2$—C(O)—.

As used herein, an "alkoxycarbonyl" used alone or in connection with another group refers to a carbonyl group such as alkyl-O—C(O)—.

As used herein, an "alkoxyalkyl" refers to an alkyl group such as alkyl-O-alkyl-, wherein alkyl has been defined above.

As used herein, an "aminocarbonyl" refers to an amido group such as —$NR^X$—C(O)—, wherein $R^X$ has been defined above.

As used herein, an "aminosulfonyl" refers to the structure —$N(R^X)_2$—$S(O)_2$—, wherein $R^X$ has been defined above.

As used herein, an "oxo" refers to =O.

As used herein, an "aminoalkyl" refers to the structure $N(R^X)_2$-alkyl-.

As used herein, a "cyanoalkyl" refers to the structure (CN)-alkyl-.

As used herein, an "alkylsulfonyl" group refers to the structure alkyl-$S(O)_2$—.

As used herein, a "sulfonylamino" group refers to the structure $R^X$—$S(O)_2$—$N(R^X)_2$—, wherein $R^X$ has been defined above.

As used herein, an "imino" group refers to the functional group =N— and covers the structure =$NR^X$ and oximes (e.g., =$NOR^X$) where $R^X$ is defined above.

As used herein, a "hydroxyl" group refers to the structure —OH.

As used herein, a "guanidinyl" group refers to the structure $NH_2C(NH)NH$—.

As used herein, an "aliphatic chain" refers to a branched or straight aliphatic group (e.g., alkyl groups, alkenyl groups, or alkynyl groups). A straight aliphatic chain has the structure —$[CH_2]_p$—, where p is 1-6. A branched aliphatic chain is a straight aliphatic chain that is substituted with one or more aliphatic groups. A branched aliphatic chain has the structure —$[CHW]_p$— where W is hydrogen or an aliphatic group; however, W shall be an aliphatic group in at least one instance. The term aliphatic chain includes alkyl chains, alkenyl chains, and alkynyl chains, where alkyl, alkenyl, and alkynyl are defined above.

As used herein, a "urea" group refers to the structure —$NR^X$—CO—$NR^YR^Z$ and a "thiourea" group refers to the structure —$NR^X$—CS—$NR^YR^Z$. $R^X$, $R^Y$, and $R^Z$ have been defined above.

In general, the term "vicinal" refers to the placement of substituents on a group that includes two or more carbon atoms, wherein the substituents are attached to adjacent carbon atoms.

In general, the term "geminal" refers to the placement of substituents on a group that includes two or more carbon atoms, wherein the substituents are attached to the same carbon atom.

In general, the term "substituted," whether preceded by the term "optionally" or not, refers to the replacement of hydrogen radicals in a given structure with the radical of a specified substituent. Specific substituents are described above in the definitions and below in the description of compounds and examples thereof. Unless otherwise indicated, an optionally substituted group may have a substituent at each substitutable position of the group, and when more than one position in any given structure may be substituted with more than one substituent selected from a specified group, the substituent may be either the same or different at every position. For instance, a substituted group may be substituted with two substituents vicinally or geminally. A ring substituent, such as a heterocycloalkyl, may be bound to another ring, such as a cycloalkyl, to form a spiro-bicyclic ring system, e.g., both rings share one common atom. As one of ordinary skill in the art will recognize, combinations of substituents envisioned by this invention are those combinations that result in the formation of stable or chemically feasible compounds.

The phrase "stable or chemically feasible," as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

As used herein, an effective amount is defined as the amount required to confer a therapeutic effect on the treated patient, and is typically determined based on age, surface area, weight, and condition of the patient. The interrelationship of dosages for animals and humans (based on milligrams per meter squared of body surface) is described by Freireich et al., *Cancer Chemother. Rep.*, 50: 219 (1966). Body surface area may be approximately determined from height and weight of the patient. See, e.g., Scientific Tables, Geigy Pharmaceuticals, Ardsley, N.Y., 537 (1970). As used herein, "patient" refers to a mammal, including a human.

As used herein, "patient" refers to a mammal, including a human.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$- or $^{14}C$-enriched carbon are within the scope of this invention. Such compounds are useful, for example, as analytical tools or probes in biological assays.

II. Compounds

A. Generic Compounds

The present invention provides methods of modulating the activity of a muscarinic receptor comprising the step of contacting said receptor with a compound of formula I:

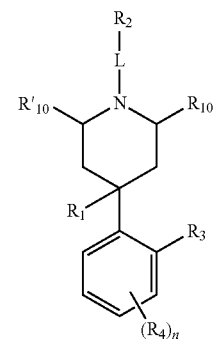

or a pharmaceutically acceptable salt thereof.

$R_1$ is $-Z^A R_5$, wherein each $Z^A$ is independently a bond or an optionally substituted branched or straight $C_{1-6}$ aliphatic chain wherein up to two carbon units of $Z^A$ are optionally and independently replaced by $-CO-$, $-CS-$, $-CONR^A-$, $-CONR^A NR^A-$, $-CO_2-$, $-OCO-$, $-NR^A CO_2-$, $-O-$, $-NR^A CONR^A-$, $-OCONR^A-$, $-NR^A NR^A-$, $-NR^A CO-$, $-S-$, $-SO-$, $-SO_2-$, $-NR^A-$, $-SO_2 NR^A-$, $-NR^A SO_2-$, or $-NR^A SO_2 NR^A-$.

Each $R_5$ is independently $R^A$, halo, $-OH$, $-NH_2$, $-NO_2$, $-CN$, or $-OCF_3$.

Each $R^A$ is independently hydrogen, an optionally substituted $C_{1-8}$ aliphatic group; an optionally substituted cycloaliphatic, an optionally substituted heterocycloaliphatic, an optionally substituted aryl, or an optionally substituted heteroaryl.

$R_2$ is independently a monocyclic cycloalkyl, a monocyclic heterocycloaliphatic, a bicyclic cycloaliphatic, a bridged bicyclic heterocycloaliphatic, or adamantanyl, each of which is optionally substituted with 1-3 of $R_6$.

Each $R_6$ is independently $=O$ or $-Z^B R_7$, wherein each $Z^B$ is independently a bond, or an optionally substituted branched or straight $C_{1-4}$ aliphatic chain wherein up to two carbon units of $Z^B$ are optionally and independently replaced by $-CO-$, $-CS-$, $-CONR^B-$, $-CONR^B NR^B-$, $-CO_2-$, $-OCO-$, $-NR^B CO_2-$, $-O-$, $-NR^B-CONR^B-$, $-OCONR^B-$, $-NR^B NR^B-$, $-NR^B CO-$, $-S-$, $-SO-$, $-SO_2-$, $-NR^B-$, $-SO_2 NR^B-$, $-NR^B SO_2-$, or $-NR^B SO_2 NR^B-$.

Each $R_7$ is independently $R^B$, halo, $-OH$, $-NH_2$, $-NO_2$, $=NR^B$, $=NOR^B$, $-CN$, or $-OCF_3$.

Each $R^B$ is independently hydrogen, an optionally substituted $C_{1-8}$ aliphatic group; an optionally substituted cycloaliphatic, an optionally substituted heterocycloaliphatic, an optionally substituted aryl, or an optionally substituted heteroaryl.

$R_3$ is $-Z^C R_8$, wherein each $Z^C$ is independently a bond or an optionally substituted branched or straight $C_{1-6}$ aliphatic chain wherein up to two carbon units of $Z^C$ are optionally and independently replaced by $-CO-$, $-CS-$, $-CONR^C-$, $-CONR^C NR^C-$, $-CO_2-$, $-OCO-$, $-NR^C CO_2-$, $-O-$, $-NR^C CONR^C-$, $-OCONR^C-$, $-NR^C NR^C-$, —NR$^C$CO—, —S—, —SO—, —SO$_2$—, —NR$^C$—, —SO$_2$NR$^C$—, —NR$^C$SO$_2$—, or —NR$^C$SO$_2$NR$^C$—.

Each R$_8$ is independently R$^C$, halo, —OH, —NH$_2$, —NO$_2$, —CN, or —OCF$_3$.

Each R$^C$ is independently an optionally substituted C$_{1-8}$ aliphatic group; an optionally substituted cycloaliphatic, an optionally substituted heterocycloaliphatic, an optionally substituted aryl, or an optionally substituted heteroaryl.

Each R$_4$ is independently —Z$^D$R$_9$, wherein each Z$^D$ is independently a bond or an optionally substituted branched or straight C$_{1-6}$ aliphatic chain wherein up to two carbon units of Z$^D$ are optionally and independently replaced by —CO—, —CS—, —CONR$^D$—, —CONR$^D$NR$^D$—, —CO$_2$—, —OCO—, —NR$^D$CO$_2$—, —O—, —NR$^D$CONR$^D$—, —OCONR$^D$—, —NR$^D$NR$^D$—, —NR$^D$CO—, —S—, —SO—, —SO$_2$—, —NR$^D$—, —SO$_2$NR$^D$—, —NR$^D$SO$_2$—, or —NR$^D$SO$_2$NR$^D$—.

Each R$_9$ is independently R$^D$, halo, —OH, —NH$_2$, —NO$_2$, —CN, or —OCF$_3$;

Each R$^D$ is independently a hydrogen, an optionally substituted C$_{1-8}$ aliphatic group, an optionally substituted cycloaliphatic, an optionally substituted heterocycloaliphatic, an optionally substituted aryl, or an optionally substituted heteroaryl.

Alternatively, R$_3$ and a vicinal R$_4$, together with the atoms to which they are attached, form an optionally substituted 5-6 membered cycloaliphatic or heterocycloaliphatic ring.

Each L is a bond or a —CH$_2$—.

Each n is 0-4.

1. Substituent R$_1$:

R$_1$ is —Z$^A$R$_5$, wherein each Z$^A$ is independently a bond or an optionally substituted branched or straight C$_{1-6}$ aliphatic chain wherein up to two carbon units of Z$^A$ are optionally and independently replaced by —CO—, —CS—, —CONR$^A$—, —CONR$^A$NR$^A$—, —CO$_2$—, —OCO—, —NR$^A$CO$_2$—, —O—, —NR$^A$CONR$^A$—, —OCONR$^A$—, —NR$^A$NR$^A$—, —NR$^A$CO—, —S—, —SO—, —SO$_2$—, —NR$^A$—, —SO$_2$NR$^A$—, —NR$^A$SO$_2$—, or —NR$^A$SO$_2$NR$^A$—; each R$_5$ is independently R$^A$, halo, —OH, —NH$_2$, —NO$_2$, —CN, or —OCF$_3$; and each R$^A$ is independently hydrogen, an optionally substituted C$_{1-8}$ aliphatic group; an optionally substituted cycloaliphatic, an optionally substituted heterocycloaliphatic, an aryl, or a heteroaryl.

In several embodiments, R$_1$ is independently hydrogen, halo, hydroxy, cyano, nitro, or optionally substituted C$_{1-6}$ aliphatic, optionally substituted C$_{1-6}$ alkoxy, optionally substituted cycloaliphatic, optionally substituted heterocycloaliphatic, optionally substituted alkylaminocarbonyl, optionally substituted alkylcarbonylamino, optionally substituted alkoxycarbonyl, optionally substituted aryl, optionally substituted heteroaryl, optionally substituted aralkyl, optionally substituted (cycloaliphatic)alkylaminocarbonyl, optionally substituted aliphaticsulfinyl, optionally substituted aliphaticsulfanyl, optionally substituted aliphaticsulfonyl, or optionally substituted (cycloaliphatic)alkylcarbonylamino.

In several embodiments, R$_1$ is an alkylaminocarbonyl, ((alkoxycarbonyl)amino)aliphatic, ((alkylamino)carbonylamino)aliphatic, (cycloaliphatic)aminocarbonyl, [((cycloaliphatic)oxycarbonyl)amino]aliphatic, or ((cycloaliphaticamino)carbonylamino)aliphatic. For example, R$_1$ is —Z$^A$R$_5$, wherein Z$^A$ is selected from —C(O)NR$^A$R$_5$, —CH$_2$NR$^A$C(O)R$_5$, —CH$_2$NR$^A$C(O)NR$^A$R$_5$, or —CH$_2$NR$^A$C(O)OR$_5$. In other examples, R$_1$ is —C(O)NHR$_5$, —CH$_2$NHC(O)R$_5$, —CH$_2$NHC(O)NHR$_5$, or —CH$_2$NHC(O)OR$_5$.

In several embodiments, R$_1$ is a cycloalkyl that is optionally substituted with 1-3 of R$_5$. For example, R$_1$ is a monocyclic cycloalkyl or a bicyclic cycloalkyl, each of which is optionally substituted with 1-3 of R$_5$. In another example, R$_1$ is an optionally substituted 3-8 membered monocyclic cycloalkyl. In several embodiments, R$_1$ is cyclopropyl, cyclobutyl, cyclopentyl, cyclohexyl, cycloheptyl, or cyclooctyl, each of which is optionally substituted with 1-3 of R$_5$. In another example R$_1$ is an optionally substituted 5-10 membered bicyclic cycloalkyl. In several embodiments, R$_1$ is bicyclo[1.1.1]pentyl, bicyclo[2.1.1]hexyl, bicyclo[2.2.1]heptyl, bicyclo[3.1.1]heptyl, bicyclo[2.2.2]octyl, bicyclo[3.2.1]octyl, bicyclo[3.3.1]nonyl, or bicyclo[3.3.2]decyl; each of which is optionally substituted with 1-3 of R$_5$. In another embodiment, R$_1$ is an optionally substituted monocyclic cycloalkenyl or an optionally substituted bicyclic cycloalkenyl. For example, R$_1$ is an optionally substituted 3-8 membered monocyclic cycloalkenyl. In several embodiments, R$_1$ is cyclopropenyl, cyclobutenyl, cyclopentenyl, cyclohexenyl, cycloheptenyl, or cyclooctenyl; each of which is optionally substituted. In another example, R$_1$ is an optionally substituted 5-10 membered bicyclic cycloalkenyl. In several embodiments, R$_1$ is bicyclo[1.1.1]pentenyl, bicyclo[2.1.1]hexenyl, bicyclo[2.2.1]heptenyl, bicyclo[3.1.1]heptenyl, bicyclo[2.2.2]octenyl, bicyclo[3.2.1]octenyl, bicyclo[3.3.1]nonenyl, or bicyclo[3.3.2]decenyl; each of which is optionally substituted. In more examples, R$_1$ is optionally substituted with 1-3 of halo, hydroxy, alkylcarbonyl, alkoxy, amino, alkoxycarbonyl, alkylaminocarbonyl, alkylcarbonylamino, aryl, heteroaryl, heterocycloaliphatic, or combinations thereof.

In other embodiments, R$_1$ is an optionally substituted heterocycloaliphatic. For example, R$_1$ is an optionally substituted heterocycloalkyl or an optionally substituted heterocycloalkenyl, each of which has 1-3 heteroatoms selected from nitrogen, oxygen, and sulfur. In another example, R$_1$ is an optionally substituted 4-8 membered monocyclic heterocycloalkyl. In several embodiments, R$_1$ is tetrahydrofuranyl, pyrrolidinyl, piperidinyl, piperazinyl, imidazolidinyl, hexahydropyrimidinyl, morpholinyl, thiomorpholinyl, oxazolidinyl, or 1,3-oxazinanyl; each of which is optionally substituted. In more examples, R$_1$ is optionally substituted with 1-3 of halo, hydroxy, alkylcarbonyl, alkoxy, amino, alkoxycarbonyl, alkylaminocarbonyl, alkylcarbonylamino, aryl, heteroaryl, heterocycloaliphatic, or combinations thereof.

In other embodiments, R$_1$ is an optionally substituted C$_{1-8}$ aliphatic. For example, R$_1$ is an optionally substituted C$_{1-6}$ aliphatic. In several embodiments, R$_1$ is methyl, ethyl, propyl, butyl, sec-butyl, pentyl, sec-pentyl, or hexyl; each of which are optionally substituted with 1-3 of R$_5$. In other embodiments, R$_1$ is ethenyl, propenyl, butenyl, sec-butenyl, pentenyl, sec-pentenyl, or hexenyl, each of which is optionally substituted with 1-3 of R$_5$. In other examples, R$_1$ is optionally substituted with 1-3 of halo, hydroxy, cycloaliphatic, amino, or combinations thereof.

In several embodiments, R$_1$ is an optionally substituted aryl. For example, R$_1$ is a monocyclic or a bicyclic aryl, each of which is optionally substituted with 1-3 of R$_5$. In other examples, R$_1$ is an optionally substituted phenyl. In still another example, R$_1$ is an optionally substituted naphthalenyl or indenyl. In several embodiments, R$_1$ is an optionally substituted with 1-3 of halo, cyano, nitro, or optionally substituted aliphatic, optionally substituted cycloaliphatic, optionally substituted heterocycloaliphatic, optionally substituted alkylaminocarbonyl, or combinations thereof.

In several embodiments, R$_1$ is an optionally substituted aralkyl. For example, R$_1$ is an optionally substituted —C$_{1-5}$ alkyl-aryl. In several embodiments, R$_1$ is a phenylmethyl, phenylethyl, phenylpropyl, phenylbutyl, or phenylpentyl; each of which is optionally substituted.

In several examples, $R_1$ is an optionally substituted alkoxy. For example, $R_1$ is a straight or branched alkoxy. In several embodiments, $R_1$ is an alkoxy that includes an optionally substituted -straight $C_{1-5}$ alkyl-O— or -branched $C_{1-5}$ alkyl-O—. In other embodiments, $R_1$ is a methoxy, ethoxy, propoxy, butoxy, or pentoxy; each of which is optionally substituted with 1-3 of $R_5$.

In several embodiments, $R_1$ is hydrogen.

In several embodiments, $R_1$ is one selected from hydrogen, methyl, fluoro, chloro, hydroxy, cyano, methoxy, and ethoxy.

2. -L-$R_2$ Group

2a. Substituent $R_2$ $R_2$ is independently a monocyclic cycloalkyl, a monocyclic heterocycloaliphatic, a bicyclic cycloaliphatic, a bridged bicyclic heterocycloaliphatic, or adamantanyl, each of which is optionally substituted with 1-3 of $R_6$; each $R_6$ is independently =O or —$Z^B R_7$, wherein each $Z^B$ is independently a bond, or an optionally substituted branched or straight $C_{1-4}$ aliphatic chain wherein up to two carbon units of $Z^B$ are optionally and independently replaced by —CO—, —CS—, —CONR$^B$—, —CONR$^B$NR$^B$—, —CO$_2$—, —OCO—, —NR$^B$CO$_2$—, —O—, —NR$^B$CONR$^B$—, —OCONR$^B$—, —NR$^B$NR$^B$—, —NR$^B$CO—, —S—, —SO—, —SO$_2$—, —NR$^B$—, —SO$_2$NR$^B$—, —NR$^B$SO$_2$—, or —NR$^B$SO$_2$NR$^B$—; each $R_7$ is independently $R^B$, halo, —OH, —NH$_2$, —NO$_2$, =NR$^B$, =NOR$^B$, —CN, or —OCF$_3$; and each $R^B$ is independently hydrogen, an optionally substituted $C_{1-8}$ aliphatic group; an optionally substituted cycloaliphatic, an optionally substituted heterocycloaliphatic, an optionally substituted aryl, or an optionally substituted heteroaryl.

In several embodiments, $R_2$ is a 3-12 membered fully saturated monocyclic ring, a bicyclic ring, or adamantanyl, each of which is optionally substituted with 1-3 of $R_6$.

In several examples, $R_2$ is an optionally substituted 3-10 membered fully saturated or partially unsaturated monocyclic or bicyclic cycloaliphatic. In several embodiments, $R_2$ is an optionally substituted 3-8 membered monocyclic cycloaliphatic. In several examples, $R_2$ is an optionally substituted 3-8 membered monocyclic cycloalkyl. In several more examples, $R_2$ is a cyclopropyl, cyclobutyl, cyclopentyl, cyclohexyl, cycloheptyl, or cyclooctyl, each of which is optionally substituted with 1-3 of hydrogen, hydroxy, cyano, nitro, oxo, or aliphatic, alkoxy, alkoxycarbonyl, aryl, imino, alkylcarbonyl. In other examples, $R_2$ is an optionally substituted 3-8 membered monocyclic cycloalkenyl. In several embodiments, $R_2$ is a cyclopropenyl, cyclobutenyl, cyclopentenyl, cyclohexenyl, cycloheptenyl, or cyclooctenyl, each of which is optionally substituted with 1-3 of hydrogen, hydroxy, cyano, nitro, oxo, or aliphatic, alkoxy, alkoxycarbonyl, aryl, imino, alkylcarbonyl, or combinations thereof. In more examples, $R_2$ is an unsubstituted monocyclic cycloalkyl. In several embodiments, $R_2$ is a 5-10 membered bicyclic cycloaliphatic optionally substituted with 1-3 of $R_6$. For example, $R_2$ is an optionally substituted 6-10 membered cycloaliphatic fused or bridged bicyclic cycloalkyl. In other examples, $R_2$ is a bicyclo[2.1.1]hexyl, bicyclo[2.2.1]heptyl, bicyclo[3.1.1]heptyl, bicyclo[2.2.2]octyl, bicyclo[3.2.1]octyl, bicyclo[3.3.1]nonyl, or bicyclo[3.3.3]undecyl, each of which is optionally substituted with 1-3 of hydrogen, hydroxy, cyano, nitro, oxo, or aliphatic, alkoxy, alkoxycarbonyl, aryl, imino, alkylcarbonyl, or combinations thereof. In still other examples, $R_2$ is an optionally substituted 6-10 membered bridged bicyclic alkenyl. In several embodiments, $R_2$ is a bicyclo[2.1.1]hexenyl, bicyclo[2.2.1]heptenyl, bicyclo[3.1.1]heptenyl, bicyclo[2.2.2]octenyl, bicyclo[3.2.1]octenyl, bicyclo[3.3.1]nonenyl, or bicyclo[3.3.3]undecenyl, each of which is optionally substituted with 1-3 of $R^6$. In several examples, $R_2$ is an optionally substituted cycloaliphatic fused bicyclic cycloaliphatic optionally substituted with 1-3 of $R_6$. In several examples, $R_2$ is a decahydronaphthalenyl, octahydropentalenyl, or octahydro-1H-indene, each of which is optionally substituted with 1-3 of $R_6$. In alternative embodiments, $R_2$ is an unsubstituted decahydronaphthalenyl, octahydropentalenyl, or octahydro-1H-indene.

In several embodiments, $R_2$ is a heterocycloaliphatic that is optionally substituted with 1-3 of $R_6$. For example, $R_2$ is a 4-9 membered optionally substituted monocyclic heterocycloalkyl or a 5-9 membered optionally substituted monocyclic heterocycloalkenyl, each of which is optionally substituted with 1-3 of hydrogen, hydroxy, cyano, nitro, oxo, or aliphatic, alkoxy, alkoxycarbonyl, aryl, imino, alkylcarbonyl, or combinations thereof. In several embodiments, $R_2$ is an optionally substituted monocyclic heterocycloalkyl selected from tetrahydrofuranyl, tetrahydrothiophenyl, 1,3-dioxolanyl, tetrahydrooxazolyl, pyrrolidinyl, imidazolidinyl, pyrazolidinyl, tetrahydropyran, piperidinyl, tetrahydro-2H-thiopyranyl, piperazinyl, 1,2,3-triazolidinyl, dioxanyl, oxazolidinyl, morpholinyl, thiepanyl, dithianyl, octahydropyranyl, trithianyl, thiomorpholinyl, hexahydropyrimidinyl, hexahydropyridazinyl, and thiocane each of which is optionally substituted with 1-3 of $R_6$. In other embodiments, $R_2$ is an optionally substituted monocyclic heterocycloalkenyl selected from 2H-pyrrolyl, pyrrolyl, 2-pyrrolinyl, 3-pyrrolinyl, oxazolyl, 2-imidazolinyl, 2-pyrazolinyl and 2,3,4,5-tetrahydropyridinyl, each of which is optionally substituted with 1-3 of $R_6$. In several embodiments, $R_2$ is an optionally substituted bridged bicyclic heterocycloaliphatic having 1-3 heteroatoms independently selected from nitrogen, oxygen, and sulfur. For example, $R_2$ is an optionally substituted 5-9 membered bicyclic heterocycloalkyl that is substituted with 1-3 of $R_6$. In several embodiments, $R_2$ is 2-azabicyclo[1.1.1]pentyl, 5-azabicyclo[2.1.1]hexyl, 7-azabicyclo[2.2.1]heptyl, 6-azabicyclo[3.1.1]heptyl, 2-azabicyclo[2.2.2]octyl, 8-azabicyclo[3.2.1]octyl, or 9-azabicyclo[3.3.1]nonyl, each of which is optionally substituted with 1-3 of hydrogen, hydroxy, cyano, nitro, oxo, or aliphatic, alkoxy, alkoxycarbonyl, aryl, imino, alkylcarbonyl, or combinations thereof.

In several embodiments, $R_2$ is an optionally substituted adamantly.

Each $R_6$ is independently =O or —$Z^B R_7$, wherein each $Z^B$ is independently a bond or an optionally substituted branched or straight $C_{1-4}$ aliphatic chain wherein up to two carbon units of $Z^C$ are optionally and independently replaced by —CO—, —CS—, —COCO—, —O$_2$—, —OCO—, —O—, NR$^B$-NR$^B$—, —S—, —SO—, —SO$_2$—, —SO$_2$NR$^B$—, —NR$^B$SO$_2$—, or —NR$^C$SO$_2$NR$^B$—; each $R_7$ is independently $R^C$, halo, =O, —OH, —NH$_2$, —NO$_2$, =NR$^B$—, =NOR$^B$, —CN, —CF$_3$, or —OCF$_3$; and each $R^B$ is independently hydrogen, an optionally substituted $C_{1-8}$ aliphatic group; a cycloaliphatic, a heterocycloaliphatic, an aryl or a heteroaryl; or two occurrences of $R^B$ are taken together with the atom(s) to which they are attached to form an optionally substituted cycloaliphatic or heterocycloaliphatic. In several embodiments, $R_6$ is a hydrogen, halo, hydroxy, cyano, nitro, or oxo; or $R_6$ is aliphatic, cycloaliphatic, heterocycloaliphatic, alkylcycloaliphatic, alkylheterocycloaliphatic, aryl, heteroaryl, aralkyl, heteroaralkyl, alkoxy, imino, or alkoxycarbonyl, each of which is optionally substituted. In alternative embodiments, two occurrences of $R^B$ are attached to the same carbon atom of $R_3$ and together with the atom to which they are attached form an optionally substituted 5 or 6 membered cycloalkyl or heterocycloalkyl. For example, in several embodiments, $R_2$ together with two occurrences of $R^B$ is optionally substituted spiro[5.5]undecyl or 1,4-dioxaspiro[4.5]decyl.

In other embodiments, $R_6$ is hydrogen, hydroxy, cyano, nitro, oxo, or aliphatic, alkoxy, alkoxycarbonyl, aryl, imino, alkylcarbonyl, or $R_2$ together with two occurrences of $R^B$ is optionally substituted spiro[5.5]undecyl or 1,4-dioxaspiro[4.5]decyl, each of which is optionally substituted.

2b. Linking Group L

Each L is independently a bond or a branched or straight $C_{1-6}$ aliphatic chain optionally substituted with 1-3 of $R^E$, wherein up to two carbon units of L are optionally and independently replaced by —CO—, —CS—, —CONR$^E$—, —CO$_2$—, —OCO—, —NR$^E$CO$_2$—, —O—, —OCONR$^E$—, —NR$^E$CO—, —S—, —SO—, —SO$_2$—, —NR$^E$—, —SO$_2$NR$^E$—, —NR$^E$SO$_2$—, or —NR$^E$SO$_2$NR$^E$—; and each $R^E$ is independently hydrogen, halo, hydroxy, or an optionally substituted $C_{1-8}$ aliphatic group; an optionally substituted cycloaliphatic, an optionally substituted heterocycloaliphatic, an optionally substituted aryl, or an optionally substituted heteroaryl.

In several embodiments, L is a bond or an optionally substituted aliphatic. For example, L is a methylene group, an ethylene group, a propylene group, a butylene group, a pentylene group, or a hexylene group, each of which is optionally substituted with 1-2 of halo, hydroxyl, cyano, nitro, cycloaliphatic, heterocycloaliphatic, aryl, heteroaryl, or combinations thereof.

In several embodiments, L is a bond, a methylene group, or an ethylene group.

2c. -L-$R_2$ Group

In several embodiments, -L-$R_2$ is one selected from 1-ethoxycarbonylpiperidin-4-yl; 1-ethoxycarbonylpiperidin-4-yl-methyl; 4-tetrahydropyranyl; 7-aza-7-ethoxycarbonyl-bicyclo[3.2.1]heptan-3-yl; 4-methyltetrahydropyran-4-yl; cyclohexyl; 4-(ethyoxyimino)cyclohexyl; (bicyclo[2.2.1]hept-2-ene-5-yl-)methyl; 4-[(3-allyloxy)imino]cyclohexyl; 4-[(tetrahydropyran-2-yloxy)]iminocyclohexyl; bicyclo[3.2.1]octan-3-yl, bicyclo[3.2.1]octan-2-yl; bicyclo[2.2.1]heptan-2-yl; bicyclo[2.2.1]heptan-2-ylmethyl; cycloheptyl; 4-oxocyclohexyl; 1,4-dioxaspiro[4.5]decan-8-yl; 4-(1,1-dimethylethyl)-oximinocyclohexyl; 3-methylcyclohexyl; 1-methylcyclohexyl; 4-methylcyclohexyl; 4-n-propylcyclohexyl; 3-methylcyclopentyl; 4-[(phenoxy)imino]cyclohexyl; 2-adamantanyl; 4-[(benzyloxy)imino]cyclohexyl; 4-ethyl-4-hydroxycyclohexyl; cyclopentyl; morpholin-4-ylmethyl; 3-(ethoxycarbonylmethyl)cyclohexyl-; 7-aza-7-(1-ethoxycarbonylpiperidin-4-yl)-bicyclo[3.2.1]octan-3-yl; 7-oxa-bicyclo[2.2.1]heptan-2-yl; cyclohexylmethyl; 4,4-diflourocyclohexyl; cyclopentylmethyl; 1,1-dioxothiacycloheptan-3-yl; bicyclo[2.2.2]octan-2-ylmethyl; (4-oxocyclohexyl)cyclohex-4-yl, cyclohexen-4-ylmethyl; tetrahydrofuran-3-ylmethyl; 5-hydroxycyclooctanyl; 4-benzoyloxycyclohexyl; tetrahydropyran-3-ylmethyl; 1-acetylpiperidin-4-yl; decalin-2-yl; 1-oxythiacyclohexan-4-yl; 3,4-diphenylcyclopentan-1-yl; 7-methylbicyclo[3.3.1]nonan-3-yl; spiro[5.5]undecan-2-yl; cyclopropylmethyl; 4-isopropylcyclohexyl; 4-phenylcyclohexyl; 3,3,5,5-tetramethylcyclohex-1-yl; 3,5-dimethylcyclohex-1-yl; 4-isobutylcyclohexyl; 4-cyclohexyl-cyclohexyl; 1-benzoyloxypiperidin-4-yl; 4-(1,1dimethylpropyl)cyclohexyl; pyrazin-2-yl; 3,6-dimethylpyrazine-2-yl; thiazol-2-yl; 1-oxa-2-aza-3-methylspiro[5.4]dec-2-en-8-yl; 4-methylthiazol-2-yl; pyrimidin-2-yl; pyrimidin-5-yl; (1-(pyrazin-2-yl)pyrrolidin-3-yl))methyl; (1-(thiazol-2-yl)pyrrolidin-3-yl))methyl; 2-pyridinyl; 1-(pyrazine-2-yl)piperidine-4-yl-; 1-(thiazole-2-yl)piperidine-4-yl-; 2-aza-3-methyl-1-oxaspiro[4.5]dec-2-ene-8-yl-; 1-(3-methyl-1,2,4-thiadiazole-5-yl) piperidine-4-yl-; 1-(3,6-dimethylpiperazine-2-yl)piperidine-4-yl-; 1-(2-fluorophenyl)piperidine-4-yl-; 1-(3-fluorophenyl)piperidine-4-yl-; 1-(4-fluorophenyl)piperidine-4-yl-; 1-(2-methoxyphenyl)piperidine-4-yl-; 1-(3-methoxyphenyl)piperidine-4-yl-; 1-(4-methoxyphenyl)piperidine-4-yl-; 1-(5-fluoro-2-methoxyphenyl)piperidine-4-yl-; 1-(pyrimidine-2-yl)piperidine-4-yl-; 1-(pyrimidine-5-yl)piperidine-4-yl-; (1-(pyrazine-2-yl) pyrrolidine-3-yl)methyl-; (1-(thiazole-2-yl)pyrrolidine-3-yl)methyl-; 1-(pyridine-2-yl)piperidine-4-yl-; 1-(pyridine-3-yl)piperidine-4-yl-; 1-(thiophene-3-yl)piperidine-4-yl-; and 3-thiopheneyl.

3. Substituent $R_3$

Each $R_3$ is —$Z^C R_8$, wherein each $Z^C$ is independently a bond or an optionally substituted branched or straight $C_{1-6}$ aliphatic chain wherein up to two carbon units of $Z^C$ are optionally and independently replaced by —CO—, —CS—, —CONR$^C$—, —CONR$^C$NR$^C$—, —CO$_2$—, —OCO—, —NR$^C$CO$_2$—, —O—, —NR$^C$CONR$^C$—, —OCONR$^C$—, —NR$^C$NR$^C$—, —NR$^C$CO—, —S—, —SO—, —SO$_2$—, —NR$^C$—, —SO$_2$NR$^C$—, —NR$^C$SO$_2$—, or —NR$^C$SO$_2$NR$^C$—; each $R_8$ is independently $R^C$, halo, —OH, —NH$_2$, —NO$_2$, —CN, —CF$_3$, or —OCF$_3$; and each $R^C$ is independently an optionally substituted $C_{1-8}$ aliphatic group, an optionally substituted cycloaliphatic, an optionally substituted heterocycloaliphatic, an optionally substituted aryl, or an optionally substituted heteroaryl.

In several embodiments, $R_3$ is halo, hydroxy, or cyano. In alternative embodiments, $R_3$ is aliphatic, alkoxy, aryl, aralkyl, heteroaryl, heteroaralkyl, heteroarylcarbonyl, alkylcarbonylamino, arylcarbonyl, alkylcarbonyl, alkylsulfonyl, sulfonylheterocycloaliphatic, (cycloaliphatic)carbonyl, (heterocycloaliphatic)carbonyl, or combinations thereof.

In several embodiments, $R_3$ is an optionally substituted alkoxy. For example, $R_3$ is a straight or branched $C_{1-6}$ alkoxy. In other embodiments, $R_3$ is a methoxy, ethoxy, propoxy, isopropoxy, butoxy, sec-butoxy, tert-butoxy, isobutoxy, pentoxy, tert-pentoxy, sec-pentoxy, isopentoxy, or hexyoxy, each of which is optionally substituted with 1-3 halo, hydroxyl, alkylcarbonyl, heterocycloalkyl, alkoxy, aryl, arylcarbonyl, heterocycloaliphaticarylcarbonyl, haloarylcarbonyl, alkoxyarylcarbonyl, alkylarylcarbonyl, or combinations thereof.

In several embodiments, $R_3$ is an optionally substituted straight or branched $C_{1-6}$ aliphatic. In other embodiments, $R_3$ is an optionally substituted alkyl. For example, $R_3$ is a methyl, ethyl, propyl, isopropyl, butyl, sec-butyl, isobutyl, pentyl, tert-pentyl, sec-pentyl, isopentyl, or hexyl, each of which is optionally substituted with 1-3 of halo, hydroxy, cyano, or optionally substituted alkylcarbonyl, alkoxy, aryl, heteroaryl, cycloaliphatic, heterocycloaliphatic, or combinations thereof. In several embodiments, $R_3$ is an optionally substituted alkenyl. For example, $R_3$ is ethenyl, propenyl, butenyl, sec-butenyl, pentenyl, sec-pentenyl, or hexenyl, each of which is optionally substituted with 1-3 of halo, hydroxy, cyano, or optionally substituted alkylcarbonyl, alkoxy, aryl, heteroaryl, cycloaliphatic, heterocycloaliphatic, or combinations thereof. In other embodiments, $R_3$ is an optionally substituted alkynyl. For example, $R_3$ is optionally substituted ethynyl, propynyl, butynyl, pentynyl, or hexynyl.

In several embodiments, $R_3$ is an optionally substituted aryl. For example, $R_3$ is a phenyl or bicyclic aryl, each of which is optionally substituted. In several examples, $R_3$ is a phenyl optionally substituted with 1-3 of halo, cyano, alkylsulfonyl, aminocarbonyl, alkylaminocarbonyl, cyanoalkyl, aliphatic, (heterocycloaliphatic)carbonyl, (heterocycloaliphatic)sulfonyl, (heteroaryl)aminocarbonyl, or combinations thereof. In other embodiments, $R_3$ is an optionally substituted naphthalenyl, or indenyl.

In several embodiments, $R_3$ is an optionally substituted heteroaryl. For example, $R_3$ is a monocyclic heteroaryl or a bicyclic heteroaryl, each of which is optionally substituted. In several examples, $R_3$ is a furanyl, thiophenyl, thiazolyl, imidazolyl, pyrazolyl isooxazolyl, isothiazolyl, 2H-pyranyl, 4H-pyranyl, pyridinyl, pyrimindinyl, pyrazinyl, or triazinyl, each of which is optionally substituted. In other embodiments, $R_3$ is a benzo[b]furanyl, benzo[b]thiophenyl, 1H-indazolyl, benzimidazolyl, benzthiazolyl, quinolinyl, isoquinolinyl, cinnolinyl, phthalazinyl, quinazolinyl, quinoxalinyl, indenyl, naphthalenyl, benzo[d][1,3]dioxole, 2,3-dihydrobenzofuran, purinyl, or 4H-quinazolinyl, each of which is optionally substituted.

In several embodiments, $R_3$ is one selected from hydrogen, methoxy; chloro; fluoro; trifluoromethoxy; methyl; cyano; trifluromethyl; (4-methylsulfonyl)phenyl; (4-methylaminocarbonyl)phenyl; nitro; (2-oxo)-1-propoxy; ethenyl; (4-methylaminocarbonyl)-3-chlorophenyl; 2-methoxyethoxy; 2-(1-hydroxycyclopent-1-yl)ethynyl; methylenedioxy; tetrahydropyran-2-ylmethoxy; 4-aminocarbonylphenyl; isopropoxy; (2-phenyl-2-oxo)ethoxy; ((2-(2-chlorophenyl)-2-oxo))ethoxy; 3,4-methylenedioxyphenyl; 2-(1-hydroxycyclohex-1-yl)ethynyl; ethyl; (4-cyclopentasulfonamido)phenyl; 4-cyanomethylphenyl; (1-cyano-1-methyl)ethyl; ((2-(4-cyclopentylaminophenyl)-2-oxo))ethoxy; 4-cyanophenyl; 3-thiophenecarbonyl; 4-methoxycarbonylphenyl; hydroxy; 3,4-methylenedioxyphenyl; ((2-(4-fluorophenyl)-2-oxo))ethoxy; ((2-(4-methoxyphenyl)-2-oxo))ethoxy; 3-methoxyphenyl; 4-methoxyphenyl; methylcarbonylamino; 4-((thiazol-2-ylamino)carbonyl)phenyl; benzoyl; ((2-(4-methylphenyl)-2-oxo))ethoxy; propoxy; 2-fluorophenyl; 2,3-dimethoxyphenyl; furan-3-ylcarbonyl; (1-methyl)propoxy; 3-flurophenyl; 3-thiopheneyl; 4-flurophenyl; (morpholin-4-yl)methyl; propionyl; 4-(cyclopentylaminocarbonyl)phenyl; 3-furanyl; 2-chlorophenyl; 2-methoxyphenyl; 4-acetylphenyl; isobutyl; 2-aminocarbonylphenyl; phenyl; ((2-(3-chlorophenyl)-2-oxo))ethoxy; 2-methylphenyl; 4-((piperidin-1yl)carbonyl)phenyl; 4-((dimethylamino)carbonyl)phenyl; 2-phenylethynyl; 4-((diethylamino)carbonyl)phenyl; 4-ethylsulfonylphenyl; 4-chlorophenyl; 4-isopropylsulfonylphenyl; (2-ethoxy-2-oxo-1,1-dimethyl)ethoxy; 3-methylphenyl; benzyloxy; 2,2-dimethylpropionyl; acetyl; cyclopropylcarbonyl; 4-trifluoromethoxyphenyl; 3-fluorophenyl; 4-methylpentyn-1-yl; 2,3-difluorophenyl; 4-trifluoromethylphenyl; 2-methylpropionyl; 4-methylphenyl; 3-aminocarbonylphenyl; 4-acetylaminophenyl; 4-methylsulfinylphenyl; 3-pyridyl; 4-ethylaminocarbonylphenyl; and cyclopentyloxy.

4. Substituent $R_4$

Each $R_4$ is —$Z^D R_9$, wherein each $Z^D$ is independently a bond or an optionally substituted branched or straight $C_{1-6}$ aliphatic chain wherein up to two carbon units of $Z^D$ are optionally and independently replaced by —CO—, —CS—, —CONR$^D$—, —CONR$^D$NR$^D$—, —CO$_2$—, —OCO—, —NR$^D$CO$_2$—, —O—, —NR$^D$CONR$^D$—, —OCONR$^D$—, —NR$^D$NR$^D$—, —NR$^D$CO—, —S—, —SO—, —SO$_2$—, —NR$^D$—, —SO$_2$NR$^D$—, —NR$^D$SO$_2$—, or —NR$^D$SO$_2$NR$^D$—; each $R_9$ is independently $R^D$, halo, —OH, —NH$_2$, —NO$_2$, —CN, —CF$_3$, or —OCF$_3$; and each $R^D$ is independently hydrogen or an optionally substituted $C_{1-8}$ aliphatic group, an optionally substituted cycloaliphatic, an optionally substituted heterocycloaliphatic, an optionally substituted aryl, or an optionally substituted heteroaryl.

Alternatively, $R_3$ and a vicinal $R_4$, together with the atoms to which they are attached, form an optionally substituted 5-6 membered cycloaliphatic or heterocycloaliphatic ring.

In several embodiments, $R_4$ is hydrogen, halo, hydroxy, cyano, or combinations thereof. In several more embodiments, $R_4$ is aliphatic, alkoxy, aryl, heteroaryl, heteroarylcarbonyl, alkylcarbonylamino, arylcarbonyl, alkylcarbonyl, alkylsulfonyl, sulfonylheterocycloaliphatic, cycloaliphaticcarbonyl, heterocycloaliphaticcarbonyl, or combinations thereof; each of which is optionally substituted.

In several embodiments, $R_4$ is a halo selected from chlorine, fluorine, and bromine. In other embodiments, $R_4$ is a halo that is attached at the 4 position or at the 5 position of the phenyl of formula I. In several embodiments, there are two of $R_4$, wherein one $R_4$ is attached at the 5 position and one $R_4$ is attached at the 6 position of the phenyl of formula I, wherein each $R_4$ is a halo. In other embodiments, there are two of $R_4$, where one $R_4$ is attached at the 5 position and one $R_4$ is attached at the 3 position of the phenyl of formula I, wherein each $R_4$ is independently selected from halo, alkyl, and alkoxy. In another embodiment, there are two of $R_4$, one $R_4$ is attached at the 4 position, and one $R_4$ is attached at the 5 position of the phenyl of formula I and each $R_4$ is a halo.

In several embodiments, $R_4$ is an optionally substituted $C_{1-8}$ aliphatic group. For example, $R_4$ is an alkyl, alkenyl, or alkynyl, each of which is optionally substituted. In several examples, $R_4$ is an optionally substituted alkyl. In other examples, $R_4$ is methyl, ethyl, propyl, isopropyl, butyl, sec-butyl, isobutyl, pentyl, tert-pentyl, sec-pentyl, isopentyl, or hexyl, each of which is optionally substituted with 1-3 of halo, hydroxy, cyano, or combinations thereof. In other examples, $R_4$ is optionally substituted with 1-3 of alkylcarbonyl, alkoxy, aryl, heteroaryl, cycloaliphatic, heterocycloaliphatic, hydroxycycloalkyl, or combinations thereof. In several embodiments, $R_4$ is an optionally substituted aliphatic that is attached at the 4 position of the phenyl of formula I. In other embodiments, $R_4$ is an optionally substituted alkyl that is attached at the 5 position of the phenyl of formula I. In several embodiments, $R_4$ is an optionally substituted alkenyl or alkynyl. For example, $R_4$ is an optionally substituted ethenyl, propenyl, isopropenyl, butenyl, sec-butyenl, isobutenyl, pentenyl, tert-pentenyl, sec-pentenyl, isopentenyl, or hexenyl. In other examples, $R_4$ is a substituted ethynyl or an unsubstituted hexynyl.

In several embodiments, $R_4$ is an optionally substituted aryl. For example, $R_4$ is a monocyclic aryl or a bicyclic aryl, each of which is optionally substituted. In other examples, $R_4$ is a phenyl that is optionally substituted with 1-2 of halo, hydroxy, cyano, alkoxy, aliphatic, cyanoalkyl, heteroarylaminocarbonyl, alkylsulfonyl, alkylaminocarbonyl, heterocycloaliphaticsulfonyl, alkoxycarbonyl, (heterocycloaliphatic)carbonyl, alkylcarbonyl, aminocarbonyl, hydroxyalkylaminocarbonyl, alkoxyalkylaminocarbonyl, cycloalkylaminocarbonyl, or combinations thereof. In several examples, $R_4$ is an optionally substituted phenyl that is attached to 5 position of the phenyl of formula I. In other embodiments, $R_4$ is an optionally substituted bicyclic aryl selected from naphthalenyl, indenyl, or azulenyl.

In several embodiments, $R_4$ is an optionally substituted heteroaryl. For example, $R_4$ is a monocyclic or bicyclic heteroaryl, each of which is optionally substituted. In other examples, $R_4$ is a furanyl, thiophenyl, 2H-pyrrolyl, pyrrolyl, thiazolyl, imidazolyl, pyrazolyl, isothiazolyl, 2H-pyranyl, 4H-pyranyl, pyridinyl, pyrimidinyl, pyridazinyl, pyrazinyl, 1,3,4-thiadiazolyl, 1,3,5-triazinyl, or combinations thereof, each of which is optionally substituted. In several embodiments, $R_4$ is a indolizinyl, indolyl, isoindolyl, 3H-indolyl, indolinyl, benzo[b]furanyl, benzo[b]thiophenyl, 1H-indazolyl, benzimidazolyl, purinyl, quinolinyl, isoquinolinyl, cinnolinyl, phthalazinyl, quinazolinyl, quinoxalinyl, 1,8-naphthyridinyl, pteridinyl, benzo[d][1,3]dioxole, or combinations thereof, each of which is optionally substituted. In several more embodiments, $R_4$ is an unsubstituted monocyclic or bicyclic heteroaryl that is attached to the 5 position of the phenyl of formula I. For example, $R_4$ is an unsubstituted furanyl, thiophenyl, pyrrolyl, pyridinyl, benzo[d][1,3]dioxole, or combinations thereof.

In several embodiments, $R_4$ is an optionally substituted cycloaliphatic. In several embodiments, $R_4$ is an optionally substituted $C_{1-8}$ cycloaliphatic. For example, $R_4$ is an optionally substituted monocyclic $C_{1-8}$ cycloaliphatic. In other examples, $R_4$ is a cyclopropyl, cyclobutyl, cyclopenytyl, cyclohexyl, cycloheptyl, or cyclooctyl, each of which is optionally substituted. In several embodiments, $R_4$ is cyclopropyl, cyclobutyl, cyclopenytyl, cyclohexyl, cycloheptyl, or cyclooctyl, each of which is optionally substituted with 1-3 of halo, cyano, hydroxyl, oxo, aliphatic, alkylcarbonyl, alkoxy, or combinations thereof. In several embodiments, $R_4$ is a monocyclic cycloalkyl that is attached at the 4 position or at the 5 position of the phenyl of formula I.

In several embodiments, $R_4$ is an (alkylamino)carbonyl, aminocarbonyl, arylcarbonyl, heteroarylcarbonyl, alkoxycarbonyl, or combinations thereof. For example, each $R_4$ is a (methyl)aminocarbonyl, aminocarbonyl, phenylcarbonyl, furanylcarbonyl, thiophenylcarbonyl, methoxycarbonyl, ethoxycarbonyl, or pyrrolidinylcarbonyl. In several embodiments, $R_4$ is an (alkyl)aminocarbonyl, aminocarbonyl, arylcarbonyl, heteroarylcarbonyl, alkoxycarbonyl, or combinations thereof, wherein $R_4$ is attached to the 5 position of the phenyl of formula I.

In several embodiments, $R_4$ is an optionally substituted alkoxy. For example, $R_4$ is an optionally substituted methoxy, ethoxy, propoxy, isopropoxy, butoxy, sec-butoxy, isobutoxy, pentoxy, sec-pentoxy, isopentoxy, or hexoxy.

In several embodiments, $R_3$ and a vicinal $R_4$, together with the atoms to which they are attached form an optionally substituted 5-6 membered cycloaliphatic or heterocycloaliphatic ring. In other embodiments, $R_3$ and a vicinal $R_4$ are taken together with the phenyl to which they are attached to form an optionally substituted benzo fused bicyclic aryl or an optionally substituted benzo fused bicyclic heteroaryl. In other examples, $R_3$ and a vicinal $R_4$, together with the phenyl to which they are attached form a benzo[b]furanyl, benzo[b]thiophenyl, 1H-indazolyl, benzimidazolyl, benzthiazolyl, quinolinyl, isoquinolinyl, cinnolinyl, phthalazinyl, quinazolinyl, quinoxalinyl, indenyl, naphthalenyl, benzo[d][1,3]dioxolyl, 2,3-dihydrobenzofuranyl, purinyl, or 4H-quinazolinyl, each of which is optionally substituted.

4. Substituent $R_{10}$, $R'_{10}$, and n

In several embodiments, each $R_{10}$ and $R'_{10}$ are independently hydrogen, halo, $C_{1-4}$ aliphatic, or $C_{1-4}$ alkoxy. In several embodiments, both $R_{10}$ and $R'_{10}$ are hydrogen.

In several embodiments, n is 1, 2, 3, or 4.

B. Sub-Generic Compounds

Another aspect of the present invention provides additional methods of modulating the activity of a muscarinic receptor comprising the step of contacting said receptor with a compound of formula Ia:

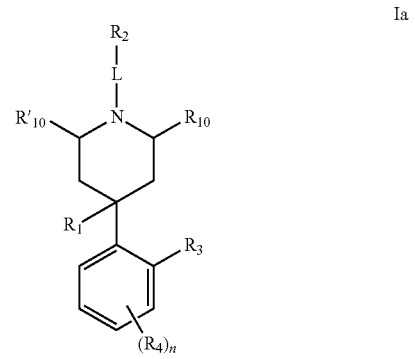

Ia or a pharmaceutically acceptable salt thereof.

$R_1$ is hydrogen, halo, cyano, nitro, trifluoromethyl, hydroxy, —$OCF_3$, —S-aliphatic, —S(O)-aliphatic, —$SO_2$-aliphatic, —COOH, —C(O)O-aliphatic, or —O-aliphatic.

Each $R_2$, $R_3$, $R_4$, $R_{10}$, $R'_{10}$, n, and L are as defined above in formula I.

An additional aspect of the present invention provides compounds of formula Ib that are useful for modulating the activity and/or activities of muscarinic receptor(s) in accordance to formula Ib:

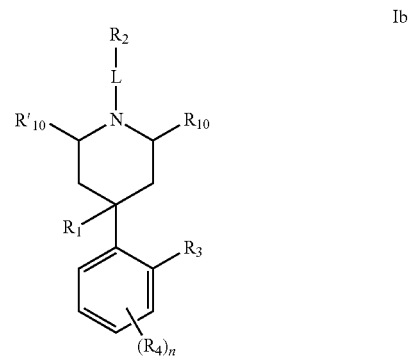

Ib or a pharmaceutically acceptable salt thereof.

Each $R_1$ is hydrogen, halo, cyano, nitro, trifluoromethyl, hydroxy, —$OCF_3$, —S— aliphatic, —S(O)-aliphatic, —$SO_2$-aliphatic, —COOH, —C(O)O-aliphatic, or —O-aliphatic.

Each $R_2$ is a monocyclic heterocycloaliphatic, a bridged bicyclic cycloaliphatic, a bridged bicyclic heterocycloaliphatic, or an adamantanly, each of which is optionally substituted with 1-3 of $R_6$.

Each $R_6$ is independently =O or —$Z^B R_7$, wherein each $Z^B$ is independently a bond or an optionally substituted branched or straight $C_{1-4}$ aliphatic chain wherein up to two carbon units of $Z^B$ are optionally and independently replaced by —CO—, —CS—, —$CONR^B$—, —$CONR^B NR^B$—, —$CO_2$—, —OCO—, —$NR^B CO_2$—, —O—, —$NR^B CONR^B$—, —OCONR$^B$—, —NR$^B$NR$^B$—, —NR$^B$CO—, —S—, —SO—, —SO$_2$—, —NR$^B$—, —SO$_2$NR$^B$—, —NR$^B$SO$_2$—, or —NR$^B$SO$_2$NR$^B$—.

Each R$_7$ is independently R$^B$, halo, —OH, —NH$_2$, —NO$_2$, =NR$^B$, =NOR$^B$, —CN, or —OCF$_3$.

Each R$^B$ is independently hydrogen, an optionally substituted C$_{1-8}$ aliphatic group; an optionally substituted cycloaliphatic, an optionally substituted heterocycloaliphatic, an optionally substituted aryl, or an optionally substituted heteroaryl.

Each R$_3$ is —Z$^C$R$_8$, wherein each Z$^C$ is independently a bond or an optionally substituted branched or straight C$_{1-6}$ aliphatic chain wherein up to two carbon units of Z$^C$ are optionally and independently replaced by —CO—, —OCO—, or —O—.

R$_8$ is independently R$^C$, halo, —OH, —NH$_2$, —NO$_2$, —CN, or —OCF$_3$.

Each R$^C$ is independently hydrogen, halo, an optionally substituted C$_{1-8}$ aliphatic group, an optionally substituted aryl, or an optionally substituted heteroaryl.

Each R$_4$ is —Z$^D$R$_9$, wherein each Z$^D$ is independently a bond or an optionally substituted branched or straight C$_{1-6}$ aliphatic chain wherein up to two carbon units of Z$^D$ are optionally and independently replaced by —CO—, —CS—, —CONR$^D$—, —CONR$^D$NR$^D$—, CO$_2$—, —OCO—, —NR$^D$CO$_2$—, —O—, —NR$^D$CONR$^D$—, —OCONR$^D$—, —NR$^D$NR$^D$, —NR$^D$CO—, —S—, —SO—, —SO$_2$—, —NR$^D$—, —SO$_2$NR$^D$—, —NR$^D$SO$_2$—, or —NR$^D$SO$_2$NR$^D$—.

Each R$_9$ is independently R$^D$, halo, —OH, —NH$_2$, —NO$_2$, —CN, or —OCF$_3$.

Each R$^D$ is independently hydrogen, halo, an optionally substituted C$_{1-8}$ aliphatic group; an optionally substituted cycloaliphatic, an optionally substituted heterocycloaliphatic, an optionally substituted aryl, or an optionally substituted heteroaryl.

Alternatively, R$_3$ and a vicinal R$_4$ together with the atoms to which they are attached, form an optionally substituted 5-6 membered cycloaliphatic or heterocycloaliphatic ring.

Each L is a bond or —CH$_2$—.

R$_{10}$ and R'$_{10}$ are each independently hydrogen or C$_{1-4}$ aliphatic, and n is 0-4. In some embodiments, n is 1 or 2.

C. Exemplary Compounds

Exemplary compounds of the present invention include, but are not limited to, those illustrated in Table 1 below.

TABLE 1

Exemplary compounds of the present invention.

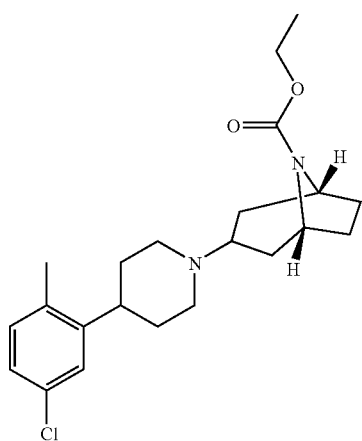

1

TABLE 1-continued

Exemplary compounds of the present invention.

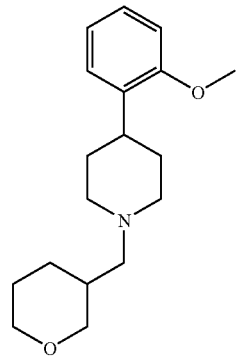

2

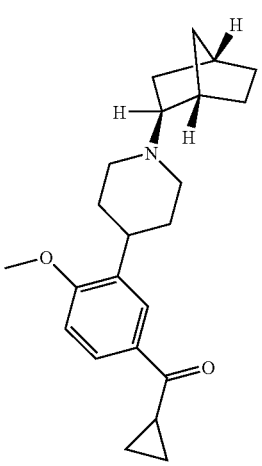

3

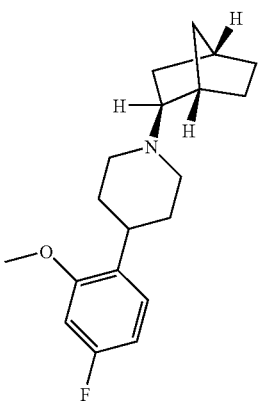

4

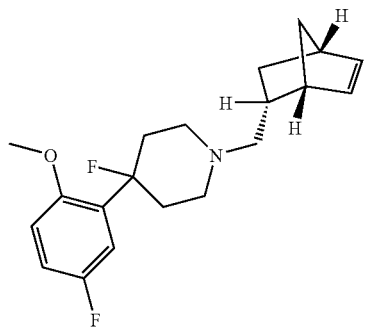

5

TABLE 1-continued
Exemplary compounds of the present invention.
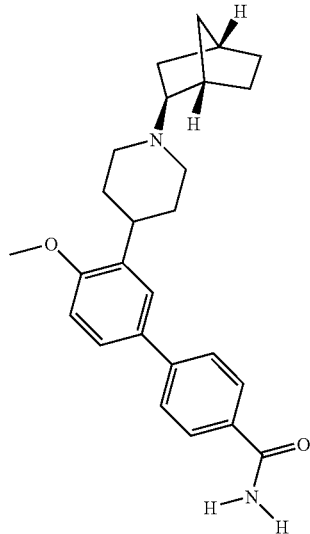
6
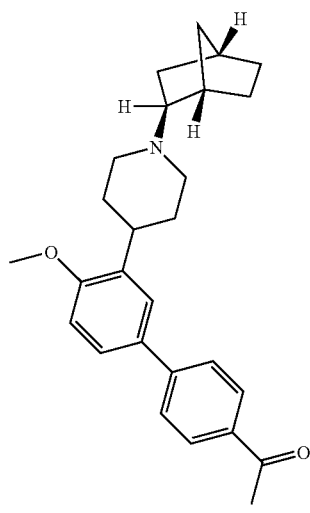
7
TABLE 1-continued
Exemplary compounds of the present invention.
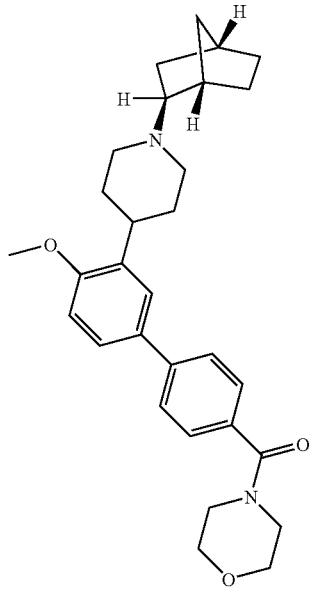
8
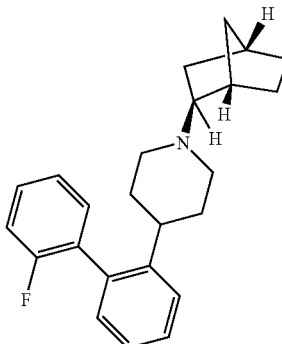
9
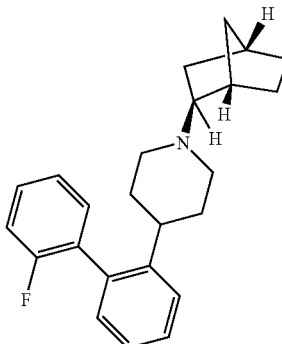
10

TABLE 1-continued
Exemplary compounds of the present invention.
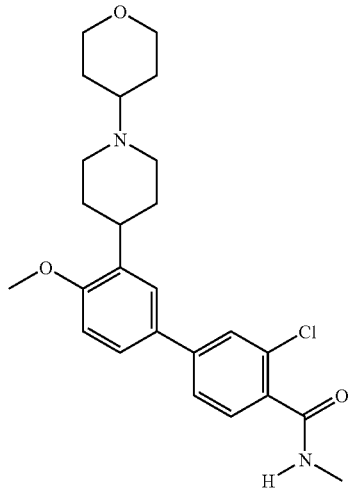
11
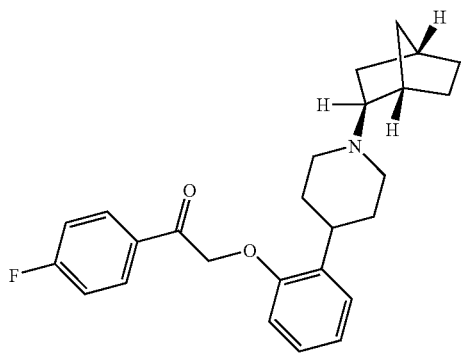
12
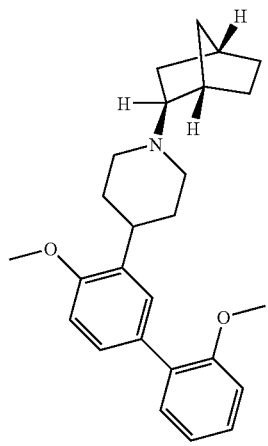
13
TABLE 1-continued
Exemplary compounds of the present invention.
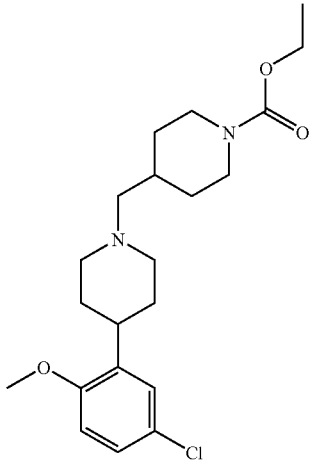
14
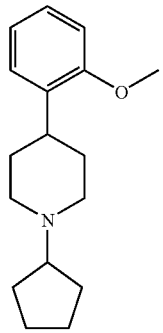
15
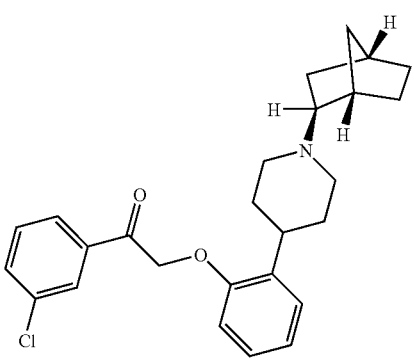
16

TABLE 1-continued
Exemplary compounds of the present invention.
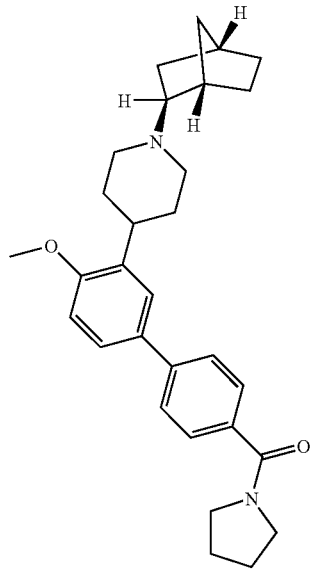
17
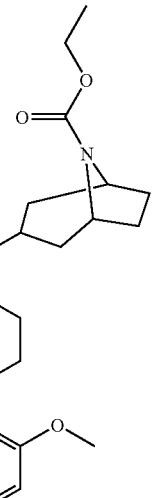
20
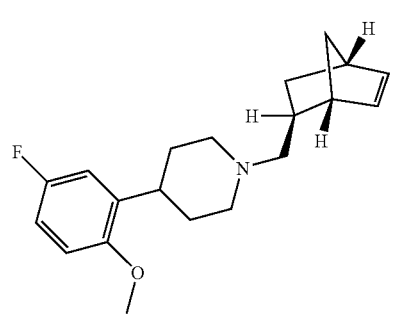
18
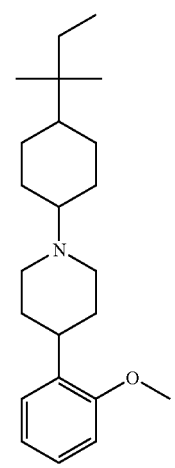
21
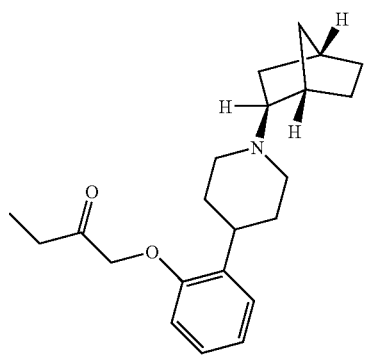
19
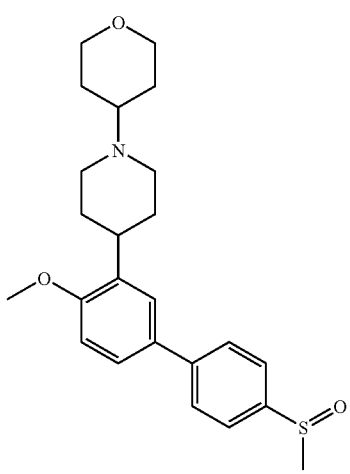
22

TABLE 1-continued
Exemplary compounds of the present invention.
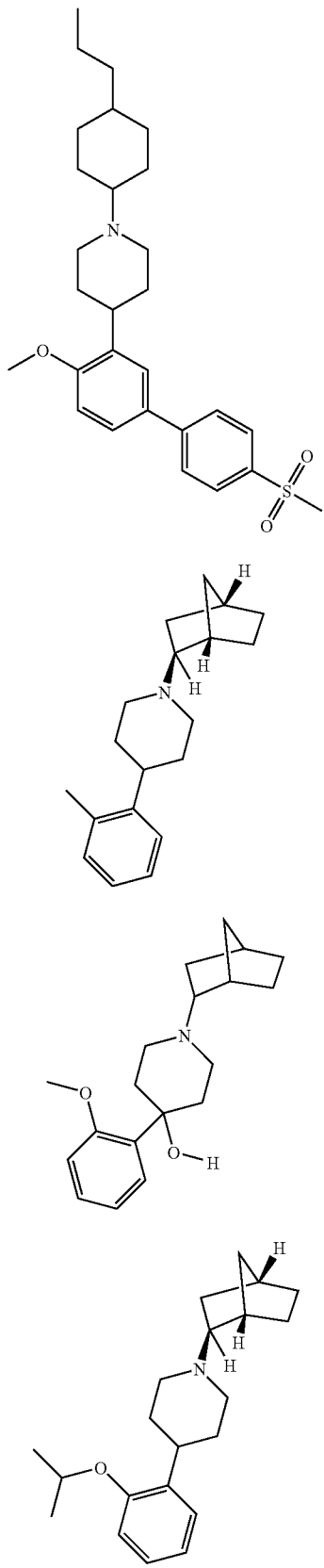
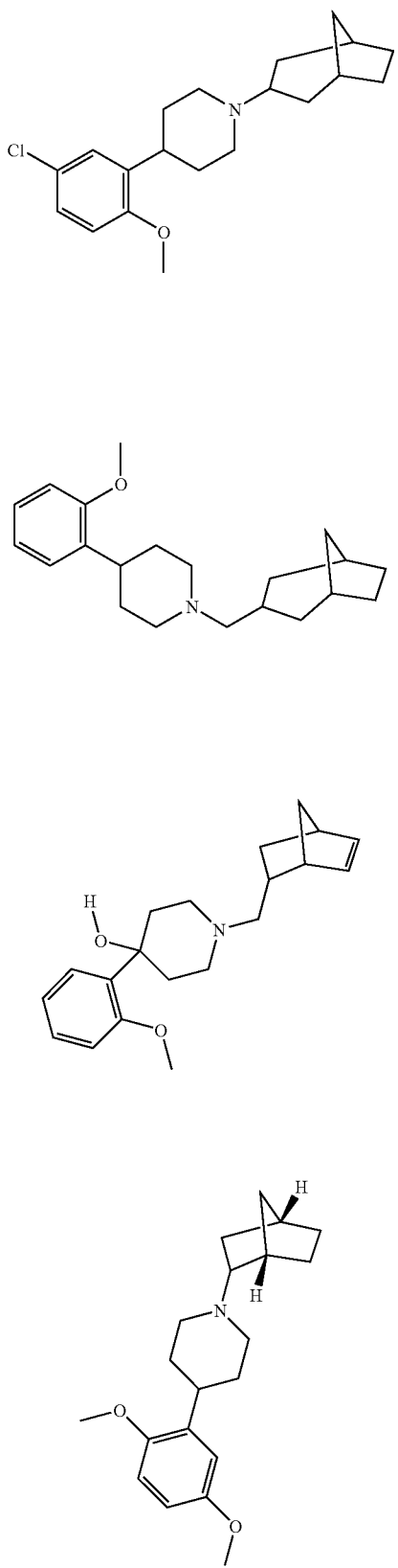

TABLE 1-continued
Exemplary compounds of the present invention.
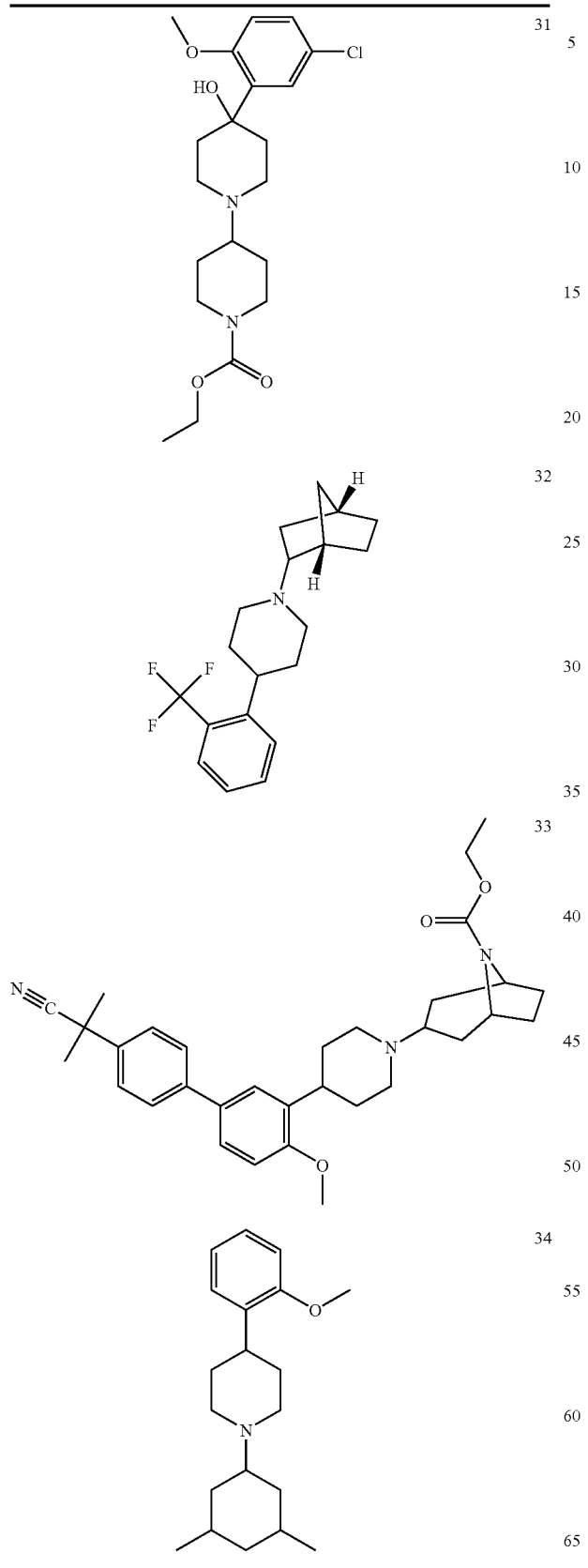
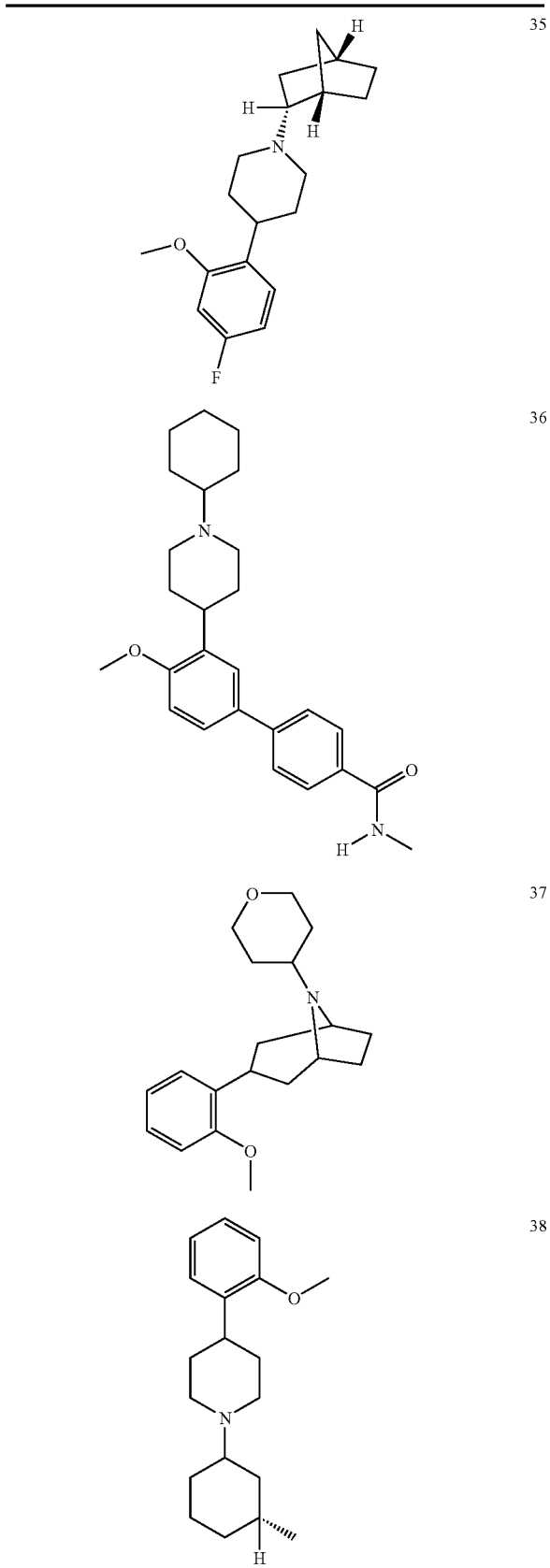

TABLE 1-continued
Exemplary compounds of the present invention.
| | |
|---|---|
| 39 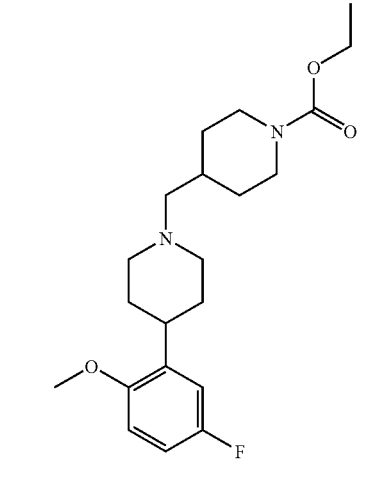 | 43 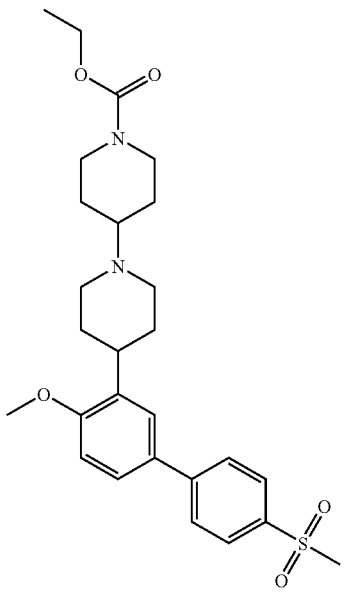 |
| 40 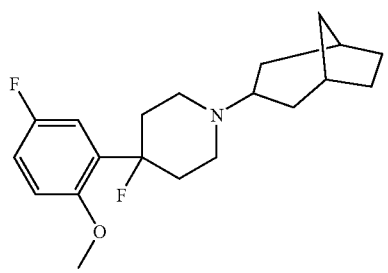 | 44 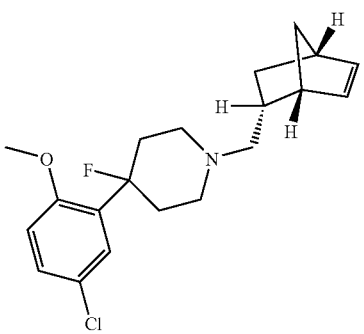 |
| 41 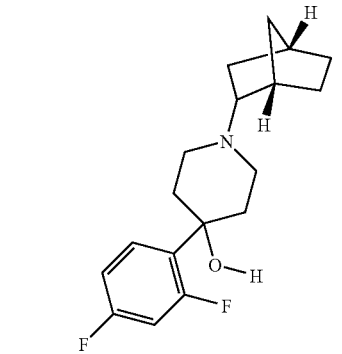 | 45 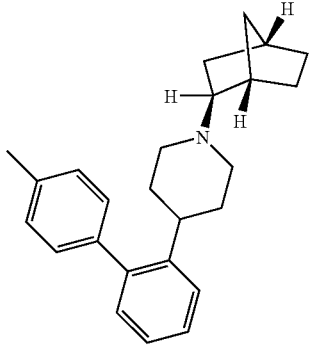 |
| 42 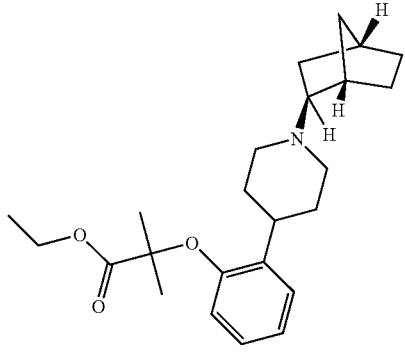 | 46 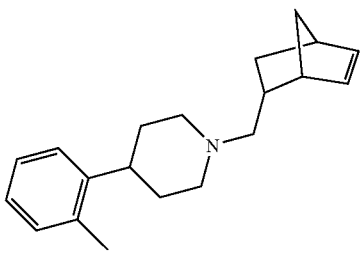 |

TABLE 1-continued
Exemplary compounds of the present invention.
| | |
|---|---|
| 47 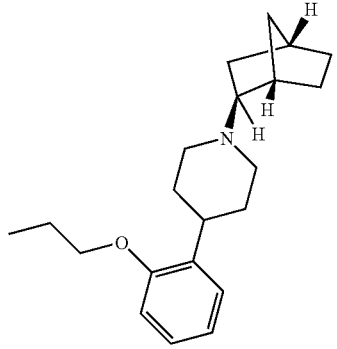 | 50 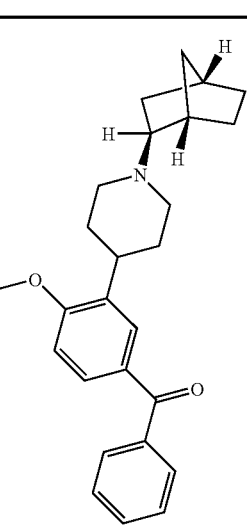 |
| 48 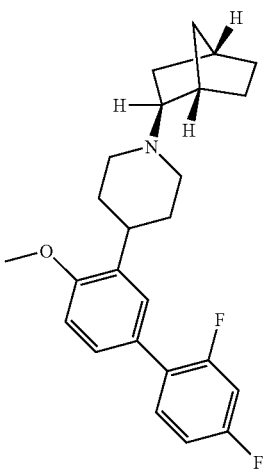 | 51 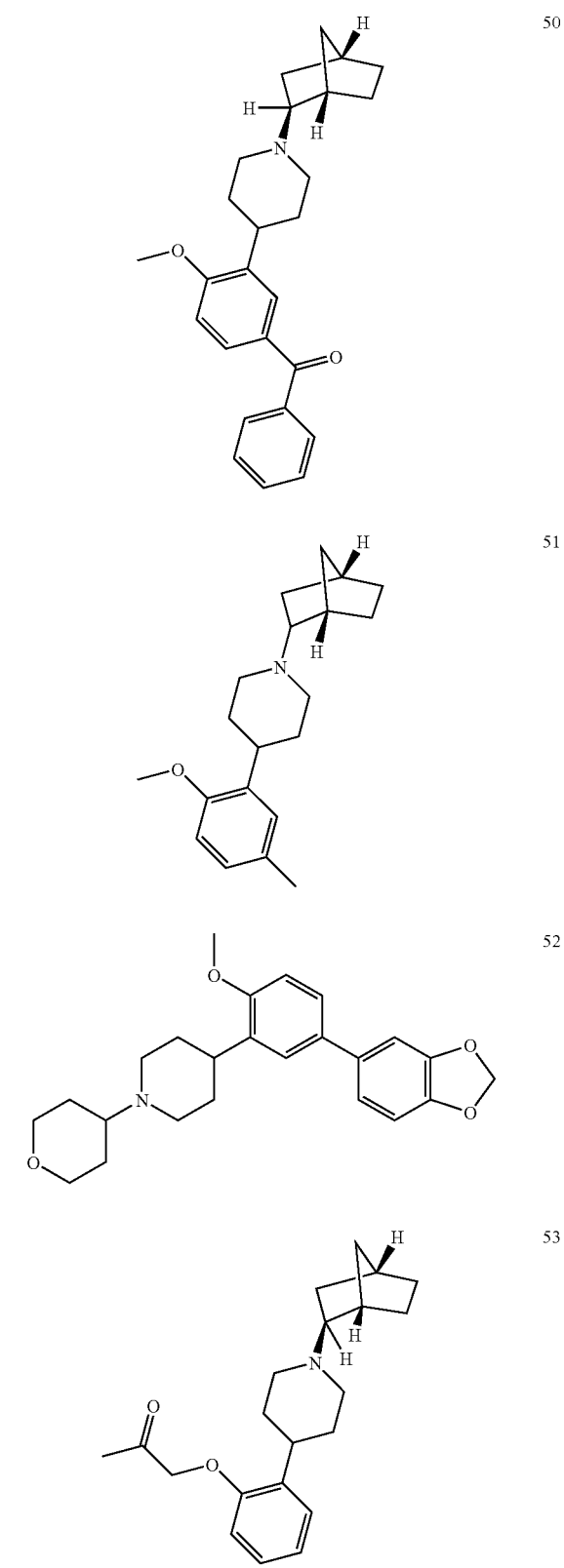 |
| 49 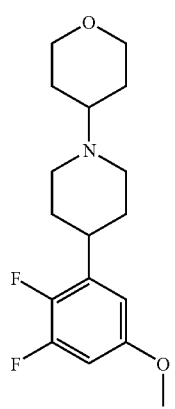 | 52 |
| | 53 |

TABLE 1-continued

Exemplary compounds of the present invention.

TABLE 1-continued
Exemplary compounds of the present invention.
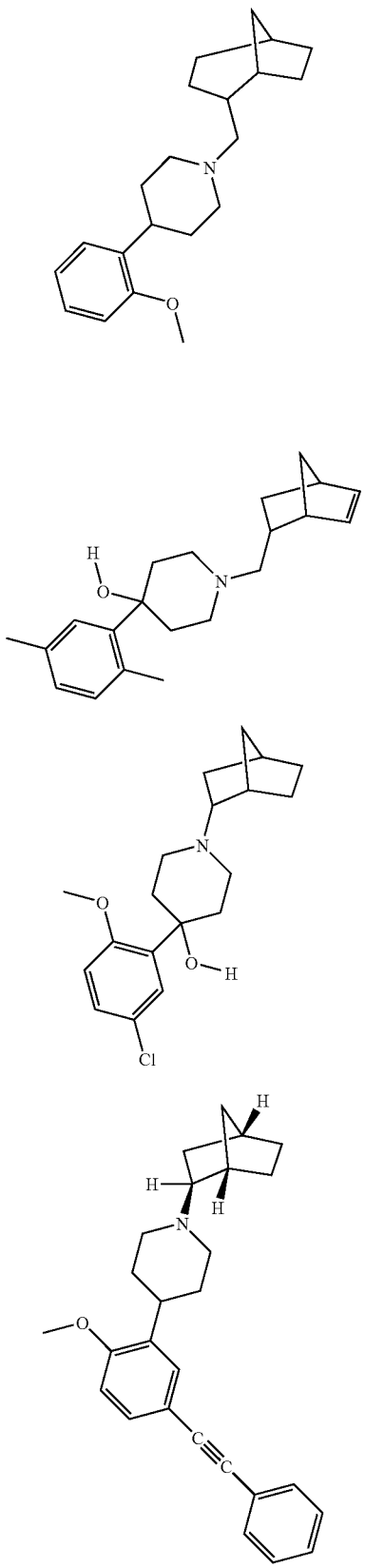
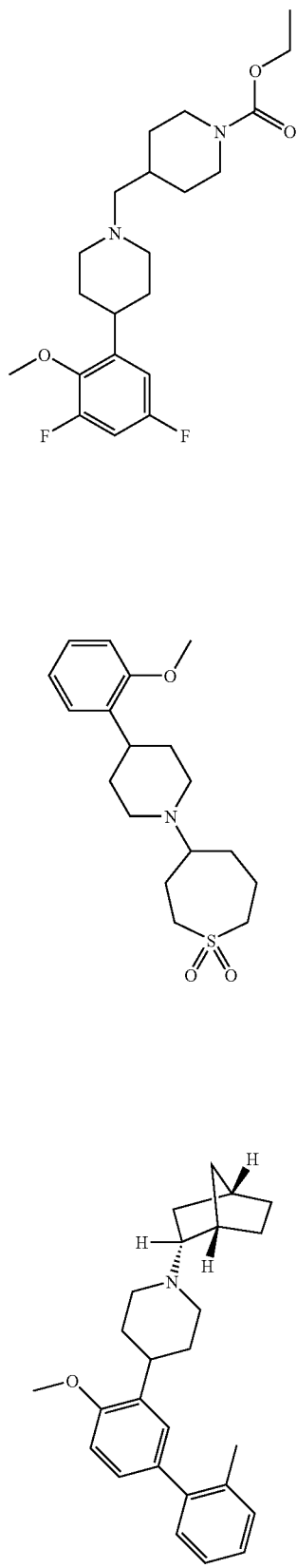

TABLE 1-continued
Exemplary compounds of the present invention.
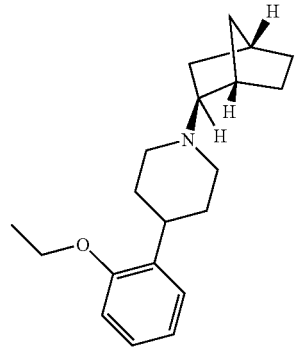 68
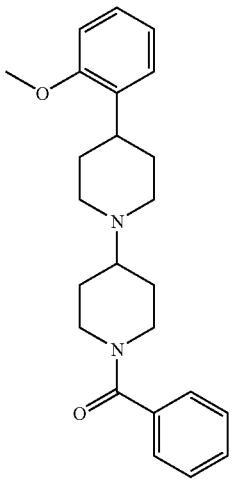 71
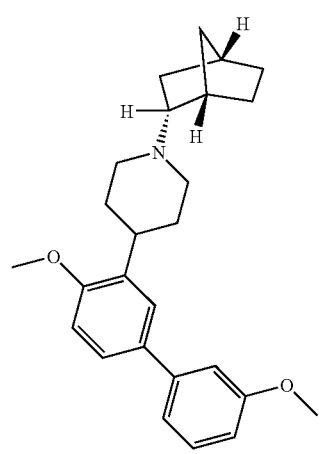 69
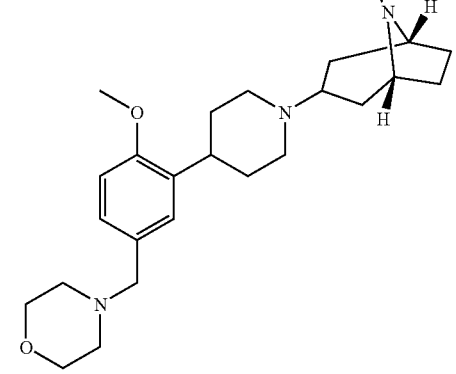 72
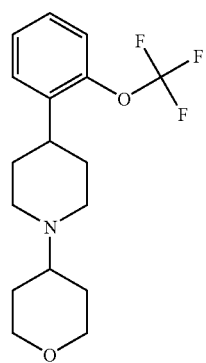 70
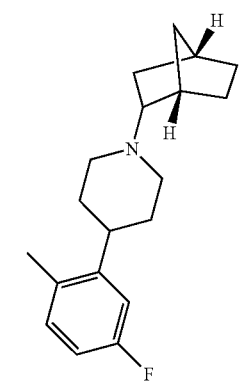 73

TABLE 1-continued
Exemplary compounds of the present invention.
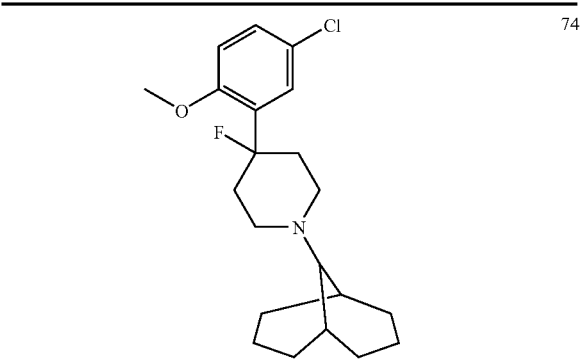
74
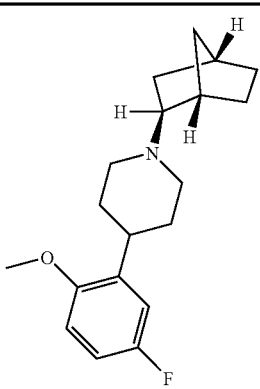
78
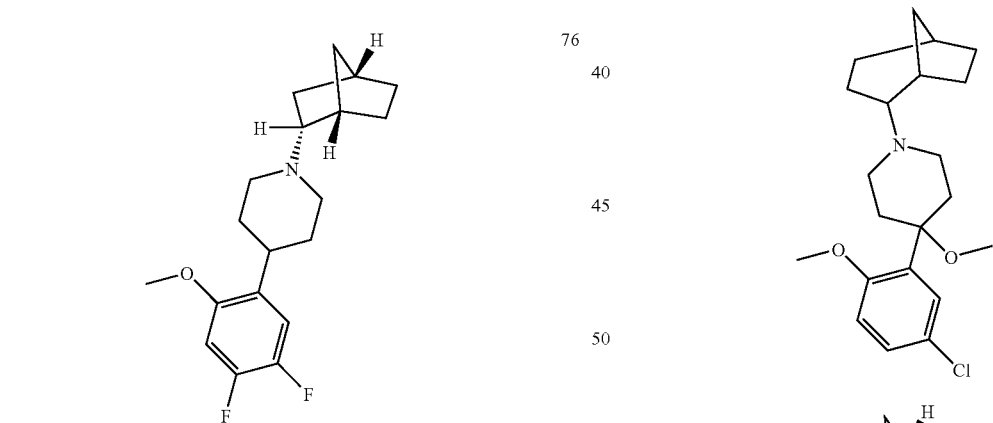
75, 76, 77
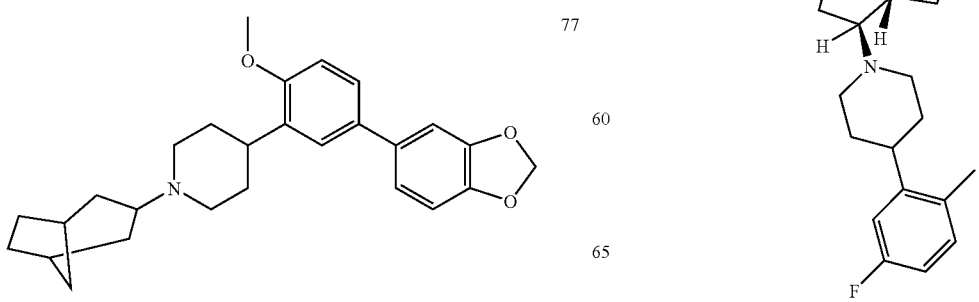
79, 80, 81

TABLE 1-continued
Exemplary compounds of the present invention.
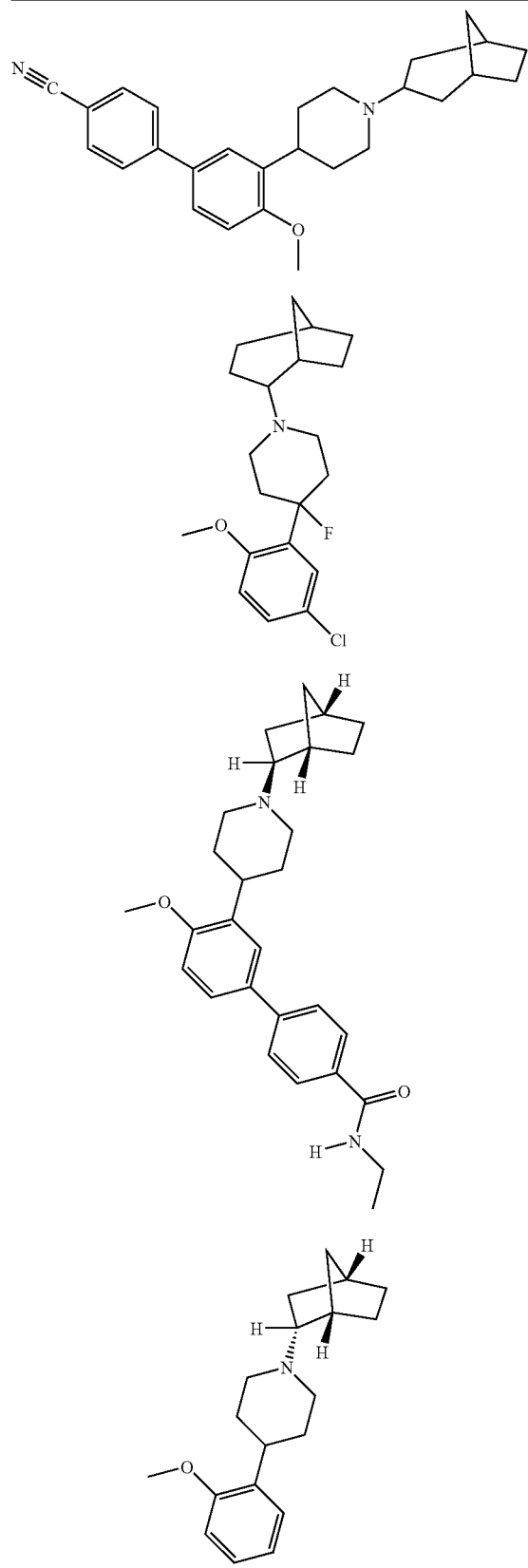
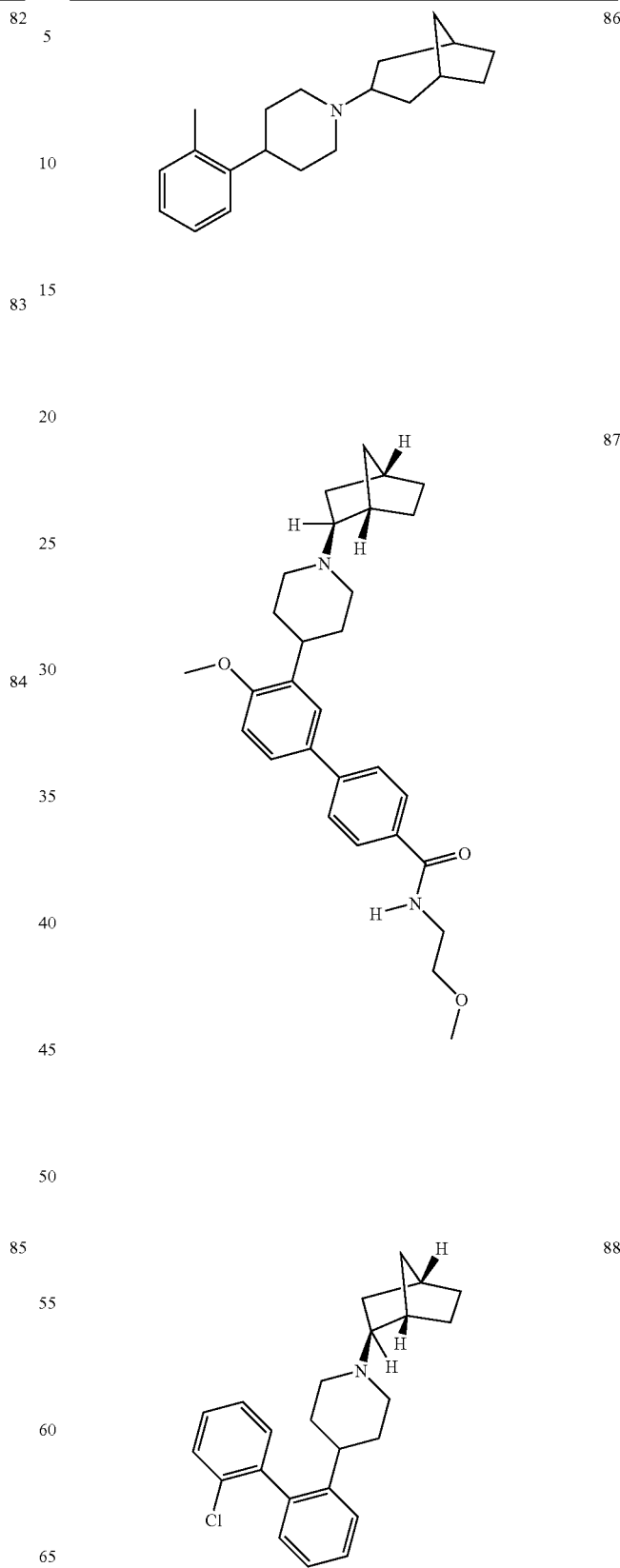

TABLE 1-continued
Exemplary compounds of the present invention.
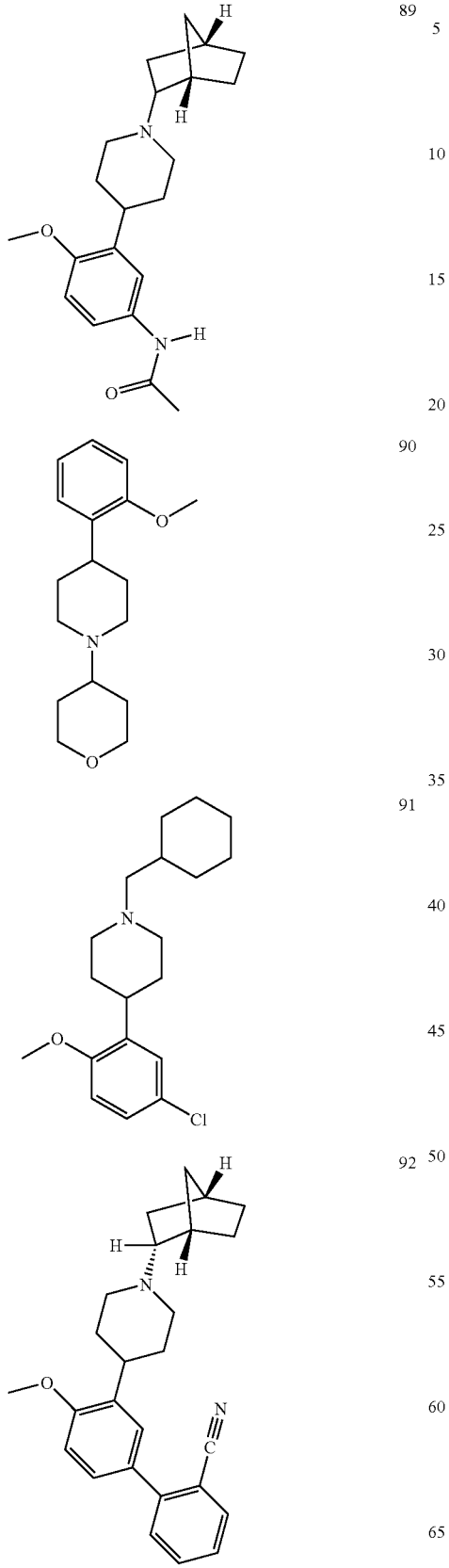
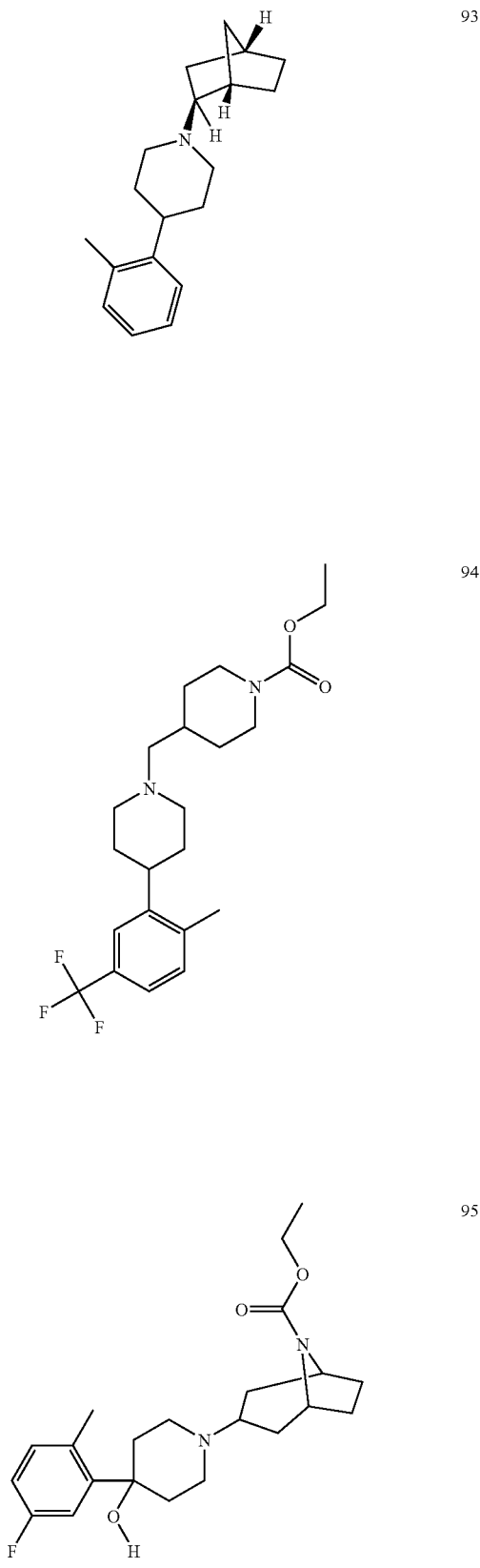

TABLE 1-continued
Exemplary compounds of the present invention.
96 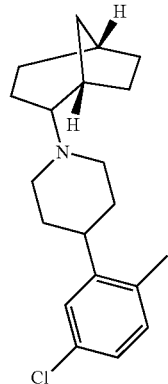
97 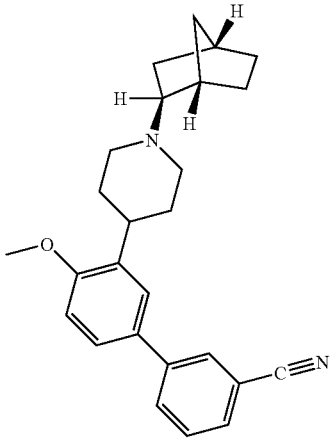
98 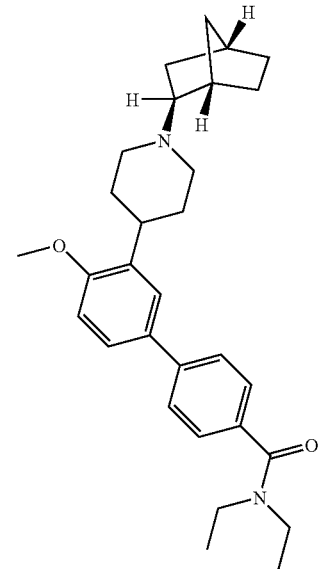
TABLE 1-continued
Exemplary compounds of the present invention.
99 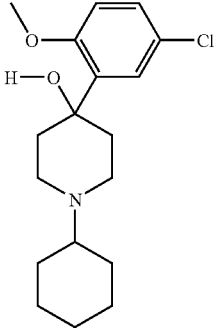
100 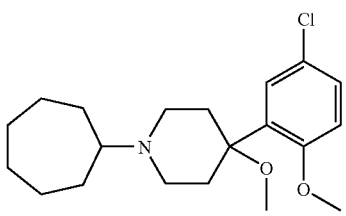
101 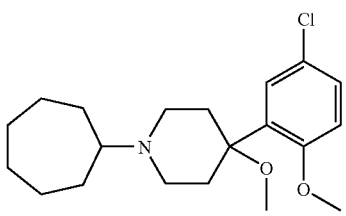
102 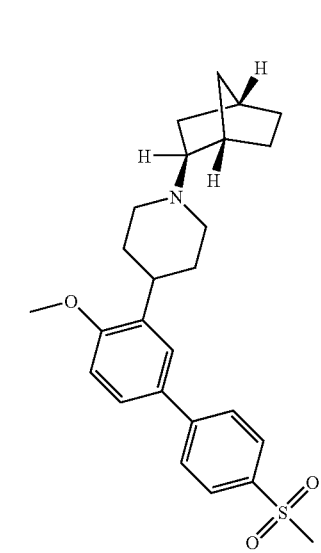

TABLE 1-continued
Exemplary compounds of the present invention.
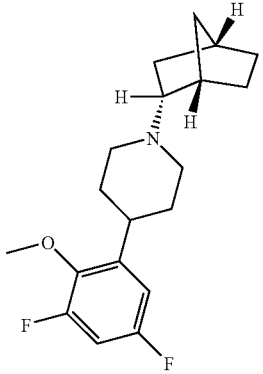 103
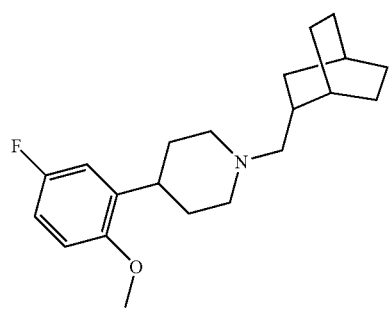 104
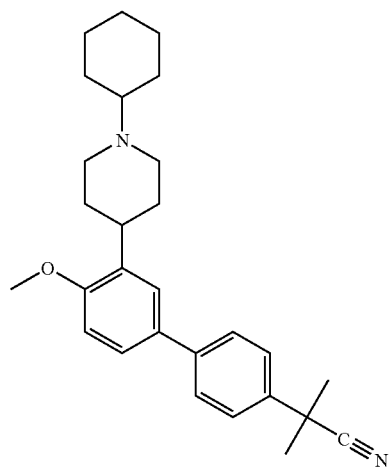 105
TABLE 1-continued
Exemplary compounds of the present invention.
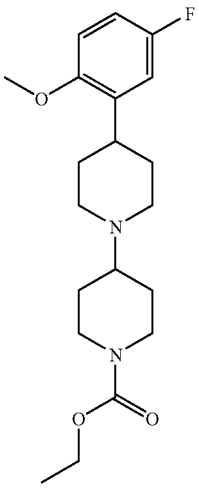 106
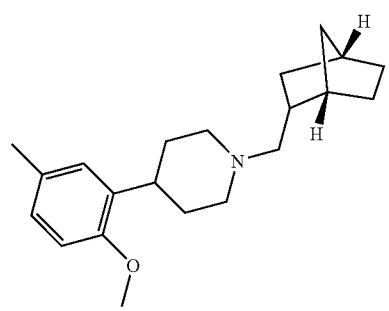 107
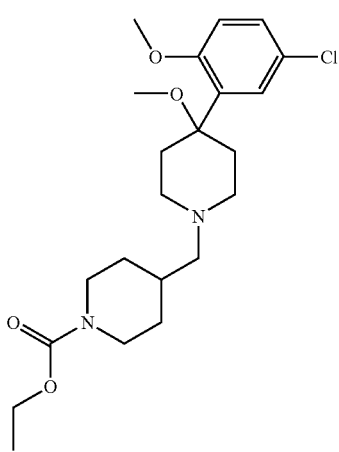 108

TABLE 1-continued
Exemplary compounds of the present invention.
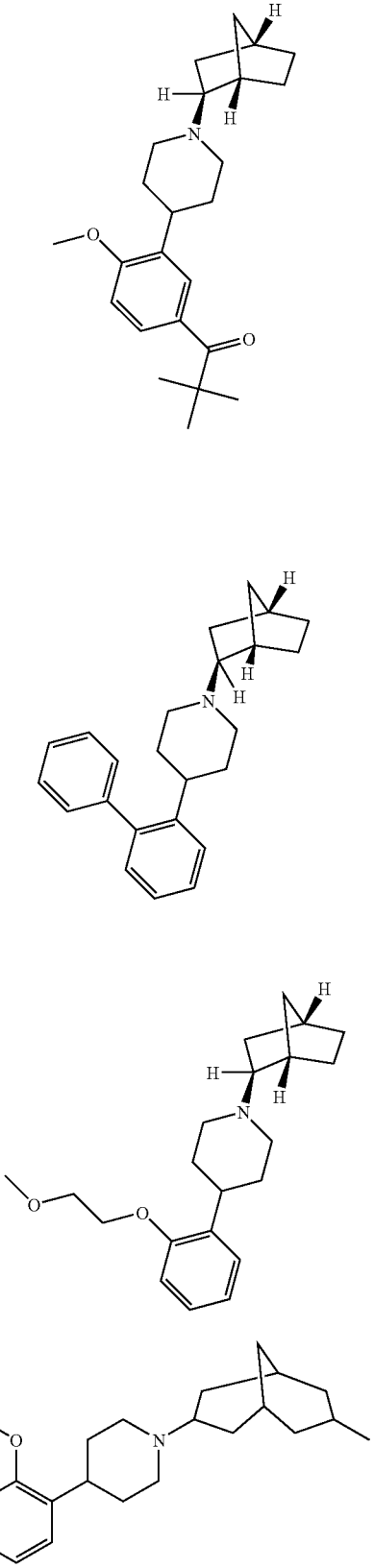
109
110
111
112
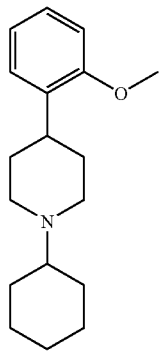
113
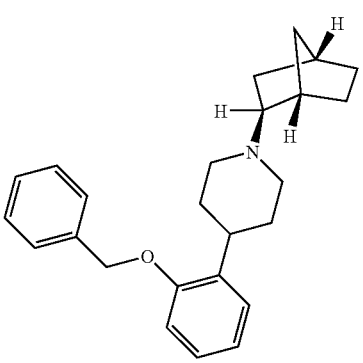
114
115
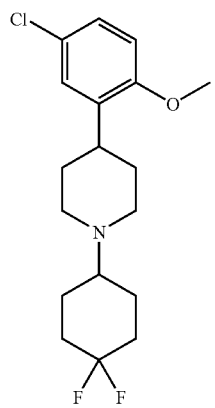
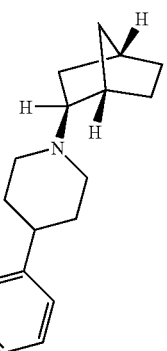
116

TABLE 1-continued
Exemplary compounds of the present invention.
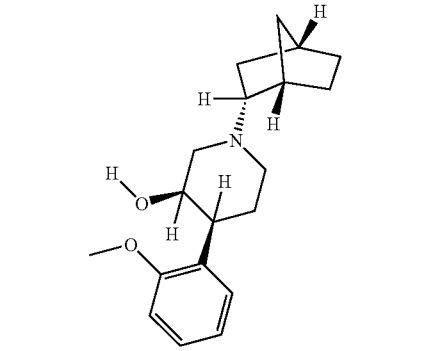 117
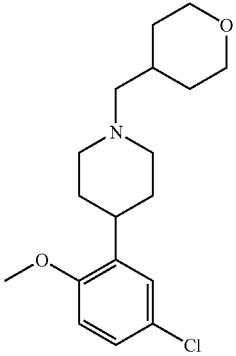 121
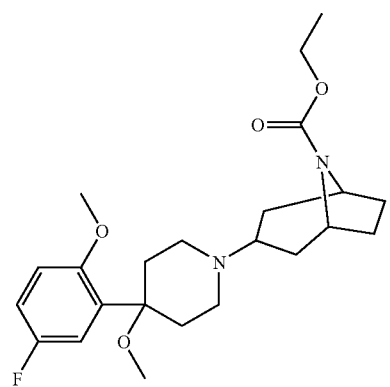 118
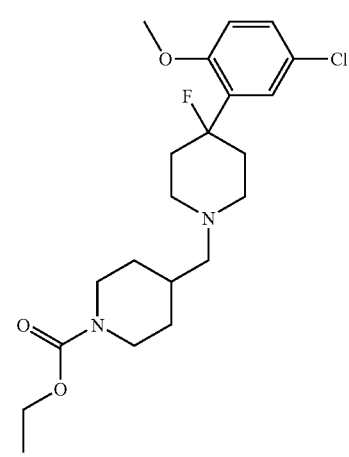 122
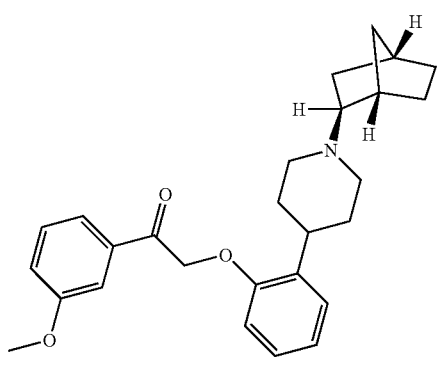 119
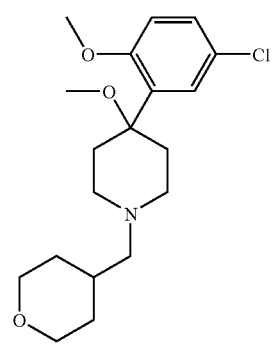 123
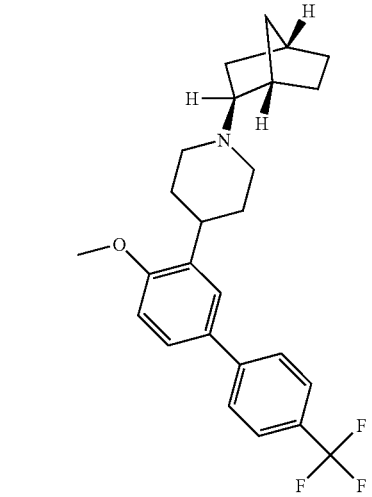 120
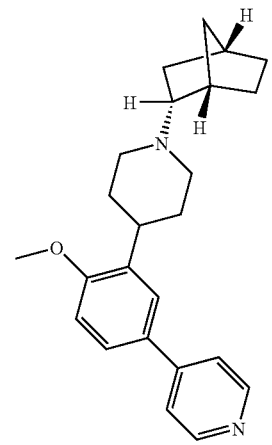 124

TABLE 1-continued
Exemplary compounds of the present invention.
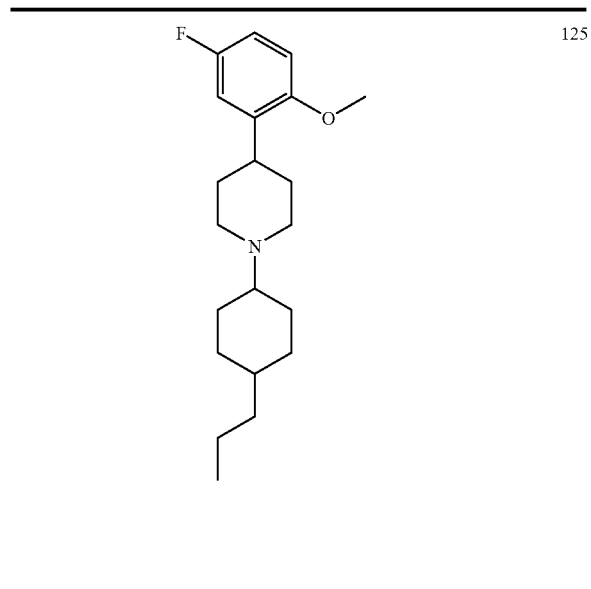
125
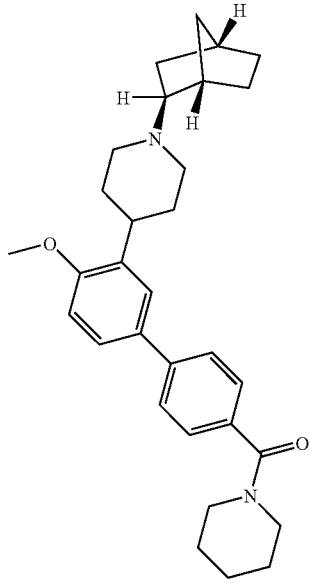
128
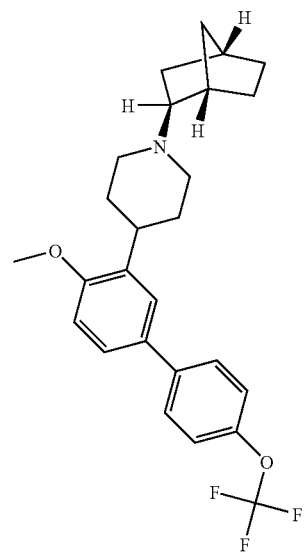
126
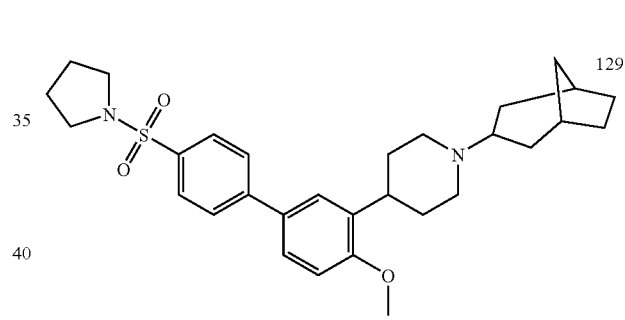
129
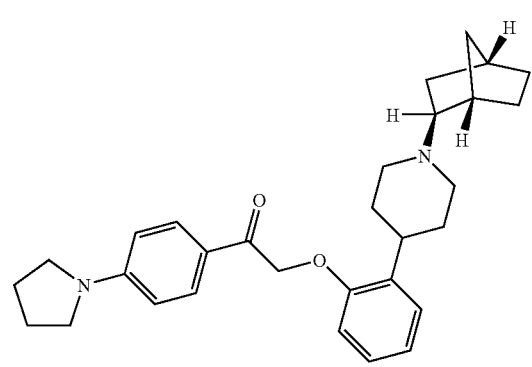
127
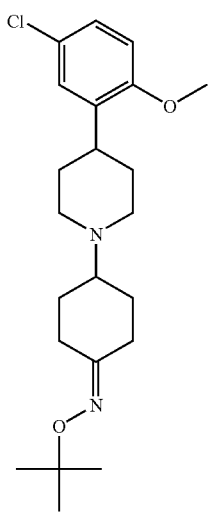
130

TABLE 1-continued
Exemplary compounds of the present invention.
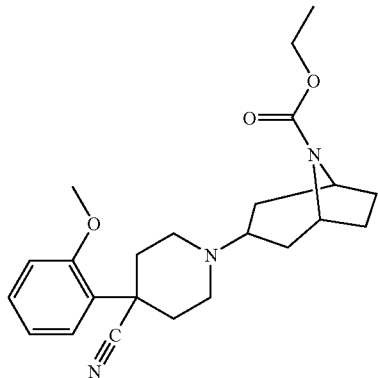 131
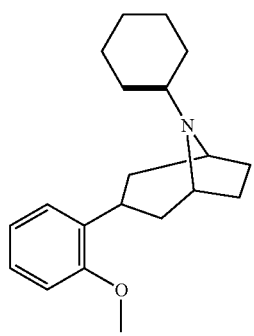 132
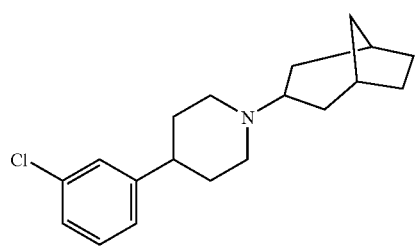 133
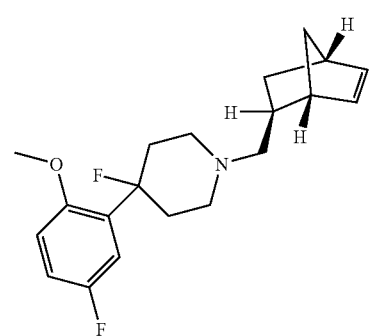 134
TABLE 1-continued
Exemplary compounds of the present invention.
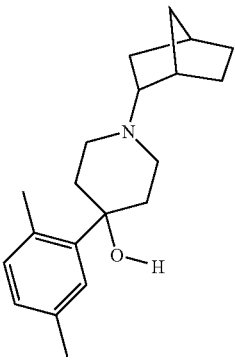 135
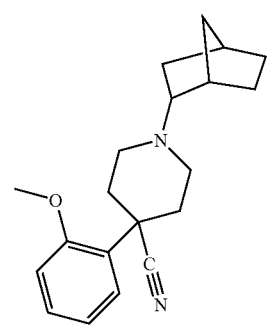 136
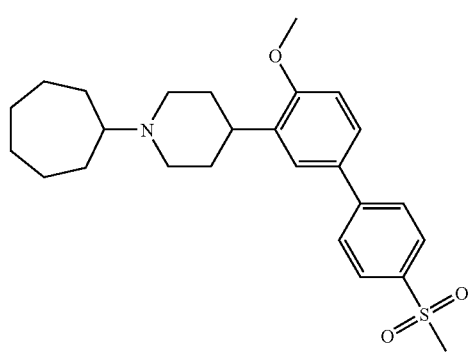 137
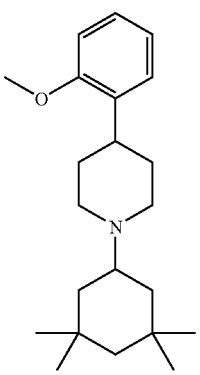 138

TABLE 1-continued
Exemplary compounds of the present invention.
139 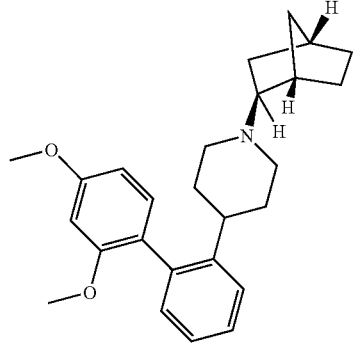
140 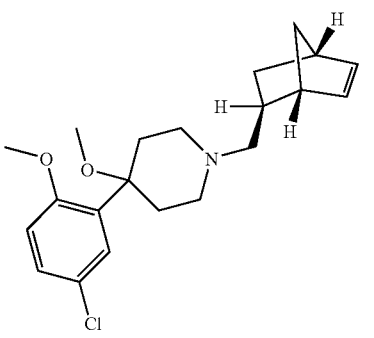
141 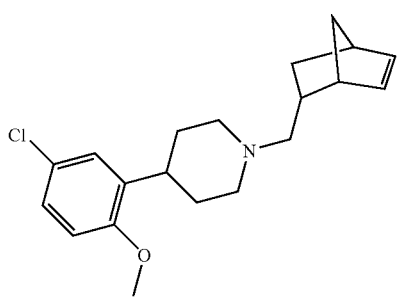
142 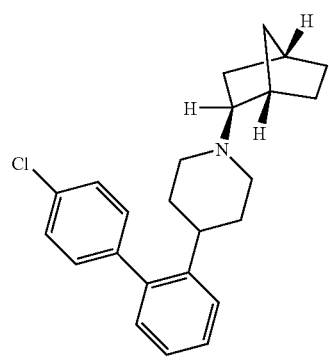
TABLE 1-continued
Exemplary compounds of the present invention.
143 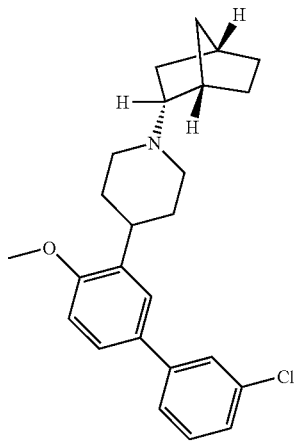
144 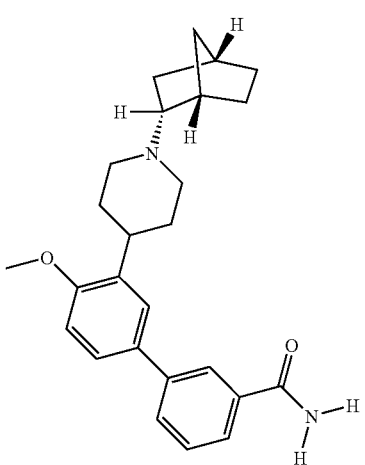
145 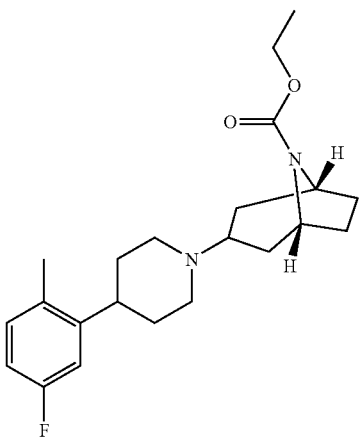

TABLE 1-continued
Exemplary compounds of the present invention.
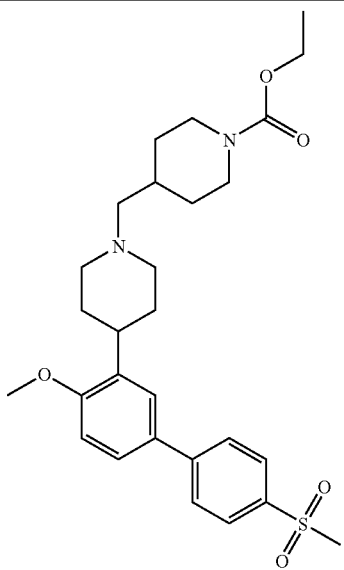 146
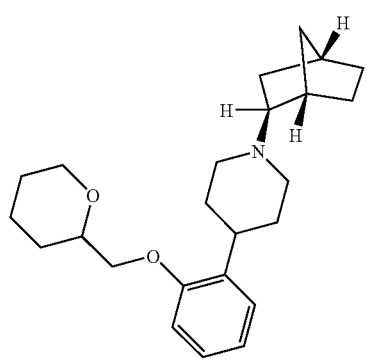 147
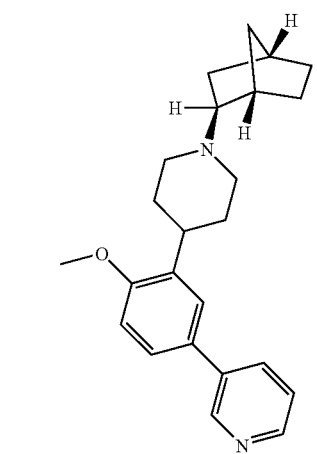 148
TABLE 1-continued
Exemplary compounds of the present invention.
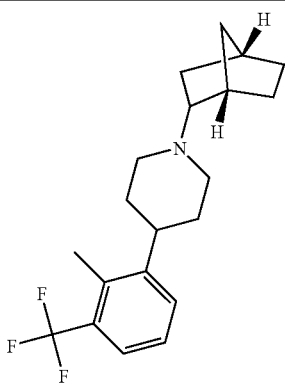 149
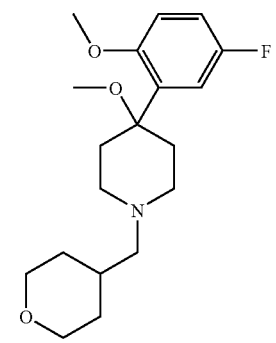 150
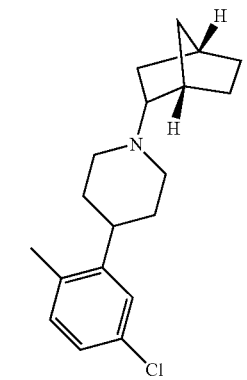 151
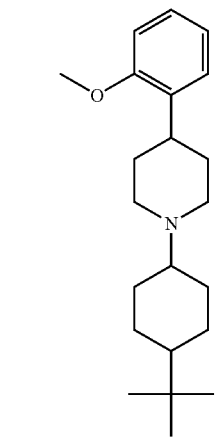 152

TABLE 1-continued
Exemplary compounds of the present invention.
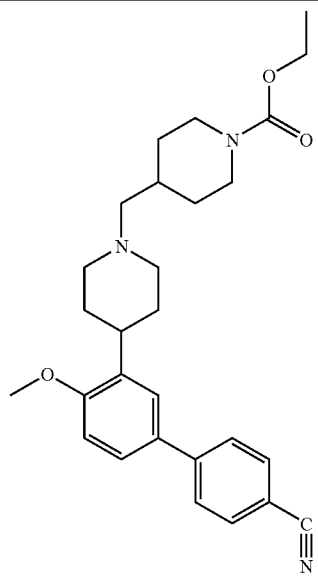
153
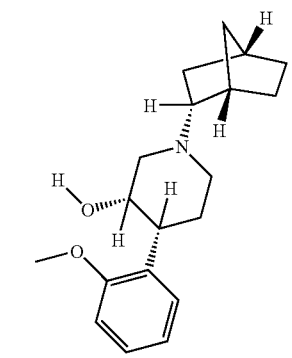
154
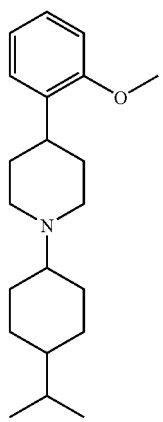
155
TABLE 1-continued
Exemplary compounds of the present invention.
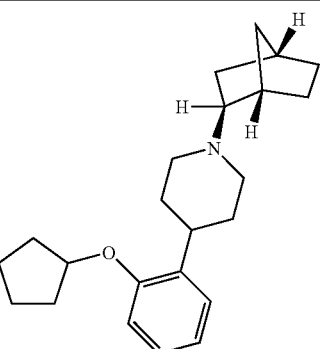
156
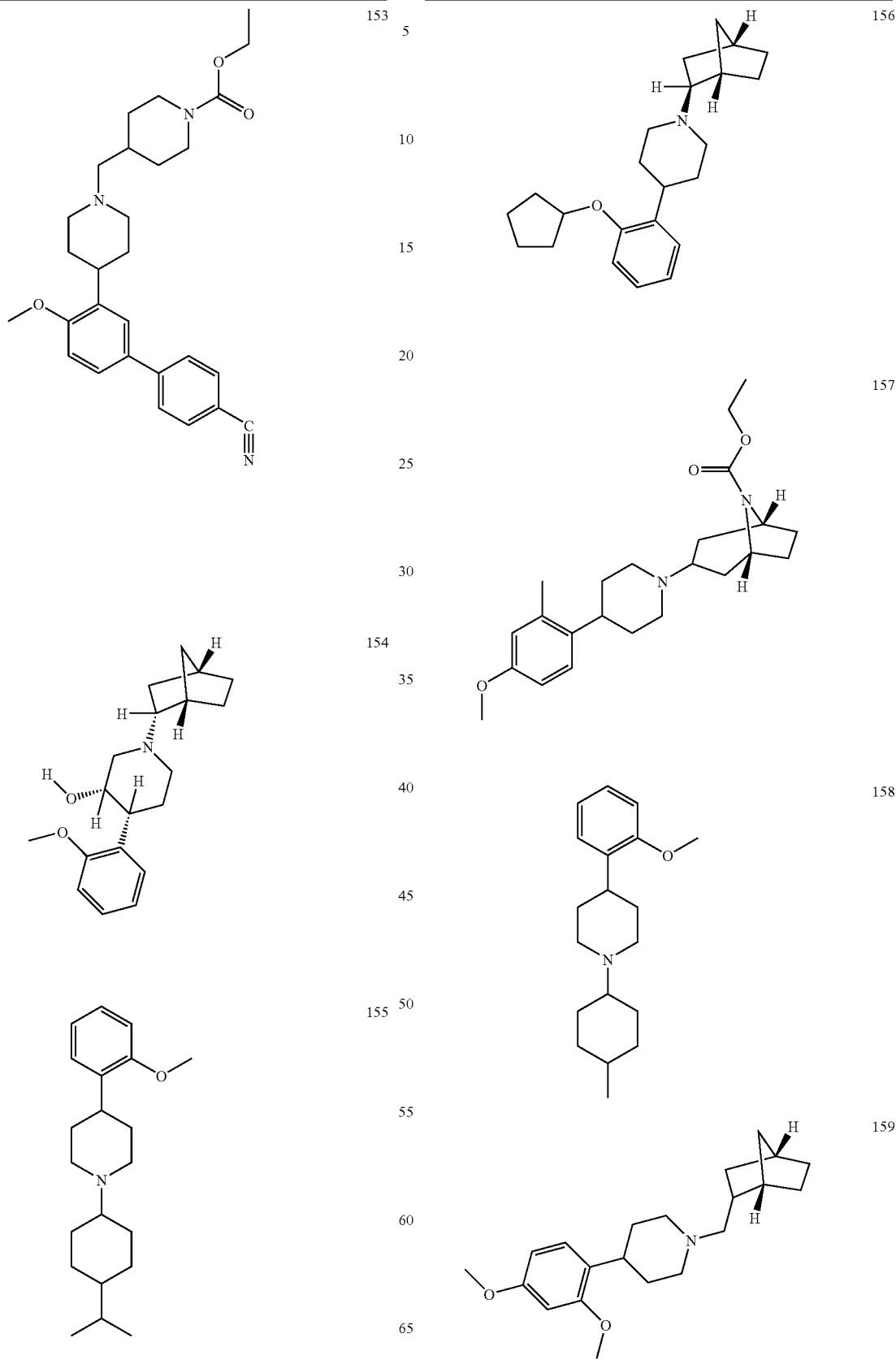
157
158
159

TABLE 1-continued
Exemplary compounds of the present invention.
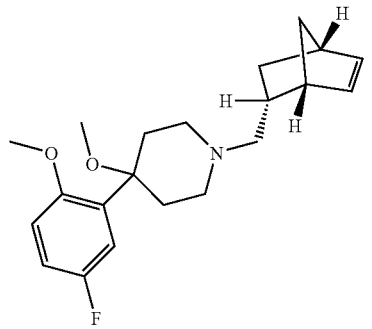 160
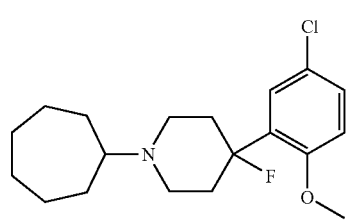 161
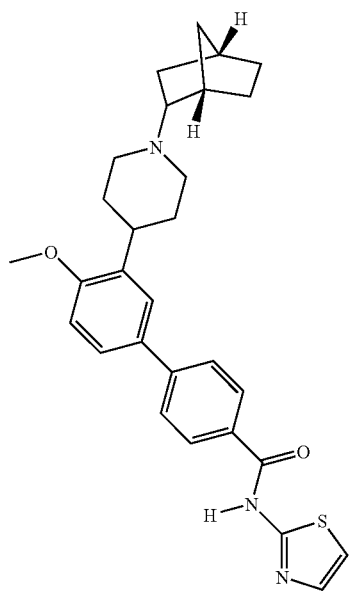 162
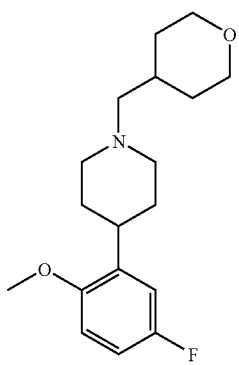 163
TABLE 1-continued
Exemplary compounds of the present invention.
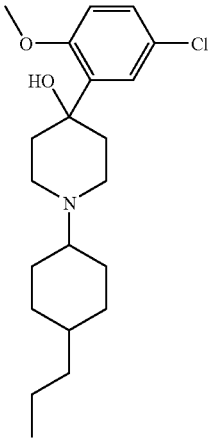 164
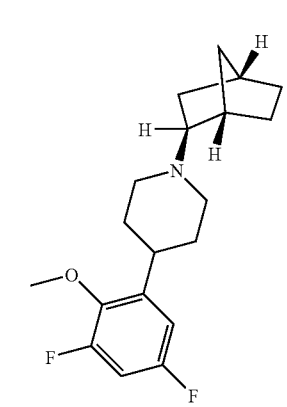 165
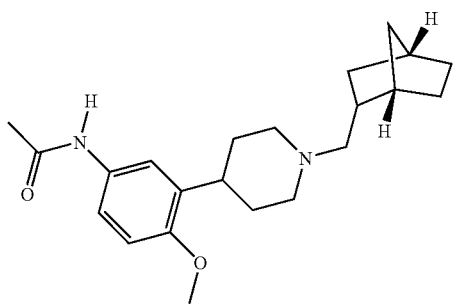 166
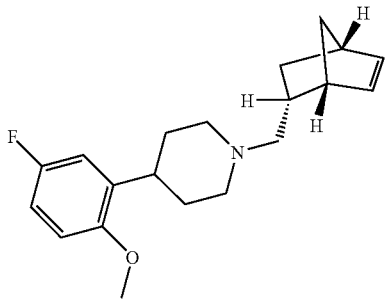 167

TABLE 1-continued
Exemplary compounds of the present invention.
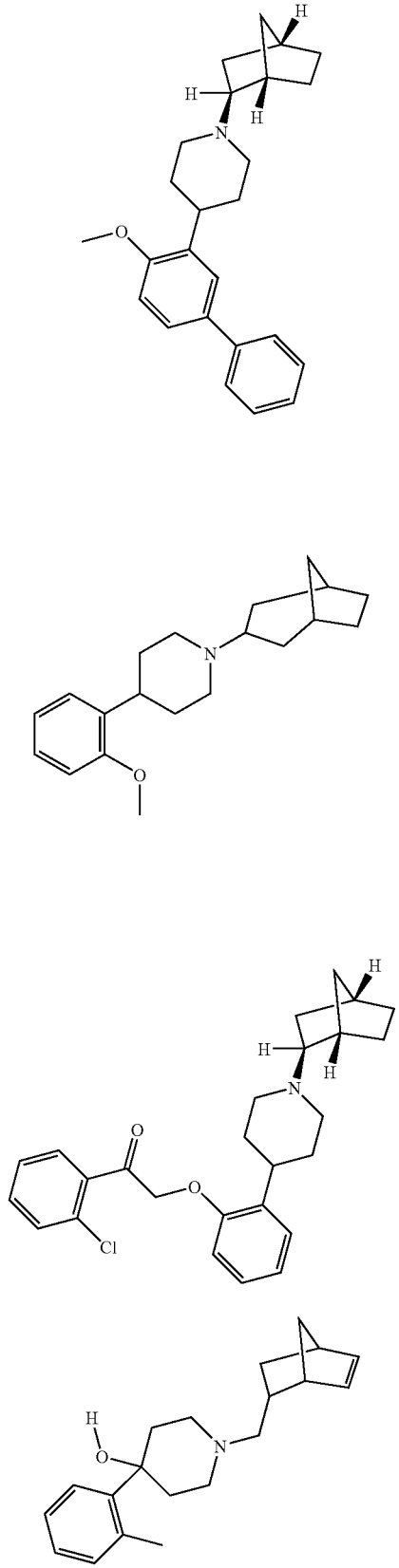
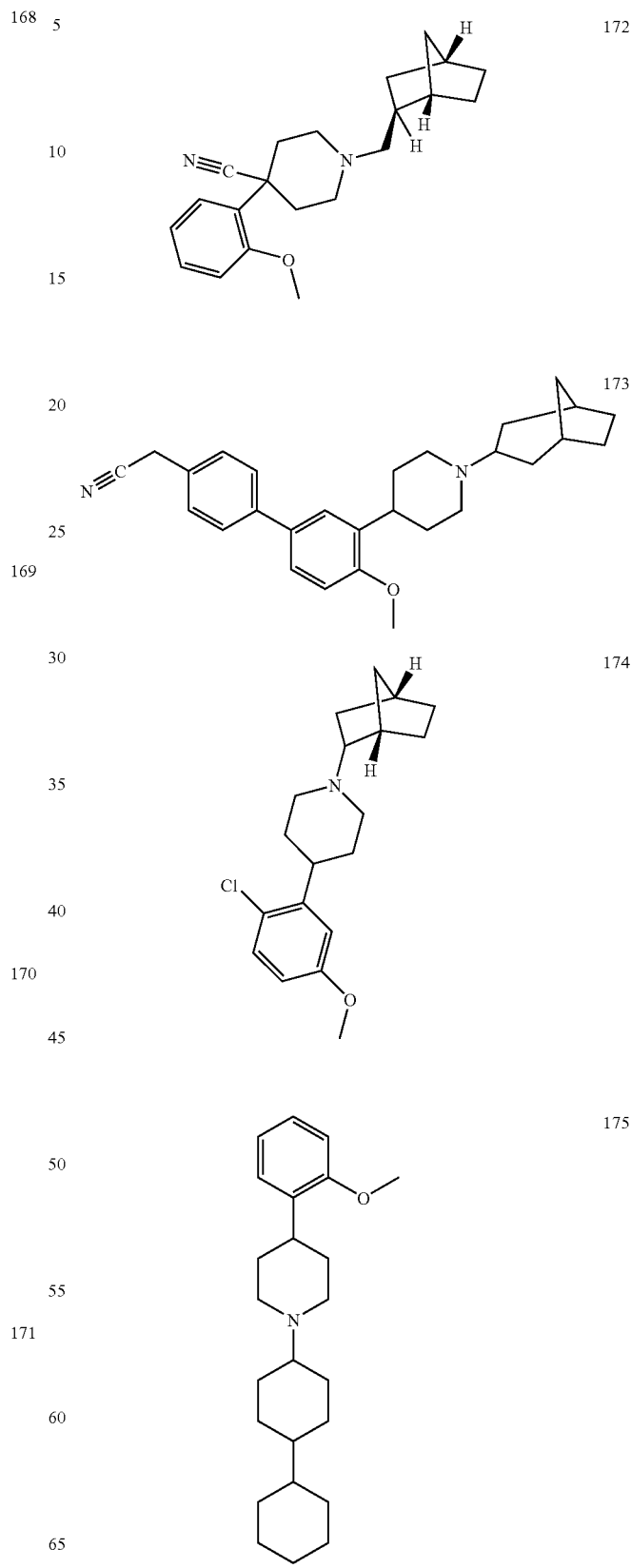

TABLE 1-continued
Exemplary compounds of the present invention.
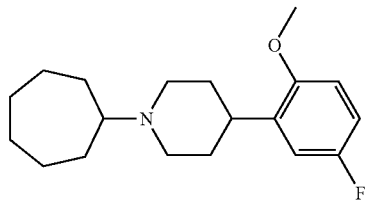
176
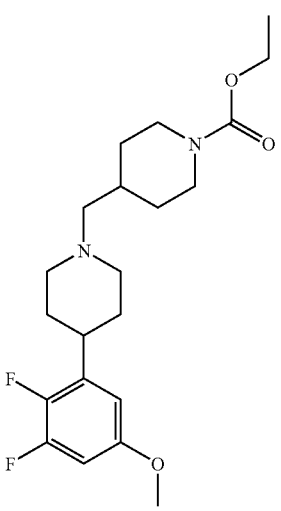
177
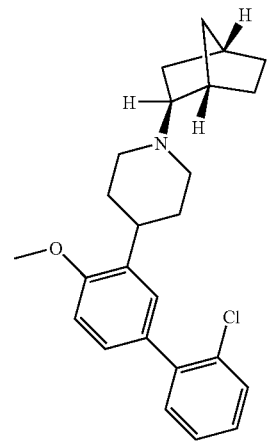
178
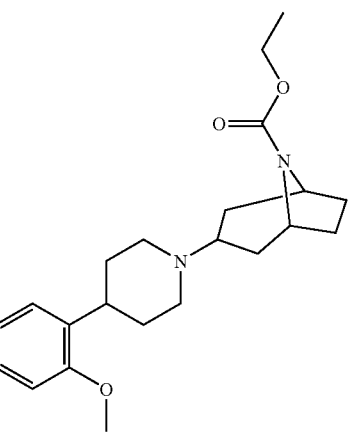
179
TABLE 1-continued
Exemplary compounds of the present invention.
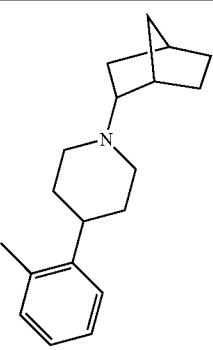
180
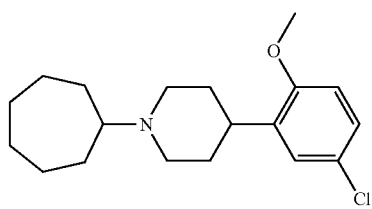
181
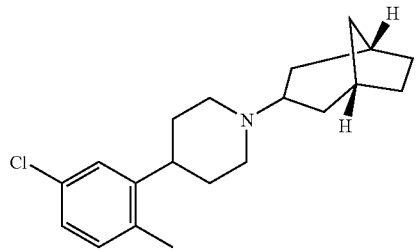
182
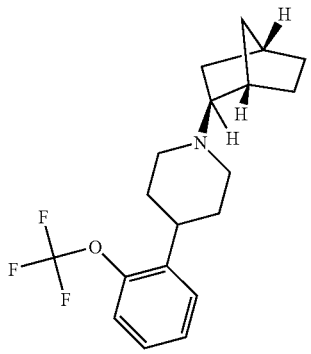
183

TABLE 1-continued
Exemplary compounds of the present invention.
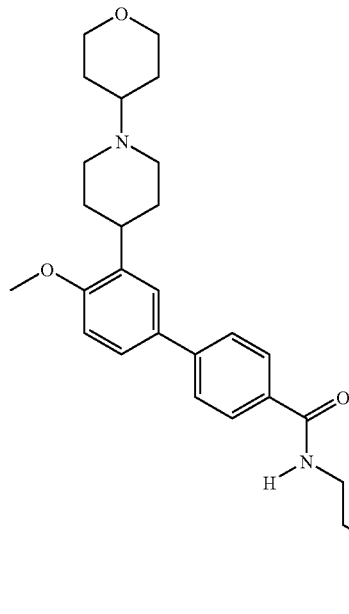
184
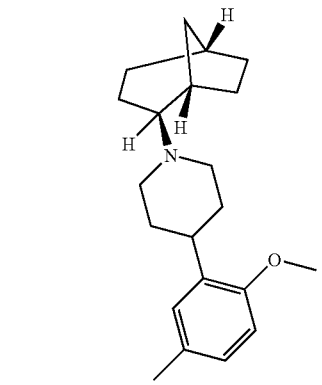
185
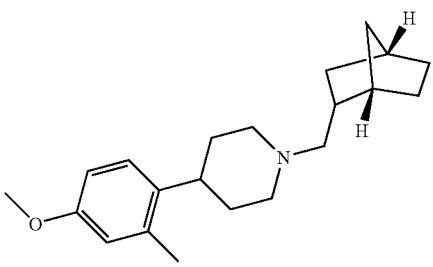
186
TABLE 1-continued
Exemplary compounds of the present invention.
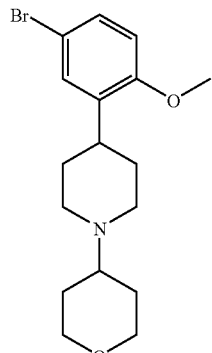
187
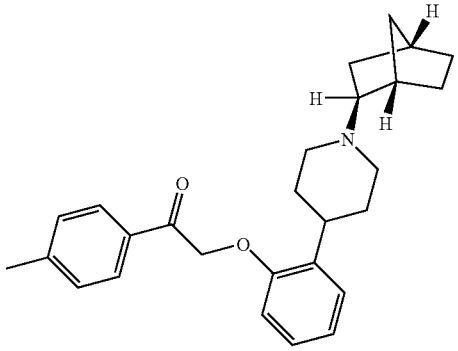
188
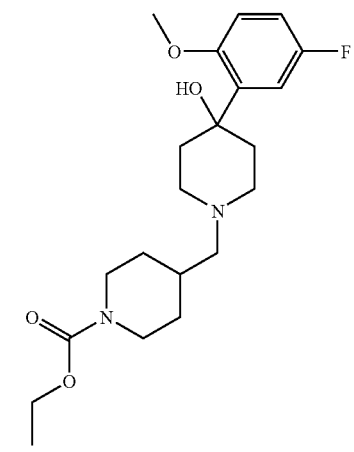
189

TABLE 1-continued
Exemplary compounds of the present invention.
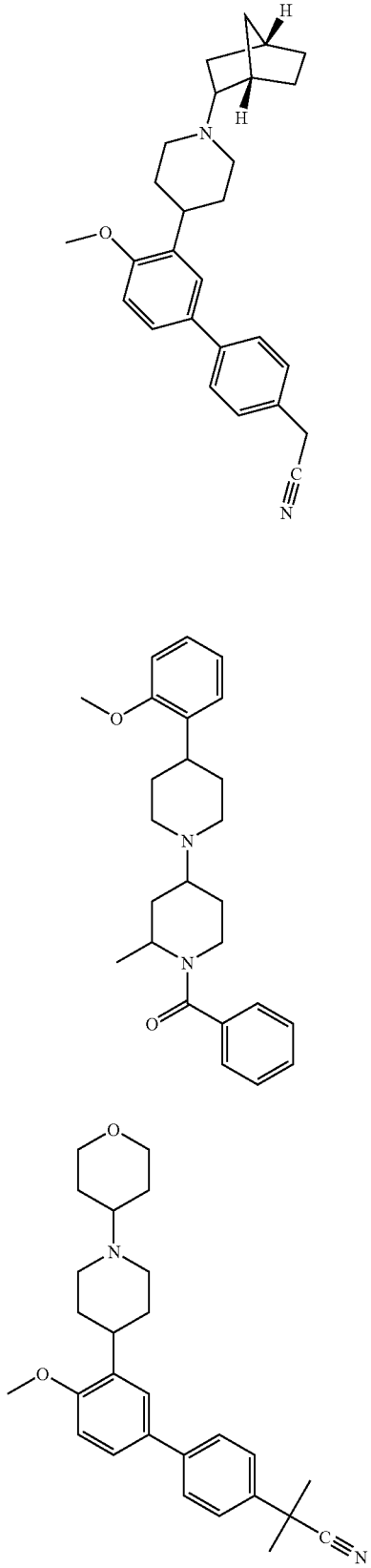
190
191
192
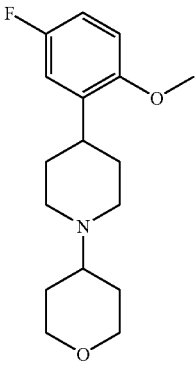
193
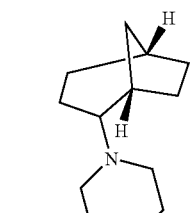
194
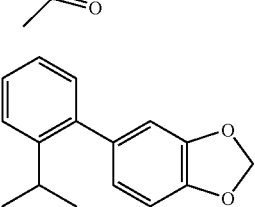
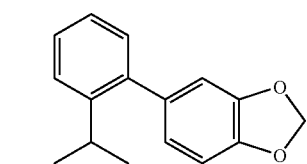
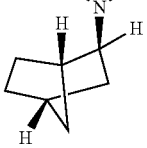
195
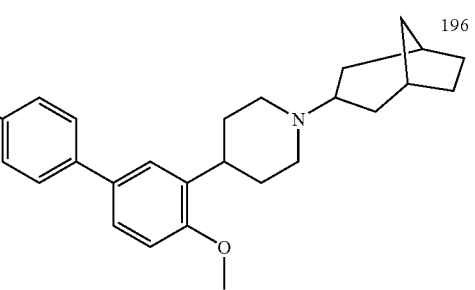
196

TABLE 1-continued
Exemplary compounds of the present invention.
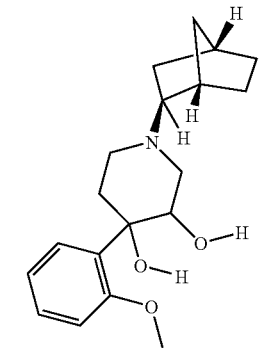 197
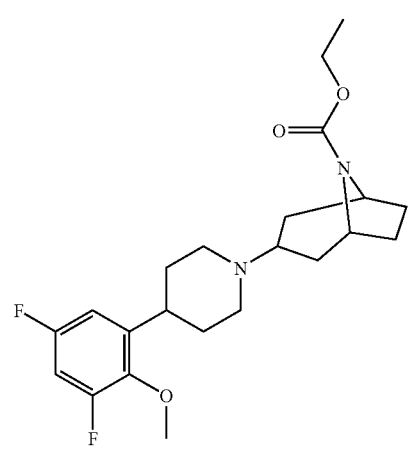 198
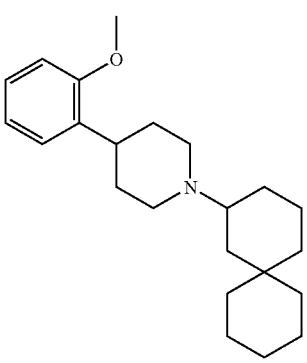 199
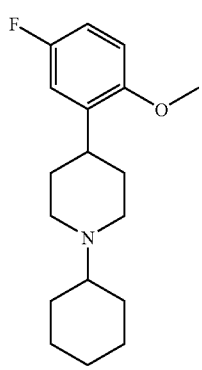 200
TABLE 1-continued
Exemplary compounds of the present invention.
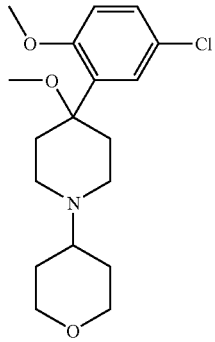 201
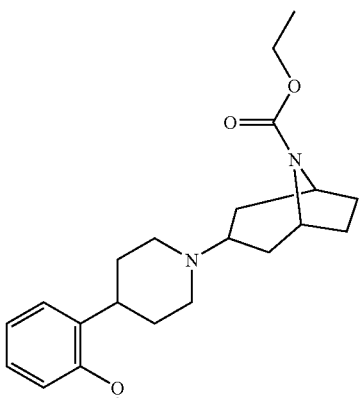 202
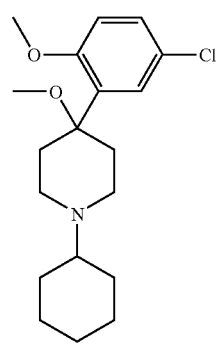 203
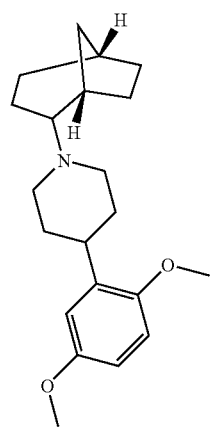 204

TABLE 1-continued
Exemplary compounds of the present invention.
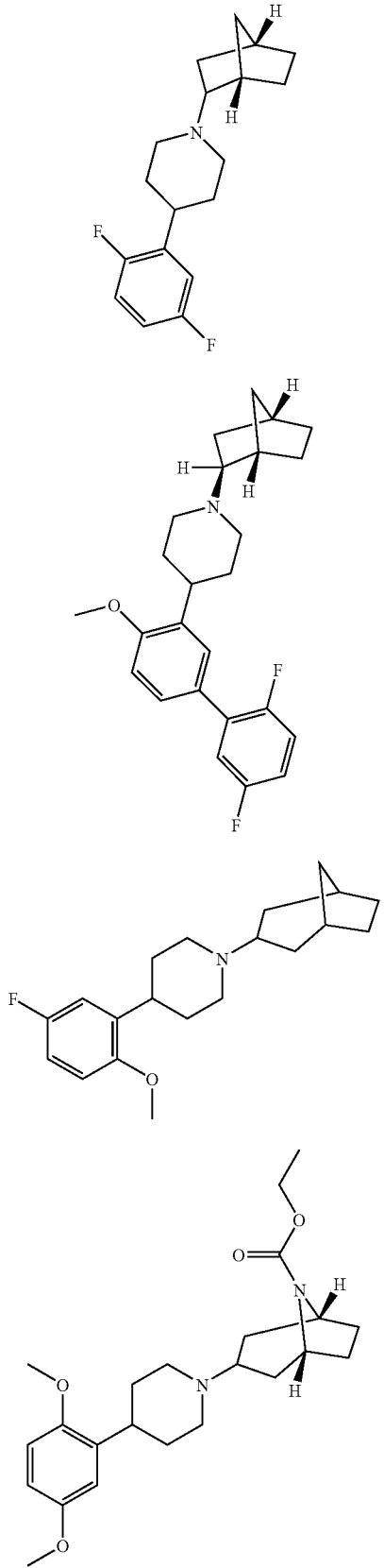
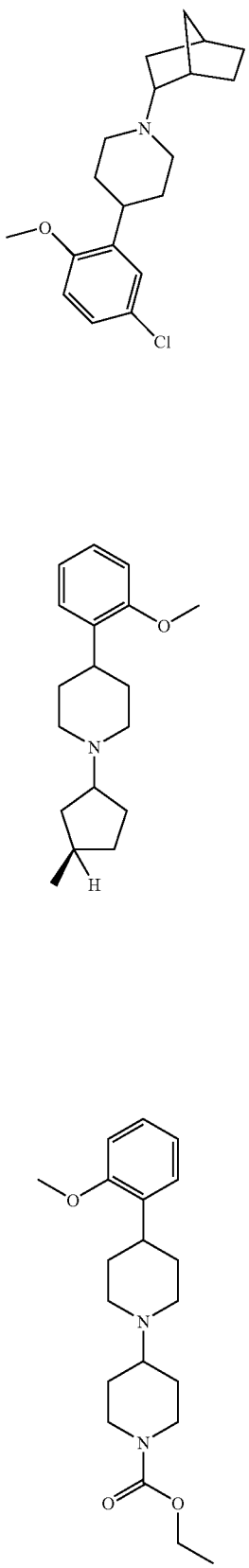

TABLE 1-continued
Exemplary compounds of the present invention.
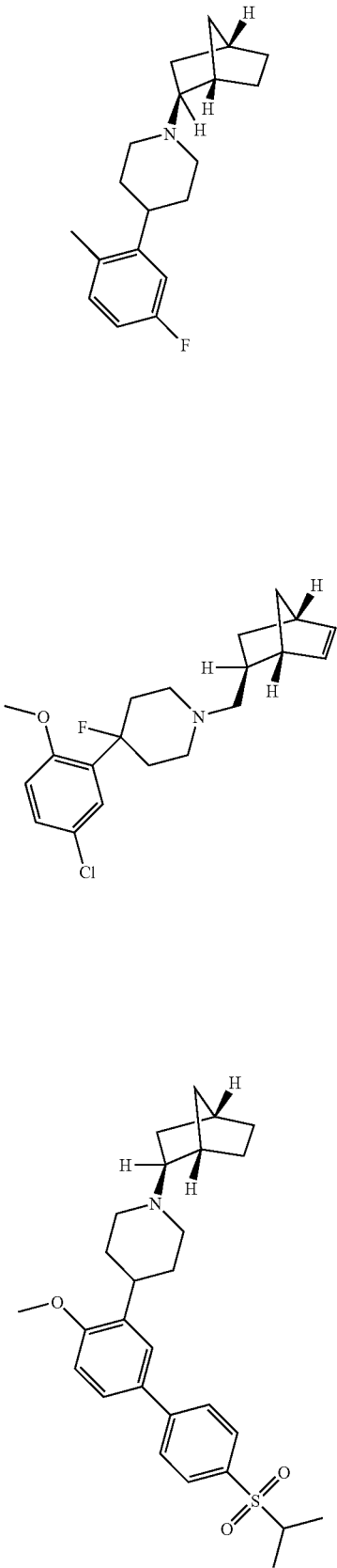
212
213
214
215
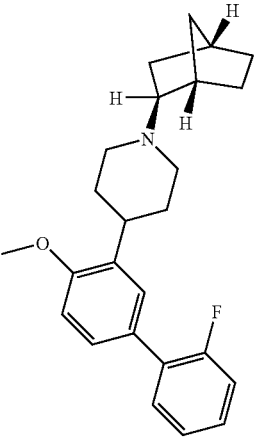
216
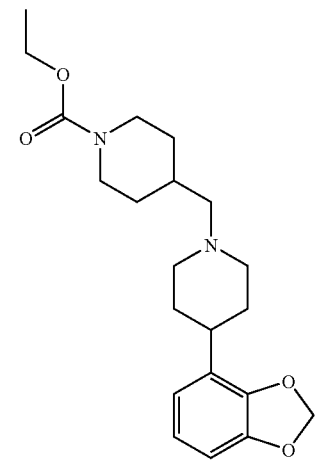
217

TABLE 1-continued
Exemplary compounds of the present invention.
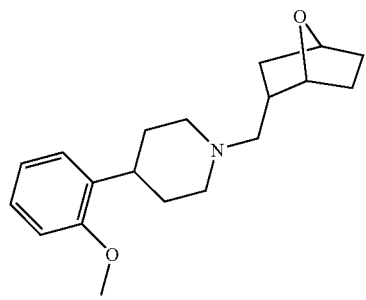 218
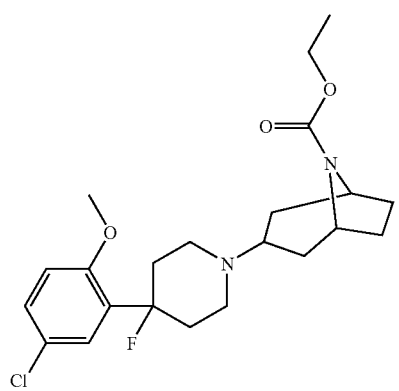 219
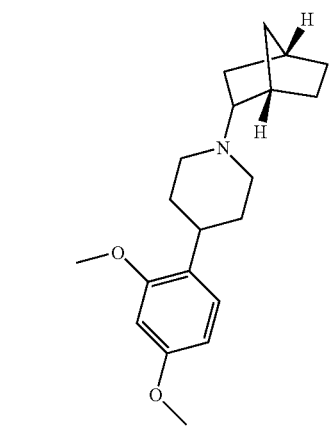 220
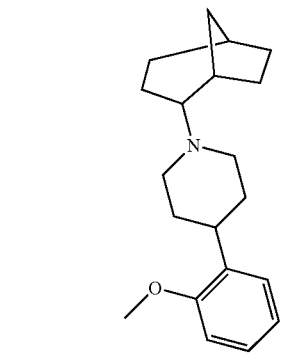 221
TABLE 1-continued
Exemplary compounds of the present invention.
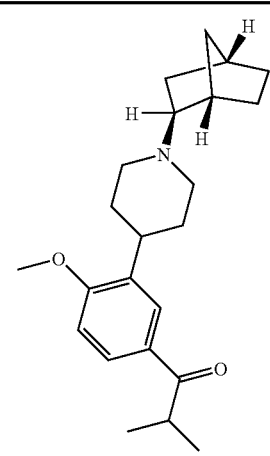 222
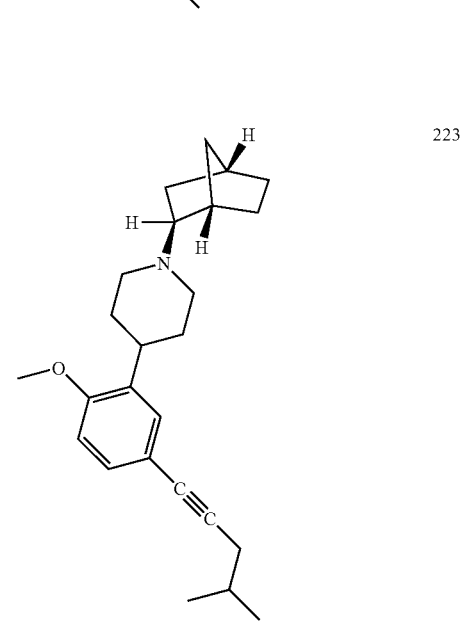 223
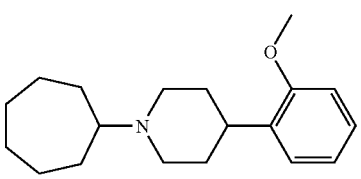 224
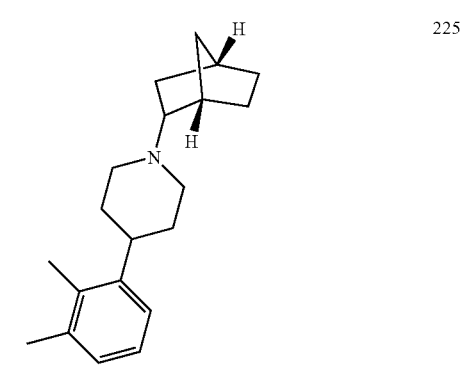 225

TABLE 1-continued
Exemplary compounds of the present invention.
226
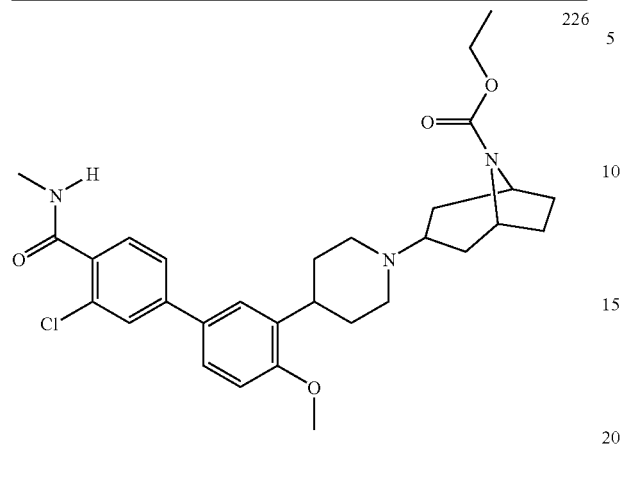
227
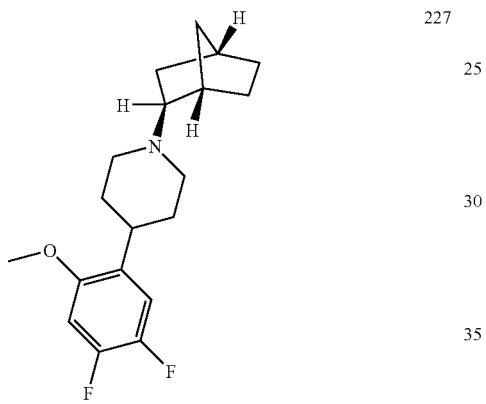
228
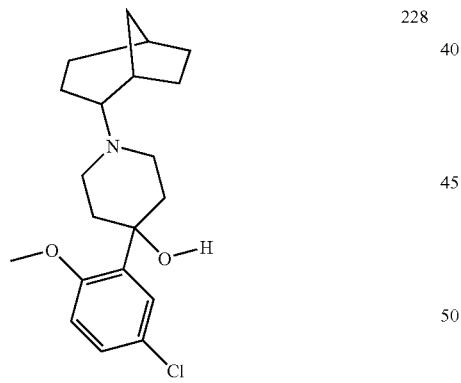
229
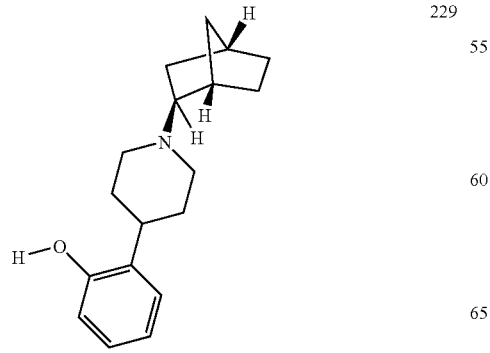
TABLE 1-continued
Exemplary compounds of the present invention.
230
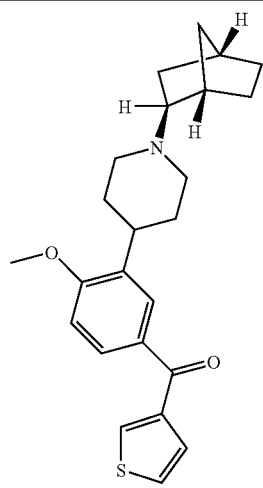
231
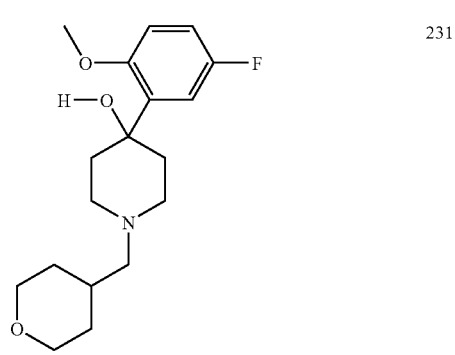
232
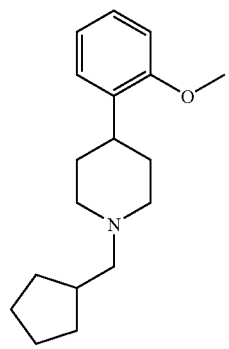
233
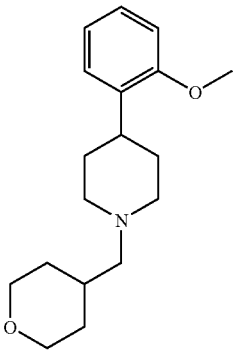

TABLE 1-continued
Exemplary compounds of the present invention.
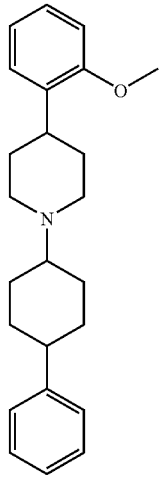 234
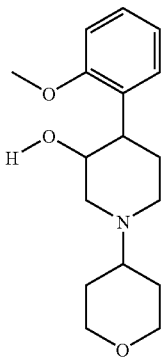 235
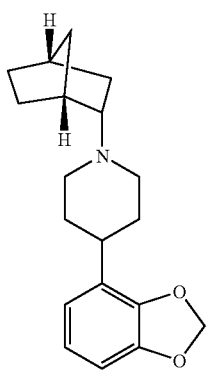 236
TABLE 1-continued
Exemplary compounds of the present invention.
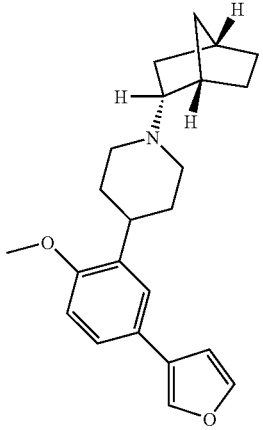 237
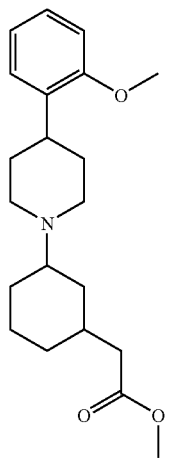 238
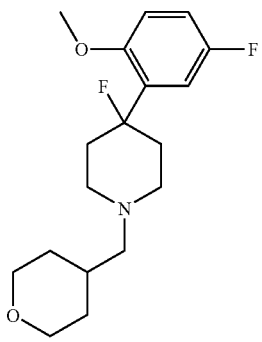 239
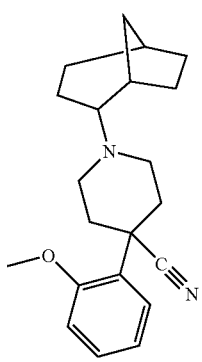 240

TABLE 1-continued
Exemplary compounds of the present invention.
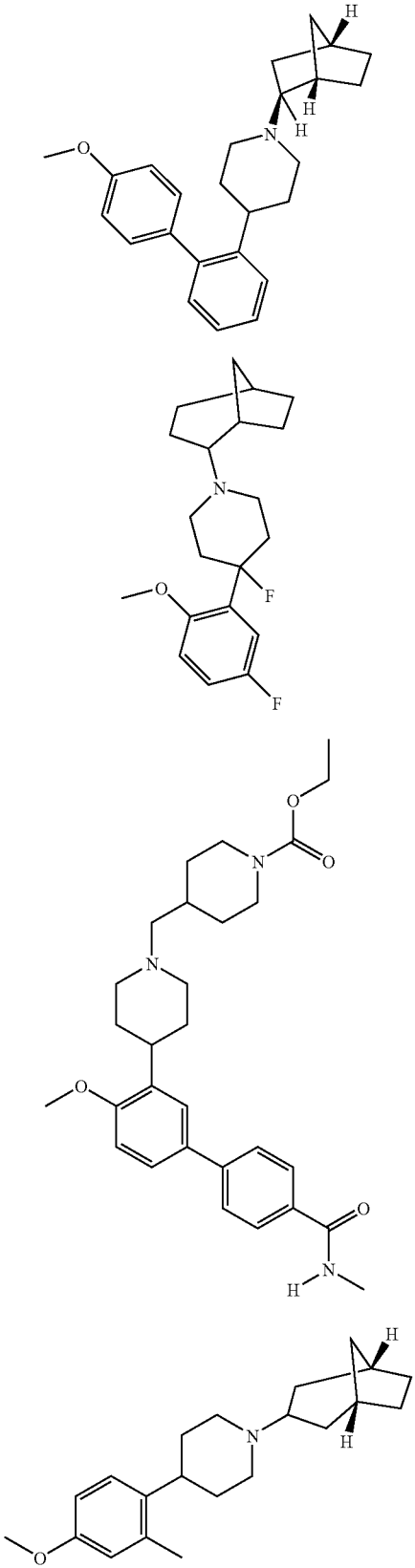
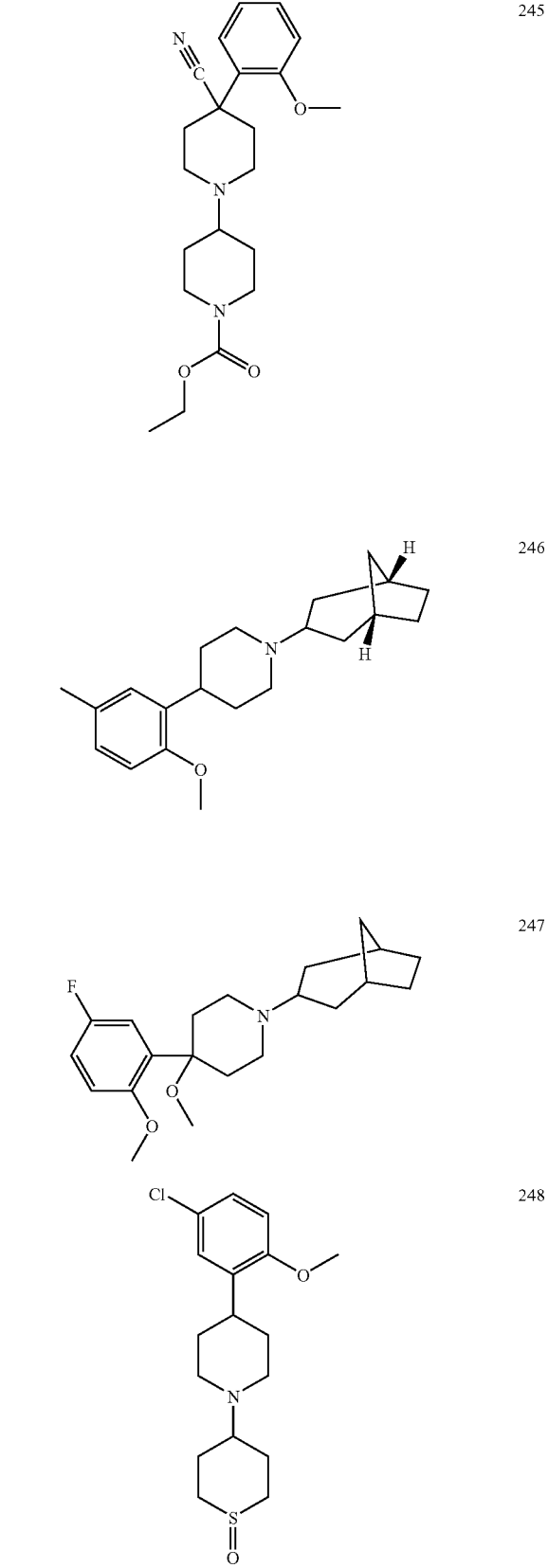

TABLE 1-continued
Exemplary compounds of the present invention.
249 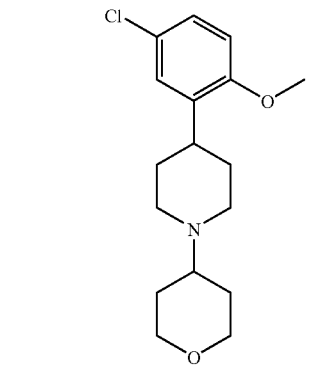
250 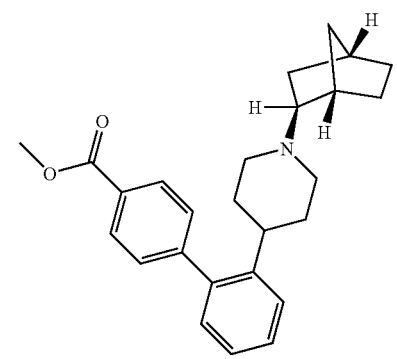
251 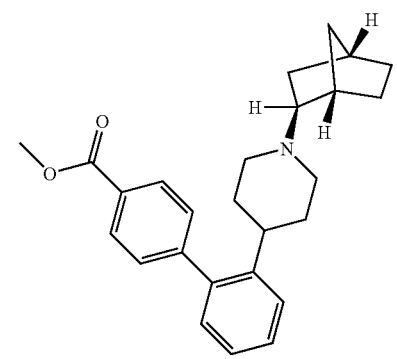
252 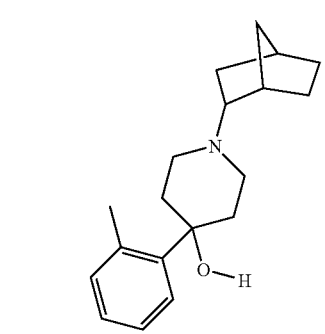
TABLE 1-continued
Exemplary compounds of the present invention.
253 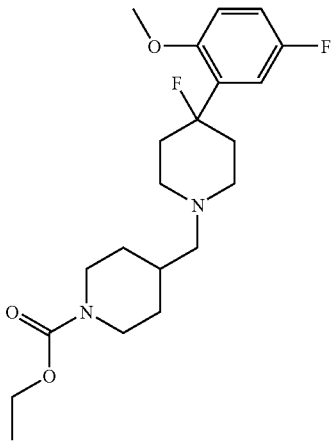
254 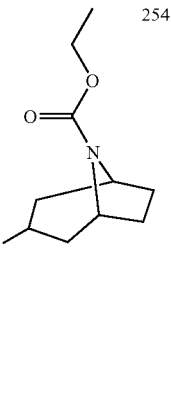
255 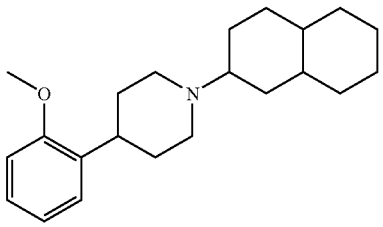
256 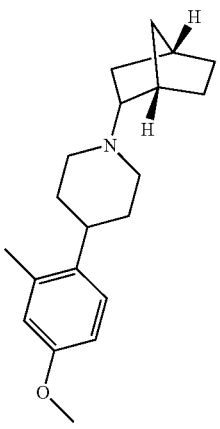

TABLE 1-continued
Exemplary compounds of the present invention.
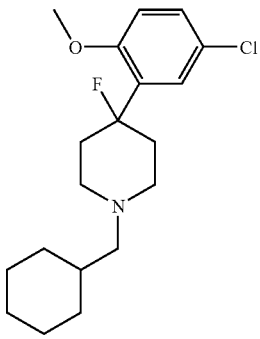 257
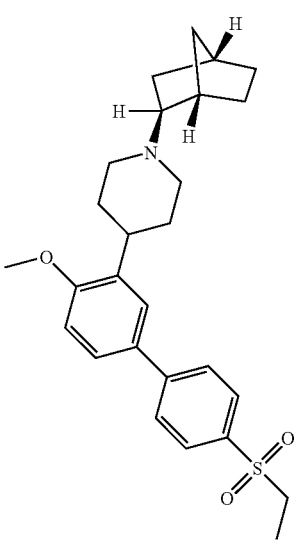 258
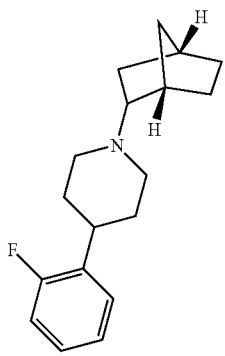 259
TABLE 1-continued
Exemplary compounds of the present invention.
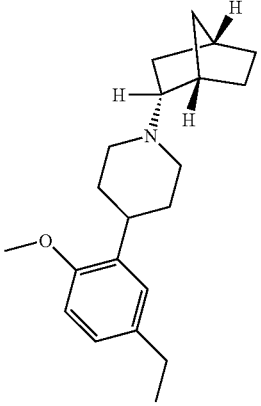 260
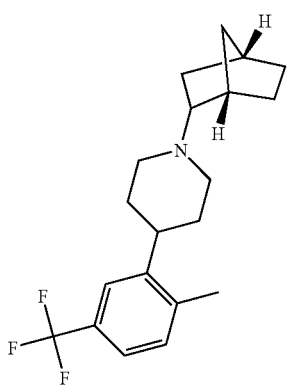 261
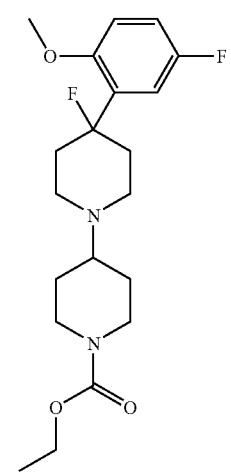 262

TABLE 1-continued
Exemplary compounds of the present invention.
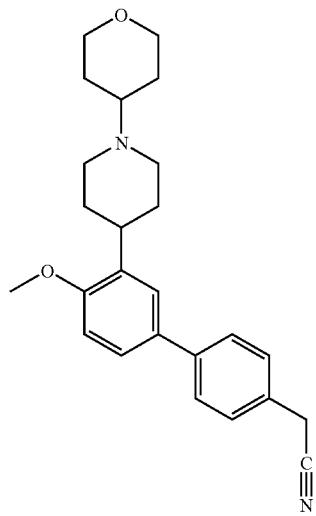
263
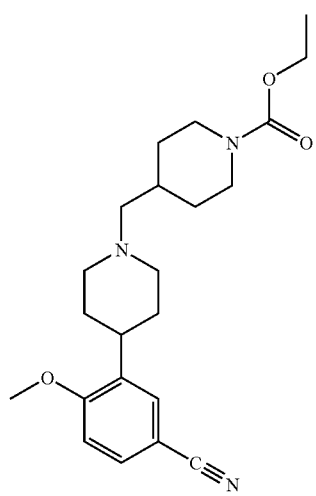
264
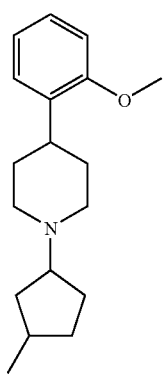
265
TABLE 1-continued
Exemplary compounds of the present invention.
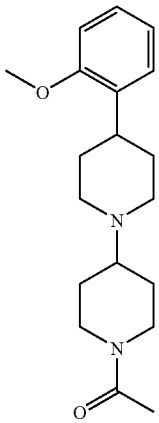
266
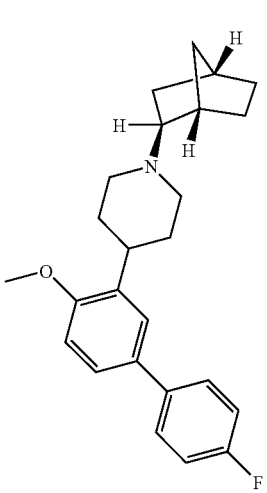
267
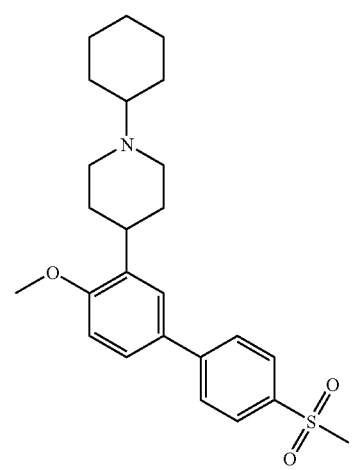
268

TABLE 1-continued
Exemplary compounds of the present invention.
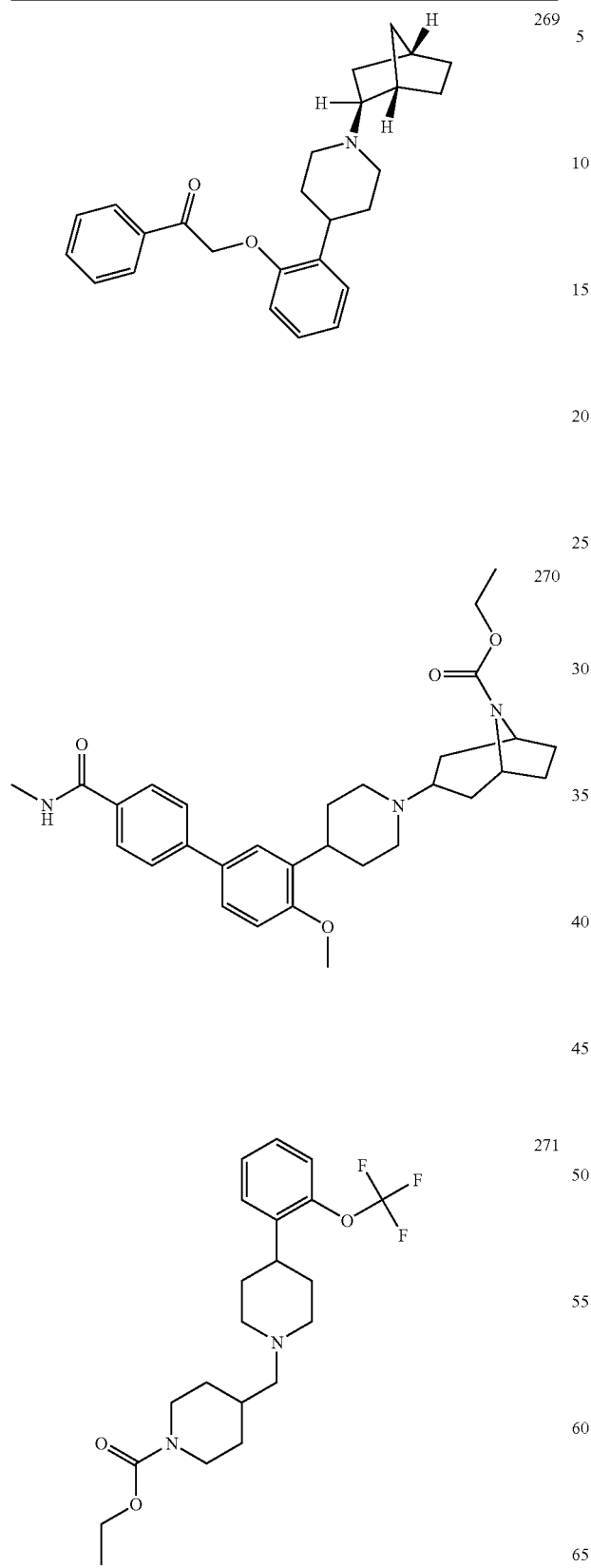
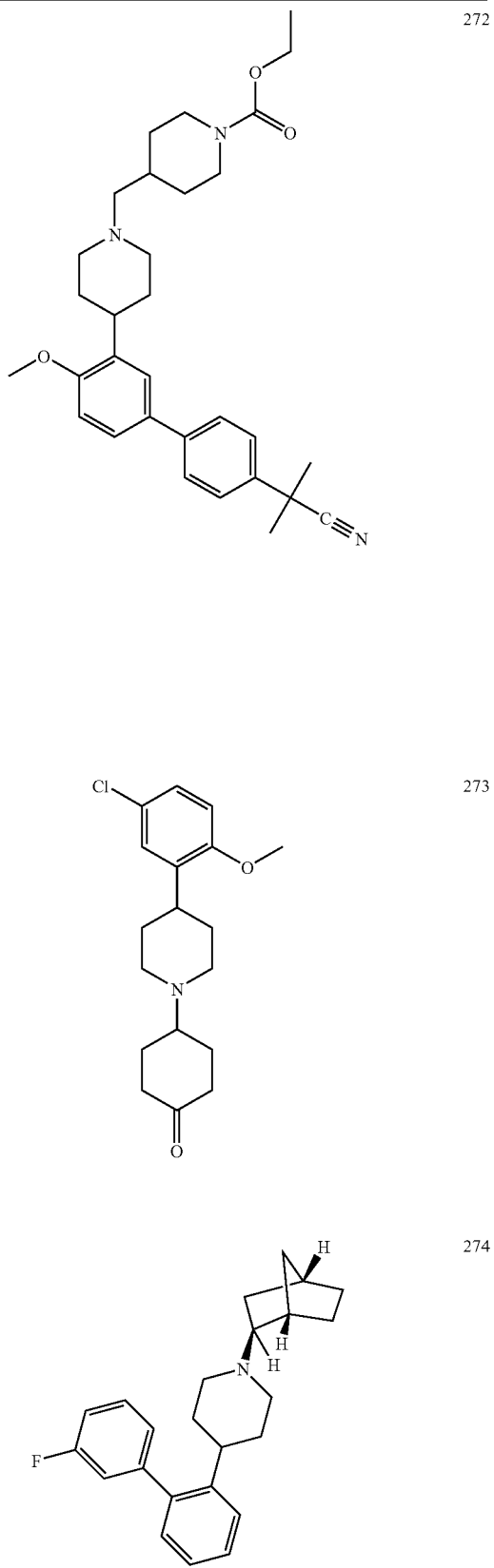

TABLE 1-continued
Exemplary compounds of the present invention.
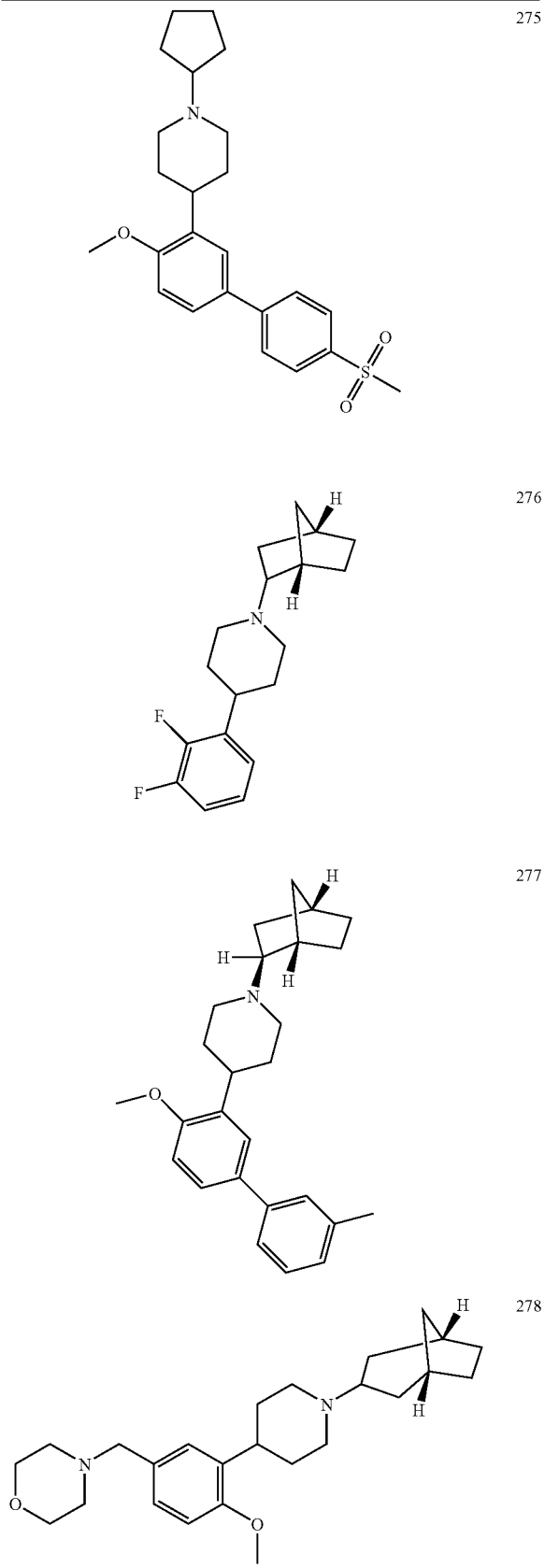
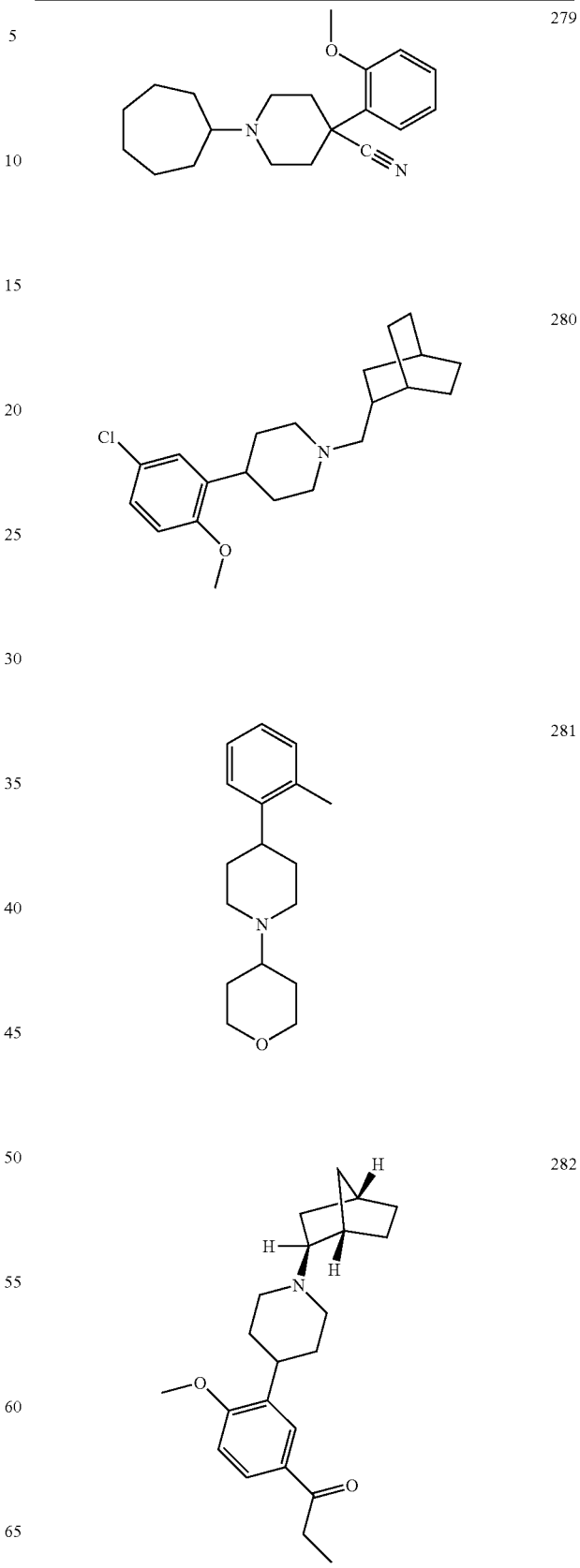

TABLE 1-continued
Exemplary compounds of the present invention.
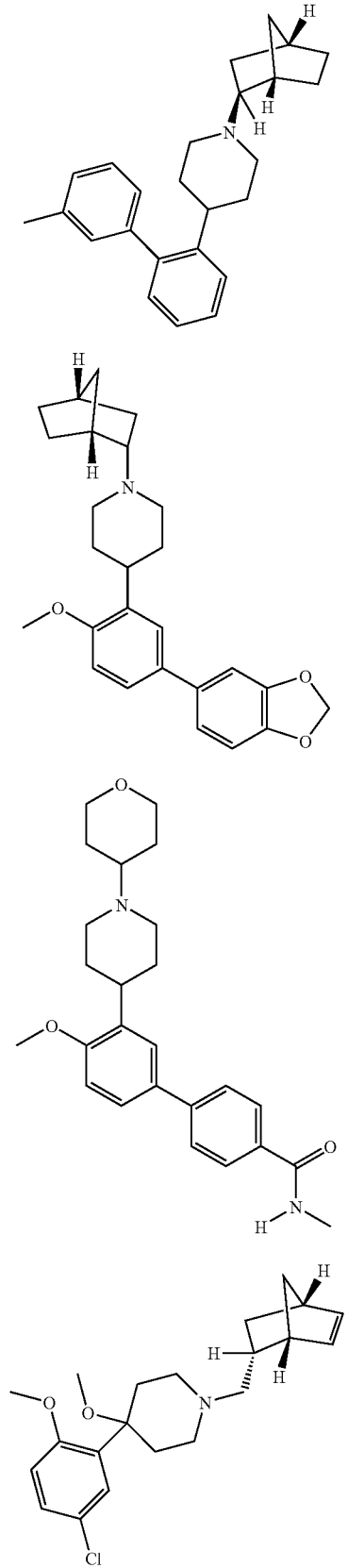
283
284
285
286
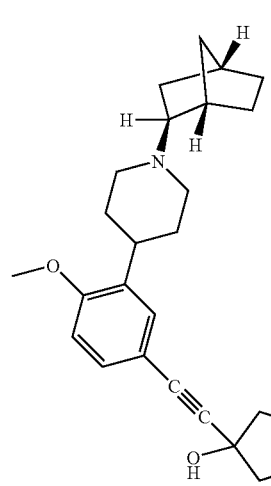
287
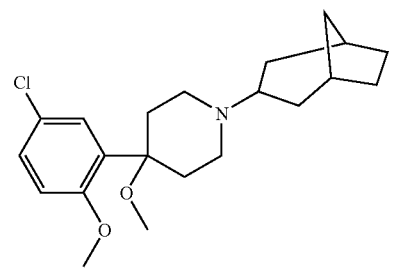
288
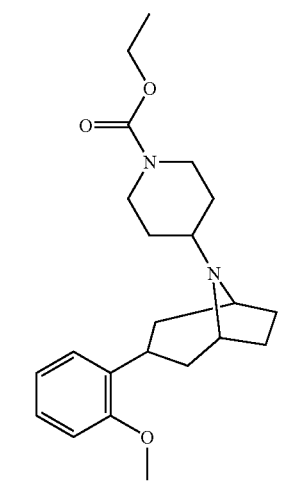
289
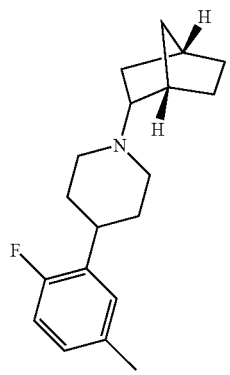
290

TABLE 1-continued
Exemplary compounds of the present invention.
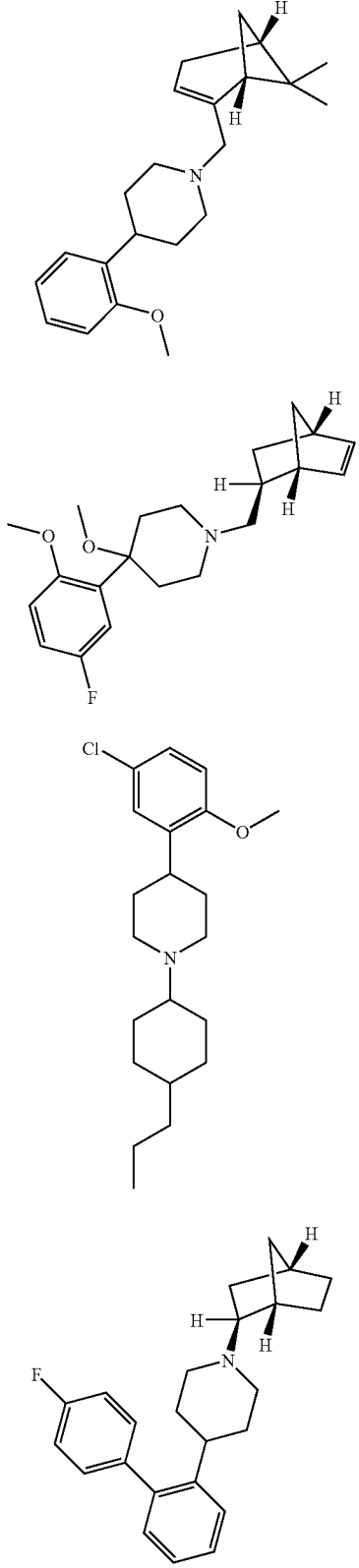
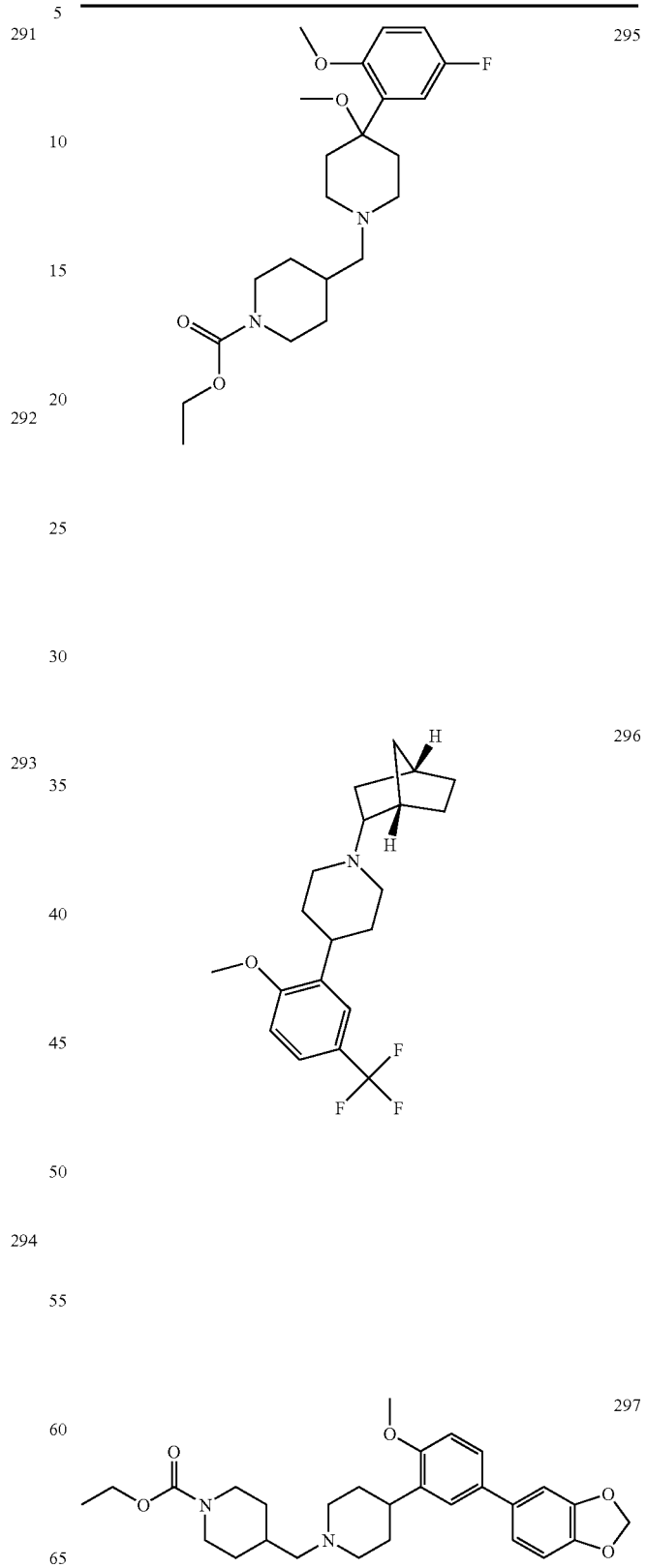

TABLE 1-continued
Exemplary compounds of the present invention.
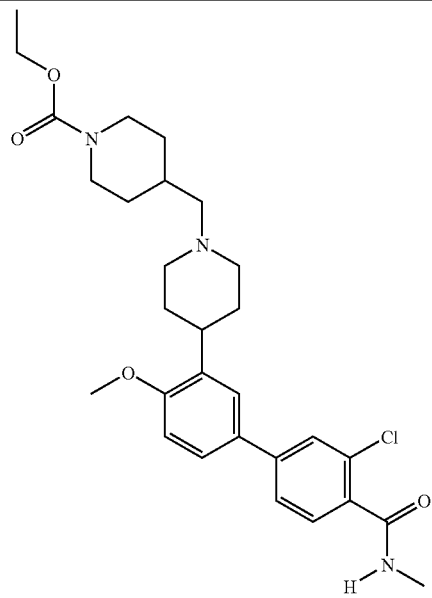
298
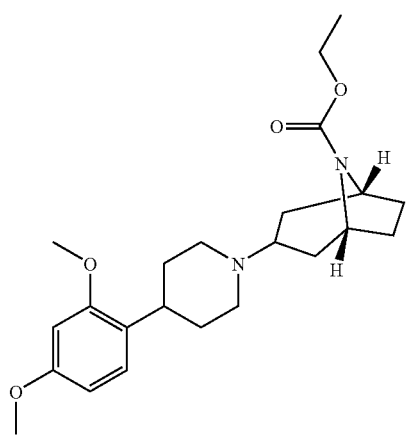
299
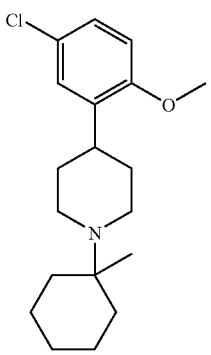
300
TABLE 1-continued
Exemplary compounds of the present invention.
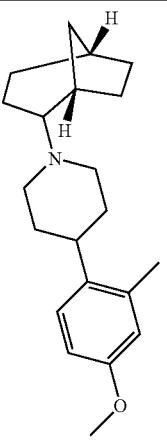
301
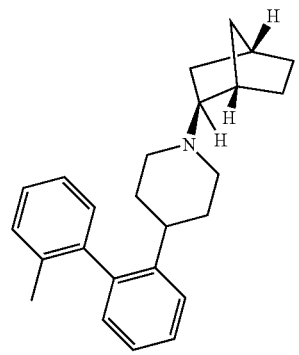
302
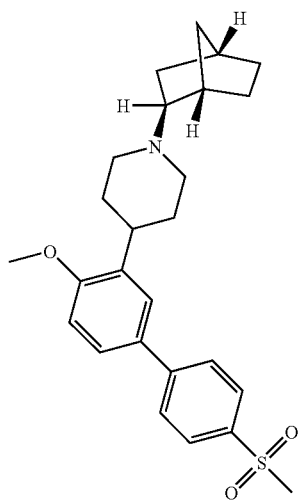
303

TABLE 1-continued
Exemplary compounds of the present invention.
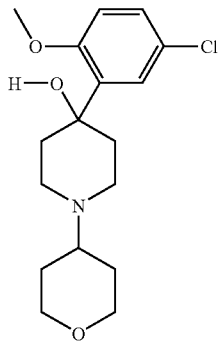 304
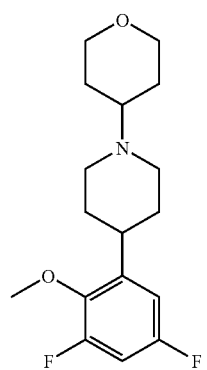 305
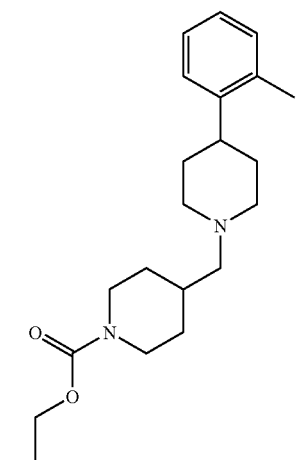 306
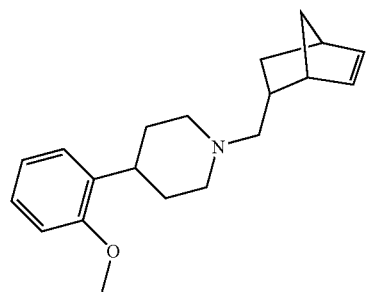 307
TABLE 1-continued
Exemplary compounds of the present invention.
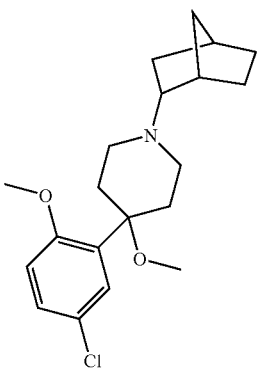 308
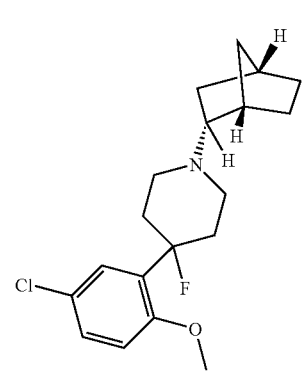 309
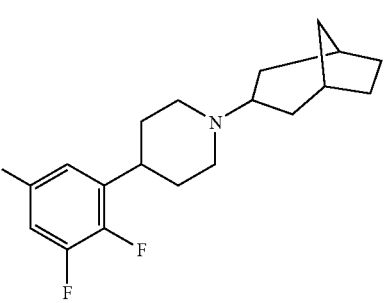 310
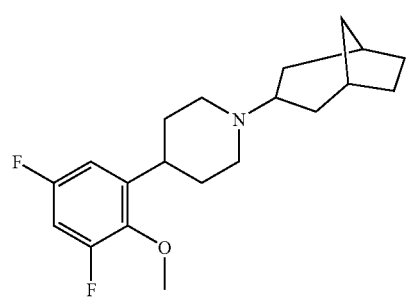 311

TABLE 1-continued
Exemplary compounds of the present invention.
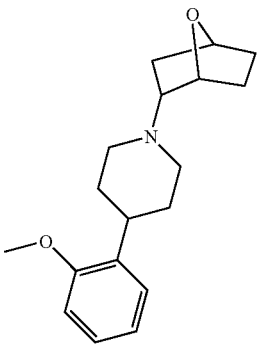
312
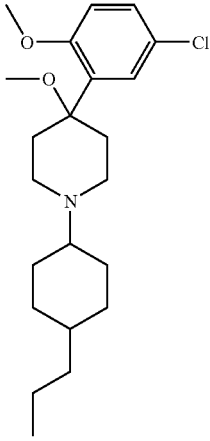
316
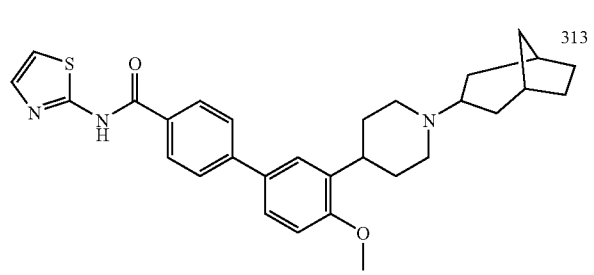
313
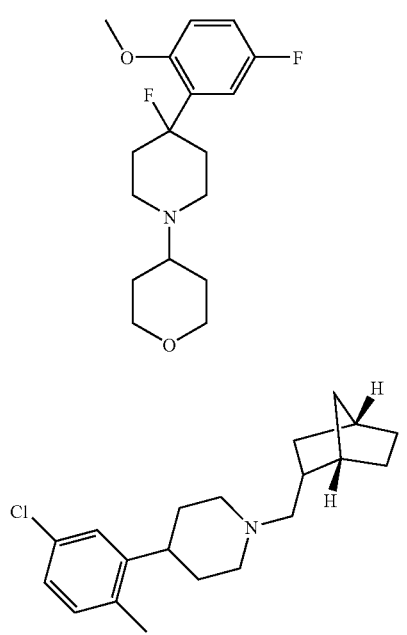
314
315
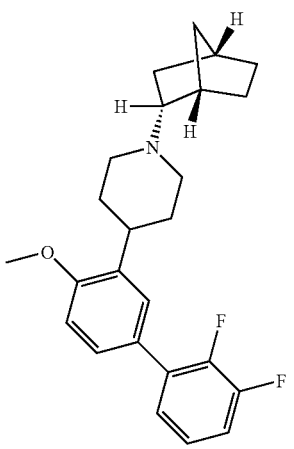
317
318

TABLE 1-continued
Exemplary compounds of the present invention.
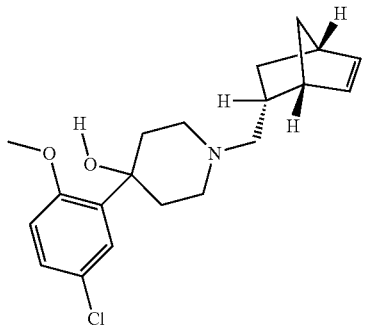 319
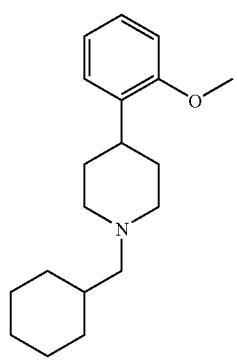 320
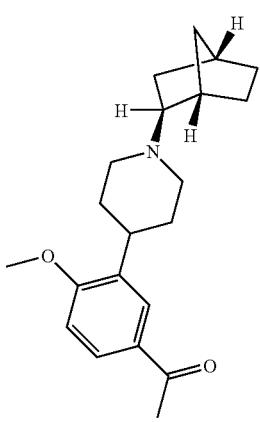 321
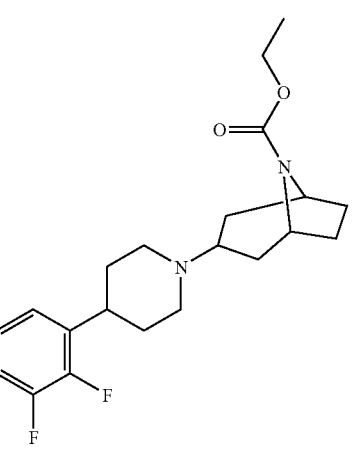 322
TABLE 1-continued
Exemplary compounds of the present invention.
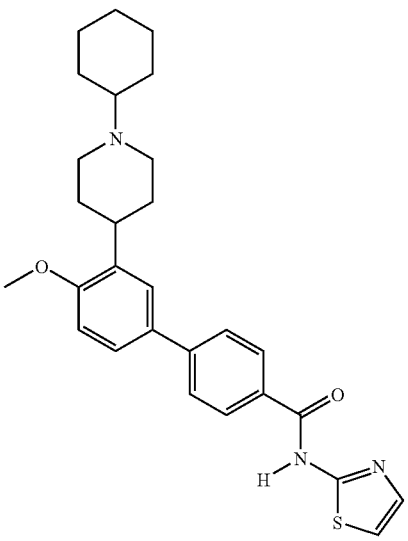 323
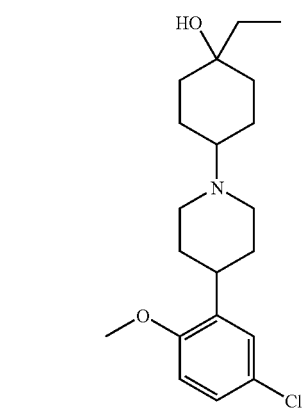 324
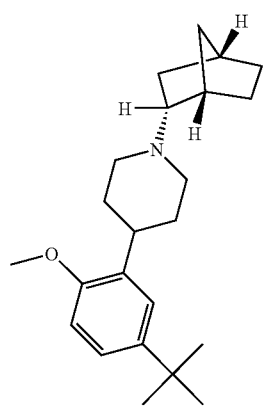 325

TABLE 1-continued
Exemplary compounds of the present invention.
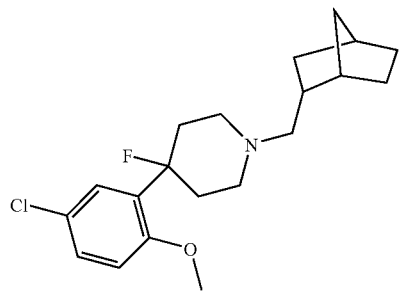
326
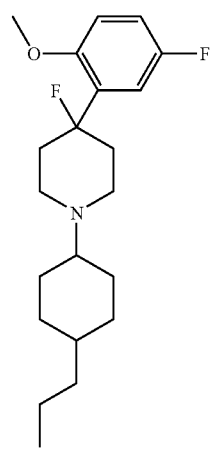
327
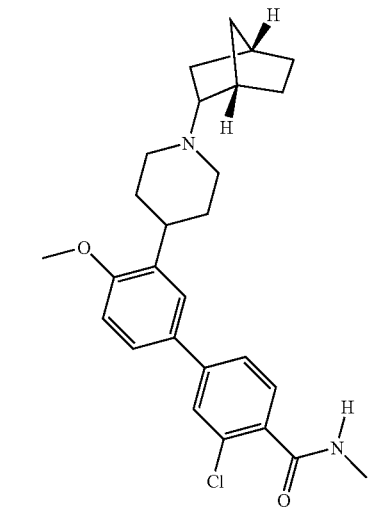
328
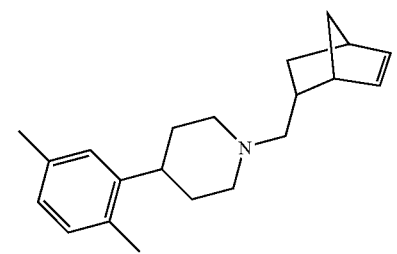
329
TABLE 1-continued
Exemplary compounds of the present invention.
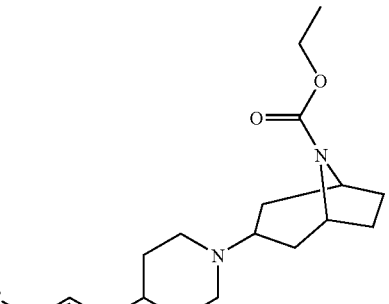
330
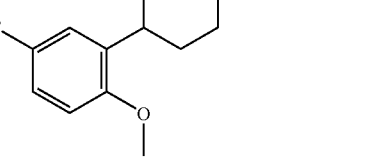
331
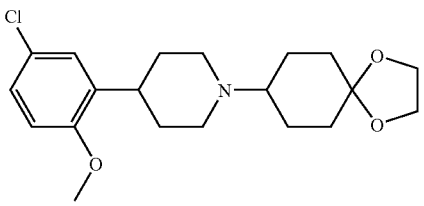
332
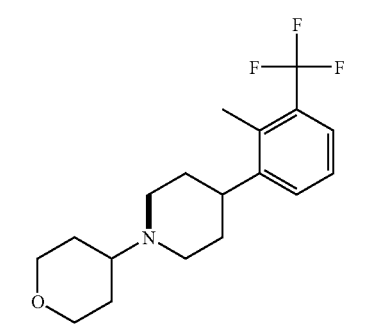
333

TABLE 1-continued
Exemplary compounds of the present invention.
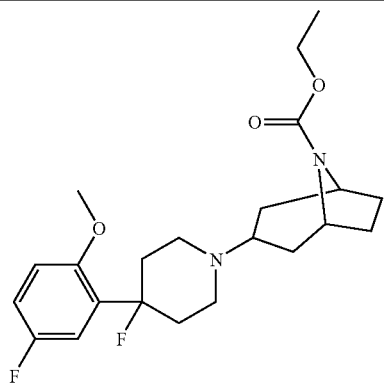 334
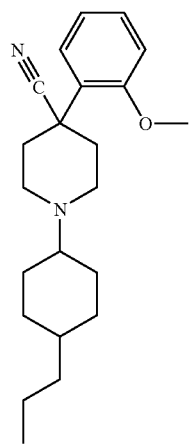 335
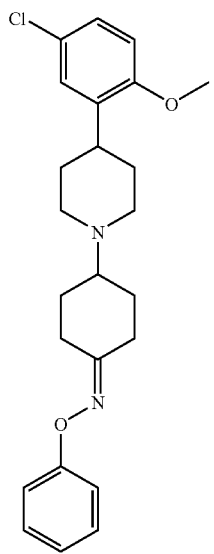 336
TABLE 1-continued
Exemplary compounds of the present invention.
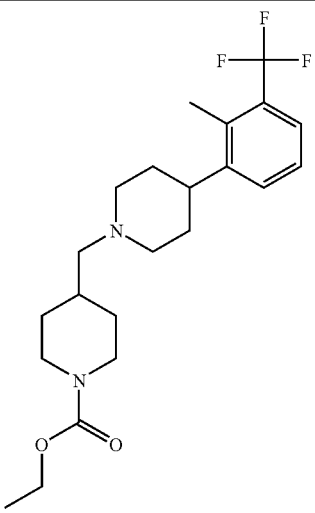 337
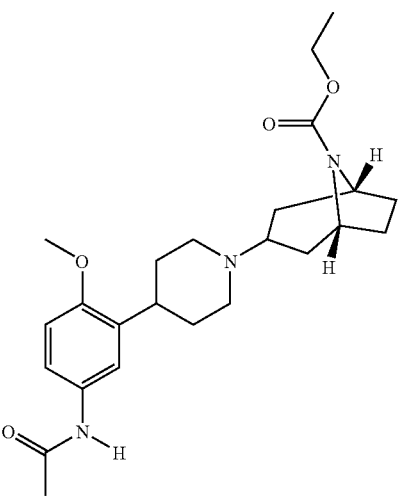 338
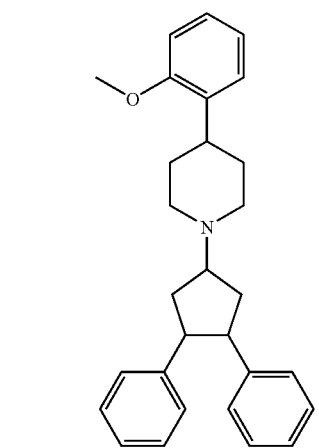 339

TABLE 1-continued
Exemplary compounds of the present invention.
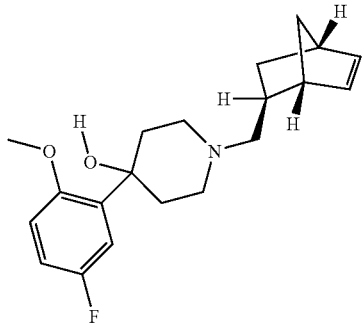
340
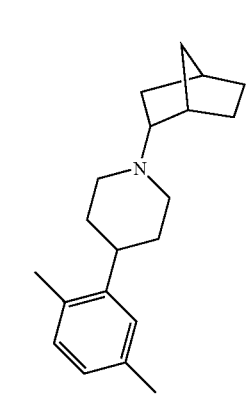
341
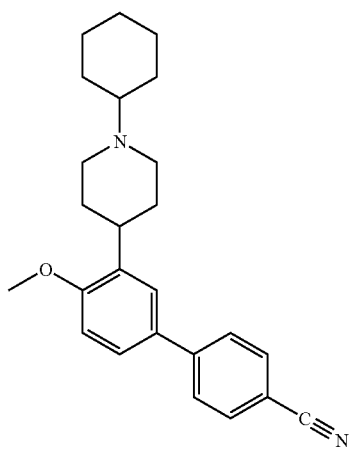
342
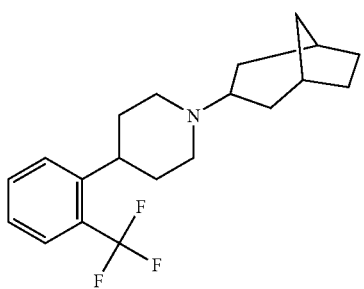
343
TABLE 1-continued
Exemplary compounds of the present invention.
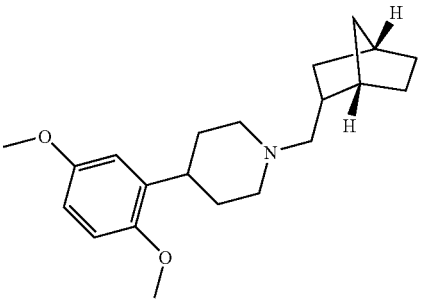
344
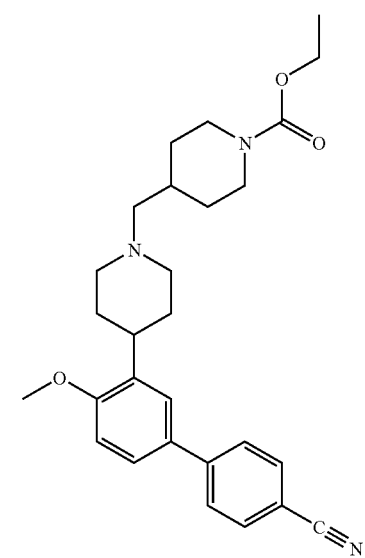
345
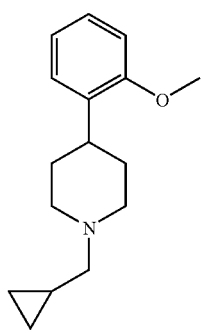
346

TABLE 1-continued
Exemplary compounds of the present invention.
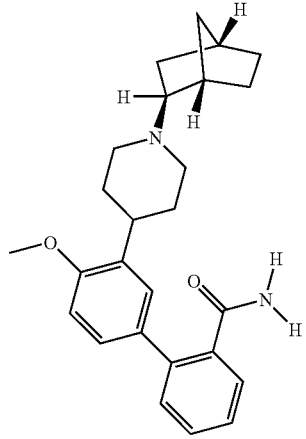
347
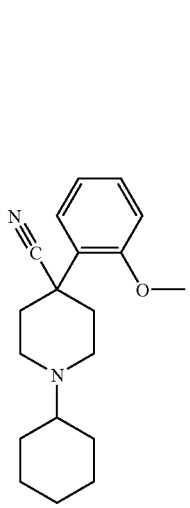
348
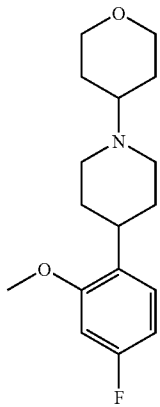
349
TABLE 1-continued
Exemplary compounds of the present invention.
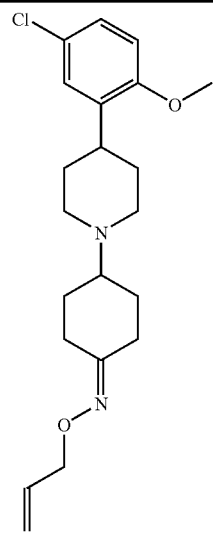
350
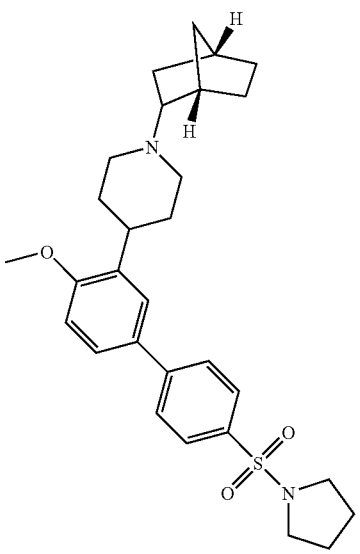
351
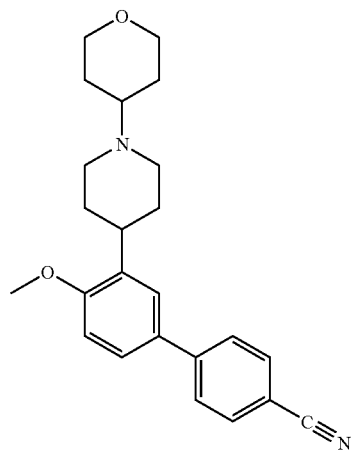
352

TABLE 1-continued
Exemplary compounds of the present invention.
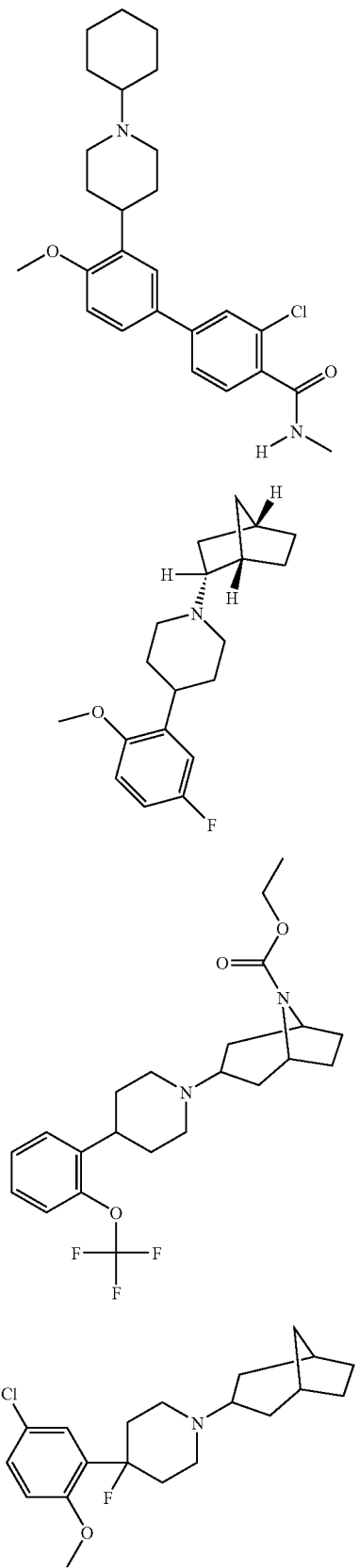
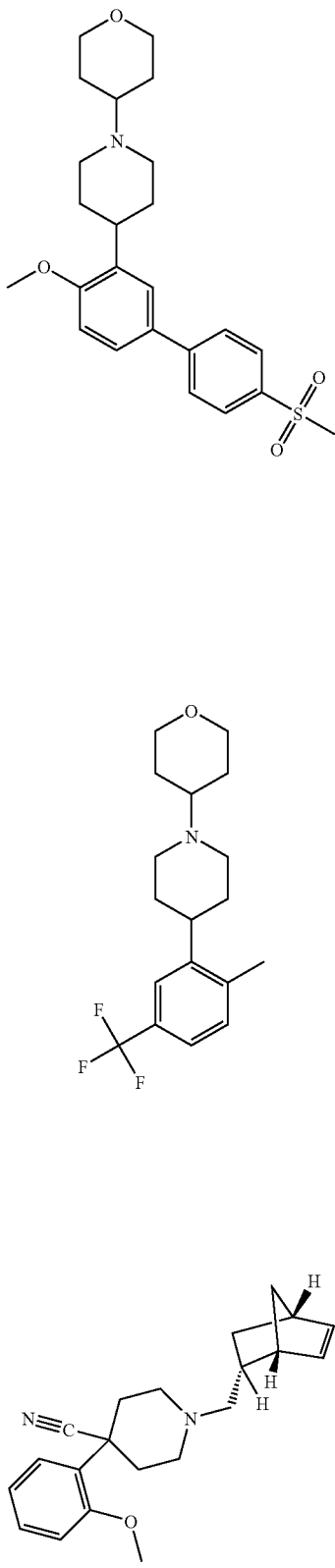

TABLE 1-continued
Exemplary compounds of the present invention.
360
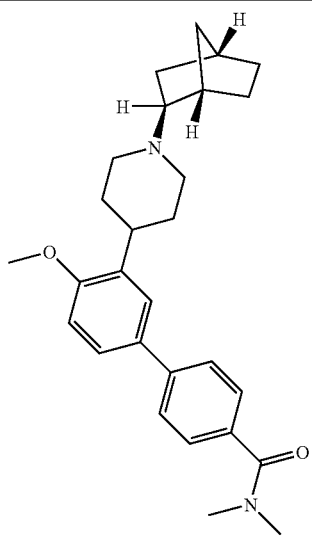
361
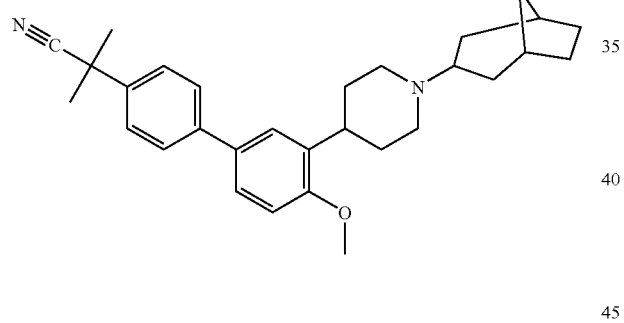
362
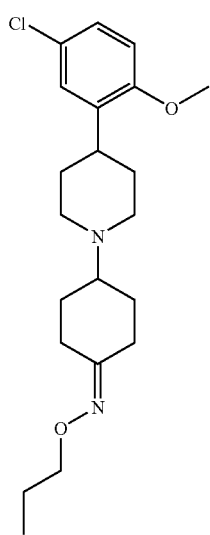
TABLE 1-continued
Exemplary compounds of the present invention.
363
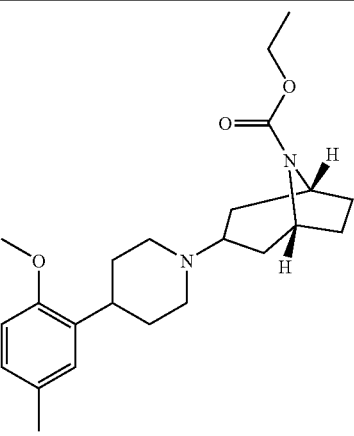
364
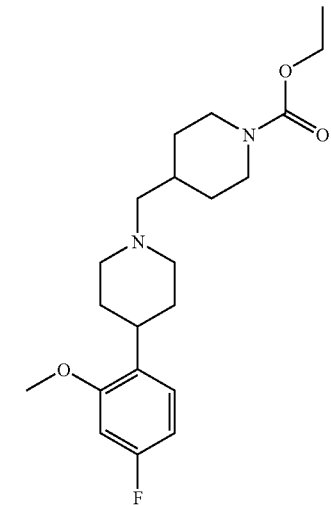
365
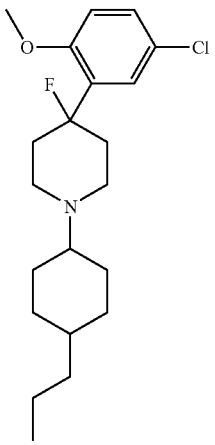

TABLE 1-continued
Exemplary compounds of the present invention.
| | |
|---|---|
| 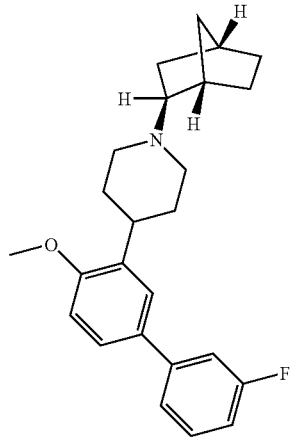 | 366 |
| 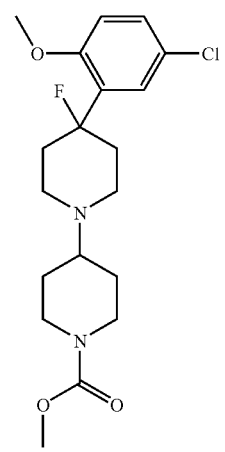 | 367 |
| 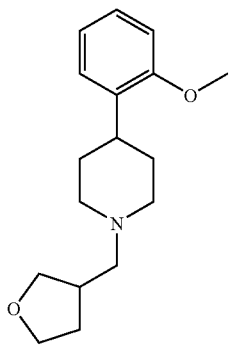 | 368 |
| | 369 |
TABLE 1-continued
Exemplary compounds of the present invention.
| | |
|---|---|
| 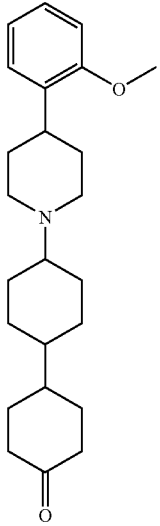 | 370 |
| 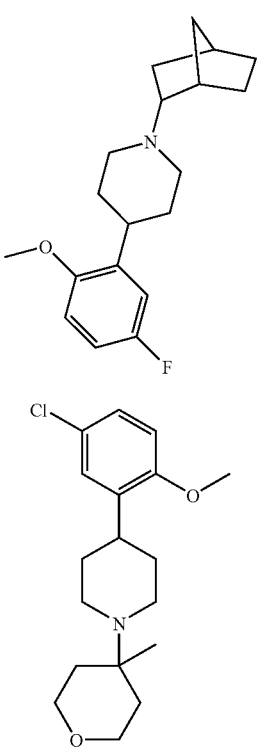 | 371 |
| | 372 |
| 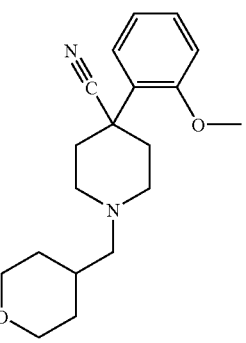 | 373 |

TABLE 1-continued
Exemplary compounds of the present invention.
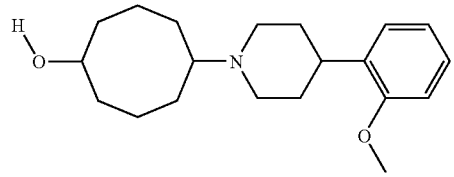
374
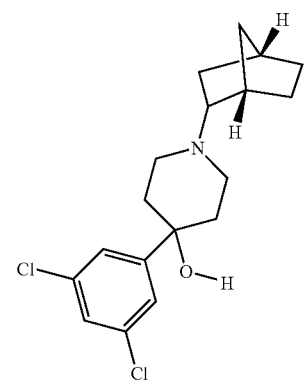
375
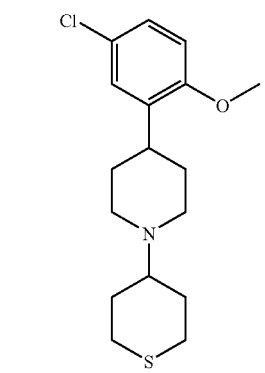
376
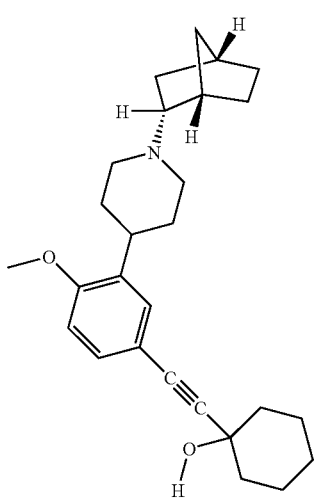
377
TABLE 1-continued
Exemplary compounds of the present invention.
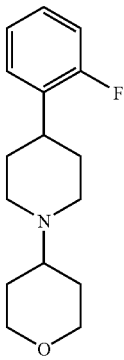
378
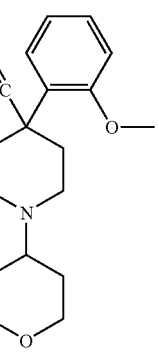
379
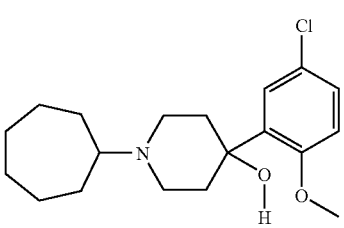
380
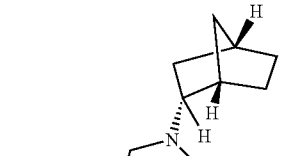
381
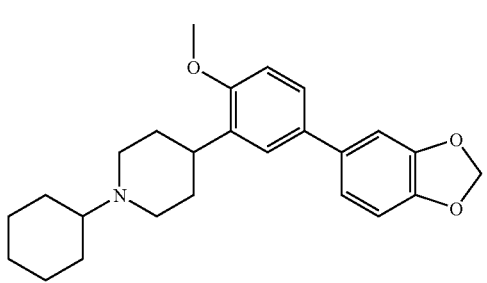
382

TABLE 1-continued
Exemplary compounds of the present invention.
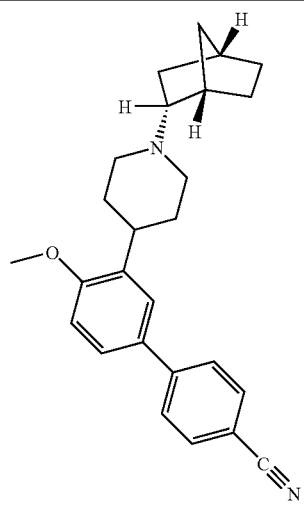
383
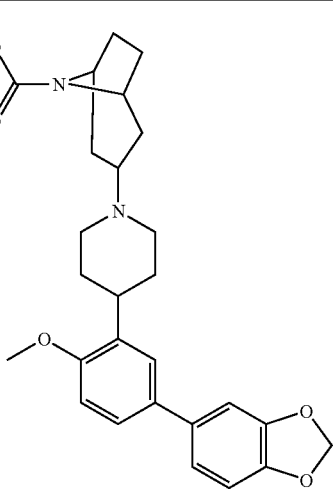
387
384
385
386
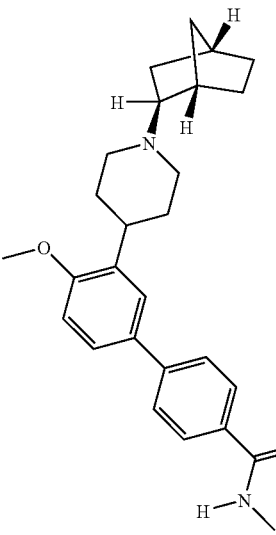
388
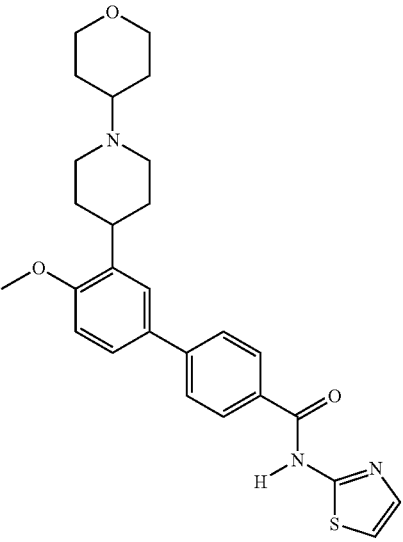
389

TABLE 1-continued
Exemplary compounds of the present invention.
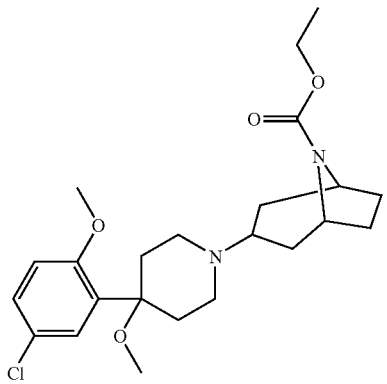
390
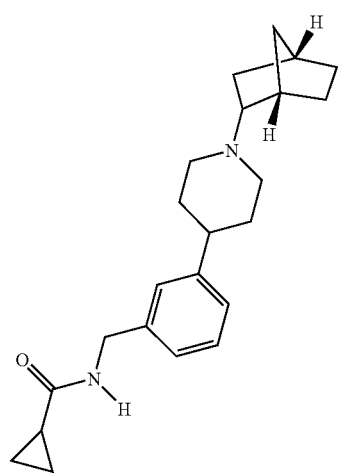
391
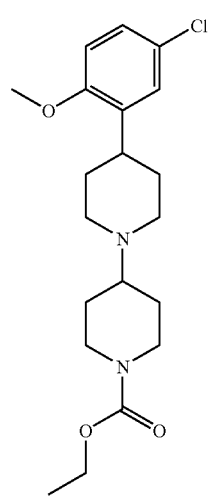
392
TABLE 1-continued
Exemplary compounds of the present invention.
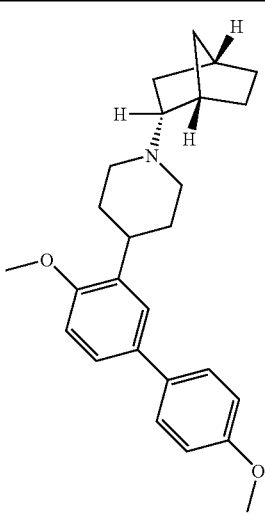
393
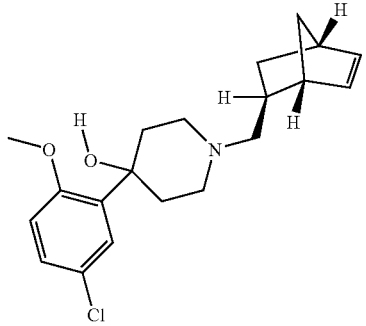
394
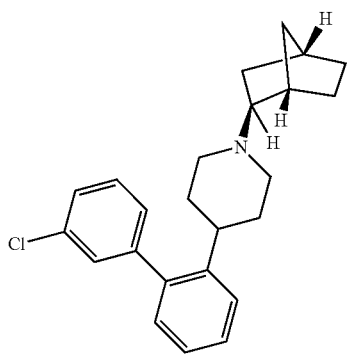
395

TABLE 1-continued
Exemplary compounds of the present invention.
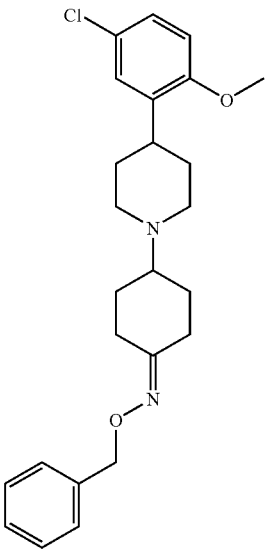
396
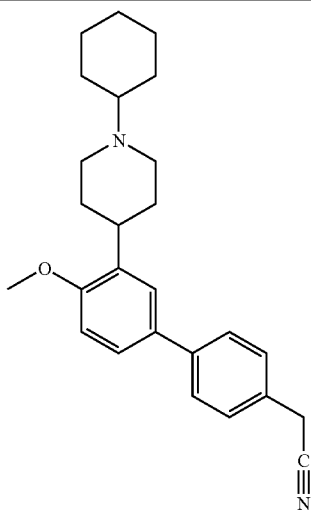
399
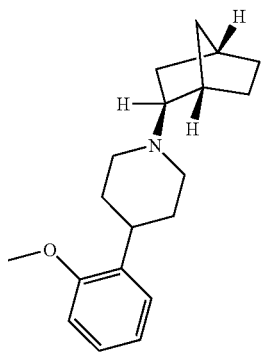
397
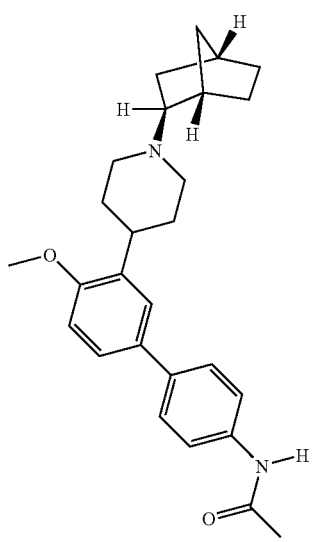
400
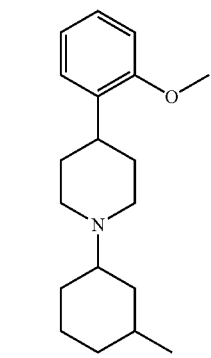
398
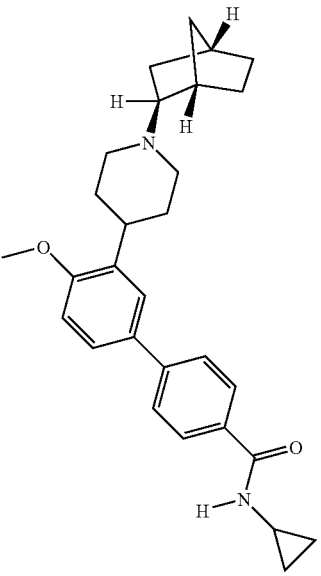
401

TABLE 1-continued
Exemplary compounds of the present invention.
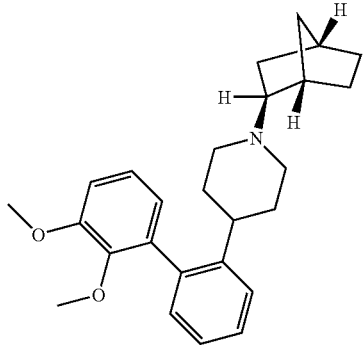
402
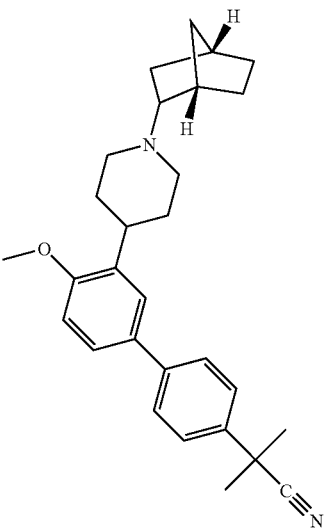
403
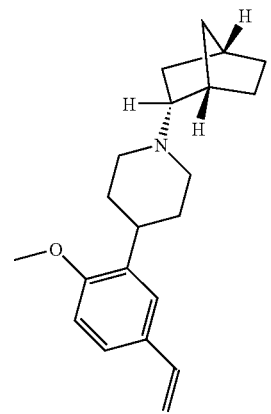
404
TABLE 1-continued
Exemplary compounds of the present invention.
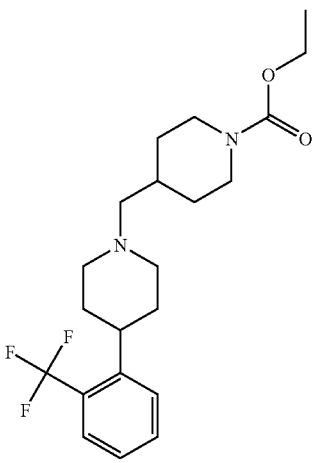
405
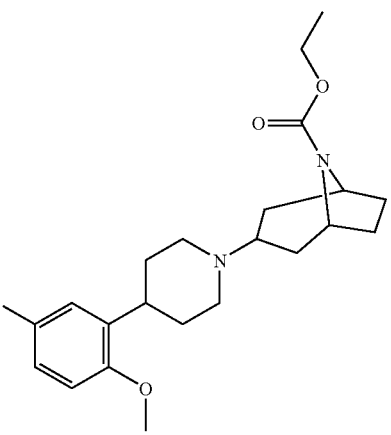
406
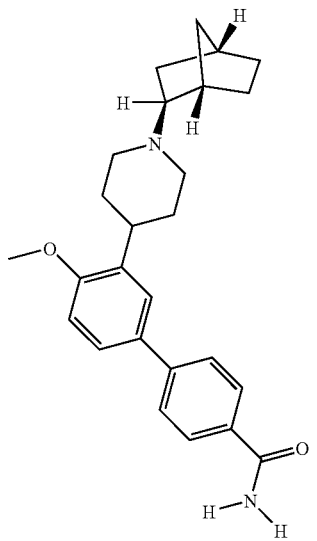
407

TABLE 1-continued
Exemplary compounds of the present invention.
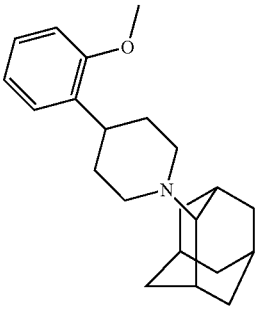 408
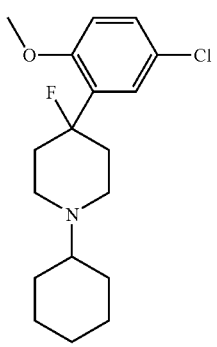 409
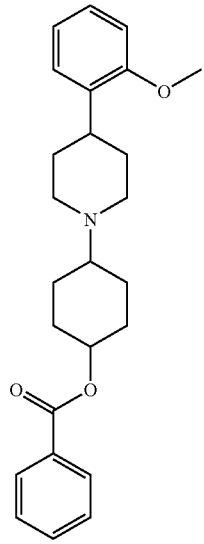 410
TABLE 1-continued
Exemplary compounds of the present invention.
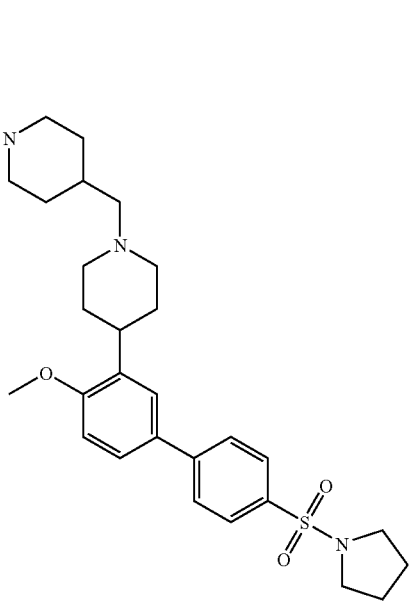 411
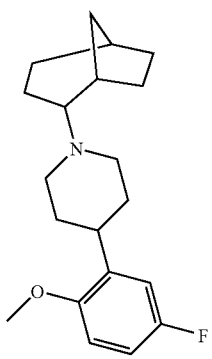 412
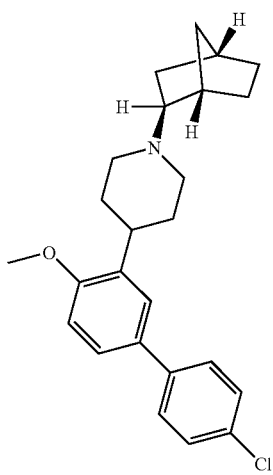 413

TABLE 1-continued
Exemplary compounds of the present invention.
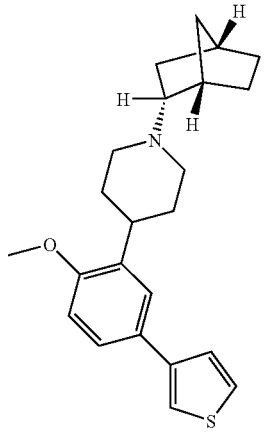
414
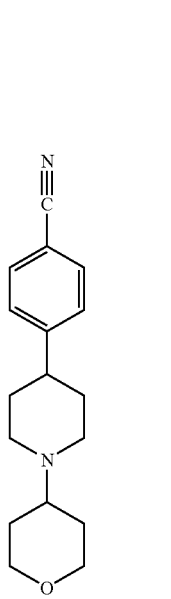
415
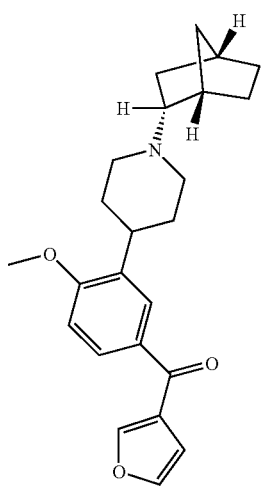
416
TABLE 1-continued
Exemplary compounds of the present invention.
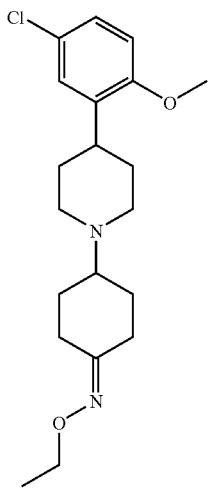
417
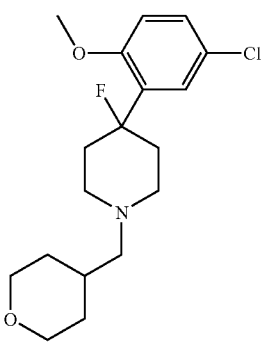
418
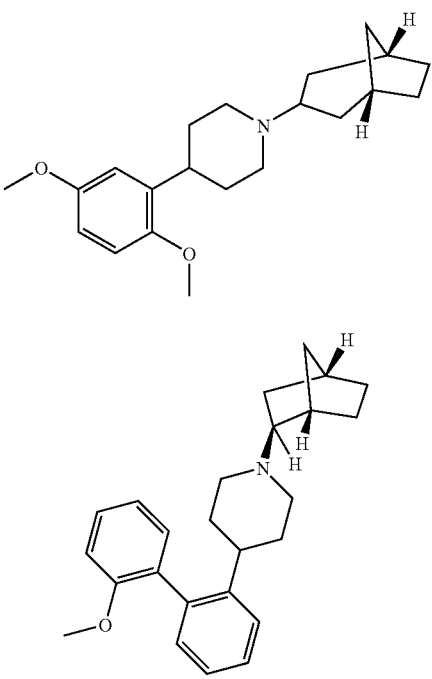
419
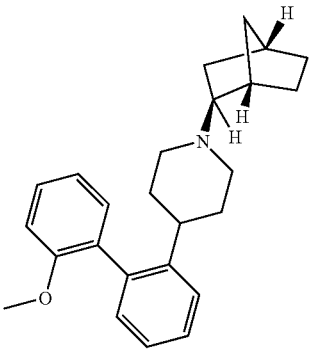
420

TABLE 1-continued

Exemplary compounds of the present invention.

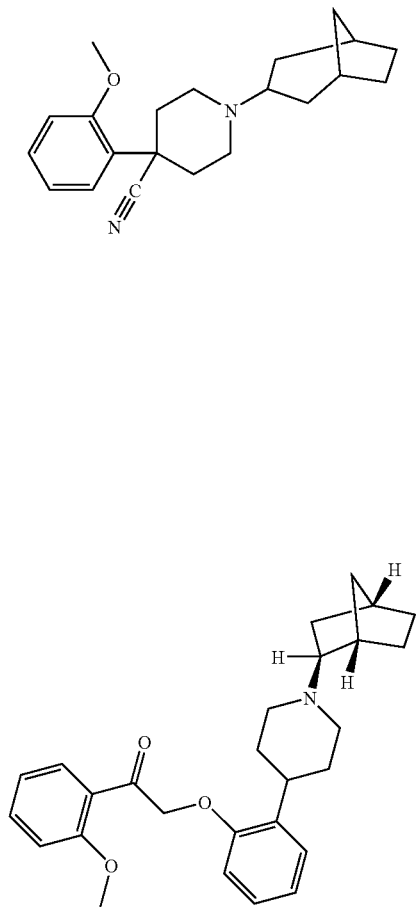

421

422

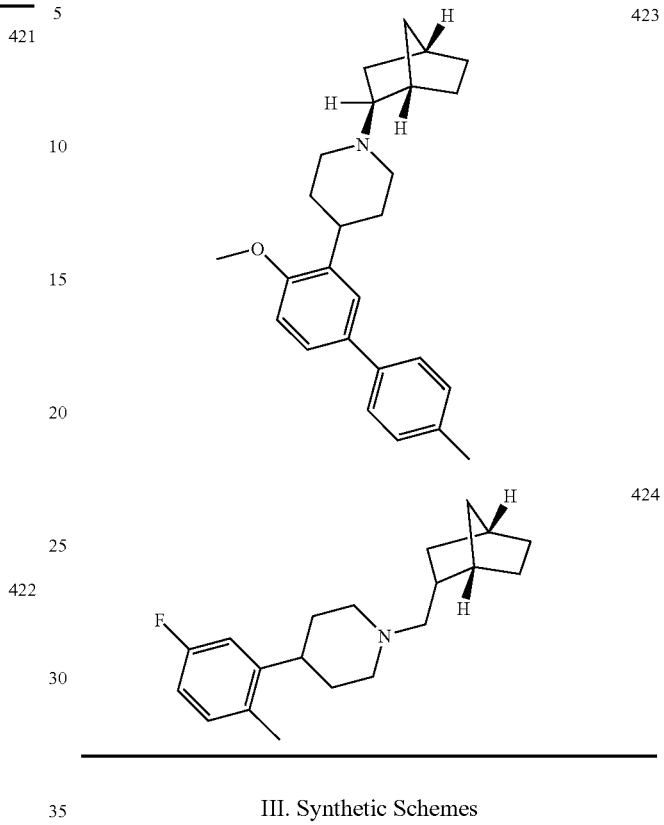

423

424

III. Synthetic Schemes

The compounds of formulae (I, Ia, and Ib) may be readily synthesized from commercially available or known starting materials by known methods. Exemplary synthetic routes to produce compounds of formulae (I, Ia, and Ib) are provided below in Preparations A-D and Schemes A-I below.

Scheme A:

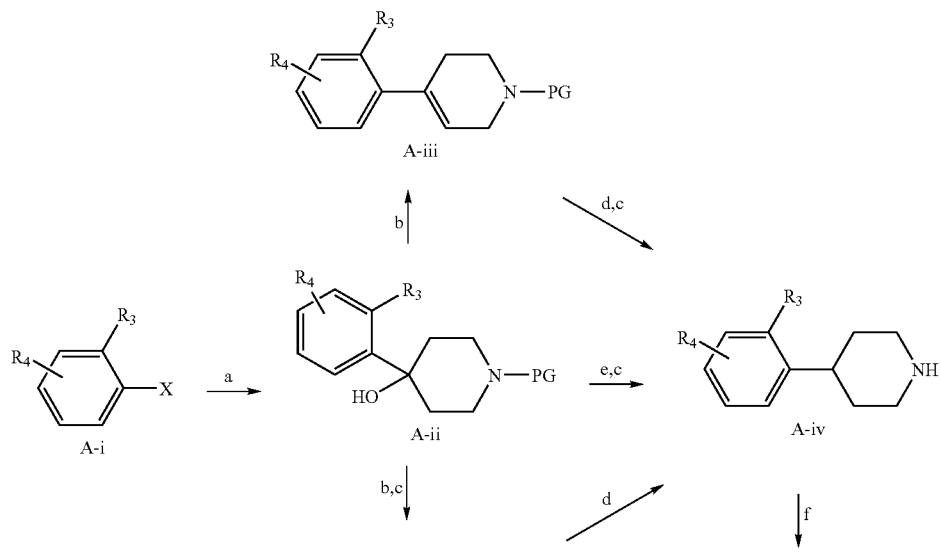

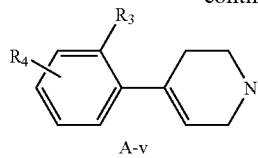

A-v

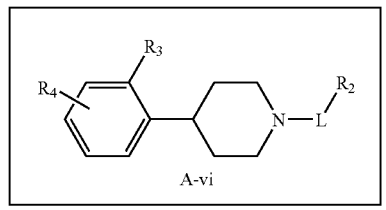

A-vi

PG = Protecting Group

Lithiation of aryl halide A-i followed by treatment with the appropriately protected ketone (e.g. 1-benzylpiperidin-4-one) yields the corresponding protected amine A-ii (step a). Alternatively, compounds of type A-ii may also be generated from the reaction of an aryl Grignard with the appropriately protected ketone. Dehydration to form intermediates of type A-iii and type A-v (step b) may be performed using a variety of known conditions, such as TFA, or TFA/MsOH, $P_2O_5$/refluxing toluene, or refluxing EtOH/conc HCl. Deprotection of the amine (step c) may be concurrent with the alkene reduction (step d, e.g. PG=N-benzyl or N-Cbz) using a variety of conditions, such as Pd/C under $H_2$, or $Rh(PPh_3)_3Cl$ under $H_2$ pressure to yield intermediate A-iv. Alternatively, intermediate A-iv may be obtained by the stepwise amine deprotection (e.g. orthogonal PG=methyl, removed with 1-chloroethyl chloroformate) and alkene reduction. Intermediate A-ii may be converted directly to amine A-iv by treatment with $TFA/Et_3SiH$ followed by the appropriate deprotection. See, for example, Shaomeng Wang, et al, *Bioorganic & Medicinal Chemistry Letters*, 2001, 11, 495, and Geraldine C. B. Harriman, Jianxing Shao and Jay R. Luly, *Tetrahedron Letters*, 2000, 41, 8853.

The dehydration and deprotection may be performed in a single step to generate the alkene of type A-v if an acid-labile amine-protecting group (e.g., Boc) and acidic dehydration conditions are utilized.

The reaction of amine A-iv or A-v with an appropriate aldehyde or ketone under reductive amination conditions (step f), using, for example, $NaBH(OAc)_3$ in DCE/AcOH/TEA at room temperature, may be used to provide the desired compounds of formulae (I, Ia, and Ib). For less reactive ketones, more forceful conditions may be used. For example, the treatment of the amine and the ketone in a neat solution of $Ti(OiPr)_4$, followed by treatment with $NaBH_4$ in MeOH, may be used to provide the desired compounds of formulae (I, Ia, and Ib). See Abdel-Magid, A. F. et al., "Reductive Amination of Aldehydes and Ketones with Sodium Triacetoxyborohydride. Studies on Direct and Indirect Reductive Amination Procedures," *J. Org. Chem.*, 61, pp. 3849-3862 (1996) and the references cited therein.

Alternatively, the amine may be alkylated with an alkyl halide in the presence of an appropriate base in step f to provide the desired compounds of formula A-vi. Typically, the amine is reacted with an alkyl iodide, bromide, or chloride in the presence of an appropriate base. Bases may be organic such as triethylamine, or inorganic such as $Na_2CO_3$ or $Cs_2CO_3$. Typical reaction solvents include but are not limited to DMF, acetone, and acetonitrile.

Additional compounds in which $R_1$ is other than hydrogen can be produced using the methods illustrated in Schemes A and B.

Scheme B:

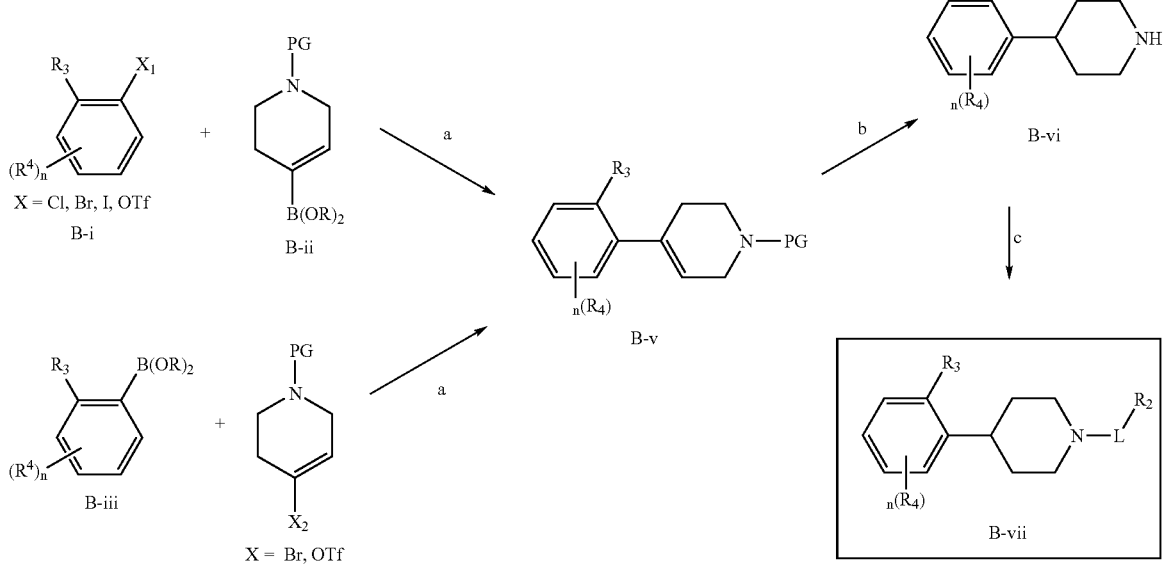

PG = Protecting Group

Treatment of B-i with B-ii using palladium-catalyzed conditions (step a) such as Pd(dppf)Cl$_2$, Na$_2$CO$_3$, in acetonitrile under microwave or conventional heating yields intermediate B-v. Treatment of B-iii with B-iv under similar reaction conditions (step a) also provides intermediate B-v. See references: Eastwood, P. R., *Tetrahedron Letters*, 2000, 41, 3705 and Wustrow, D. J., Wise, L. D., *Synthesis*, 1991, 11, 993. Simultaneous deprotection (e.g. PG=N-benzyl or N-Cbz) of the amine and alkene reduction in compounds of type B-v (step b) may be accomplished using a variety of conditions, such as Pd/C under H$_2$, or Rh(PPh$_3$)$_3$Cl under H$_2$ pressure (e.g. PG=Bn or Cbz). The reaction of amines B-vi provide compounds of type B-vii when subjected to reductive amination or alkylation conditions as described above in Scheme A.

Additional compounds in which R$_1$ is other than hydrogen can be produced using the methods illustrated in Schemes C, D, and E.

Scheme C:

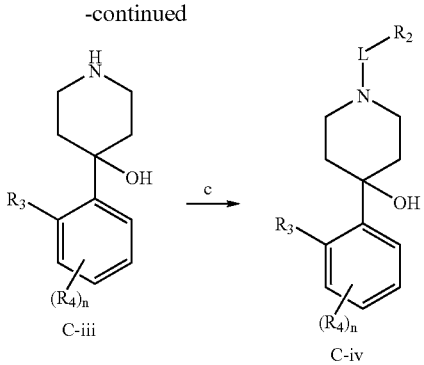

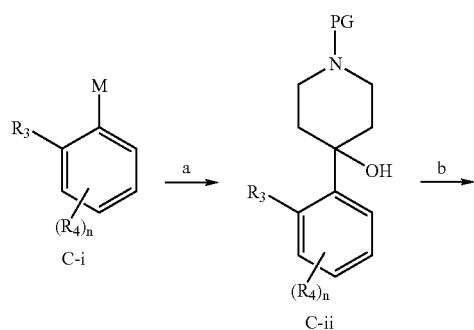

Addition of the aryl organometallic reagent (e.g. aryllithium or Grignard) C-i to the appropriately protected ketone (e.g. 1-benzylpiperidin-4-one) provides the adduct C-ii (step a). Deprotection (step b) using known methods provides the piperidine intermediate amine C-iii, which can be converted to the final compound C-iv through reductive amination or alkylation as described above in Scheme A.

Scheme D:

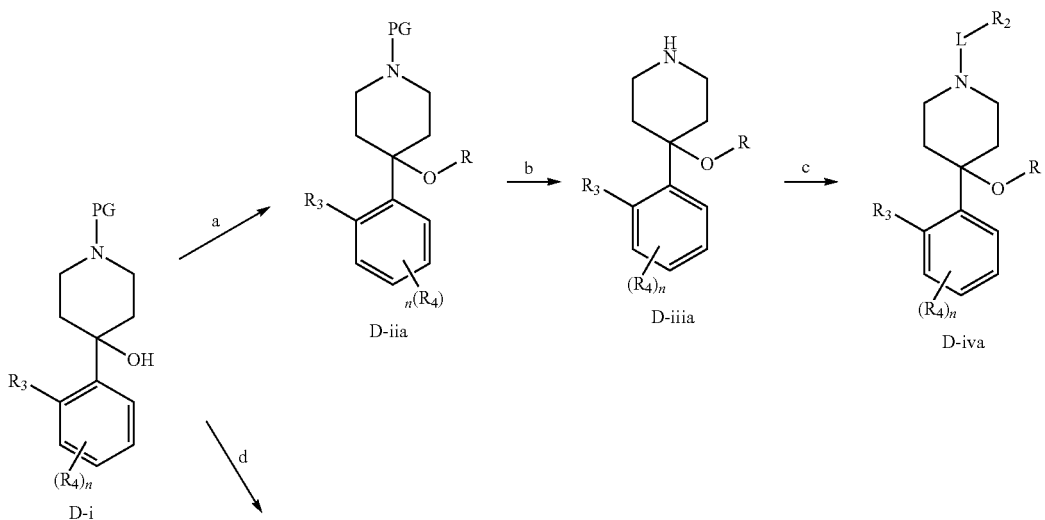

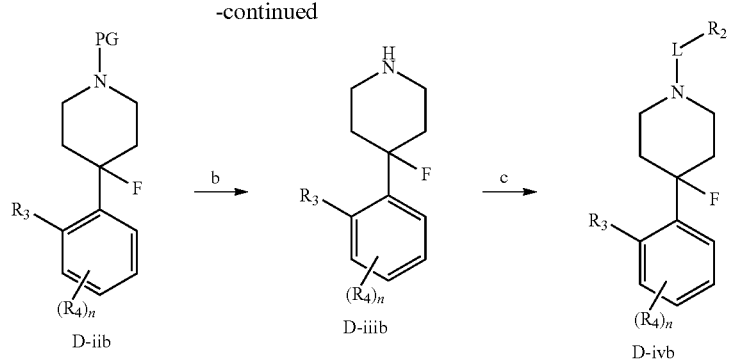

As shown in Scheme D, alkylation of the protected 4-hydroxypiperidine D-i (step a) using a strong base and alkylating agent (e.g. NaH, R—X), followed by deprotection of the amine, provides 4-alkoxy intermediate D-iiia. Reaction of D-i with a fluorinating agent (e.g., DAST), followed by deprotection of the amine, yields the 4-fluoropiperidine intermediate D-iiib. Both intermediate D-iiia and D-iiib may be converted to the final product D-iva/b by way of reductive amination or alkylation as described above in Scheme A.

Scheme E:

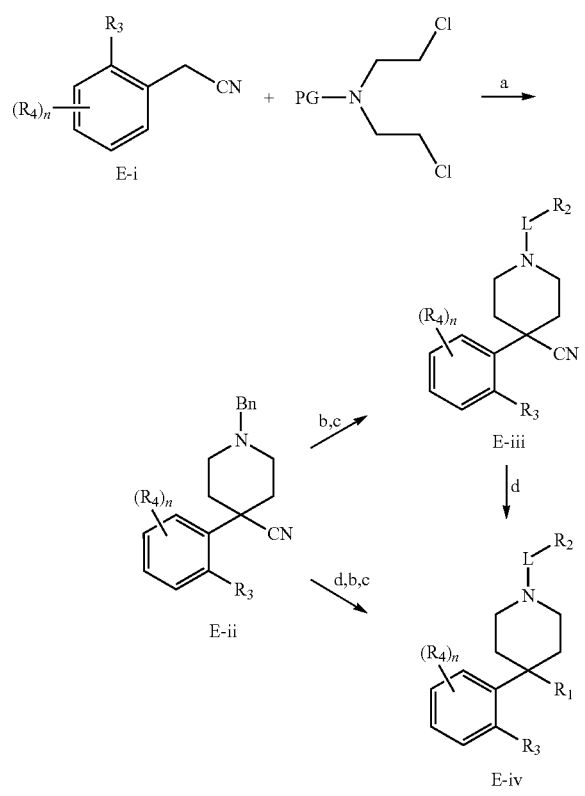

Conditions: (a) NaHMDS/THF reflux; (b) e.g. PG=Bn: Pd(OH)$_2$; (c) NaBH(OAc)$_3$, DCE, AcOH, TEA, appropriate ketone or aldehyde; or 1) neat Ti(OiPr)$_4$, appropriate ketone, 2) NaBH$_4$, MeOH; or the appropriate alkyl halide, Cs$_2$CO$_3$, acetonitrile, heat; The nitrile in E-ii may either be retained to yield compounds of type E-iii or utilized for reactions characteristic of the functional group (step d) to produce compounds of type E-iv.

Scheme F:

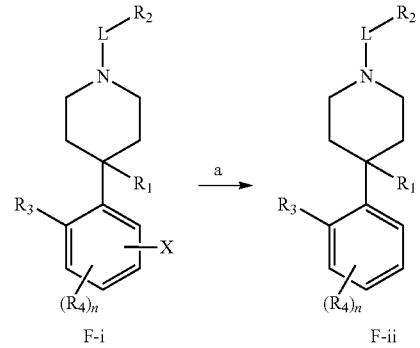

Reaction of F-i (e.g. X=Cl, Br, I, or trilflate) with an appropriate boronic acid or ester under palladium-catalyzed cross coupling conditions (step a) Pd(dppf)Cl$_2$ or (Ph$_3$P)$_4$Pd, 2 M K$_2$CO$_3$, in acetonitrile under microwave irradiation at 150° C. for 10-20 minutes yields compound F-ii. Alternative, reaction of intermediate F-i (e.g. X=boronic acid or ester) with an appropriate aryl or alkyl halide (step a) yields compound F-ii. Intermediate F-i may also be treated with an appropriately substituted terminal acetylene under Sonogashira Pd-coupling conditions (Pd(dppf)Cl$_2$, CuI, CH$_3$CN, TEA, microwave or conventional heating) to yield compounds of type F-ii.

Scheme G:

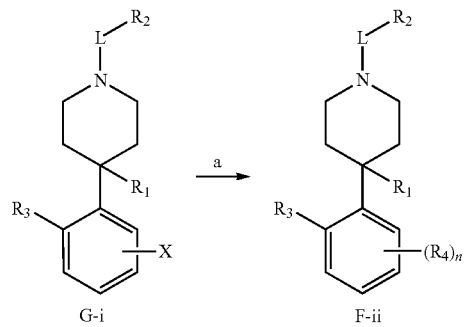

Alkylation: treatment of intermediate G-i (X=OH, SH, NH2, NH-alkyl) with an electrophile (e.g. $R_4$—X, or $R_4$—C(O)Cl) under basic conditions (e.g. $K_2CO_3$, $Cs_2CO_3$, or TEA) in DMF at ambient or elevated temperature yields compounds of type G-ii.

Scheme H:

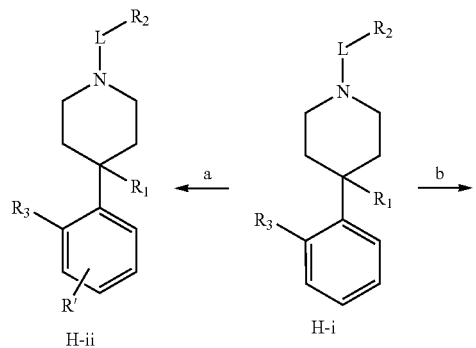

Freidel Crafts: Treatment of intermediate i with a strong Lewis acid (e.g. $AlCl_3$) and an appropriate alcohol (e.g. tert-butanol) at room temperature in nitrobenzene (step a) yields compounds of type ii. Treatment of intermediate i with a strong Lewis acid (e.g. $AlCl_3$) and an appropriate acid chloride at room temperature in toluene (step b) yields compounds of type iii.

Scheme I outlines the general preparation of the appropriate aldehydes from the corresponding ketone.

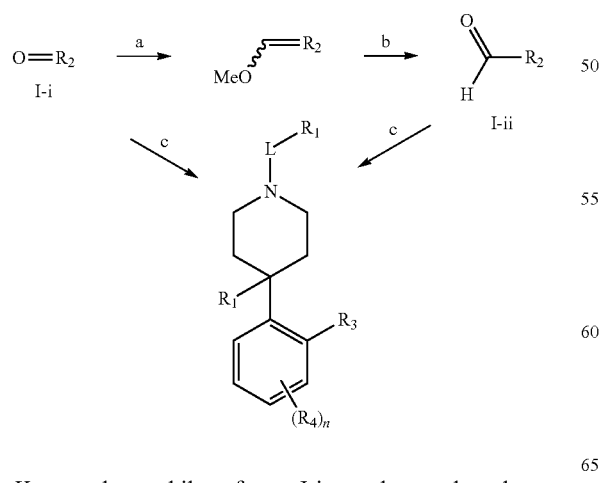

Ketone electrophiles of type I-i may be purchased commercially, produced by methods disclosed above, or by other known methods. Aldehydes of type I-ii may be purchased commercially or produced from compounds of type I-i using the following conditions: (a) $Ph_3P^+CH_2OMeCl^-$, NaN$(SiMe_3)_2$; (b) aqueous HCl, $CH_3CN$. The following conditions may be used for the synthesis of compounds of formulae (I, Ia, and Ib) using ketones of type I-i and aldehydes of type I-ii: (c) Amine of type A-vi (see Scheme A), $NaBH(OAc)_3$, DCE, AcOH, TEA, appropriate ketone or aldehyde; or i. neat $Ti(OiPr)_4$, appropriate ketone; ii. $NaBH_4$, MeOH.

Those skilled in the art will recognize that alternative methods to reductive amination of the piperidine intermediates to give the compounds of the invention are well known. For example, amidation of the piperidine followed by reduction with an appropriate reagent such as diborane or alkylation of the piperidine nitrogen with an alkyl halide or sulfonate ester provides the desired compounds.

Additionally, compounds of formulae (I, Ia, and Ib) in which the piperidine ring is replaced by:

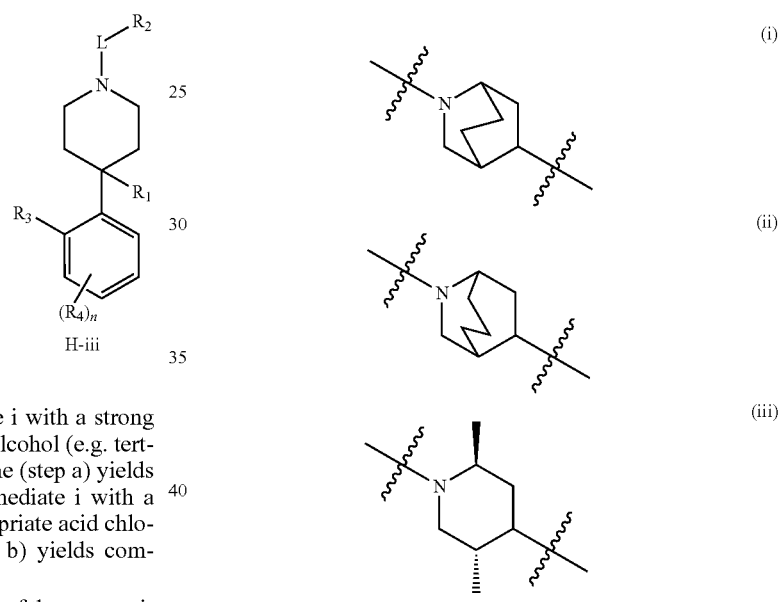

(vii)
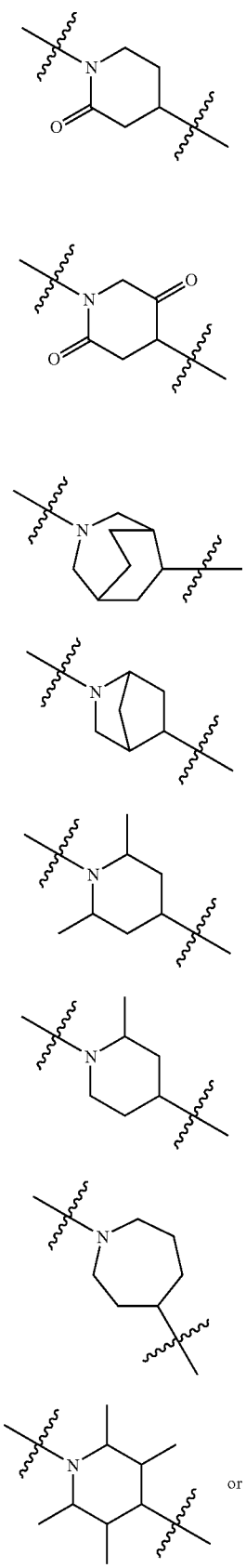
(viii)

(ix)

(x)

(xi)

(xii)

(xiii)

(xiv) or

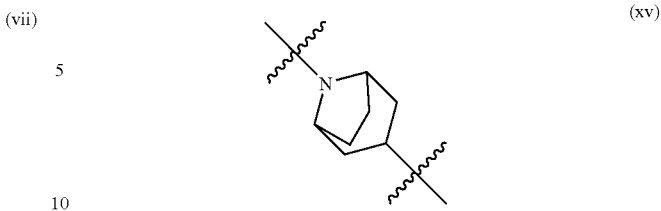
(xv)

may be produced using the methods described herein or other known methodologies.

IV. Formulations, Administrations, and Uses

A. Pharmaceutically Acceptable Compositions

The present invention includes within its scope pharmaceutically acceptable prodrugs of the compounds of the present invention. A "pharmaceutically acceptable prodrug" means any pharmaceutically acceptable salt, ester, salt of an ester, or other derivative of a compound of the present invention which, upon administration to a recipient, is capable of providing (directly or indirectly) a compound of this invention or an active metabolite or residue thereof. Preferred prodrugs are those that increase the bioavailability of the compounds of this invention when such compounds are administered to a mammal or which enhance delivery of the parent compound to a biological compartment relative to the parent species.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., calcium or magnesium), ammonium and $N^+(C_{1-4}\text{ alkyl})_4$ salts or salts of lysine and arginine. This invention also envisions the quaternization of any basic nitrogen-containing groups of the compounds disclosed herein. Water or oil-soluble or dispersible products may be obtained by such quaternization. Other salts can be found in "Practical Process, Research, & Development," Anderson, Neal G., Academic Press, 2000, the contents of which are incorporated herein by reference.

The compositions of the present invention may be administered orally, parenterally, by inhalation spray, topically, rectally, intermuscularly, subcutaneously, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, the pharmaceutically acceptable compositions of this invention are formulated for oral administration.

The amount of the compounds of the present invention that may be combined with the carrier materials to produce a composition in a single dosage form will vary depending upon the host treated, the particular mode of administration. Preferably, the compositions should be formulated so that a dosage of between 0.01-100 mg/kg body weight/day of the modulator can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Depending upon the particular condition, or disease, to be treated or prevented, additional therapeutic agents, which are normally administered to treat or prevent that condition, may also be present in the compositions of this invention. As used herein, additional therapeutic agents that are normally administered to treat or prevent a particular disease, or condition, are known as "appropriate for the disease, or condition, being treated."

According to a preferred embodiment, the compounds of formulae (I, Ia, and Ib) are selective modulators of $M_1$, $M_2$ and $M_4$. More preferably, the compounds of formulae (I, Ia, and Ib) are selective modulators of $M_1$ and $M_4$. Or, the compounds of formula (I, Ia, and Ib) are selective modulators of $M_2$ and $M_4$. Yet more preferably, the compounds of formula (I, Ia, and Ib) are selective modulators of one of $M_1$, $M_2$, and $M_4$. The compounds of formula (I, Ia, and Ib) are selective modulators of $M_4$. The compounds of formula (I, Ia, and Ib) are selective modulators of $M_1$.

Applicants believe that the ability of the compounds of the present invention to modulate the activity of muscarinic receptors is derived from the affinity of these compounds to the muscarinic receptors. Such affinity, applicants believe, activates a muscarinic receptor (i.e, an agonist) or inhibits the activity of a muscarinic receptor.

According to another embodiment, the compounds of formulae (I, Ia, and Ib) are selective activators of all of $M_1$, $M_2$, and $M_4$. In other embodiments, the compounds of formulae (I, Ia, and Ib) are selective activators of one of $M_1$, $M_2$, and $M_4$ and selective inhibitors of the other two of $M_1$, $M_2$, and $M_4$. In another embodiment, the compounds of formulae (I, Ia, and Ib) are selective activators of up to two of $M_1$, $M_2$, and $M_4$ and selective inhibitors of the other of $M_1$, $M_2$, and $M_4$. In still another embodiment, the compounds of formulae (I, Ia, and Ib) are selective inhibitors of all of $M_1$, $M_2$, and $M_4$.

According to another embodiment, the compounds of compounds of formulae (I, Ia, and Ib) are selective inhibitors of one or more of $M_1$, $M_2$, or $M_4$. In one embodiment, preferably, the compounds of formulae (I, Ia, and Ib) are selective inhibitors of $M_4$. In another embodiment, the compounds of formulae (I, Ia, and Ib) are selective inhibitors of $M_1$. In yet another embodiment, the compounds of formulae (I, Ia, and Ib) are selective inhibitors of $M_1$ and $M_4$. In still another embodiment, the compounds of formulae (I, Ia, and Ib) are selective inhibitors of $M_1$ and $M_2$ or $M_4$ and $M_2$.

The term "selective" as used herein means a measurably greater ability to modulate one muscarinic receptor subtype when compared to the other muscarinic receptor subtypes. E.g., the term "selective $M_4$ agonist" means a compound that has a measurably greater ability to act as an $M_4$ agonist when compared to that compound's agonist activity with the other muscarinic receptor subtype(s).

According to an alternative embodiment, the present invention provides a method of treating a muscarinic receptor mediated disease in a mammal, comprising the step of administering to said mammal a composition comprising a compound of formulae (I, Ia, and Ib), or a preferred embodiment thereof as set forth above.

According to a preferred embodiment, the present invention provides a method of treating a disease mediated by one or more of $M_1$, $M_2$, or $M_4$, comprising the step of administering to said mammal a composition comprising a compound of formulae (I, Ia, and Ib), or a preferred embodiment thereof as set forth above. Or in another embodiment the disease is mediated by $M_2$. Or, said disease is mediated by $M_1$. Yet more preferably, said disease is mediated by $M_4$. In still further embodiments, the disease is mediate by all of $M_1$, $M_2$, and $M_4$. In another embodiment, the disease is mediate by two of $M_1$, $M_2$, and $M_4$.

According to a preferred embodiment, the present invention provides a method of treating or reducing the severity of a disease in a patient, wherein said disease is selected from CNS derived pathologies including cognitive disorders, Attention Deficit Hyperactivity Disorder (ADHD), obesity, Alzheimer's disease, various dementias such as vascular dementia, psychosis associated with CNS disorders including schizophrenia, mania, bipolar disorders, pain conditions including acute and chronic syndromes, Huntington's Chorea, Friederich's ataxia, Gilles de la Tourette's Syndrome, Downs Syndrome, Pick disease, clinical depression, Parkinson's disease, peripheral disorders such as reduction of intra ocular pressure in Glaucoma and treatment of dry eyes and dry mouth including Sjögren's Syndrome, and wound healing, wherein said method comprises the step of contacting said patient with a compound according to the present invention.

In one embodiment, the present invention provides a method for the treatment or lessening the severity of acute, chronic, neuropathic, or inflammatory pain, arthritis, migrane, cluster headaches, trigeminal neuralgia, herpetic neuralgia, general neuralgias, epilepsy or epilepsy conditions, neurodegenerative disorders, psychiatric disorders such as anxiety and depression, myotonia, arrythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, or cancer pain is provided comprising administering an effective amount of a compound, or a pharmaceutically acceptable composition comprising a compound to a subject in need thereof. In certain embodiments, a method for the treatment or lessening the severity of acute, chronic, neuropathic, or inflammatory pain is provided comprising administering an effective amount of a compound or a pharmaceutically acceptable composition to a subject in need thereof. In certain other embodiments, a method for the treatment or lessening the severity of radicular pain, sciatica, back pain, head pain, or neck pain is provided comprising administering an effective amount of a compound or a pharmaceutically acceptable composition to a subject in need thereof. In still other embodiments, a method for the treatment or lessening the severity of severe or intractable pain, acute pain, post-surgical pain, back pain, or cancer pain is provided comprising administering an effective amount of a compound or a pharmaceutically acceptable composition to a subject in need thereof.

According to an alternative embodiment, the present invention provides a method of treating or reducing the severity of a disease in a patient, wherein said disease is selected from pain, psychosis (including schizophrenia, hallucinations, and delusions), Alzheimer's disease, Parkinson's disease, glaucoma, bradhycardia, gastric acid secretion, asthma, GI disturbances or wound healing.

According to a preferred embodiment, the present invention is useful for treating or reducing the severity of psychosis, Alzheimer's disease, pain, or Parkinson's disease.

In order that the invention described herein may be more fully understood, the following examples are set forth. It should be understood that these examples are for illustrative purposes only and are not to be construed as limiting this invention in any manner.

All references cited above are incorporated herein by reference. Other embodiments of the compounds of formulae (I, Ia, and Ib) are shown below. The following examples are illustrative of the compounds of formulae (I, Ia, and Ib) and are not meant to be limiting.

IV. Preparations And Examples

Preparation A: Synthesis of N-(ethoxycarbonyl)-8-aza-bicyclo[3.2.1]octane-3-carbaldehyde

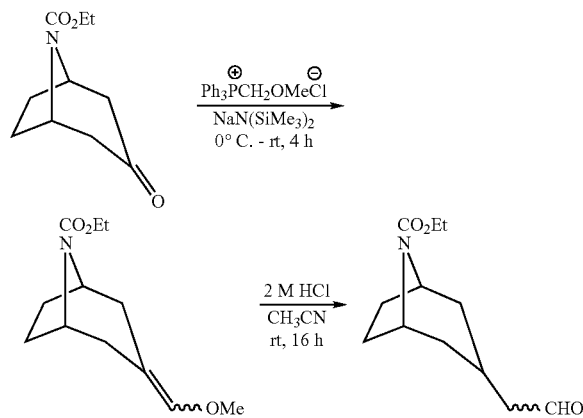

Sodium bis(trimethylsilyl)amide (6 mmol, 6 mL of 1 M solution in THF) was added to a suspension of 2.06 g (6.0 mmol) of methoxymethyltriphenylphosphonium chloride in 6 mL of THF at 0° C. under argon. After stirring at 0° C. for 15 min, the resulting dark red solution was added via syringe to a solution of 0.79 g (4.0 mmol) of N-(ethoxycarbonyl) tropinone (6) in 8 mL of THF at 0° C. and then stirred at room temperature for 4 h (an orange color persisted). The reaction mixture was quenched by adding sat. aq. NaCl (15 mL) and then extracted with ether (25 mL×3). The combined organic extracts were dried over $Na_2SO_4$. The solid residue obtained after solvent evaporation was loaded onto a short silica gel column (3.5 cm×4 cm) to remove the phosphorous impurities. The product was eluted with ether. After the solvent was evaporated, the product enol ether was obtained as a brown oil which was used in the next step without further purification.

The enol ether intermediate was dissolved in a solution of 12 mL of 2 N HCl and 20 mL of acetonitrile, and stirred at room temperature for 16 h. After removing the acetonitrile on a rotary evaporator, the aqueous solution was extracted with ether (25 mL×3). The combined organic extracts were washed with sat. aq. $NaHCO_3$ (15 mL×2), sat. aq. NaCl (15 mL) and then dried over $Na_2SO_4$. After the solution was evaporated to dryness, the residue was purified by chromatography ($SiO_2$, 10%-20% EtOAc in Hexane as eluent). N-(ethoxycarbonyl)-8-aza-bicyclo[3.2.1]octane-3-carbaldehyde (0.65 g) was obtained as a colorless oil in an approximately 1:1 ratio of endo and exo isomers (77%). ESI-MS m/z 212.1 (MH+); $^1$H NMR (300 MHz, $CDCl_3$) δ 9.53 (s, 1H), 4.54 (br s, 1H), 4.38 (br s, 1H), 4.16 (m, 2H), 2.72 (m, 2H), 2.38 (s, 1H), 2.32 (s, 1H), 2.10 (m, 3H), 1.69 (m, 2H), 1.29 (m, 3H).

Preparation B: Synthesis of bicyclo[3.2.1]octane-2-carbaldehyde

Bicyclo[3.2.1]octane-2-carbaldehyde was prepared using an analogous procedure as for Intermediate 1 from commercially available bicyclo[3.2.1]octan-2-one. The crude products were used in the next step without further purification.

Preparation C: Synthesis of 7-oxa-bicyclo[2.2.1]hept-5-ene-2-carbaldehyde

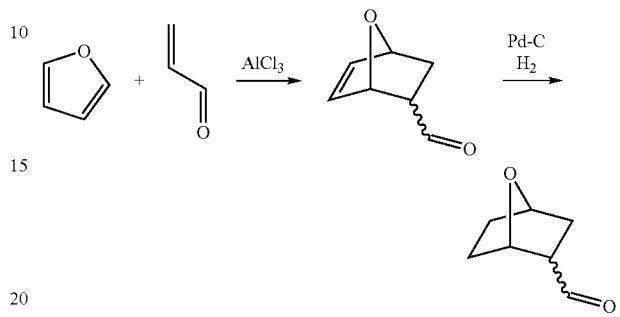

To a stirred solution of furan (9) (15 mL, 200 mmol) and acrolein (13) (6.7 mL, 100 mmol) in DCM (25 mL) was slowly added $AlCl_3$ (666 mg, 5 mmol) under argon at −43° C. (dry ice/isopropanol bath). The reaction mixture was stirred at −43° C. under argon for 30 min, and then quenched with sat. aq. $K_2CO_3$ (50 mL). After the reaction mixture was gradually warmed to room temperature, it was extracted with ether (200 mL×5). The combined ether extracts were washed with sat. aq. $K_2CO_3$ (200 mL×2) and sat. aq. NaCl (200 mL×2), dried over $MgSO_4$, filtered, and concentrated to give 2.6 g of oily crude product 7-oxa-bicyclo[2.2.1]hept-5-ene-2-carbaldehyde which was used in the next step without further purification. See references Laszlo, P.; Lucchetti, J. *Tetrahedron Lett*. 1984, 25, 4387-4388. Moore, J. A., Partain, E. M. III. *J. Org. Chem*. 1983, 48, 1105-1106. Dauben, W. G.; Krabbenhoft, H. O. *J. Am. Chem. Soc*. 1976, 98, 1992-1993. Nelson, W. L.; Allen, D. R.; Vincenzi, F. F. *J. Med. Chem*. 1971, 14, 698-702.

To a stirred solution of crude product 7-oxa-bicyclo[2.2.1]hept-5-ene-2-carbaldehyde (2.6 g. 20 mmol) in 95% EtOH (200 mL) was added 10% Pd—C (0.25 g) at room temperature under argon. The mixture was shaken on a Parr hydrogenation apparatus for 4 h at room temperature under 30 psi of hydrogen. After the Pd catalyst was removed by filtration through a Celite pad, the Celite was washed with MeOH (15 mL×2), the combined extracts were concentrated under vacuum to yield crude 7-oxa-bicyclo[2.2.1]hept-5-ene-2-carbaldehyde as a pale yellow oil, which was used in the next step without further purification.

Preparation D: Synthesis of ethyl 4-formylpiperidine-1-carboxylate

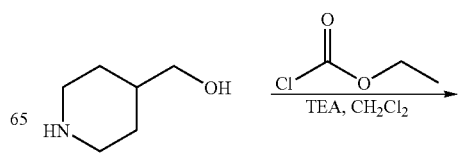

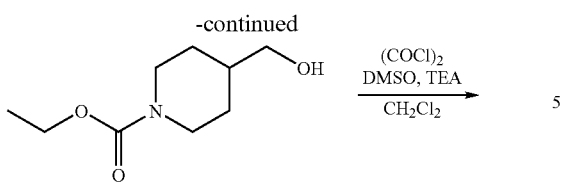

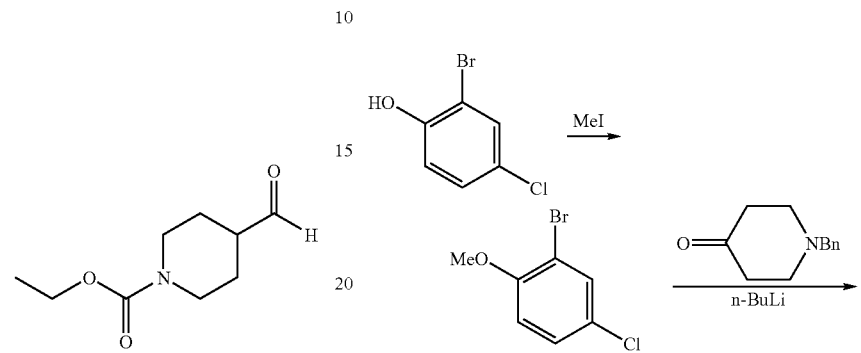

1.0 eq 4-piperidinemethanol (10.00 g, 86.8 mmol) was dissolved in dichloromethane (350 mL), cooled in an ice-H$_2$O bath and treated dropwise with a solution of 1.05 eq ethyl chloroformate (9.89 g, 91.1 mmol) in dichloromethane (50 mL), followed by the dropwise addition of a solution of 1.0 eq triethylamine (8.78 g) in dichloromethane (50 mL). The reaction was stirred at ≈0° C. for 15 minutes, then at room temperature for 10 minutes. The reaction was diluted with dichloromethane (250 mL) and washed successively with (150 mL each) H$_2$O, 0.1 NHCl (aq) (×2), saturated brine, then dried (Na$_2$SO$_4$) and filtered. The filtrate was concentrated in vacuo to afford 15.60 g ethyl 4-(hydroxymethyl)-piperidine-1-carboxylate as a viscous, pale bluish-green oil. $^1$H-NMR (400 MHz, CDCl$_3$) δ 4.15 (br m, 2H), 4.09 (q, J=7.1 Hz, 2H), 3.46 (d, J=6.4 Hz, 2H), 2.72 (br t, J=12.4 Hz, 2H), 2.07 (s, 1H), 1.70 (m, 2H), 1.63 (m, 1H), 1.23 (t, J=7.2 Hz, 3H), 1.12 (m, 2H); t$_R$=1.56 min [10-99% CH$_3$CN gradient over 5 mins with 0.1% TFA (aq)]; Theoretical (M+H)$^+$ m/z for C$_9$H$_{17}$NO$_3$=188.1; Found 188.0.

A solution of 1.2 eq oxalyl chloride (12.69 g, 0.10 mol) in dichloromethane (150 mL) was cooled to approximately −78° C. and treated dropwise, under nitrogen, with a solution of 2.4 eq anhydrous dimethylsulfoxide (15.63 g, 0.20 mol) in dichloromethane (50 mL). 15 minutes after the addition was complete, a solution of 1.0 eq ethyl 4-(hydroxymethyl)-piperidine-1-carboxylate (15.60 g, 83.3 mmol) in dichloromethane (50 mL) was added dropwise. 30 minutes after the addition was complete, a solution of 3.0 eq triethylamine (25.30 g, 0.25 mol) in dichloromethane (50 mL) was added dropwise and the reaction warmed to room temperature. The reaction was stirred at room temperature for 1 hour, then quenched with saturated sodium bicarbonate (500 mL). The layers were separated and the aqueous layer extracted once with dichloromethane (200 mL). The pooled organic layers were washed with H$_2$O (3×100 mL), saturated sodium bicarbonate (1×100 mL) and saturated brine, then dried (Na$_2$SO$_4$) and filtered. The filtrate was concentrated in vacuo to afford 13.84 g ethyl 4-formylpiperidine-1-carboxylate as a viscous amber oil. $^1$H-NMR (400 MHz, CDCl$_3$) δ 9.64 (s, 1H), 4.10 (q, J=7.2 Hz, 2H), 4.00 (br m, 2H), 2.97 (m, 2H), 2.40 (m, 1H), 1.87 (br m, 2H), 1.54 (m, 2H), 1.23 (t, J=7.0 Hz, 3H).

Example 1

4-(5-chloro-2-methoxyphenyl)piperidine
(Compound No. 209)

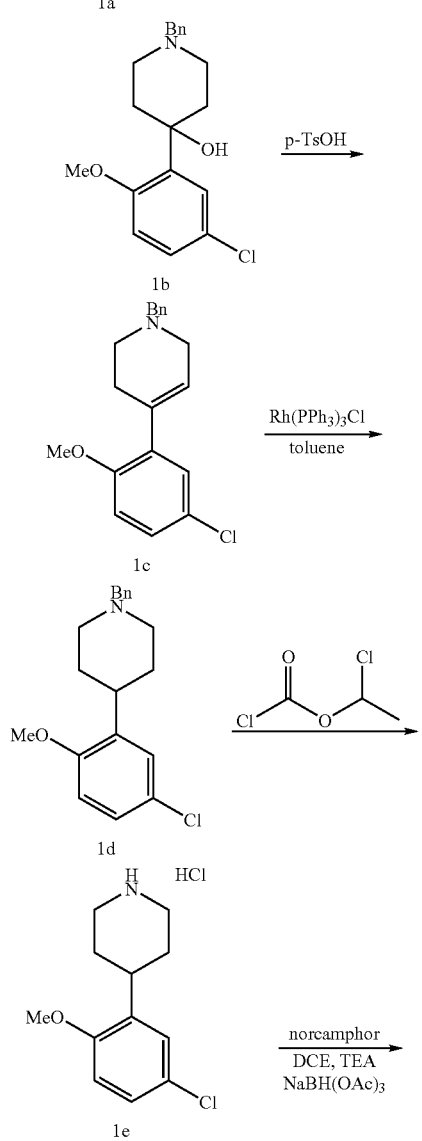

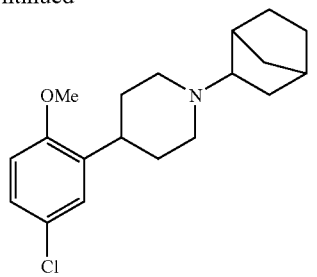

Compound No. 209

A mixture of K$_2$CO$_3$ (68 g, 0.5 mol), 2-bromo-4-chlorophenol (50 g, 0.24 mol) and MeI (42.6 g, 0.3 mol) in acetone (1000 mL) was heated to reflux for 5 hr and then cooled to room temperature. The solid was filtered off and washed with dichloromethane (100 mL×3). The combined filtrate was concentrated to dryness. The residue was diluted with diethyl ether (500 mL) and washed with HCl (1 M, 100 mL×2), H$_2$O (100 mL×2) and brine (200 mL). The separated organic layer was dried over Na$_2$SO$_4$ and concentrated to give 2-bromo-4-chloroanisole 1a as a light yellow liquid. $^1$H NMR (CDCl$_3$): δ 7.52 (d, J=2.8 Hz, 1H), 7.24 (q, J$_1$=8.8 Hz, J$_2$=2.8 Hz, 1H), 6.81 (d, J=8.8 Hz, 1H), 3.86 (s, 3H).

To a solution of 2-bromo-4-chloroanisole (1a, 51 g, 0.23 mol) in THF (500 mL) was added dropwise n-BuLi (2.5 M in hexane, 138 mL, 0.345 mol) at −78° C. under nitrogen atmosphere. After being stirred at −78° C. for 1 h, 1-benzyl-piperidin-4-one (42 g, 0.22 mol) was added dropwise. After addition, the mixture was stirred at this temperature for 1 h, and then warmed to room temperature. The reaction was quenched with saturated NH$_4$Cl (300 mL) and the separated aqueous layer was extracted with ethyl acetate (150 mL×3). The combined extracts were washed with water and brine, dried over Na$_2$SO$_4$, concentrated to dryness. The residue was purified by silica gel column to obtain 1-benzyl-4-(5-chloro-2-methoxy-phenyl)-piperidin-4-ol 1b as a white solid. $^1$H NMR (CDCl$_3$): δ 7.37-7.24 (m, 6H), 7.21 (q, J$_1$=8.8 Hz, J$_2$=2.8 Hz, 1H), 6.85 (d, J=8.8 Hz, 1H), 3.88 (s, 3H), 3.80 (s, 1H), 3.59 (s, 2, H), 2.77-2.74 (m, 2, H), 2.59-2.54 (t, 2H), 2.13-2.06 (m, 2H), 2.00-1.96 (m, 2H).

A solution of 1-benzyl-4-(5-chloro-2-methoxy-phenyl)-piperidin-4-ol 1b (1.2, 17 g, 0.05 mol) and p-TsOH (29.3 g, 0.15 mol) in toluene (300 mL) was heated to reflux for 6 h with water being removed through a Dean-Stark apparatus. The mixture was cooled to room temperature and was washed with saturated NaHCO$_3$ (100 mL×3). The organic layer was dried over Na$_2$SO$_4$ and concentrated to afford 1-benzyl-4-(5-chloro-2-methoxy-phenyl)-1,2,3,6-tetrahydro-pyridine 1c as a brown liquid.

A solution of 1-benzyl-4-(5-chloro-2-methoxy-phenyl)-1,2,3,6-tetrahydro-pyridine 1c (13.5 g, 0.043 mol) and Rh(PPh$_3$)Cl (1.5 g, 0.00375 mol) in toluene (200 mL) was stirred under hydrogen atmosphere (P$_{H2}$=50 PSI) at 75° C. for 24 hr. The mixture was concentrated to dryness and the residue was purified by silica gel column to afford 1-benzyl-4-(5-chloro-2-methoxyphenyl)-piperidine 1d as a colorless liquid.

To a solution of 1-benzyl-4-(5-chloro-2-methoxy-phenyl)-piperidine 1d (12 g, 0.038 mol) in dichloromethane (150 mL) was added 1-chloroethyl chloroformate (6.5 g, 0.046 mol) dropwise. The mixture was stirred at room temperature for 2 hr and then concentrated to dryness. The residue was dissolved in methanol (30 mL) and then heated to reflux for 30 min. The mixture was concentrated to dryness in vacuo and ether (30 mL) was added with stirring. The precipitated solid was filtered and washed with ether to obtain 4-(5-chloro-2-methoxyphenyl)piperidine 1e as its hydrochloride salt. $^1$H NMR (DMSO): δ 8.90-8.84 (m, 2H), 7.27 (d, J=8.8 Hz, 1H), 7.08 (s, 1H), 7.02 (d, J=8.8 Hz, 1H), 3.78 (m, 4H), 3.15-2.97 (m, 4H), 1.84-1.82 (m, 4H). ESI-MS m/z 226.2.

To a suspension of 4-(5-chloro-2-methoxyphenyl)-piperidine hydrochloride 1e (52 mg, 0.2 mmol) in 1 mL 1,2-dichloroethane was added triethylamine (28 uL, 0.2 mmol), norcamphor (22 mg, 0.2 mmol), and NaBH(OAc)$_3$ (85 mg, 0.4 mmol). The reaction was stirred vigorously under nitrogen at room temperature for ≈72 h. The reaction mixture was diluted with 0.5 mL methanol, filtered, and purified by reverse-phase HPLC (10-99% CH$_3$CN/0.05% TFA, 50 mL/min). The combined pure fractions were concentrated under reduced pressure to 1-(bicyclo[2.2.1]heptan-2-yl)-4-(5-chloro-2-methoxyphenyl)-piperidine (compound no. 209) as the TFA salt. LC/MS (10-99% CH$_3$CN/0.05% TFA gradient over 5 min): m/z 319.0, retention time 2.32 minutes.

Example 2

1-bicyclo[2.2.1]hept-2-yl-4-(4-methoxy-2-methylphenyl)-piperidine (Compound No. 51)

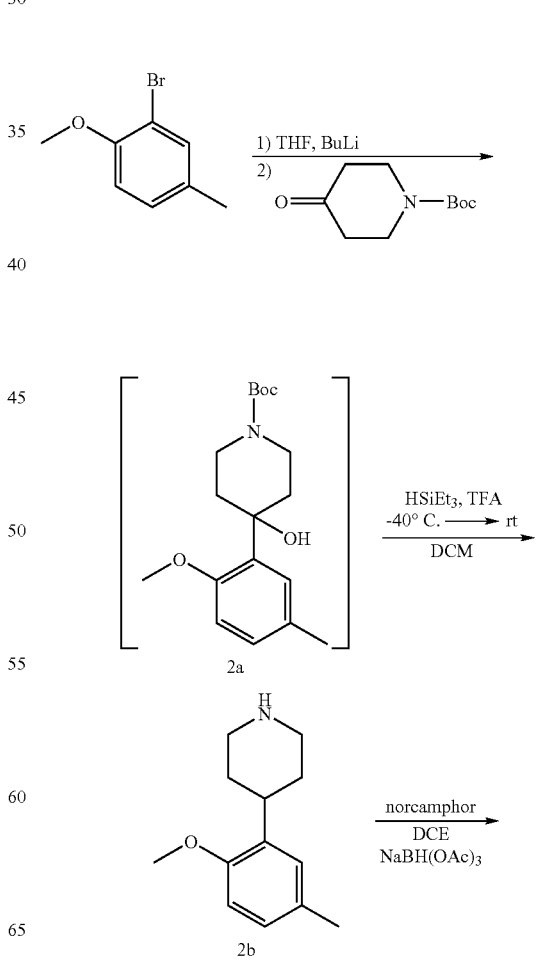

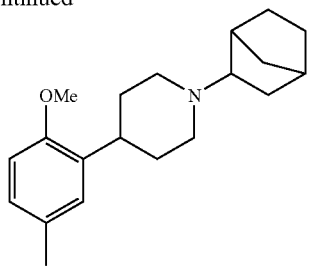

Compound No. 51

A dry 100 mL flask was charged with 2-methoxy-5-methyl-bromobenzene (2.21 g, 11.0 mmol, 1.1 equiv) and THF (20 mL), and purged with nitrogen. The mixture was cooled to −78° C. and butyllithium (4.45 mL of a 2.36 M solution in hexanes, 10.5 mmol, 1.05 equiv) was added dropwise over 10 min. The resulting mixture was stirred at −78° C. for 35 min before 4-oxo-piperidine-1-carboxylic acid tert-butyl ester (1.99 g, 10.0 mmol,) in THF (10 mL) was added dropwise over 10 min. The reaction mixture was stirred at −78° C. for 1 h, then at 0° C. for 30 min. The reaction was quenched with 1 M $NH_4Cl$ (25 mL), and then partitioned between EtOAc (100 mL) and 1 M $NH_4Cl$ (75 mL). The organic layer was washed with water (50 mL), brine (50 mL), dried ($Na_2SO_4$), filtered, and concentrated in vacuo to yield the crude alcohol 2a, which was used directly in the next step.

A 100-mL flask was charged with the crude alcohol 2a (assumed 10 mmol from previous reaction) and dichloromethane (40 mL). The system was purged with nitrogen then triethylsilane (8.0 mL, 50 mmol) was added. The solution was cooled to −40° C., and TFA (3.9 mL, 50 mmol, ca 5 equiv) was added over 25 min. The reaction mixture was stirred for 2 h while allowing the mixture to slowly warm. Additional TFA (3.9 L, 50 mmol, ca 5 eq) was added over 3 min (solution was −10° C.). The reaction mixture was allowed to warm to room temperature slowly and stirred for 22 h. The reaction mixture was diluted with ether (150 mL) and extracted with 1 N HCl (3×50 mL). The combined aqueous extracts were basified to pH>12 with 6 N NaOH and extracted with dichloromethane (2×100 mL). The combined organic extracts were dried over $Na_2SO_4$, filtered, and concentrated in vacuo to yield 4-(2-methoxy-5-methylphenyl)piperidine 2b. ESI-MS m/z 205.9 (M+H)$^+$.

To a 4-mL vial was added solid NaBH(OAC)$_3$ (170 mg, 0.8 mmol, 2 equiv) followed by a solution of 4-(2-methoxy-5-methyl-phenyl)-piperidine (82 mg, 0.4 mmol, 1 equiv) in 1,2-dichloroethane (0.3 mL). Bicyclo[2.2.1]heptan-2-one (49 mg, 0.44 mmol, 1.1 equiv) in 1,2-dichloroethane (0.6 mL) was added and the mixture was shaken at room temperature for 22 h. The contents were transferred to a 20 mL scintillation vial, and the solvent removed in a centrifugal evaporator. The residue was dissolved in methanol (3 mL) and transferred to a 20 mL fritted syringe containing washed sulfonic acid resin (1.65 g, 2.8 mmol, 7 equiv, 1.7 mmol/g loading). The vial was rinsed with methanol (1 mL) and added to the syringe. The syringe was capped and placed in an orbital shaker at 35° C. for 17 h. The resin was washed with methanol (3×10 mL), dichloromethane (3×10 mL), methanol (2×10 mL), dichloromethane (2×10 mL) and methanol (2×10 mL). Each wash was about 3 to 4 minutes with 1 min of shaking. The washed resin was extracted with 7 M $NH_3$/methanol (2×5 mL for 1 h; 5 mL for 4 days; 4 mL for 15 min) and dichloromethane (4 mL for 15 min). The combined extracts were concentrated in a centrifugal evaporator, and the residue was then purified by preparative HPLC to afford 1-bicyclo[2.2.1]hept-2-yl-4-(4-methoxy-2-methyl-phenyl)-piperidine (compound no. 51) as the TFA salt. LC/MS m/z 299.5, retention time 1.94 minutes (10-99% $CH_3CN$/0.05% TFA gradient over 5 min).

Example 3

1-((bicyclo[2.2.1]hept-5-en-2-yl)methyl)-4-(2,5-dimethylphenyl)piperidin-4-ol (Compound No. 62)

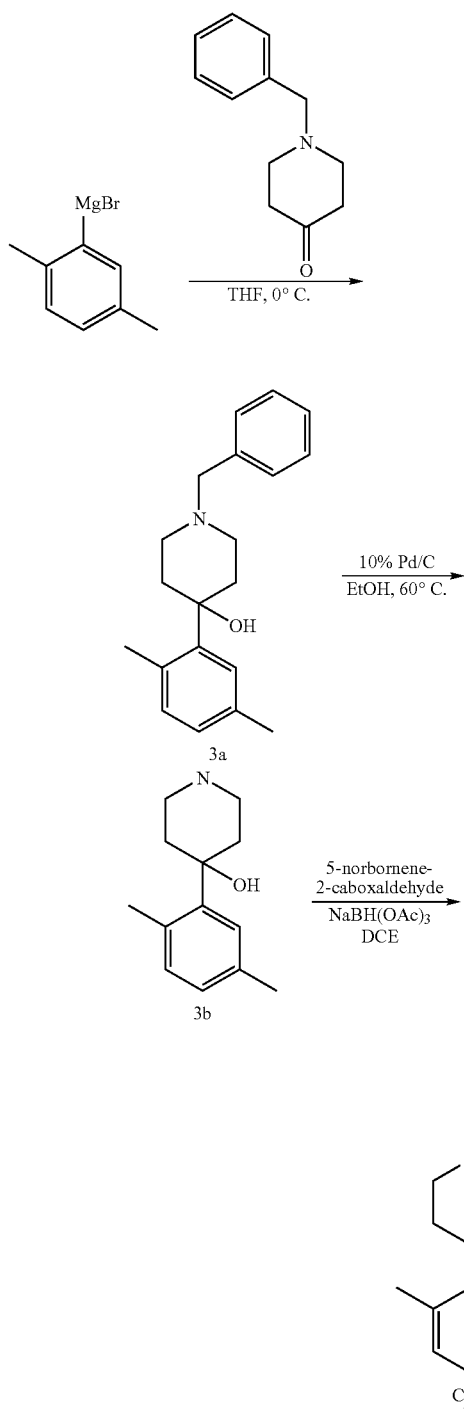

Compund No. 62

1-Benzyl-4-piperidinone (946 mg, 5 mmol) was added to 5 mL anhydrous THF and cooled to 0° C. under nitrogen. 10 mL of 2,5-dimethylphenylmagnesium bromide (0.5 M solution in THF) was added drop-wise. The reaction was stirred at 0° C. for 10 minutes, then allowed to warm to room temperature and stirred for 1 h. The reaction was concentrated, and brought back up in methanol/H$_2$O/acetic acid (1:1:0.5). The solution was filtered and purified by reverse-phase HPLC (2-99% CH$_3$CN/0.085% TFA) to yield 1-benzyl-4-(2,5-dimethyl-phenyl)-piperidin-4-ol 3a. MS (ESI) m/z (M+H$^+$) 296.2.

1-Benzyl-4-(2,5-dimethyl-phenyl)-piperidin-4-ol (100 mg, 0.48 mmol) was dissolved in ethanol (5 mL) in a 25-mL flask, followed by the addition of 10% Pd/C (25 mg) under nitrogen atmosphere. The flask was fixed with a hydrogen balloon and heated to 60° C. for 18 h, leading to quantitative conversion to 4-(2,5-dimethyl-phenyl)-piperidin-4-ol. The reaction mixture was filtered through Celite and concentrated to yield 4-(2,5-dimethyl-phenyl)-piperidin-4-ol 3b as a colorless oil. LC/MS (RP-C$_{18}$, 10-99% CH$_3$CN/0.05% TFA gradient over 5 min) m/z 206.2 [M+H]$^+$, 188.0 [M—H$_2$O]$^+$, retention time 2.19 min.

4-(2,5-Dimethyl-phenyl)-piperidin-4-ol (41 mg, 0.2 mmol) was dissolved in 1.5 mL anhydrous 1,2-dichloroethane. 5-Norbornene-2-carboxaldehyde (25 mg, 0.2 mmol) was added, followed by followed by NaBH(OAc)$_3$ (63 mg, 0.3 mmol). The reaction was stirred overnight, then quenched with 1.0 mL DMSO:methanol (1:1). The reaction mixture was filtered, purified by reverse-phase HPLC (2-99% CH$_3$CN in 0.085% TFA (aq), 50 mL/min, 2.0 mL injected) and the product 1-((bicyclo[2.2.1]hept-5-en-2-yl)methyl)-4-(2,5-dimethylphenyl)piperidin-4-ol (compound no. 62) isolated as the TFA salt. $^1$H-NMR (400 MHz, DMSO-d$_6$) δ 9.54 (br s, 1H), 7.20 (d, J=6.6 Hz, 1H), 7.03-7.13 (m, 2H), 6.25 (m, 0.8H), 6.15 (m, 0.2H), 6.03 (m, 0.8H), 3.45 (m, 2H), 3.29 (m, 2H), 2.84-2.97 (m, 2H), 2.75-2.83 (m, 2H), 2.45 (s, 3H), 2.20-2.25 (m+Ph-CH$_3$, 6H), 2.06-2.10 (m, 2H), 1.96-2.01 (m, 1H), 1.27-1.37 (m, 3H), 0.70 (m, 1H); LC/MS (RP-C$_{18}$, 10-99% CH$_3$CN/0.05% TFA gradient over 5 min) m/z 312.4 [M+H]$^+$, retention time 2.19 min.

Example 4

4-(5-chloro-2-methoxyphenyl)-4-fluoropiperidine tropane ethyl carbamate (Compound No. 219)

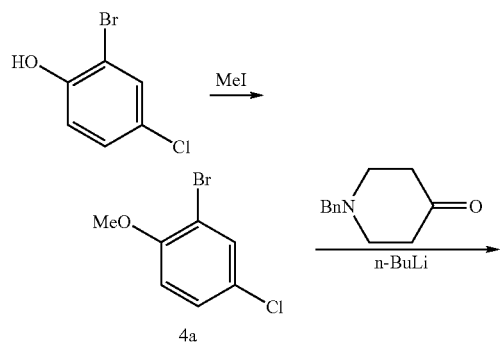

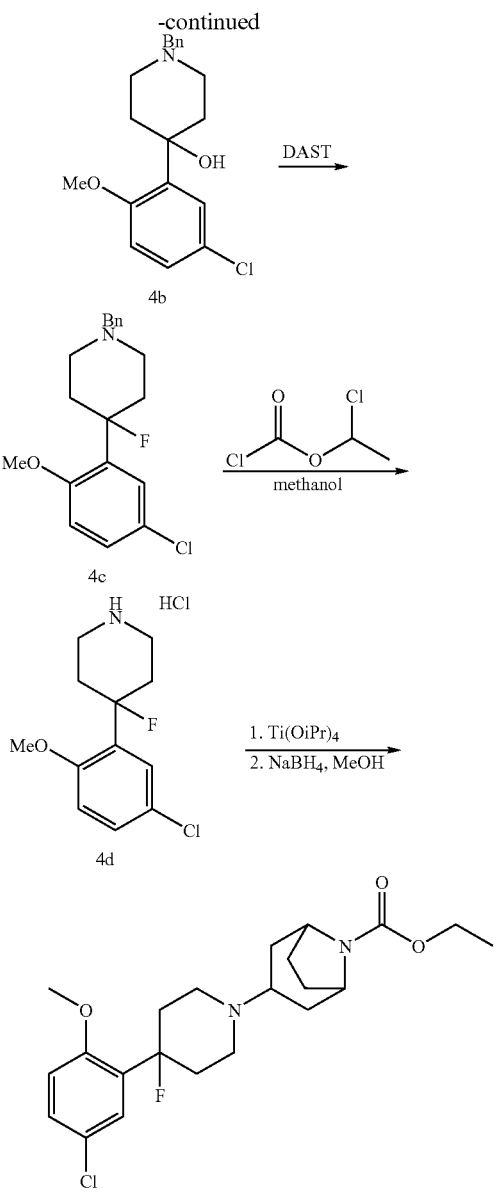

Compound No. 219

A mixture of K$_2$CO$_3$ (68 g, 0.5 mol), 2-bromo-4-chlorophenol (50 g, 0.24 mol) and MeI (42.6 g, 0.3 mol) in acetone (1000 mL) was heated to reflux for 5 h and then cooled to room temperature. The solid was filtered off and washed with dichloromethane (100 mL×3). The combined filtrate was concentrated to dryness. The residue was diluted with diethyl ether (500 mL) and washed with 1N HCl (100 mL×2), H$_2$O (100 mL×2) and brine (200 mL). The separated organic layer was dried over Na$_2$SO$_4$ and concentrated to give 2-bromo-4-chloroanisole 4a as light yellow liquid. $^1$H NMR (CDCl$_3$): δ 7.52 (d, J=2.8 Hz, 1H), 7.24 (q, J$_1$=8.8 Hz, J$_2$=2.8 Hz, 1H), 6.81 (d, J=8.8 Hz, 1H), 3.86 (s, 3H).

To a solution of 2-bromo-4-chloro-1-methoxybenzene (51 g, 0.23 mol) in THF (500 mL) was added dropwise n-BuLi (2.5 M in hexane, 138 mL, 0.345 mol) at −78° C. at nitrogen atmosphere. After being stirred at this temperature for 1 h, 1-benzyl-piperidin-4-one (42 g, 0.22 mol) was added dropwise. After addition, the mixture was stirred at −78° C. for 1 h, and then warmed to room temperature. The reaction was quenched with NH₄Cl (Sat. aq., 300 mL), and the separated aqueous layer was extracted with ethyl acetate (150 mL×3). The combined organic layer was washed with water and brine, dried over Na₂SO₄, concentrated to dryness. The residue was purified by silica gel column to obtain 1-benzyl-4-(5-chloro-2-methoxy-phenyl)-piperidin-4-ol 4b as white powder product. $^1$H NMR (CDCl₃): δ 7.37-7.24 (m, 6H), 7.21 (q, J₁=8.8 Hz, J₂=2.8 Hz, 1H), 6.85 (d, J=8.8 Hz, 1H), 3.88 (s, 3H), 3.80 (s, 1H), 3.59 (s, 2, H), 2.77-2.74 (m, 2, H), 2.59-2.54 (t, 2H), 2.13-2.06 (m, 2H), 2.00-1.96 (m, 2H).

To a solution of 1-benzyl-4-(5-chloro-2-methoxy-phenyl)-piperidin-4-ol (4b, 17 g, 0.05 mol) in dry dichloromethane (70 mL) was added dropwise DAST (10 g, 0.061 mol) at –78° C. under N₂ atmosphere. The mixture was stirred at this temperature for 1 h and then warmed to room temperature slowly. NaHCO₃ (sat., aq., 200 mL) was carefully added dropwise to quench the reaction. The separated aqueous was extracted with dichloromethane (150 mL×3), the combined extracts was washed with water and brine, dried over Na₂SO₄, concentrated to dryness. The residue was titrated with petroleum ether and the precipitated solid was filtered and washed with petroleum ether to afford 1-benzyl-4-(5-chloro-2-methoxy-phenyl)-4-fluoro-piperidine 4c as white powder.

To a stirred solution of 1-benzyl-4-(5-chloro-2-methoxyphenyl)-4-fluoro-piperidine 4c (13.8 g, 0.04 mol) in dichloromethane (50 mL) was added 1-chloroethylchloroformate. (7.1 g, 0.05 mol). The mixture was stirred at room temperature for 2 h and then concentrated to dryness. The residual was dissolved in methanol (50 mL) and then heated to reflux for 30 min. The mixture was concentrated to dryness in vacuo, ether was added, the precipitate solid was filtered and washed with ether to obtain 4-(5-chloro-2-methoxyphenyl)-4-fluoropiperidine 4d as its hydrochloride salt. $^1$H NMR (DMSO-d₆): δ 9.10-9.01 (m, 2H), 7.25 (q, J₁=8.4 Hz, J₂=8.8 Hz, 1H), 7.33 (d, J=2.8 Hz, 1H), 7.12 (d, J=8.8 Hz, 1H), 3.82 (s, 3H), 3.27 (s, 2H), 3.13-3.04 (m, 2H), 2.79-2.66 (m, 2H), 1.924-1.864 (t. 2H). MS (ESI) m/z (M+H⁺) 243.98.

To a 20-mL vial was added 4-(5-chloro-2-methoxyphenyl)-4-fluoropiperidine hydrohloride 4d (84 mg, 0.3 mmol) followed by ethyl 3-oxo-8-azabicyclo[3.2.1]octane-8-carboxylate (71 mg, 0.36 mmol) and triethylamine (41 uL, 0.3 mmol). The mixture was suspended in Ti(OiPr)₄ and stirred slowly for 24 h at room temperature. The reaction was diluted with methanol (1.5 mL) and treated with NaBH₄ (23 mg, 0.6 mmol). The reaction was stirred for an additional hour and was then treated with 200 uL 1 N NaOH to create a white precipitate. The mixture was centrifuged (3,000 rpm, 10 minutes) and the supernatant filtered and purified by reverse-phase HPLC (10-99% CH₃CN/0.05% TFA). The combined pure fractions were concentrated under reduced pressure to afford 4-(5-chloro-2-methoxyphenyl)-4-fluoropiperidine tropane ethyl carbamate (compound no. 219) as the TFA salt. LC/MS (RP-C₁₈, 10-99% CH₃CN/0.05% TFA gradient over 5 min) m/z 325.3 [M+H]⁺, retention time 2.40 min.

Example 5

1-(((1S,2S,4S)-bicyclo[2.2.1]hept-5-en-2-yl)methyl)-4-(5-chloro-2-methoxyphenyl)-4-methoxypiperidine (Compound No. 140)

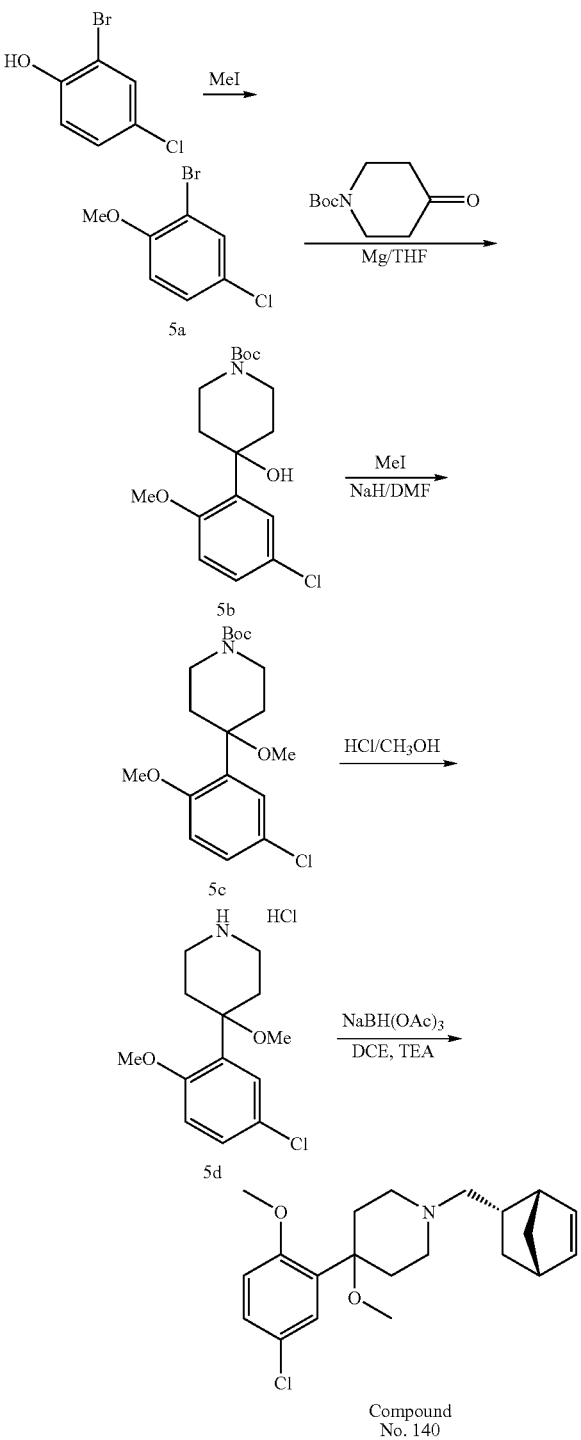

Compound No. 140

A mixture of K₂CO₃ (68 g, 0.5 mol), 2-bromo-4-chorophenol (50 g, 0.24 mol) and MeI (42.6 g, 0.3 mol) in acetone (1000 mL) was heated to reflux for 5 h and then cooled to room temperature. The solid was filtered off and washed with dichloromethane (100 mL×3). The combined filtrate was concentrated to dryness. The residue was diluted with diethyl ether (500 mL) and washed HCl (1 M, 100 mL×2), H$_2$O (100 mL×2) and brine (200 mL). The separated organic layer was dried over Na$_2$SO$_4$ and concentrated to give 2-bromo-4-chloroanisole 5a as light yellow liquid. $^1$H NMR (CDCl$_3$): δ 7.52 (d, J=2.8 Hz, 1H), 7.24 (q, J$_1$=8.8 Hz, J$_2$=2.8 Hz, 1H), 6.81 (d, J=8.8 Hz, 1H), 3.86 (s, 3H).

To a mixture of Mg (2.64 g, 0.11 mol) and a small crystal of iodine in THF (250 mL) was added dropwise 2-bromo-4-chloroanisole 5a (22.1 g, 0.1 mol). After addition, the mixture was heated to reflux for 30 min and then cooled to −78° C., to which 1-benzyl-piperidin-4-one (17 g, 0.085 mol) was added dropwise at this temperature. After being stirred at −78° C. for 1 h, the mixture was warmed to room temperature slowly. Water was added and the mixture was extracted with ethyl acetate (150 mL×3). The combined organic layer was washed with water and brine, dried over Na$_2$SO$_4$, concentrated to give a crude product, which was purified by silica gel column to obtain pure 4-(5-chloro-2-methoxy-phenyl)-4-hydroxy-piperidine-1-carboxylic acid tert-butyl ester 5b as off-white powder (7 g, 20.5%).

To a suspension of NaH (0.7 g, 60% in mineral oil, 17.5 mol) in DMF (30 mL) was added dropwise a solution of 4-(5-chloro-2-methoxy-phenyl)-4-hydroxy-piperidine-1-carboxylic acid tert-butyl ester 5b (4.0 g, 11.7 mol) in DMF (10 mL) at 0° C. After being stirred at this temperature for 30 min, MeI (0.9 ml 0.0145 mol) was added dropwise. The reaction mixture was stirred at 0° C. for 30 min and then warmed to room temperature. Water (100 mL) was added and the mixture was extracted with ethyl acetate (100 mL×3). The combined organic layers were washed with water and brine, dried over Na$_2$SO$_4$, and concentrated to obtain crude 4-(5-chloro-2-methoxy-phenyl)-4-methoxy-piperidine-1-carboxylic acid tert-butyl ester 5c (3.8 g), which was used directly in next step.

A solution of 4-(5-chloro-2-methoxy-phenyl)-4-methoxy-piperidine-1-carboxylic acid tert-butyl ester 5c (3.8 g, crude from last step) in methanol/HCl (2 M, 50 mL) was stirred at room temperature for 4 h, then the mixture was concentrated to half of volume under 40° C. and then ether was added. The precipitated was filtered and washed with ether to obtain 4-(5-chloro-2-methoxyphenyl)-4-methoxypiperidine 5d as its HCl salt. $^1$H NMR (DMSO-d$_6$): δ 8.95 (b, 2H), 7.37-7.34 (q, J$_1$=8.8 Hz, J$_2$=8.8 Hz, 1H), 7.21-7.20 (d, J=2.8 Hz, 1H), 7.09-7.07 (d, J=8.8 Hz, 1H), 3.78 (s, 3H), 3.16-3.13 (m, 2H), 3.13-2.98 (m, 5H), 2.35-2.28 (m, 2H), 2.19-2.16 (m, 2H). ESI-MS m/z 256.8.

4-(5-Chloro-2-methoxyphenyl)-4-methoxypiperidine 5d (51 mg, 0.2 mmol) was dissolved in 1,2-dichloroethane (1.5 mL) and treated with (S,S,S)-norbornene carboxaldehyde (24 mg, 0.2 mmol, 1.0 eq), followed by the addition of NaBH(OAc)$_3$ (65 mg, 0.3 mmol, 1.5 eq). The reaction was allowed to stir at room temperature for 1 h, quenched with methanol (1 mL) and allowed to stir for another 30 min (until gas evolution stopped). The crude reaction mixture was purified by HPLC (10-99 CH$_3$CN gradient, 0.05% TFA) to provide the desired product 1-(((1S,2S,4S)-bicyclo[2.2.1]hept-5-en-2-yl)methyl)-4-(5-chloro-2-methoxyphenyl)-4-methoxypiperidine (compound no. 140) as the TFA salt. LC/MS (RP-C$_{18}$; 10-99% CH$_3$CN/0.05% TFA gradient over 5 min) m/z 362.2 [M+H]$^+$, retention time 2.53 min.

Example 6

4-(5-chloro-2-methoxyphenyl)-1-(1,4-dioxaspiro[4.5]decan-8-yl)piperidine (Compound No. 331); 4-(4-(5-chloro-2-methoxyphenyl)piperidin-1-yl)cyclohexanone (Compound No. 273); and 4-(4-(5-chloro-2-methoxyphenyl)piperidin-1-yl)cyclohexanone O-ethyl oxime (Compound no. 417)

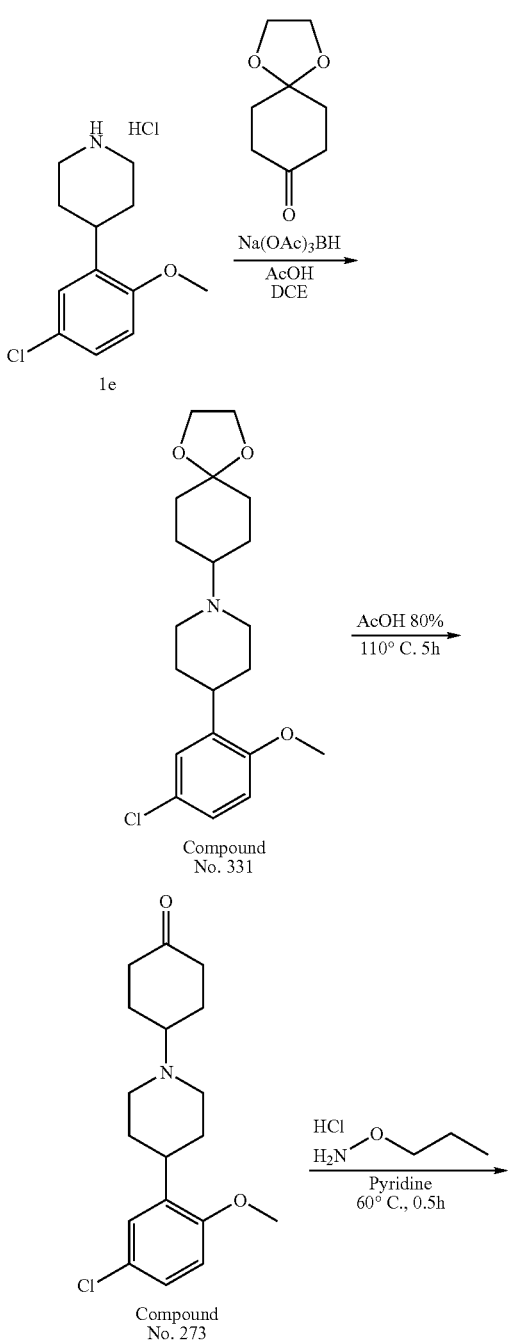

-continued

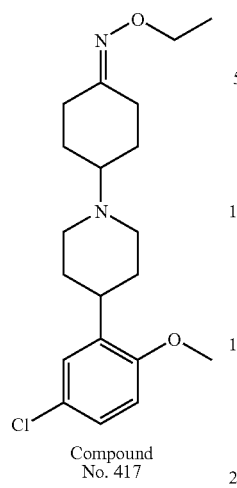

Compound No. 417

4-(2-methoxy-5-chlorophenyl)piperidine hydrochloride (1.5, 393.3 mg, 1.5 mmol) was dissolved in anhydrous 1,2-dichloroethane (3 mL) in a 100-mL round bottom flask and treated with triethylamine (0.25 mL 1 eq). 1,4-cyclohexanedione-mono-ethylene ketal (1.8 mmol, 281.12 mg) was added to the solution and the mixture stirred for 5 min. Na(OAc)$_3$BH (3.0 mmol, 635.7 mg) was added followed by addition of AcOH (0.2 mL, 0.3 mmol.). The reaction was stirred at room temperature for 16 h. The crude reaction was washed with saturated NaHCO$_3$, brine, dried over Na$_2$SO$_4$ and filtered. The filtrate was concentrated under reduced pressure to afford the desired product as pale yellow oil and carried to the next step without further purification. An analytical and screening sample was purified by HPLC (10-99 CH$_3$CN gradient, 0.05% TFA) to provide the 4-(5-chloro-2-methoxyphenyl)-1-(1,4-dioxaspiro[4.5]decan-8-yl)piperidine (compound no. 331) as the TFA salt. LC/MS (RP-C$_{18}$, 10-99% CH$_3$CN/0.05% TFA gradient over 5 min) m/z 366.2 [M+H]$^+$, retention time 2.13 min.

Crude 4-(5-chloro-2-methoxyphenyl)-1-(1,4-dioxaspiro [4.5]decan-8-yl)piperidine was brought up in 20 mL of 80% aq. AcOH in a 100-mL flask and heated for 5 h at 110° C. The reaction was brought to pH 8-9 with 1N NaOH and extracted with dichlorometane (3×20 mL). The organic layer washed with saturated brine, dried over Na$_2$SO$_4$ and filtered. The filtrate was concentrated under reduced pressure to give crude desired product as pale yellow oil and carried to the next step without further purification. An analytical and screening sample was purified by HPLC (10-99 CH$_3$CN gradient, 0.05% TFA) to provide the desired product 4-(4-(5-chloro-2-methoxyphenyl)piperidin-1-yl)cyclohexanone (compound no. 273) as the TFA salt. LC/MS (RP-C$_{18}$, 10-99% CH$_3$CN/ 0.05% TFA gradient over 5 min) m/z 322.0 [M+H]$^+$, retention time 1.98 min.

Crude 4-(4-(5-chloro-2-methoxyphenyl)piperidin-1-yl) cyclohexanone (45.5 mg) was dissolved in pyridine (0.5 mL) in 20 mL vial and ethylhydroxylamine hydrochloride (17 mg, 1.2 eq) added to the solution. Mixture was stirred at 60° C. for 0.5 h. All pyridine was evaporated under reduced pressure. Desired crude product redissolved in 2 mL of methanol, and purified by reverse phase HPLC (C-18, 10-99% acetonitrile/ 0.05% TFA gradient over 10 min). Pure fractions were pooled and concentrated to yield compound no. 417 as yellow oil.

LC/MS (RP-C$_{18}$, 10-99% CH$_3$CN/0.05% TFA gradient over 5 min) m/z 365.0 [M+H]$^+$, retention time 2.19 min.

Example 7 ethyl 4-cyano-4-(2-methoxyphenyl)-1,4'-bipiperidine-1'-carboxylate (Compound No. 245)

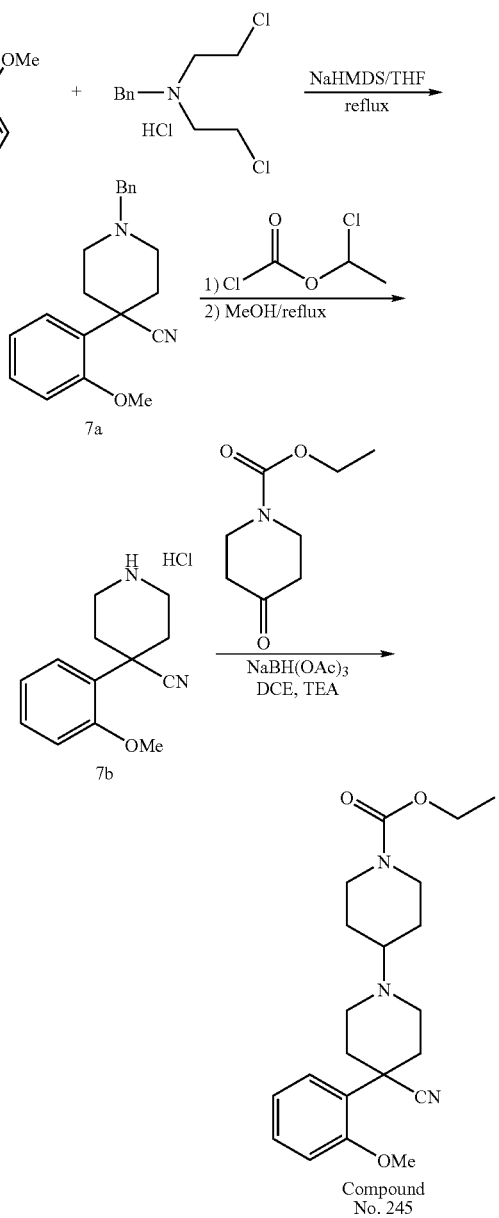

To a solution of (2-methoxy-phenyl)-acetonitrile (4.14 g, 0.03 mol) in THF (100 mL) was added dropwise NaHMDS (2 M, 36 mL) at 0° C. After the mixture was stirred for 30 min, benzyl-bis-(2-chloro-ethyl)-amine hydrochloride (8 g, 0.03 mol) was added gradually, and then the mixture was heated under reflux for 2 h. The mixture was quenched with H$_2$O (50 mL), then extracted with EtOAc (100 mL). The combined organic layers were washed with brine, dried over Na$_2$SO$_4$, filtered, and concentrated under vacuum. The residue was triturated with diethyl ether, and then the precipitate was filtered and washed with diethyl ether to give a white solid 1-benzyl-4-(2-methoxy-phenyl)-piperidine-4-carbonitrile 7a as the HCl salt. $^1$H NMR (CDCl$_3$): δ 7.35-7.28 (m, 7H), 6.99-6.96 (m, 2H), 3.93 (s, 3H), 3.62 (s, 2H), 3.98 (d, J=12.4 Hz, 2H), 2.61 (t, J=1.6 Hz, 2H), 2.39 (d, J=13.2 Hz, 2H), 2.06 (t, J=13.2 Hz, 2H).

To a solution of 1-benzyl-4-(2-methoxy-phenyl)-piperidine-4-carbonitrile 7a (6.17 g, 0.02 mol) in CH$_2$Cl$_2$ (200 mL) was added dropwise chloroformic acid 1-chloroethyl ester (3.66 g, 0.03 mol). After stirred for 5 h the mixture was concentrated under reduced pressure and methanol (200 mL) was added. The mixture was then heated to reflux for 30 min. The solvent was removed under vacuum. Diethyl ether (100 mL) was added and the white precipitate was collected by filtration to afford 4-(2-methoxyphenyl)piperidine-4-carbonitrile 7b as HCl salt. $^1$H NMR (CDCl$_3$) δ 9.5-9.1 (br, 2H), 7.41 (t, J=7.6 Hz, 1H), 7.30 (d, J=7.6 Hz, 1H), 7.15 (d, J=8.4 Hz, 1H), 7.02 (t, J=7.6 Hz, 1H), 3.87 (s, 3H). 3.44 (d, J=13.2 Hz, 2H), 3.08 (m, 2H), 2.48 (m, 2H), 2.28 (m, 2H). MS (ESI) m/z (M+H+) 217.2.

4-(2-methoxyphenyl)piperidine-4-carbonitrile HCl (7.2, 50.5 mg, 0.2 mmol) was suspended in 1,2-dichloroethane (1.5 mL) and treated with ethyl 4-oxopiperidine-1-carboxylate (34 mg, 0.2 mmol), followed by the addition of NaBH(OAc)$_3$ (65 mg, 0.3 mmol). The reaction was allowed to stir at room temperature for 16 h and was then quenched with methanol (1 mL) and allowed to stir for another 30 min (until gas evolution stopped). The crude reaction mixture was purified by HPLC (10-99 CH$_3$CN gradient, 0.05% TFA) to provide the desired product ethyl 4-cyano-4-(2-methoxyphenyl)-1,4'-bipiperidine-1'-carboxylate (compound no. 245) as the TFA salt. LC/MS (RP-C$_{18}$, 10-99% CH$_3$CN/0.05% TFA gradient over 5 min) m/z 372.0 [M+H]$^+$, retention time 2.18 min.

Example 8

[4-(3-(1-((1S,2R,4R)-bicyclo[2.2.1]heptan-2-yl)piperidin-4-yl)-4-methoxyphenyl) pyridine] (Compound No. 124)

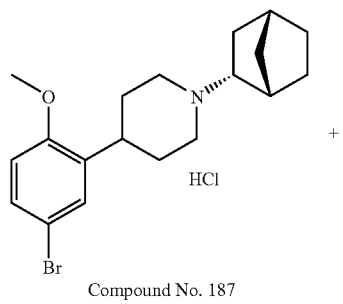

Compound No. 187

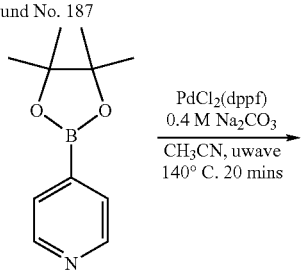

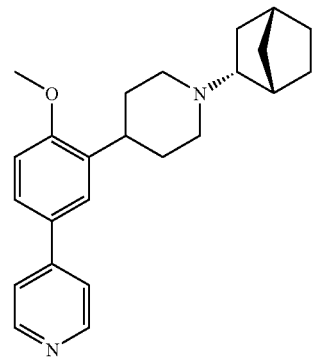

Compound No. 124

Dichloro[1,1'-bis(diphenylphosphino)ferrocene]-palladium(II)dichloromethane adduct (12 mg, 0.015 mmol), acetonitrile (500 µL), 2.0 M sodium carbonate (aq) (250 µL), 1-((1S,2R,4R)-bicyclo[2.2.1]heptan-2-yl)-4-(5-bromo-2-methoxyphenyl)piperidine hydrochloride (compound no. 187) (60 mg, 0.15 mmol) and 4-(4,4,5,5-tetramethyl-1,3,2-dioxaborolan-2-yl)pyridine (31 mg, 0.15 mmol) were combined in a microwave vial. The vial was flushed with nitrogen, capped and microwaved at 140° C. for 20 min. The reaction was diluted with methanol (750 µL), mixed well and then filtered (Whatman 0.20 µM PTFE) and subjected to reverse-phase HPLC purification (2-40% CH$_3$CN/0.08% TFA) to yield [4-(3-(1-((1S,2R,4R)-bicyclo[2.2.1]heptan-2-yl)piperidin-4-yl)-4-methoxyphenyl) pyridine] (compound no. 124) as the TFA salt. LC/MS (RP-C$_{18}$, 10-99% CH$_3$CN/ 0.05% TFA gradient over 5 min) m/z 363.4 [M+H]$^+$, retention time 1.67 min.

Example 9

1-((1S,2R,4R)-bicyclo[2.2.1]heptan-2-yl)-4-(2-methoxy-5-(phenyl-ethynyl)phenyl)piperidine (Compound No. 64)

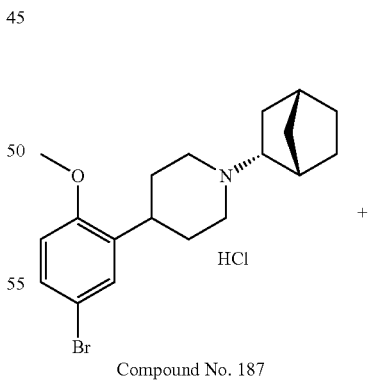

Compound No. 187

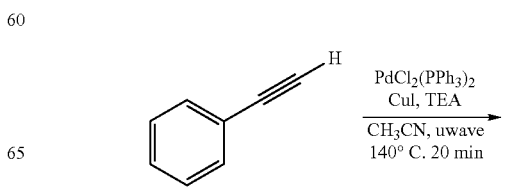

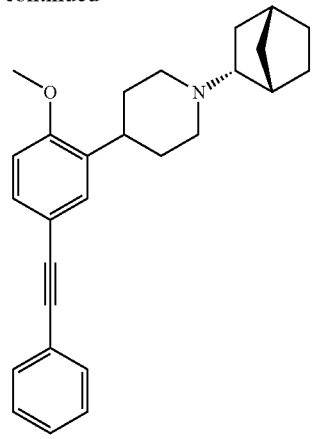

Compound No. 64

1-((1S,2R,4R)-bicyclo[2.2.1]heptan-2-yl)-4-(5-bromo-2-methoxyphenyl) piperidine hydrochloride (compound no. 187) (60 mg, 0.15 mmol), trans-dichlorobis(triphenylphosphine) palladium (II) (11 mg, 0.015 mmol) and copper iodide (6 mg, 0.030 mmol) were suspended in anhydrous acetonitrile (500 μL) in a microwave vial and treated with phenylacetylene (77 mg, 0.75 mmol), followed by triethylamine (250 μL). The vial was flushed with nitrogen, capped and microwaved at 140° C. for 20 min. The reaction was diluted with methanol (750 μL), filtered (Whatman 0.20 μm PTFE) and subjected to reverse-phase HPLC purification (5-50% $CH_3CN$/0.08% TFA) to yield 1-((1S,2R,4R)-bicyclo[2.2.1]heptan-2-yl)-4-(2-methoxy-5-(phenyl-ethynyl)phenyl)piperidine (compound no. 64) as the TFA salt. LC/MS (RP-$C_{18}$, 10-99% $CH_3CN$/0.05% TFA gradient over 5 min) m/z 386.2 $[M+H]^+$, retention time 2.86 min.

Example 10 ethyl 4-(3-(2-methoxyphenyl)-8-azabicyclo-[3.2.1]octan-8-yl)piperidine-1-carboxylate (Compound No. 289)

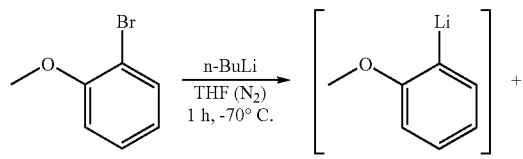

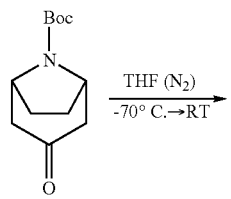

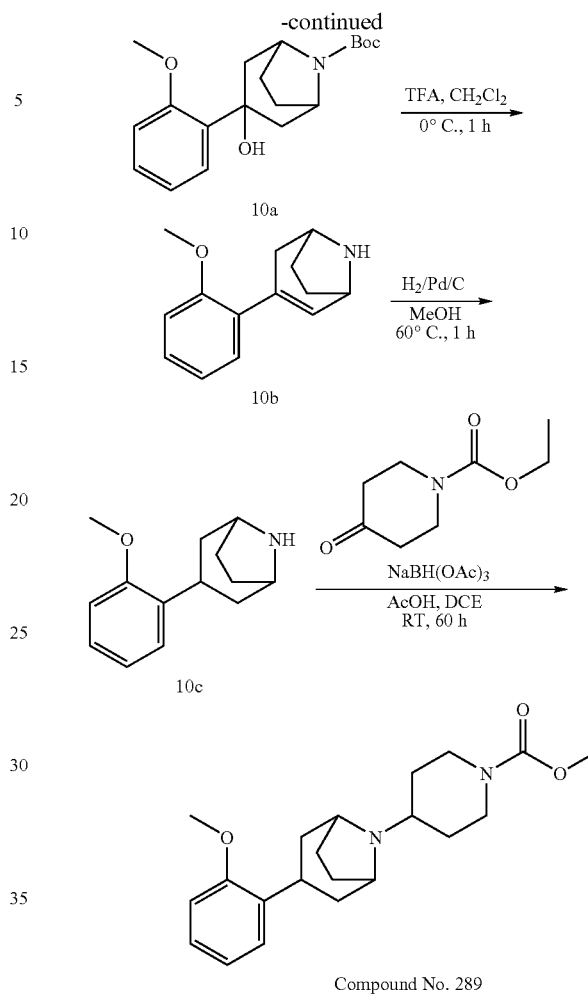

Compound No. 289

A solution of 2-bromoanisole (2.08 g, 11.1 mmol) in anhydrous tetrahydrofuran (20 mL) was cooled to approximately −70° C. and treated dropwise, under nitrogen, with n-butyllithium in hexanes (9 mL 2.5 M solution, 22.5 mmol). After the addition, the reaction was stirred at −70° C. for 1 h, then treated dropwise with a solution of N-Boc-nortropinone (2.50 g, 11.1 mmol) in anhydrous tetrahydrofuran (20 mL). After the addition, the reaction was slowly warmed to room temperature and stirred overnight under nitrogen. The reaction was diluted with diethyl ether (100 mL), cooled in an ice-$H_2O$ bath and slowly treated with ice-cold 1.0 N HCl (adjusted to pH 7; solution changes from cloudy white to clear). The layers were separated and the aqueous layer extracted once with diethyl ether (50 mL). The pooled organic layers were washed with $H_2O$ and saturated brine, then dried ($Na_2SO_4$) and filtered. The filtrate was concentrated in vacuo to afford 4.124 g crude product tert-butyl 3-hydroxy-3-(2-methoxyphenyl)-8-azabicyclo[3.2.1]octane-8-carboxylate 10a as a pale yellow oil, which was taken to the next step without further purification. LC/MS (RP-$C_{18}$, 10-99% $CH_3CN$/0.05% TFA gradient over 5 min) m/z 334.2 $[M+H]^+$, retention time 3.20 min.

Crude 10a from above (4.124 g) was dissolved in dichloromethane (10 mL) and cooled in an ice-$H_2O$ bath. The solution was slowly treated with ice-cold trifluoroacetic acid (10 mL) and stirred at 0° C. for 1 h. The reaction was then concentrated under reduced pressure and the oil obtained re-dissolved in acetonitrile and re-concentrated under reduced pressure. The crude TFA salt was cooled in an ice-H₂O bath and treated slowly with ice-cold 1.0 N NaOH (75 mL). The product was extracted into dichloromethane (2×75 mL) and the pooled extracts washed successively with H₂O, saturated NaHCO₃ and saturated brine, dried over Na₂SO₄ and filtered. The filtrate was concentrated in vacuo to afford 1.223 g crude 3-(2-methoxyphenyl)-8-azabicyclo[3.2.1]oct-2-ene 10b as a pale amber oil, which was taken to the next step without further purification. LC/MS (RP-C$_{18}$, 10-99% CH₃CN/0.05% TFA gradient over 5 min) m/z 216.2 [M+H]⁺, retention time 1.75 min.

Crude 10b from above (1.223 g) was dissolved in methanol (20 mL) and the solution purged with nitrogen gas for several minutes. 10% Palladium on carbon (500 mg, wet) was added and the flask flushed with nitrogen, followed by hydrogen (balloon). The reaction was heated at 60° C. for 1 h under a hydrogen balloon, then filtered through a pad of Celite and rinsed with methanol (3×25 mL). The filtrate was concentrated in vacuo to afford 1.030 g crude 3-(2-methoxyphenyl)-8-azabicyclo[3.2.1]octane 10c as a pale amber oil, which was taken to the next step without further purification. A small sample was purified via reverse-phase HPLC for analysis. ¹H-NMR (400 MHz, DMSO-d₆) δ 8.66 (br s, 2H), 7.33 (d, J=9.0 Hz, 1H), 7.23 (t, J=7.8 Hz, 1H), 6.99 (d, J=8.2 Hz, 1H), 6.93 (t, J=7.5 Hz, 1H), 4.00 (m, 2H), 3.80 (s, 3H), 3.34 (m, 1H), 2.35 (m, 2H), 1.99 (m, 2H), 1.86 (m, 2H), 1.78 (m, 2H). LC/MS (RP-C$_{18}$, 10-99% CH₃CN/0.05% TFA gradient over 5 min) m/z 218.2 [M+H]⁺, retention time 1.81 min.

Intermediate 10c from above (43 mg, 0.20 mmol) was dissolved in anhydrous 1,2-dichloroethane (1.0 mL) in a scintillation vial and treated with ethyl 4-oxopiperidine-1-carboxylate (51 mg, 0.30 mmol), followed by glacial acetic acid (24 mg, 0.40 mmol) and sodium triacetoxyborohydride (85 mg, 0.40 mmol). The vial was flushed with nitrogen and stirred at room temperature for 60 h. The reaction was then quenched with methanol (1.0 mL) and stirred at room temperature for 30 min. The reaction was filtered (Whatman 0.2 μm PTFE) and subjected to reverse-phase HPLC purification (2-40% CH₃CN/0.08% TFA) to yield ethyl 4-(3-(2-methoxyphenyl)-8-azabicyclo-[3.2.1]octan-8-yl)piperidine-1-carboxylate (compound no. 289) as the TFA salt. LC/MS (RP-C$_{18}$, 10-99% CH₃CN/0.05% TFA gradient over 5 min) m/z 373.0 [M+H]⁺, retention time 2.15 min.

Example 11

[1-((1S,2R,4R)-bicyclo[2.2.1]heptan-2-yl)-4-(5-tert-butyl-2-methoxy-phenyl) piperidine] (Compound No. 325)

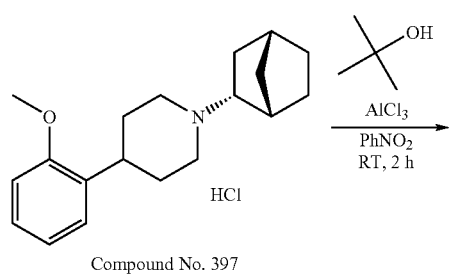

Compound No. 397

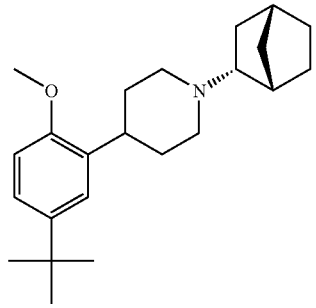

Compound No. 325

1-((1S,2R,4R)-bicyclo[2.2.1]heptan-2-yl)-4-(2-methoxyphenyl)piperidine hydrochloride (397, 64 mg, 0.20 mmol) was suspended in nitrobenzene (1.0 mL) and treated with 1.0 eq tert-butanol (15 mg), followed by 3.0 eq of aluminum trichloride in nitrobenzene (600 μL 1.0 M solution, 0.60 mmol). The reaction was stirred at room temperature for 2 hours, then quenched with 1.0 N HCl (5.0 mL). The aqueous layer was separated, basified with 1.0 N NaOH (pH 12) and extracted with dichloromethane (10 mL). The extract was dried (Na₂SO₄), filtered, concentrated in vacuo and dissolved in methanol:acetonitrile (1.0 mL, 1:1 v/v). The solution was filtered (Whatman 0.2 μm PTFE) and subjected to reverse-phase HPLC purification (5-50% CH₃CN/0.08% TFA) to yield [1-((1S,2R,4R)-bicyclo[2.2.1]heptan-2-yl)-4-(5-tert-butyl-2-methoxy-phenyl)piperidine] (compound no. 325) as the TFA salt. LC/MS (RP-C$_{18}$, 10-99% CH₃CN/0.05% TFA gradient over 5 min) m/z 342.2 [M+H]⁺, retention time 2.70 min.

Example 12

1-(3-(1-((1S,2R,4R)-bicyclo[2.2.1]heptan-2-yl)piperidin-4-yl)-4-methoxyphenyl)-2-methylpropan-1-one (Compound No. 222)

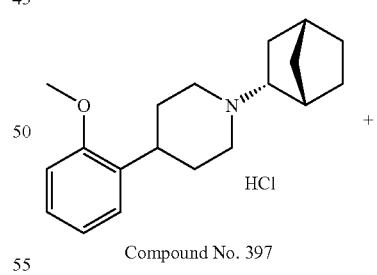

Compound No. 397

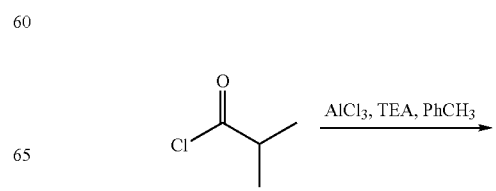

-continued

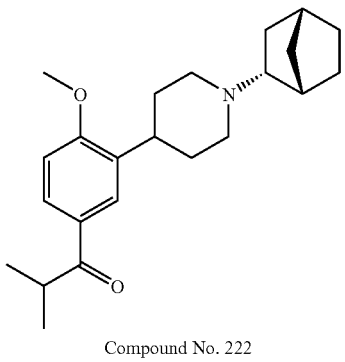

Compound No. 222

1-((1S,2R,4R)-bicyclo[2.2.1]heptan-2-yl)-4-(2-methoxyphenyl)piperidine hydrochloride (397, 32 mg, 0.1 mmol) was dissolved in 1 mL anhydrous toluene and triethylamine (14 uL, 0.1 mmol) to produce a cloudy mixture. To the solution was added the anhydrous $AlCl_3$ (27 mg, 0.2 mmol) and the reaction mixture went clear. The isobutyryl chloride (1.5 eq, 0.15 mmol) was then added to the rapidly stirring solution, resulting in a color change ranging from light yellow to brown. After 30 min, the reaction was diluted with toluene (2 mL), and quenched by the addition of 50% saturated sodium bicarbonate (2 mL). The organic layer was washed with brine, dried over $Na_2SO_4$, decanted and dried down. The crude reaction was subjected to reverse-phase HPLC purification (5-50% $CH_3CN$/0.08% TFA) to yield 1-(3-(1-((1S,2R,4R)-bicyclo[2.2.1]heptan-2-yl)piperidin-4-yl)-4-methoxyphenyl)-2-methylpropan-1-one (compound no. 222) as the TFA salt. $^1$H NMR (400 MHz, DMSO-$d_6$) δ 8.77 (bs, 1H), 7.96 (dd, J=8.7, 2.2 Hz, 1H), 7.79 (d, J=2.1 Hz, 1H), 7.14 (d, J=8.7 Hz, 1H), 3.91 (s, 3H), 3.64 (septet, J=6.8 Hz, 1H), 3.59-3.35 (m, 3H), 3.26-3.20 (m, 1H), 3.10 (quintet, J=12.6 Hz, 1H), 2.61 (bs, 1H), 2.30 (bs, 1H), 2.07-1.90 (m, 4H), 1.65-1.54 (m, 3H), 1.46-1.36 (m, 3H), 1.23-1.19 (m, 1H), 1.10 (d, J=6.8 Hz, 6H); LC/MS (RP-$C_{18}$, 10-99% $CH_3CN$/0.05% TFA gradient over 5 min) m/z 333.2 [M+H]$^+$, retention time 2.97 min.

Example 13

4-(5-chloro-2-methoxyphenyl)-1-(1-methylcyclohexyl)piperidine (Compound No. 300)

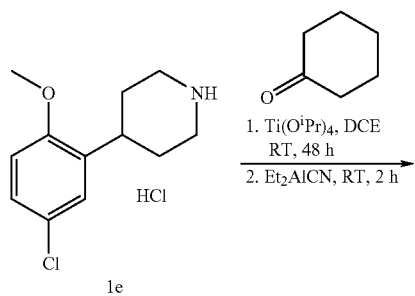

-continued

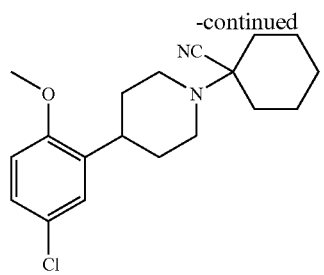

13a

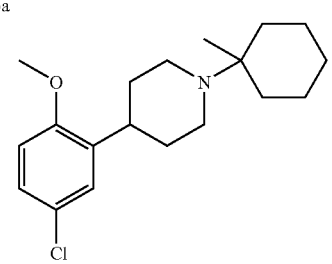

Compound No. 300

4-(5-chloro-2-methoxyphenyl)piperidine hydrochloride 1e (131 mg, 0.50 mmol) and cyclohexanone (54 mg, 0.55 mmol) were combined in anhydrous 1,2-dichloroethane (1.0 mL) in a scintillation vial and treated with triethylamine (51 mg), followed by titanium tetraisopropoxide (205 μL, 199 mg, 0.70 mmol). The vial was flushed with nitrogen and stirred at room temperature for 48 h. The reaction was then concentrated in vacuo and treated with diethyl aluminum cyanide in toluene (750 μL 1.0 M solution, 0.75 mmol). The vial was flushed with nitrogen and stirred at room temperature for 2 h. The reaction was then diluted with ethyl acetate (5 mL), quenched with $H_2O$ (1 mL) and stirred at room temperature for 1 h. The suspension obtained was centrifuged (3K rpm, 10 minutes) and the supernatant decanted, filtered (Whatman 0.20 μm PTFE) and concentrated in vacuo. The crude 1-(4-(5-chloro-2-methoxyphenyl)piperidin-1-yl)cyclohexane carbonitrile 13a was immediately taken to the next step without further purification. LC/MS (RP-$C_{18}$, 10-99% $CH_3CN$/0.05% TFA gradient over 5 min) m/z 333.2 [M+H]$^+$, retention time 2.97 min.

Intermediate 13a (0.5 mmol) from above was dissolved in anhydrous tetrahydrofuran (1.0 mL) and treated with 2.0 eq methylmagnesium bromide in butyl ether (1.0 mL 1.0 M solution, 1.0 mmol). The vial was flushed with nitrogen and stirred at room temperature for 3 h. The reaction was diluted with ethyl acetate (5.0 mL), quenched with saturated aqueous ammonium chloride (1.0 mL) and stirred overnight at room temperature. The organic layer was separated, concentrated in vacuo, then dissolved in methanol:acetonitrile (3.0 mL, 1:1 v/v) and subjected to reverse-phase HPLC purification (5-50% $CH_3CN$/0.08% TFA) to yield 4-(5-chloro-2-methoxyphenyl)-1-(1-methylcyclo-hexyl)piperidine (compound no. 300) as the TFA salt. LC/MS (RP-$C_{18}$, 10-99% $CH_3CN$/0.05% TFA gradient over 5 min) m/z 322.0 [M+H]$^+$, retention time 2.39 min.

Example 14

2-(1-((1S,2R,4R)-bicyclo[2.2.1]heptan-2-yl)piperidin-4-yl)phenol (Compound No. 229) and 1-((1S,2R,4R)-bicyclo[2.2.1]heptan-2-yl)-4-(2'-fluorobiphenyl-2-yl)piperidine (Compound No. 10)

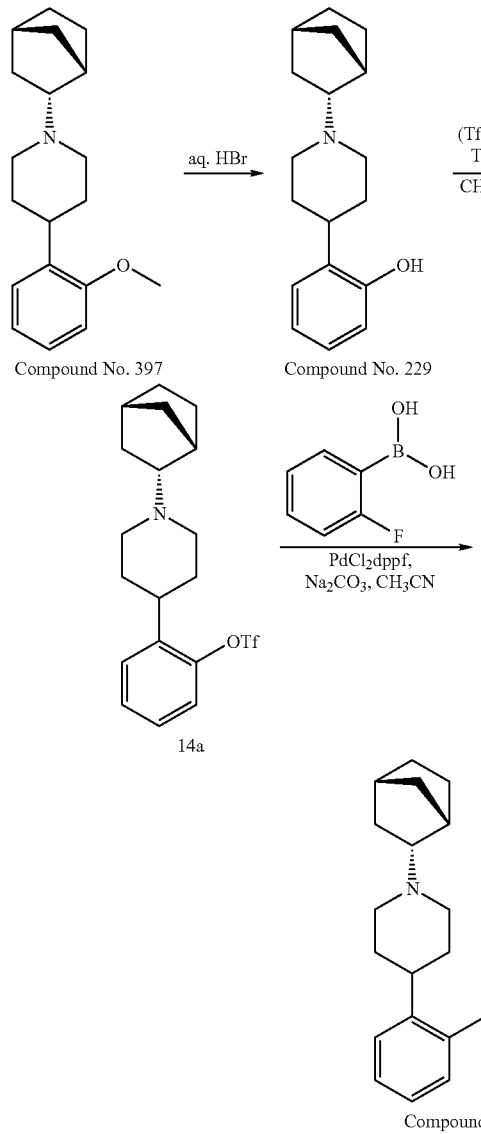

1-((1S,2R,4R)-bicyclo[2.2.1]heptan-2-yl)-4-(2-methoxyphenyl)piperidine (compound no. 397) (2.000 g, 6.21 mmol) was dissolved in acetic acid (33 mL) and treated with aq. HBr 48% (33 mL). After refluxing for 4 h the solvent was evaporated under reduced pressure, and the residue was azeotroped with dichloromethane (3×30 mL) to eliminate most of the acetic acid. Diethyl ether (100 mL) was added to the residue, and the mixture was shaken with saturated $K_2CO_3$ (100 mL) until most solids disappeared. The layers were separated, and the aqueous layer was extracted with diethyl ether (4×100 mL). The combined ethereal extracts were dried over $Na_2SO_4$ and concentrated. The crude product was dissolved in diethyl ether (40 mL) and treated with excess 1 N HCl in ether (20 mL). The pink precipitate was collected by filtration and dried under vacuum to provide 2-(1-((1S,2R,4R)-bicyclo[2.2.1]heptan-2-yl)piperidin-4-yl)phenol (compound no. 229) as a white solid. LC/MS (RP-$C_{18}$, 10-99% $CH_3CN$/0.05% TFA gradient over 5 min) m/z 272.0 $[M+H]^+$, retention time 1.83 min.

2-(1-((1S,2R,4R)-Bicyclo[2.2.1]heptan-2-yl)piperidin-4-yl)phenol (compound no. 229) (900 mg, 2.92 mmol) was dissolved in dichloromethane (100 mL) and treated with $Et_3N$ (895 uL, 650 mg, 6.43 mmol) The solution was cooled to –30° C. under $N_2$ and treated slowly with a solution of triflic anhydride (738 uL, 1237 mg, 4.39 mmol) in $CH_2Cl_2$ (12 mL). The reaction was allowed to warm up to room temperature and stirred for 48 h. The reaction was diluted with $H_2O$ (150 mL) and 1N NaOH (10 mL) and the layers were separated. The aqueous layer was extracted with dichloromethane (3×100 mL). The combined organic layers were dried over $Na_2SO_4$ and concentrated to afford the crude product as a pale-brown oil. This material was dissolved in diethyl ether (50 mL), filtered, and the solution was treated with excess 1N HCl in diethyl ether to provide the hydrochloride of the desired intermediate 14a as an off-white solid. LC/MS (RP-$C_{18}$, 10-99% $CH_3CN$/0.05% TFA gradient over 5 min) m/z 403.6 $[M+H]^+$, retention time 2.42 min.

2-(1-((1S,2R,4R)-bicyclo[2.2.1]heptan-2-yl)piperidin-4-yl)phenyl trifluoromethanesulfonate 14a (22.0 mg, 0.05 mmol) was mixed with 2-fluorophenylboronic acid (10.4 mg, 0.075 mmol) and $PdCl_2dppf(CH_2Cl_2)_2$ (10 mg, 0.013 mmol) in a microwave vial. The vial was sealed, flushed with $N_2$ and acetonitrile (0.75 mL) was added, followed by 2 M $Na_2CO_3$ (250 uL). Added 0.3 mL water to each reaction to help dissolve the inorganic base. The reactions were microwaved at 140° C. for 20 min. The reaction mixtures were filtered, the filtrate was diluted to 1 mL with methanol and the products were purified by LC/MS (10-99 $CH_3CN$—$H_2O$ gradient w/0.03% TFA, 9 min) to provide 1-((1S,2R,4R)-bicyclo[2.2.1]heptan-2-yl)-4-(2'-fluorobiphenyl-2-yl)piperidine (compound no. 10) as the TFA salt. LC/MS (RP-$C_{18}$, 10-99% $CH_3CN$/0.05% TFA gradient over 5 min) m/z 350.2 $[M+H]^+$, retention time 2.82 min.

Example 15

1-(2-(1-((1S,2R,4R)-bicyclo[2.2.1]heptan-2-yl)piperidin-4-yl)phenoxy)propan-2-one (Compound No. 53)

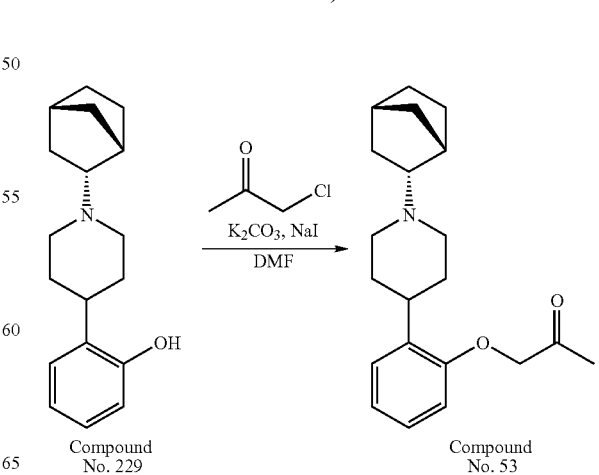

2-(1-((1S,2R,4R)-Bicyclo[2.2.1]heptan-2-yl)piperidin-4-yl)phenol (compound no. 229) (27.0 mg, 0.1 mmol) was dissolved in DMF (0.5 mL) and treated with $K_2CO_3$ (100 mg, 0.72 mmol) followed by the 1-chloropropan-2-one (19 mg, 0.4 mmol) and NaI (100 mg, 0.66 mmol) and the reaction was allowed to stir at room temperature for 48 h. The crude reaction mixture was filtered, diluted with DMSO to 1 mL and purified by LC/MS (10-99 $CH_3CN$—$H_2O$ gradient with 0.03% TFA, 9 minute) to provide 1-(2-(1-((1S,2R,4R)-bicyclo[2.2.1]heptan-2-yl)piperidin-4-yl)phenoxy)propan-2-one (compound no. 53) as the TFA salt. LC/MS (RP-$C_{18}$, 10-99% $CH_3CN$/0.05% TFA gradient over 5 min) m/z 327.0 [M+H]$^+$, retention time 2.32 min.

Example 16

The examples and schemes along with known synthetic methodologies are useful in synthesizing compounds including the compounds in Table 2 below.

Other compounds of formula I were synthesized using known methods and those described herein.

Compound 107
$^1$H-NMR (CDCl$_3$, 300 MHz), δ 7.03-6.91 (m, 2H), 6.73 (d, J=8.2 Hz, 1H), 3.77 (s, 3H), 3.87-3.63 (m, 2H), 3.58-3.27 (m, 2H), 3.27-3.15 (m, 1H, single diastereomer), 3.15-2.98 (m, 1H), 2.98-2.85 (m, 1H, single diastereomer), 2.83-2.65 (m, 2H), 2.26 (s, 3H), 2.40-2.15 (m, 4H), 2.04-1.86 (m, 3H), 1.67-1.08 (m, 7H), 0.88-0.77 (m, 1H, single diastereomer).

Compound 244
$^1$H-NMR (CDCl$_3$, 300 MHz), δ 7.08 (d, J=8.5 Hz, 1H), 6.73 (dd, J=2.8 and 8.4 Hz, 1H), 6.68 (d, J=2.7 Hz, 1H), 3.76 (s, 3H), 3.83-3.66 (m, 2H), 3.43-3.26 (m, 1H), 2.90-2.72 (m, 3H), 2.51-2.33 (m, 3H), 2.41 (s, 3H), 2.33-2.10 (m, 2H), 2.03-1.87 (m, 3H), 1.87-1.63 (m, 3H), 1.62-1.37 (m, 5H), 1.16-1.04 (m, 1H, single diastereomer).

Compound 424
$^1$H-NMR (CDCl$_3$, 300 MHz), δ 7.08 (dd, J=6.1 and 8.3 Hz, 1H), 6.91 (dt, J=10.1 and 2.9 Hz, 1H), 6.81 (dt, J=2.5 and 8.3 Hz, 1H), 3.87-3.68 (m, 2H), 3.28-2.99 (m, 1H), 2.97-2.63 (m, 4H), 2.28 (s, 3H), 2.41-2.16 (m, 3H), 2.04-1.71 (m, 5H), 1.66-1.09 (m, 7H), 0.88-0.77 (m, 1H, single diastereomer).

Compound 385
$^1$H-NMR (CDCl$_3$, 300 MHz), δ 7.19 (d, J=1.9 Hz, 1H), 7.13-7.01 (m, 2H), 3.96 (d, J=11.6 Hz, 1H), 3.68 (d, J=12.6 Hz, 1H), 3.39-3.29 (m, 1H, single diastereomer), 3.04 (br s, 1H), 2.86 (tt, J=3.4 Hz and 12.5 Hz, 1H), 2.79-2.31 (m, 4H), 2.27 (s, 3H), 2.08-1.83 (m, 4H), 1.73-1.39 (m, 7H).

Compound 166
$^1$H-NMR (CDCl$_3$, 300 MHz), δ 7.93 (br s, 1H), 7.78 (dd, J=2.4 and 8.9 Hz, 1H), 6.94 (app t, J=2.4 Hz, 1H), 6.80 (d, J=8.9 Hz, 1H), 3.78 (s, 3H), 3.88-3.63 (m, 2H), 3.53-2.87 (m, 5H), 2.87-2.68 (m, 2H), 2.16 (s, 3H), 2.39-2.19 (m, 4H), 2.11-1.83 (m, 2H), 1.77-1.07 (m, 7H), 0.88-0.74 (m, 1H, single diastereomer).

Compound 31
$^1$H-NMR (400 MHz, DMSO-d$_6$) δ 10.91 (br s, 1H), 7.54 (d, J=2.8 Hz, 1H), 7.31 (dd, J=8.7, 2.7 Hz, 1H), 7.01 (d, J=8.8 Hz, 1H), 5.61 (s, 1H), 4.12 (m, 2H), 4.05 (q, J=7.1 Hz, 2H), 3.84 (s, 3H), 3.33 (m, 3H), 3.21 (m, 2H), 2.97 (m, 2H), 2.81 (br s, 2H), 2.19 (m, 2H), 1.64 (m, 4H), 1.20 (t, J=7.1 Hz, 3H).

Compound 330
$^1$H-NMR (400 MHz, CDCl$_3$) δ 12.22 (br s, 1H), 7.00 (dd, J=9.3, 3.0 Hz, 1H), 6.88 (m, 1H), 6.77 (dd, J=9.0, 4.5 Hz, 1H), 4.46 (br s, 2H), 4.17 (q, J=7.1 Hz, 2H), 3.80 (s, 3H), 3.71 (m, 1H), 3.54 (m, 2H), 3.12 (m, 1H), 2.88 (br s, 2H), 2.57 (m, 2H), 2.03 (m, 6H), 1.79 (m, 4H), 1.28 (t, J=7.1 Hz, 3H).

Compound 207
$^1$H-NMR (400 MHz, CDCl$_3$) δ 11.91 (br s, 1H), 7.01 (m, 1H), 6.87 (m, 1H), 6.76 (dd, J=9.0, 4.5 Hz, 1H), 3.80 (s, 3H), 3.67 (m, 2H), 3.17 (m, 2H), 2.76 (m, 2H), 2.56 (m, 2H), 2.46 (m, 2H), 1.4-2.1 (m, 12H).

Compound 381
$^1$H-NMR (400 MHz, DMSO-d$_6$) δ 10.28 (br s, 1H), 7.21 (m, 1H), 6.97 (m, 2H), 3.48 (m, 2H), 3.31 (m, 1H), 3.05 (m, 3H), 2.58 (m, 1H), 2.45 (m, 1H), 2.30 (s, 3H), 2.23 (m, 2H), 1.96 (m, 2H), 1.82 (m, 2H), 1.56 (m, 3H), 1.40 (m, 3H).

Compound 354
$^1$H-NMR (400 MHz, DMSO-d$_6$) δ 10.19 (br s, 1H), 7.02 (m, 3H), 3.79 (s, 3H), 3.47 (m, 2H), 3.30 (m, 1H), 3.19 (m, 1H), 3.04 (m, 2H), 2.57 (m, 1H), 2.39 (m, 1H), 2.26 (m, 1H), 2.17 (m, 1H), 1.85 (m, 4H), 1.53 (m, 3H), 1.39 (m, 3H).

Compound 27
$^1$H-NMR (400 MHz, CDCl$_3$) δ 11.93 (br s, 1H), 7.22 (d, J=2.5 Hz, 1H), 7.15 (dd, J=8.8, 2.4 Hz, 1H), 6.76 (d, J=8.7 Hz, 1H), 3.81 (s, 3H), 3.67 (m, 2H), 3.19 (m, 1H), 3.09 (m, 1H), 2.76 (m, 2H), 2.53 (m, 2H), 2.43 (m, 2H), 1.4-2.1 (m, 12H).

Compound 187
$^1$H-NMR (400 MHz, CDCl$_3$) δ 11.70 (br s, 1H), 7.31 (d, J=2.4 Hz, 1H), 7.23 (dd, J=8.7, 2.4 Hz, 1H), 6.64 (d, J=8.7 Hz, 1H), 3.75 (s, 3H), 3.73 (br d, 1H), 3.58 (br d, 1H), 3.02 (m, 2H), 2.85 (m, 1H), 2.62 (m, 3H), 2.27 (m, 2H), 1.89 (m, 4H), 1.59 (m, 4H), 1.41 (m, 2H).

Compound 357
$^1$H NMR (400 MHz, DMSO-d$_6$) δ 10.65 (bs, 1H), 7.98 (d, J=8.5 Hz, 2H), 7.87 (d, J=8.5 Hz, 2H), 7.65 (dd, J=8.5, 2.3 Hz, 1H), 7.50 (d, J=2.2 Hz, 1H), 7.16 (d, J=8.7 Hz, 1H), 3.99 (dd, J=11.2, 3.7 Hz, 2H), 3.88 (s, 3H), 3.56 (d, J=11.5 Hz, 2H), 3.47-3.31 (m, 4H), 3.25 (s, 3H), 3.12 (q, J=11.3 Hz, 2H), 2.24 (q, J=12.1 Hz, 2H), 2.06 (d, J=11.6 Hz, 2H), 1.99 (d, J=13.2 Hz, 2H), 1.82-1.72 (m, 2H).

Compound 303
$^1$H NMR (400 MHz, DMSO-d$_6$) δ 9.03 (s, 1H), 7.98 (d, J=8.6 Hz, 2H), 7.88 (d, J=8.6 Hz, 2H), 7.67 (dd, J=8.6, 2.3 Hz, 1H), 7.50 (d, J=2.3 Hz, 1H), 7.17 (d, J=8.7 Hz, 1H), 3.88 (s, 3H), 3.57 (d, J=11.8 Hz, 1H), 3.51 (d, J=12.3 Hz, 1H), 3.41-3.36 (m, 1H), 3.32-3.23 (m, 1H), 3.25 (s, 3H), 3.18-3.06 (m, 2H), 2.62 (s, 1H), 2.30 (s, 1H), 2.17-1.95 (m, 5H), 1.68-1.53 (m, 3H), 1.46-1.38 (m, 3H), 1.27-1.23 (m, 1H).

Compound 262
$^1$H NMR (400 MHz, DMSO-d$_6$) δ 11.12 (s, 1H), 7.23-7.16 (m, 2H), 7.12-7.09 (m, 1H), 4.13 (d, J=12.2 Hz, 2H), 4.05 (q, J=7.1 Hz, 2H), 3.84 (s, 1H), 3.49-3.40 (m, 2H), 3.36 (s, 1H), 3.18 (q, J=11.2 Hz, 2H), 3.08 (dt, J=19.6, 7.0 Hz, 1H), 2.98 (dt, J=20.0, 7.2 Hz, 1H), 2.81 (bs, 2H), 2.19 (d, J=11.6 Hz, 2H), 2.01 (t, J=11.4 Hz, 2H), 1.66 (q, J=12.2 Hz, 2H), 1.20 (t, J=7.1 Hz, 3H).

Compound 397
$^1$H NMR (400 MHz, DMSO-d$_6$) δ 9.93 (bs, 1H), 3.80 (dt, J=8.97, 1.68 Hz, 1H), 3.80 (dd, J=7.6, 1.56 Hz, 1H), 3.80 (dd, J=8.3, 0.7 Hz, 1H), 3.80 (dt, J=7.48, 0.9 Hz, 1H), 3.80 (s, 3H), 3.51 (d, J=11.5 Hz, 1H), 3.45 (d, J=11.6 Hz, 1H), 3.34-3.29 (m, 1H), 3.22-3.14 (m, 1H), 3.11-2.97 (m, 2H), 2.58 (bs, 1H), 2.39-2.30 (m, 1H), 2.27 (bs, 1H), 2.19-2.08 (m, 1H), 1.95 (dt, J=17.4, 6.0 Hz, 1H), 1.88-1.80 (m, 3H), 1.56-1.46 (m, 3H), 1.43-1.36 (m, 3H).

Compound 211
$^1$H NMR (400 MHz, DMSO-$d_6$) δ 10.44 (s, 1H), 7.23 (dt, J=10.4, 4.3 Hz, 1H), 7.15 (dd, J=7.6, 1.5 Hz, 1H), 7.00 (dd, J=7.9, 0.4 Hz, 1H), 6.95 (dt, J=10.2, 3.7 Hz, 1H), 4.12 (d, J=11.8 Hz, 2H), 4.05 (q, J=7.1 Hz, 2H), 3.80 (s, 3H), 3.49 (d, J=11.3 Hz, 2H), 3.41-3.35 (m, 1H), 3.34 (s, 1H), 3.22-3.08 (m, 3H), 2.82 (bs, 1H), 2.14-2.05 (m, 4H), 1.90 (d, J=13.3 Hz, 2H), 1.65-1.55 (m, 2H), 1.20 (t, J=7.1 Hz, 3H).

Compound 249
$^1$H NMR (400 MHz, DMSO-$d_6$) δ 10.57 (s, 1H), 7.29 (dd, J=8.7, 2.4 Hz, 1H), 7.11 (d, J=2.4 Hz, 1H), 7.04 (d, J=8.8 Hz, 1H), 3.98 (dd, J=11.0, 3.5 Hz, 2H), 3.81 (s, 3H), 3.53 (d, J=11.6 Hz, 2H), 3.42-3.30 (m, 3H), 3.18 (t, J=12.2 Hz, 1H), 3.08 (q, J=10.9 Hz, 2H), 2.14-2.03 (m, 4H), 1.92 (d, J=13.2 Hz, 2H), 1.79-1.71 (m, 2H).

Compound 247
$^1$H NMR (400 MHz, DMSO-$d_6$) δ 10.21 (s, 1H), 7.19-7.14 (m, 1H), 7.10-7.04 (m, 2H), 3.79 (s, 3H), 3.41-3.26 (m, 3H), 3.09-3.00 (m, 2H), 2.99 (s, 3H), 2.48-2.39 (m, 2H), 2.32-2.29 (m, 4H), 2.01-1.97 (m, 2H), 1.70-1.56 (m, 4H), 1.50-1.34 (m, 4H).

Compound 24
$^1$H NMR (400 MHz, DMSO-d6) δ 10.09 (s, 1H), 7.25-7.10 (m, 4H), 3.52 (d, J=11.3 Hz, 1H), 3.46 (d, J=11.8 Hz, 1H), 3.35-3.22 (m, 1H), 3.11-2.99 (m, 3H), 2.58 (bs, 1H), 2.48-2.37 (m, 1H), 2.33 (s, 3H), 2.27 (bs, 1H), 2.26-2.15 (m, 1H), 2.00-1.89 (m, 2H), 1.82 (t, J=16.3 Hz, 2H), 1.60-1.47 (m, 3H), 1.45-1.37 (m, 3H).

TABLE 2

Physical Data for exemplary compounds

| Compound No. | LCMS_Plus | LCMS_RT |
|---|---|---|
| 1 | 329.2 | 1.67 |
| 2 | 290 | 1.9 |
| 3 | 354.2 | 2.25 |
| 4 | 304.2 | 2.24 |
| 5 | 334 | 2.39 |
| 6 | 405 | 2.41 |
| 7 | 404.2 | 2.51 |
| 8 | 475.2 | 2.28 |
| 9 | 308.4 | 2.52 |
| 11 | 443.4 | 1.97 |
| 12 | 408.2 | 2.77 |
| 13 | 392.4 | 2.69 |
| 14 | 396.1 | 2.5 |
| 15 | 260 | 3.74 |
| 16 | 424.2 | 2.95 |
| 17 | 459.4 | 2.4 |
| 18 | 316 | 2.47 |
| 19 | 342 | 2.45 |
| 20 | 386.26 | 1.95 |
| 21 | 344 | 2.9 |
| 22 | 414.2 | 1.89 |
| 23 | 470.4 | 2.94 |
| 25 | 302 | 1.89 |
| 26 | 314.2 | 2.66 |
| 28 | | |
| 29 | 314.2 | 2.06 |
| 30 | 356.2463 | 1.74 |
| 32 | 325 | 2.26 |
| 33 | 516.4 | 2.63 |
| 34 | 302 | 4.43 |
| 35 | 304.2 | 2.23 |
| 36 | 407 | 2.13 |
| 37 | 302 | 1.91 |
| 38 | 288 | 4.21 |
| 39 | 379.2 | 2.38 |
| 40 | 336.2 | 2.41 |
| 41 | 307 | 1.68 |
| 42 | 386.2 | 2.47 |
| 43 | 501.2 | 2.48 |
| 44 | 350.2 | 2.54 |
| 45 | 346.2 | 2.91 |
| 46 | 282.4 | 2.27 |
| 47 | 314.2 | 2.72 |
| 48 | 398.2 | 2.78 |
| 49 | 312.2 | 1.87 |
| 50 | 390 | 2.46 |
| 52 | 396.2 | 2.3 |
| 54 | 421 | 2.34 |
| 55 | 411.4 | 2.37 |
| 56 | 328.2 | 2.87 |
| 57 | 420 | 2.75 |
| 58 | 315 | 2.45 |
| 59 | 310.2 | 2.23 |
| 60 | 332 | 2.17 |
| 61 | 313.241 | 2.14 |
| 63 | 336.2 | 2.3 |
| 65 | 397.2 | 2.13 |
| 66 | 338 | 1.77 |
| 67 | 376.2 | 2.82 |
| 68 | 300.4 | 2.56 |
| 69 | 392.2 | 2.68 |
| 70 | 330 | 2.05 |
| 71 | 379 | 379 |
| 72 | 398.2933 | 1.15 |
| 73 | 287.422 | 2.1 |
| 74 | 366.2 | 2.49 |
| 75 | 356.2463 | 1.73 |
| 76 | 322 | 2.26 |
| 77 | 420.2 | 2.73 |
| 78 | 304.2 | 2.15 |
| 79 | 286.1 | 1.98 |
| 80 | 364.2 | 2.55 |
| 81 | 301.449 | 2.14 |
| 82 | 401 | 2.66 |
| 83 | 352.3 | 2.52 |
| 84 | 433.4 | 2.32 |
| 85 | 286.2 | 2.1 |
| 86 | 284.2 | 2.37 |
| 87 | 463.4 | 2.26 |
| 88 | 366.2 | 2.81 |
| 89 | 384.2776 | 1.33 |
| 90 | 275.8 | 1.74 |
| 91 | 322.2 | 2.41 |
| 92 | 387.2 | 2.5 |
| 93 | 269.8 | 2.07 |
| 94 | 413 | 2.66 |
| 95 | 391.3 | 2.15 |
| 96 | 317.191 | 1.58 |
| 97 | 387 | 2.56 |
| 98 | 461.4 | 2.53 |
| 99 | 324.2 | 2.31 |
| 100 | 467.4 | 2.36 |
| 101 | 352 | 2.56 |
| 102 | 440.4 | 2.55 |
| 103 | 322 | 2.1 |
| 104 | 332 | 2.53 |
| 105 | 417 | 2.7 |
| 106 | 365 | 2.29 |
| 108 | 425.2 | 2.46 |
| 109 | 370.5 | 2.83 |
| 110 | 332.2 | 2.79 |
| 111 | 330.2 | 2.4 |
| 112 | 328 | 2.63 |
| 113 | 274.3 | 2.37 |
| 114 | 362.2 | 2.83 |
| 115 | 344 | 2.32 |
| 116 | 362.2 | 2.73 |
| 117 | 302 | 1.78 |

TABLE 2-continued

Physical Data for exemplary compounds

| Compound No. | LCMS_Plus | LCMS_RT |
|---|---|---|
| 118 | 421.3 | 2.2 |
| 119 | 420.2 | 2.83 |
| 120 | 430.2 | 2.97 |
| 121 | 324.4 | 2.24 |
| 122 | 414 | 2.59 |
| 123 | 354 | 2.2 |
| 125 | 334.2 | 2.83 |
| 126 | 446.2 | 3.01 |
| 127 | 459.4 | 3 |
| 128 | 473.4 | 2.59 |
| 129 | 509.2 | 2.7 |
| 130 | 393 | 2.8 |
| 131 | 398.2 | 2.28 |
| 132 | 300 | 2.28 |
| 133 | 305 | 2.4 |
| 134 | 334 | 2.43 |
| 135 | 300.2 | 2.05 |
| 136 | 311 | 2.17 |
| 137 | 442.4 | 2.69 |
| 138 | 330 | 2.7 |
| 139 | 392.2 | 2.74 |
| 141 | 332.2 | 2.46 |
| 142 | 366.2 | 2.93 |
| 143 | 396.2 | 2.85 |
| 144 | 405.4 | 2.19 |
| 145 | 374.2369 | 1.49 |
| 146 | 515.5 | 2.28 |
| 147 | 370.2 | 2.41 |
| 148 | 363.2 | 1.7 |
| 149 | 338 | 2.71 |
| 150 | 338.2 | 2.06 |
| 151 | 390.2074 | 1.92 |
| 152 | 330 | 2.68 |
| 153 | 476.2 | 2.43 |
| 154 | 302 | 1.85 |
| 155 | 316 | 2.56 |
| 156 | 340.2 | 2.88 |
| 157 | 317.191 | 1.54 |
| 158 | 288 | 2.32 |
| 159 | 329.2354 | 1.7 |
| 160 | 346.2 | 2.25 |
| 161 | 340.2 | 2.75 |
| 162 | 488.4 | 2.53 |
| 163 | 308.4 | 2.07 |
| 164 | 366.2 | 2.75 |
| 165 | 322 | 2.1 |
| 167 | 316.2 | 2.48 |
| 168 | 362.2 | 2.68 |
| 169 | 300.4 | 2.51 |
| 170 | 424 | 2.85 |
| 171 | 298.2 | 2.03 |
| 172 | 323.2 | 2.33 |
| 173 | 415.2 | 2.61 |
| 174 | 318 | 2.27 |
| 175 | 356 | 2.93 |
| 176 | 306 | 2.47 |
| 177 | 397 | 2.21 |
| 178 | 396 | 2.81 |
| 179 | 391.4 | 2.22 |
| 180 | 270.2 | 2.11 |
| 181 | 322.2 | 2.35 |
| 182 | 313.2405 | 1.57 |
| 183 | 340 | 2.42 |
| 184 | 453.2 | 1.87 |
| 185 | 313.49 | 2.06 |
| 186 | 398.2933 | 1.46 |
| 188 | 404.2 | 2.85 |
| 189 | 395 | 2.21 |
| 190 | 401 | 2.52 |
| 191 | 393 | 2.16 |
| 192 | 419 | 2.44 |
| 193 | 294.2 | 2.04 |
| 194 | 398.2933 | 1.43 |
| 195 | 376.2 | 2.76 |
| 196 | 433.4 | 2.27 |
| 197 | 318 | 1.66 |
| 198 | 409.4 | 2.12 |
| 199 | 342 | 5.01 |
| 200 | 292 | 2.34 |
| 201 | 340.2 | 2.14 |
| 202 | 373 | 2.37 |
| 203 | 338.2 | 2.44 |
| 204 | 429.2627 | 1.91 |
| 205 | 291.8 | 2.1 |
| 206 | 398.2 | 2.76 |
| 208 | 386.2569 | 1.52 |
| 210 | 274 | 4.02 |
| 212 | 288.1 | 2.19 |
| 213 | 350.2 | 2.57 |
| 214 | 468.2 | 2.51 |
| 215 | 582.4 | 2.52 |
| 216 | 380.2 | 2.7 |
| 217 | 375 | 2.07 |
| 218 | 302.3 | 1.68 |
| 220 | 313.2405 | 1.51 |
| 221 | 300.4 | 2.5 |
| 223 | 366 | 2.91 |
| 224 | 288.2 | 2.46 |
| 225 | 284 | 2.3 |
| 226 | 540.4 | 2.21 |
| 227 | 322.2 | 2.24 |
| 228 | 350 | 2.42 |
| 230 | 396 | 2.34 |
| 231 | 324.4 | 1.91 |
| 232 | 274.5 | 2.16 |
| 233 | 290 | 2.01 |
| 234 | 350 | 2.61 |
| 235 | 291.8 | 1.26 |
| 236 | 300 | 2.05 |
| 237 | 352.2 | 2.54 |
| 238 | 346 | 2.19 |
| 239 | 326.6 | 2.18 |
| 240 | 325.2 | 2.32 |
| 241 | 362.2 | 2.74 |
| 242 | 336.3 | 2.44 |
| 243 | 494.4 | 2.13 |
| 246 | 313.485 | 2.26 |
| 248 | 342 | 1.86 |
| 250 | 311.2 | 2.03 |
| 251 | 390.4 | 2.75 |
| 252 | 286.2 | 1.87 |
| 253 | 397.2 | 2.44 |
| 254 | 488.4 | 2.45 |
| 255 | 328 | 4.79 |
| 256 | 329.2354 | 1.49 |
| 257 | 340.1 | 2.73 |
| 258 | 454 | 2.43 |
| 259 | 275 | 1.96 |
| 260 | 314.2 | 2.46 |
| 261 | 338 | 2.73 |
| 263 | 391.4 | 2.23 |
| 264 | 386 | 2.05 |
| 265 | 274 | 4.05 |
| 266 | 317 | 1.71 |
| 267 | 380 | 2.73 |
| 268 | 428.2 | 2.57 |
| 269 | 390 | 2.74 |
| 270 | 506.2 | 2.13 |
| 271 | 415 | 2.27 |
| 272 | 504.4 | 2.64 |
| 274 | 350 | 2.85 |
| 275 | 414.2 | 2.48 |
| 276 | 291.8 | 2.07 |
| 277 | 376.2 | 2.82 |
| 278 | 303.1753 | 1.21 |
| 279 | 313 | 2.33 |
| 280 | 347.8 | 2.65 |
| 281 | 260.1 | 1.74 |
| 282 | 342.2 | 2.23 |
| 283 | 346.2 | 2.9 |

TABLE 2-continued

Physical Data for exemplary compounds

| Compound No. | LCMS_Plus | LCMS_RT |
|---|---|---|
| 284 | 406.4 | 2.63 |
| 285 | 409.4 | 1.9 |
| 286 | 362.2 | 2.53 |
| 287 | 394 | 2.42 |
| 288 | 364.2 | 2.62 |
| 290 | 287 | 2.21 |
| 291 | 326.2 | 2.64 |
| 292 | 346.2 | 2.27 |
| 293 | 350.4 | 2.67 |
| 294 | 350 | 2.84 |
| 295 | 409.4 | 2.32 |
| 296 | 352 | 2.45 |
| 297 | 481.2 | 2.5 |
| 298 | 528.4 | 2.18 |
| 299 | 356.2463 | 1.38 |
| 301 | 402.2518 | 1.62 |
| 302 | 346.2 | 2.88 |
| 304 | 326.2 | 2.04 |
| 305 | 312 | 1.69 |
| 306 | 345.2 | 2.19 |
| 307 | 298.5 | 2.15 |
| 308 | 350.1 | 2.19 |
| 309 | 338 | 2.34 |
| 310 | 336.2 | 2.41 |
| 311 | 336.2 | 2.29 |
| 312 | 287.18 | 1.64 |
| 313 | 502.2 | 2.53 |
| 314 | 312.2 | 1.94 |
| 315 | 342.2307 | 1.83 |
| 316 | 380.2 | 2.9 |
| 317 | 474.2 | 2.46 |
| 318 | 398.2 | 2.76 |
| 319 | 348 | 2.43 |
| 320 | 288.4 | 2.54 |
| 321 | 327.8 | 1.98 |
| 322 | 409.4 | 2.24 |
| 323 | 476.2 | 2.5 |
| 324 | 352 | 2.23 |
| 326 | 352.2 | 2.57 |
| 327 | 352.2 | 2.72 |
| 328 | 453 | 2.21 |
| 329 | 296 | 2.41 |
| 332 | 483.2 | 2.6 |
| 333 | 328 | 2.47 |
| 334 | 409.22 | 2.27 |
| 335 | 341 | 2.68 |
| 336 | 413 | 2.66 |
| 337 | 413 | 2.68 |
| 338 | 315.2198 | 1.17 |
| 339 | 411.8 | 2.76 |
| 340 | 332 | 2.04 |
| 341 | 284.2 | 2.28 |
| 342 | 375.2 | 2.52 |
| 343 | 338.2 | 2.53 |
| 344 | 329.2354 | 1.68 |
| 345 | 462.2 | 2.5 |
| 346 | 246.2 | 1.9 |
| 347 | 405.4 | 2.12 |
| 348 | 299.2 | 2.2 |
| 349 | 294 | 1.84 |
| 350 | 377 | 2.38 |
| 351 | 495.2 | 2.64 |
| 352 | 377.4 | 2.23 |
| 353 | 441.4 | 2.21 |
| 355 | 427 | 2.4 |
| 356 | 352.2 | 2.44 |
| 358 | 328 | 2.53 |
| 359 | 323.2 | 2.36 |
| 360 | 433.2 | 2.28 |
| 361 | 443.2 | 2.79 |
| 362 | 379 | 2.43 |
| 363 | 386.537 | 1.98 |
| 364 | 379.2 | 2.22 |
| 365 | 368.2 | 2.7 |
| 366 | 380.2 | 2.72 |
| 367 | 338.2 | 2.34 |
| 368 | 399.2 | 2.3 |
| 369 | 276 | 1.71 |
| 370 | 370 | 2.24 |
| 371 | 304.4 | 2.32 |
| 372 | 324.2 | 2.06 |
| 373 | 315.2 | 1.97 |
| 374 | 318 | 1.94 |
| 375 | 339 | 1.93 |
| 376 | 327 | 2.15 |
| 377 | 408.4 | 2.53 |
| 378 | 263.8 | 1.59 |
| 379 | 301.2 | 1.87 |
| 380 | 338.2 | 2.44 |
| 382 | 394.2 | 2.58 |
| 383 | 387 | 2.6 |
| 384 | 328.2 | 2.82 |
| 386 | 360.2 | 2.96 |
| 387 | 493.4 | 2.52 |
| 388 | 419.2 | 2.19 |
| 389 | 478.2 | 2.27 |
| 390 | 437.2 | 2.41 |
| 391 | 353 | 1.86 |
| 392 | 381.2 | 2.24 |
| 393 | 392.4 | 2.66 |
| 394 | 348.2 | 2.43 |
| 395 | 366.2 | 2.9 |
| 396 | 426 | 2.63 |
| 398 | 288 | 4.02 |
| 399 | 389.2 | 2.48 |
| 400 | 419 | 2.29 |
| 401 | 445.4 | 2.33 |
| 402 | 392.2 | 2.73 |
| 403 | 428.4 | 2.74 |
| 404 | 312.2 | 2.39 |
| 405 | 399.2 | 2.24 |
| 406 | 407.2 | 2.6 |
| 407 | 405.4 | 2.1 |
| 408 | 326.2 | 2.4 |
| 409 | 326.2 | 2.6 |
| 410 | 394 | 2.57 |
| 411 | 570.2 | 2.53 |
| 412 | 318 | 2.48 |
| 413 | 396.2 | 2.89 |
| 414 | 368 | 2.64 |
| 415 | 271 | 1.32 |
| 416 | 380.2 | 2.23 |
| 418 | 342.2 | 2.34 |
| 419 | 317.191 | 1.47 |
| 420 | 362.2 | 2.74 |
| 421 | 325 | 2.36 |
| 422 | 420 | 2.79 |
| 423 | 376 | 2.82 |

Example 17

Assays for Detecting and Measuring Modulation Properties of Compounds

Functional Mobilization of Intracellular Calcium to Determine Muscarinic Receptor Activity:

CHO cells expressing muscarinic receptors ($M_1$ to $M_5$) are grown as monolayers in tissue culture flasks at 37° C. in a humidified atmosphere containing 5% $CO_2$ and passaged every 3-5 days. The growth media is Dulbecco's modified eagles medium (DMEM, Gibco Cat #12430-054), containing 25 mM Hepes and supplemented with Fetal Bovine Serum (Hyclone, cat #SH30071.03), 0.1 mM of MEM non-essential amino acids (GIBCO, Cat #11140-050), 1 mM MEM Sodium Pyruvate (GIBCO Cat #11360-070) and 100 units/ml of Penicillin G and 100 µg/ml of Streptomycin (GIBCO Cat #15140-122). The recombinant muscarinic receptor cell lines are grown under antibiotic pressure with media containing 25 µg/ml zeocin and 500 µg/ml G418 (M1-CHO), 4 µg/ml puromycin, 50 µg/ml zeocin and 2.5 µg/ml blasticidin (M2 and M4-CHO) or 50 µg/ml zeocin and 4 µg/ml puromycin (M3 and M5-CHO).

Cells are harvested at 80-90% confluence using Versene (GIBCO Cat #15040-066), collected by centrifugation and seeded 18-24 hrs prior to running the calcium assay at a density of 5,000-10,000 cells/well in back-walled, clear-bottomed 384-well plates (BD Biocoat, poly-D-lysine, Cat #356663). The day of the experiment, the cells are washed with a plate washer (Bioteck Instruments, ELX 405) using bath 1 buffer (140-mM NaCl, 4.5-mM KCl, 2-mM $CaCl_2$, 1-mM $MgCl_2$, 10-mM Hepes-Na, 10-mM Glucose, pH 7.4, with NaOH) containing 1 mM Probenecid. Next, the calcium dye Fluo-3 (25 µl/well of Fluo-3 AM at 4 µM, Molecular Probes F-1241, in Bath 1 buffer containing 1 mM Probenecid) is added to the 25 µl of Bath 1 remaining in each well after the plate wash and the dye is loaded at 37° C. in the tissue culture incubator for 60-90 min. The fluorescent dye is removed using the plate washer with Bath 1 containing 1 mM Probenecid, leaving 25 µl/well of this solution after the wash. Alternatively, cells can be loaded with the calcium indicator from Molecular Devices (Calcium 3 Assay Reagents, Cat #R7181) adding 5 µl of a 5× solution dye in Bath 1 containing 1 mM Probenecid (10 ml per dye flask cat #R7182 to generate a solution 20×) to 20 µl of the same buffer. After loading for 60 min, the experiment can be run without having to remove the dye.

Compounds are prepared at a 2× fold concentration in a 96-well plate (round bottom, Costar Corning cat #3656), by reconstituting the pre-spotted compounds in bath 1 containing 1 mM probenecid. The final concentration DMSO is 0.5%, and the amount of DMSO is normalized across the assay plate. To determine an agonist action of the compounds on muscarinic receptors, the reconstituted compounds are added (25 µl compound/well) to the cell assay plate (containing 25 µl/well) using the multi-channel robotic system of the FLIPR 3 Instrument (Molecular Devices, Sunnyvale, Calif.). To determine a functional inhibitory action of the compounds on muscarinic receptors, the reconstituted compounds are added (25 µl compound/well) to the assay plate and pre-incubated for 15 min prior to adding 25 µl of Carbachol at 3× the EC80 for each muscarinic subtype. Alternatively, the compounds can be co-applied simultaneously with the agonist. In both assay modes, the fluorescence is recorded for 60 sec (excitation wavelength is 488 nM and emission wavelength 540 nm) using the FLIPR 3 instrument.

The potency, efficacy and selectivity of the muscarinic compounds were evaluated by screening the compound activity across the whole family ($M_1$ to $M_5$ cells). Compounds were also screened for activity on other proteins such as other GPCRs and ion channels to determine selectivity on M4 receptors.

The compounds of the present invention were found to modulate the $M_1$ and/or $M_4$ muscarinic receptors selectively over the other receptor types.

Examples of activities and efficacies of the muscarinic compounds of formulae (I, Ia, Ib, and II) on modulating $M_1$, $M_2$, $M_3$ and $M_4$ receptors are shown below in Table 3. The compound activity for the $M_1$, $M_2$, $M_3$ and $M_4$ is illustrated with "+++" if activity was measured to be less than 1.0 µM, "++" if activity was measured to be from 1.0 µM to 5.0 µM, "+" if activity was measured to be greater than 5.0 µM, and "−" if no data was available. The efficacy for $M_1$, $M_2$, $M_3$ and $M_4$ modulation is illustrated with "+++" if efficacy was calculated to be greater than 100%, "++" if efficacy was calculated to be from 100% to 25%, "+" if efficacy was calculated to be less than 25%, and "−" if no data was available. It should be noted that 100% efficacy is the maximum response obtained with the Carbachol control.

TABLE 3

Compound activities and efficacies for modulating $M_1$ and $M_4$ receptors

| Compound No. | $M_1$ Activity | $M_2$ Activity | $M_3$ Activity | $M_4$ Activity | $M_1$ Efficacy | $M_2$ Efficacy | $M_3$ Efficacy | $M_4$ Efficacy |
|---|---|---|---|---|---|---|---|---|
| 1 | +++ | +++ | − | +++ | ++ | ++ | − | ++ |
| 2 | + | + | + | ++ | ++ | + | + | ++ |
| 3 | + | + | + | + | + | + | + | + |
| 4 | + | + | + | +++ | ++ | + | + | ++ |
| 5 | + | + | + | +++ | ++ | ++ | + | ++ |
| 6 | + | + | + | + | + | + | + | + |
| 7 | + | + | + | ++ | + | + | + | ++ |
| 8 | + | + | + | + | + | + | + | + |
| 9 | +++ | +++ | + | +++ | ++ | ++ | + | ++ |
| 10 | + | + | + | ++ | + | ++ | + | ++ |
| 11 | + | + | + | ++ | + | + | + | ++ |
| 12 | + | + | + | ++ | + | ++ | + | ++ |
| 13 | + | + | + | + | + | + | + | + |
| 14 | +++ | +++ | + | +++ | ++ | ++ | + | ++ |
| 15 | + | + | + | +++ | + | + | + | ++ |
| 16 | + | + | + | ++ | + | + | + | ++ |
| 17 | + | + | + | ++ | + | + | + | ++ |
| 18 | +++ | +++ | + | +++ | ++ | ++ | + | ++ |
| 19 | ++ | + | + | +++ | ++ | + | + | ++ |
| 20 | +++ | + | − | +++ | ++ | + | − | ++ |
| 21 | − | − | − | − | − | − | − | − |
| 22 | + | + | + | + | + | + | + | + |
| 23 | − | − | − | − | − | − | − | − |
| 24 | ++ | ++ | + | +++ | ++ | ++ | + | ++ |
| 25 | + | + | + | + | + | + | − | + |
| 26 | ++ | + | + | +++ | ++ | + | + | ++ |

TABLE 3-continued

Compound activities and efficacies for modulating $M_1$ and $M_4$ receptors

| Compound No. | $M_1$ Activity | $M_2$ Activity | $M_3$ Activity | $M_4$ Activity | $M_1$ Efficacy | $M_2$ Efficacy | $M_3$ Efficacy | $M_4$ Efficacy |
|---|---|---|---|---|---|---|---|---|
| 27 | ++ | ++ | + | +++ | ++ | ++ | + | ++ |
| 28 | + | + | − | + | + | + | − | + |
| 29 | + | + | + | ++ | ++ | + | − | ++ |
| 30 | + | + | − | ++ | ++ | + | − | ++ |
| 31 | ++ | + | + | +++ | ++ | + | + | ++ |
| 32 | + | + | + | +++ | ++ | + | + | ++ |
| 33 | ++ | + | + | ++ | ++ | + | + | ++ |
| 34 | + | + | + | + | + | + | + | + |
| 35 | + | + | + | +++ | ++ | + | + | ++ |
| 36 | + | + | + | ++ | + | + | + | ++ |
| 37 | + | + | + | + | + | + | + | + |
| 38 | + | + | + | +++ | + | + | + | ++ |
| 39 | +++ | +++ | + | +++ | ++ | ++ | + | ++ |
| 40 | ++ | + | + | +++ | ++ | ++ | + | ++ |
| 41 | + | + | + | + | + | + | + | + |
| 42 | + | + | + | ++ | + | + | + | + |
| 43 | +++ | +++ | + | +++ | +++ | ++ | ++ | ++ |
| 44 | + | + | + | ++ | ++ | ++ | + | ++ |
| 45 | + | + | + | + | + | + | + | ++ |
| 46 | ++ | + | + | +++ | ++ | ++ | − | ++ |
| 47 | + | + | + | ++ | ++ | + | + | ++ |
| 48 | + | + | + | + | ++ | + | + | ++ |
| 49 | + | + | + | +++ | ++ | + | + | ++ |
| 50 | + | + | + | ++ | ++ | + | + | ++ |
| 51 | ++ | + | + | +++ | ++ | ++ | + | ++ |
| 52 | + | + | + | + | + | + | + | ++ |
| 53 | ++ | ++ | + | +++ | ++ | ++ | + | ++ |
| 54 | ++ | + | + | +++ | ++ | + | + | ++ |
| 55 | +++ | + | − | +++ | ++ | + | − | ++ |
| 56 | − | − | − | − | − | − | − | − |
| 57 | ++ | ++ | + | ++ | ++ | ++ | + | ++ |
| 58 | + | + | + | ++ | + | + | + | ++ |
| 59 | + | + | + | ++ | ++ | + | + | ++ |
| 60 | + | + | + | ++ | + | + | + | ++ |
| 61 | + | + | − | ++ | + | + | − | ++ |
| 62 | ++ | + | + | ++ | ++ | + | − | ++ |
| 63 | + | + | − | + | + | + | − | ++ |
| 64 | + | + | + | ++ | ++ | ++ | + | ++ |
| 65 | +++ | + | + | +++ | ++ | + | + | ++ |
| 66 | + | + | + | ++ | ++ | + | + | ++ |
| 67 | + | + | + | + | + | + | + | ++ |
| 68 | ++ | + | + | +++ | ++ | + | + | ++ |
| 69 | + | + | + | + | + | + | + | ++ |
| 70 | + | + | + | ++ | ++ | + | + | ++ |
| 71 | + | + | + | + | + | + | + | + |
| 72 | + | + | − | ++ | + | + | − | ++ |
| 73 | ++ | ++ | + | +++ | ++ | ++ | + | ++ |
| 74 | + | + | + | + | + | + | + | + |
| 75 | + | + | − | ++ | + | + | − | ++ |
| 76 | + | + | + | ++ | + | + | + | ++ |
| 77 | + | + | + | + | + | + | + | ++ |
| 78 | ++ | + | + | +++ | ++ | + | + | ++ |
| 79 | + | + | + | +++ | ++ | + | + | ++ |
| 80 | ++ | ++ | − | +++ | ++ | + | − | ++ |
| 81 | + | + | − | ++ | ++ | ++ | − | ++ |
| 82 | + | + | + | + | ++ | + | + | ++ |
| 83 | + | + | + | ++ | ++ | ++ | + | ++ |
| 84 | + | + | + | + | + | + | + | + |
| 85 | + | + | + | +++ | ++ | + | + | ++ |
| 86 | ++ | + | + | +++ | ++ | + | + | ++ |
| 87 | + | + | + | + | + | + | + | + |
| 88 | + | + | + | ++ | + | + | + | ++ |
| 89 | + | + | − | + | + | + | − | + |
| 90 | + | + | + | +++ | ++ | + | + | ++ |
| 91 | ++ | + | − | ++ | + | + | − | ++ |
| 92 | + | + | + | + | + | + | + | + |
| 93 | ++ | + | + | +++ | ++ | + | + | ++ |
| 94 | +++ | +++ | ++ | +++ | ++ | ++ | + | ++ |
| 95 | +++ | + | − | +++ | ++ | + | − | ++ |
| 96 | +++ | ++ | − | +++ | ++ | ++ | − | ++ |
| 97 | + | + | + | + | + | + | + | ++ |
| 98 | + | + | + | ++ | + | + | + | + |
| 99 | + | + | − | ++ | + | + | − | ++ |

TABLE 3-continued

Compound activities and efficacies for modulating $M_1$ and $M_4$ receptors

| Compound No. | $M_1$ Activity | $M_2$ Activity | $M_3$ Activity | $M_4$ Activity | $M_1$ Efficacy | $M_2$ Efficacy | $M_3$ Efficacy | $M_4$ Efficacy |
|---|---|---|---|---|---|---|---|---|
| 100 | + | + | + | ++ | + | + | + | ++ |
| 101 | ++ | + | − | +++ | ++ | + | − | ++ |
| 102 | + | + | + | ++ | + | + | + | ++ |
| 103 | + | + | + | ++ | + | + | + | + |
| 104 | + | + | + | ++ | + | + | + | ++ |
| 105 | ++ | + | + | + | ++ | ++ | + | ++ |
| 106 | +++ | +++ | +++ | +++ | ++ | ++ | + | ++ |
| 107 | + | + | − | +++ | ++ | + | − | ++ |
| 108 | +++ | ++ | + | +++ | ++ | + | + | ++ |
| 109 | ++ | + | + | + | ++ | + | + | ++ |
| 110 | + | + | + | ++ | + | + | + | ++ |
| 111 | ++ | + | + | +++ | ++ | ++ | + | ++ |
| 112 | + | + | + | + | + | + | + | ++ |
| 113 | ++ | + | + | +++ | ++ | + | + | ++ |
| 114 | + | + | + | ++ | + | + | + | ++ |
| 115 | + | + | + | ++ | ++ | + | + | ++ |
| 116 | + | + | + | ++ | ++ | + | + | ++ |
| 117 | + | + | + | + | + | + | + | ++ |
| 118 | +++ | + | + | +++ | ++ | + | + | ++ |
| 119 | + | + | + | ++ | ++ | ++ | + | ++ |
| 120 | + | + | + | + | ++ | + | + | ++ |
| 121 | ++ | + | + | +++ | ++ | + | + | ++ |
| 122 | ++ | ++ | + | +++ | ++ | ++ | + | ++ |
| 123 | ++ | + | + | + | ++ | + | + | + |
| 124 | + | + | + | + | + | + | + | + |
| 125 | +++ | ++ | − | +++ | ++ | ++ | − | ++ |
| 126 | + | + | + | + | ++ | + | + | ++ |
| 127 | ++ | ++ | + | +++ | ++ | ++ | + | ++ |
| 128 | + | + | + | ++ | + | + | + | + |
| 129 | + | + | + | + | + | + | + | ++ |
| 130 | ++ | + | + | +++ | ++ | + | + | ++ |
| 131 | +++ | + | − | +++ | ++ | + | − | ++ |
| 132 | ++ | + | + | ++ | + | + | + | + |
| 133 | + | + | + | +++ | ++ | + | + | ++ |
| 134 | ++ | ++ | + | +++ | ++ | ++ | + | ++ |
| 135 | + | + | + | + | ++ | + | − | + |
| 136 | + | + | − | ++ | ++ | + | − | ++ |
| 137 | − | − | − | − | − | − | − | − |
| 138 | + | + | + | + | + | + | + | + |
| 139 | + | + | + | ++ | ++ | + | + | ++ |
| 140 | ++ | ++ | + | +++ | ++ | ++ | + | ++ |
| 141 | ++ | ++ | − | +++ | ++ | ++ | − | ++ |
| 142 | + | + | + | ++ | ++ | ++ | + | ++ |
| 143 | + | + | + | + | + | + | + | ++ |
| 144 | + | + | + | + | + | + | + | + |
| 145 | +++ | +++ | − | +++ | ++ | ++ | − | ++ |
| 146 | +++ | + | + | +++ | ++ | + | + | ++ |
| 147 | ++ | ++ | + | +++ | ++ | ++ | + | ++ |
| 148 | + | + | + | + | + | + | + | + |
| 149 | + | + | + | + | ++ | + | + | ++ |
| 150 | + | + | + | + | ++ | + | + | ++ |
| 151 | ++ | ++ | − | +++ | ++ | ++ | − | ++ |
| 152 | + | + | + | + | + | + | + | + |
| 153 | ++ | + | + | +++ | ++ | + | + | ++ |
| 154 | + | + | + | + | + | + | + | ++ |
| 155 | + | + | + | + | + | + | + | + |
| 156 | − | − | − | − | − | − | − | − |
| 157 | ++ | + | − | ++ | ++ | + | − | + |
| 158 | + | + | + | +++ | ++ | + | + | ++ |
| 159 | + | + | − | ++ | + | + | − | + |
| 160 | + | + | + | +++ | ++ | + | + | ++ |
| 161 | + | + | + | + | ++ | ++ | + | ++ |
| 162 | − | − | − | − | − | − | − | − |
| 163 | + | + | + | +++ | ++ | + | + | ++ |
| 164 | + | + | + | ++ | + | + | − | ++ |
| 165 | + | + | + | ++ | ++ | + | + | ++ |
| 166 | + | + | − | + | + | + | − | + |
| 167 | ++ | + | + | +++ | ++ | + | + | ++ |
| 168 | + | + | + | + | + | + | + | ++ |
| 169 | ++ | + | + | +++ | ++ | + | + | ++ |
| 170 | + | + | + | +++ | + | + | + | ++ |
| 171 | ++ | + | + | +++ | ++ | + | − | ++ |
| 172 | +++ | +++ | − | +++ | ++ | ++ | − | ++ |

TABLE 3-continued

Compound activities and efficacies for modulating $M_1$ and $M_4$ receptors

| Compound No. | $M_1$ Activity | $M_2$ Activity | $M_3$ Activity | $M_4$ Activity | $M_1$ Efficacy | $M_2$ Efficacy | $M_3$ Efficacy | $M_4$ Efficacy |
|---|---|---|---|---|---|---|---|---|
| 173 | + | + | + | + | + | + | + | ++ |
| 174 | + | + | + | + | + | + | + | + |
| 175 | + | + | + | + | + | + | + | + |
| 176 | +++ | ++ | + | +++ | ++ | ++ | + | ++ |
| 177 | +++ | + | + | +++ | ++ | + | + | ++ |
| 178 | + | + | + | + | + | + | + | ++ |
| 179 | +++ | + | + | +++ | ++ | + | + | ++ |
| 180 | ++ | + | + | +++ | ++ | + | + | ++ |
| 181 | ++ | ++ | + | +++ | ++ | ++ | + | ++ |
| 182 | +++ | ++ | − | +++ | ++ | ++ | − | ++ |
| 183 | + | + | + | +++ | ++ | + | + | ++ |
| 184 | + | + | + | + | + | + | + | + |
| 185 | ++ | + | + | +++ | ++ | ++ | + | ++ |
| 186 | + | + | − | + | + | + | − | + |
| 187 | +++ | ++ | + | +++ | ++ | ++ | + | ++ |
| 188 | + | + | + | ++ | ++ | ++ | + | ++ |
| 189 | +++ | + | + | +++ | ++ | + | + | ++ |
| 190 | + | + | + | + | + | + | + | ++ |
| 191 | − | − | − | − | − | − | − | − |
| 192 | + | + | + | + | ++ | + | + | ++ |
| 193 | ++ | + | + | +++ | ++ | ++ | + | ++ |
| 194 | + | + | − | + | + | + | − | + |
| 195 | + | + | + | +++ | ++ | + | + | ++ |
| 196 | + | + | + | +++ | + | + | + | ++ |
| 197 | + | + | + | + | + | + | + | ++ |
| 198 | ++ | + | + | +++ | ++ | + | + | ++ |
| 199 | + | + | + | + | + | + | + | + |
| 200 | +++ | ++ | + | +++ | ++ | ++ | + | ++ |
| 201 | + | + | − | + | + | + | − | + |
| 202 | +++ | ++ | + | +++ | ++ | ++ | + | ++ |
| 203 | + | + | − | ++ | ++ | + | − | ++ |
| 204 | + | + | − | +++ | + | + | − | ++ |
| 205 | ++ | ++ | + | +++ | ++ | ++ | + | ++ |
| 206 | + | + | + | + | + | + | + | ++ |
| 207 | +++ | + | + | +++ | ++ | + | + | ++ |
| 208 | +++ | + | − | +++ | ++ | + | − | ++ |
| 209 | ++ | ++ | + | +++ | ++ | ++ | + | ++ |
| 210 | + | + | + | +++ | ++ | + | + | ++ |
| 211 | +++ | +++ | + | +++ | ++ | ++ | ++ | +++ |
| 212 | + | + | + | +++ | ++ | + | + | ++ |
| 213 | + | ++ | + | +++ | ++ | ++ | + | ++ |
| 214 | + | + | + | ++ | ++ | + | + | ++ |
| 215 | + | + | + | + | ++ | + | + | + |
| 216 | + | + | + | + | + | + | + | ++ |
| 217 | +++ | + | ++ | +++ | ++ | + | + | ++ |
| 218 | + | + | − | ++ | + | + | − | ++ |
| 219 | +++ | + | + | +++ | ++ | + | + | ++ |
| 220 | + | + | − | + | ++ | + | − | ++ |
| 221 | + | + | + | +++ | ++ | + | + | ++ |
| 222 | + | + | + | + | ++ | + | + | + |
| 223 | + | + | + | + | + | + | + | ++ |
| 224 | + | + | + | +++ | ++ | + | + | ++ |
| 225 | + | + | + | ++ | ++ | + | + | ++ |
| 226 | + | + | + | ++ | + | + | + | ++ |
| 227 | + | + | + | ++ | ++ | + | + | ++ |
| 228 | + | + | − | ++ | + | + | − | ++ |
| 229 | ++ | + | + | ++ | ++ | + | + | ++ |
| 230 | + | + | + | +++ | + | + | + | ++ |
| 231 | + | + | + | + | + | + | + | + |
| 232 | + | + | + | ++ | ++ | + | + | ++ |
| 233 | + | + | + | ++ | ++ | + | + | ++ |
| 234 | + | + | + | + | + | + | + | + |
| 235 | + | + | + | + | ++ | + | + | ++ |
| 236 | ++ | + | + | +++ | ++ | + | + | ++ |
| 237 | + | + | + | ++ | + | + | + | ++ |
| 238 | + | + | + | +++ | ++ | + | + | ++ |
| 239 | + | + | + | ++ | ++ | + | + | ++ |
| 240 | ++ | ++ | − | +++ | ++ | ++ | − | ++ |
| 241 | + | + | + | ++ | ++ | + | + | ++ |
| 242 | ++ | + | + | +++ | ++ | ++ | + | ++ |
| 243 | +++ | + | + | +++ | ++ | + | + | ++ |
| 244 | + | + | − | + | + | + | − | + |
| 245 | +++ | + | − | +++ | ++ | + | − | ++ |

TABLE 3-continued

Compound activities and efficacies for modulating $M_1$ and $M_4$ receptors

| Compound No. | $M_1$ Activity | $M_2$ Activity | $M_3$ Activity | $M_4$ Activity | $M_1$ Efficacy | $M_2$ Efficacy | $M_3$ Efficacy | $M_4$ Efficacy |
|---|---|---|---|---|---|---|---|---|
| 246 | ++ | + | + | +++ | ++ | ++ | + | ++ |
| 247 | + | + | + | +++ | + | + | + | ++ |
| 248 | + | + | + | + | + | + | + | ++ |
| 249 | + | + | + | +++ | ++ | ++ | + | ++ |
| 250 | ++ | + | + | +++ | ++ | + | + | ++ |
| 251 | + | + | + | +++ | ++ | ++ | + | ++ |
| 252 | + | + | + | + | + | + | − | + |
| 253 | +++ | ++ | + | +++ | ++ | + | + | ++ |
| 254 | + | + | + | ++ | ++ | + | + | ++ |
| 255 | + | + | + | ++ | ++ | + | ++ | ++ |
| 256 | + | + | − | + | + | + | − | + |
| 257 | + | + | + | + | + | + | + | ++ |
| 258 | + | + | + | ++ | ++ | + | + | ++ |
| 259 | ++ | + | + | +++ | ++ | + | + | ++ |
| 260 | +++ | + | + | +++ | ++ | + | + | ++ |
| 261 | +++ | + | + | ++ | ++ | ++ | + | ++ |
| 262 | +++ | + | + | +++ | ++ | + | + | ++ |
| 263 | + | + | + | + | + | + | + | + |
| 264 | +++ | + | + | +++ | ++ | + | + | ++ |
| 265 | + | + | + | +++ | ++ | + | + | ++ |
| 266 | + | + | + | ++ | + | + | + | ++ |
| 267 | + | + | + | + | ++ | + | + | ++ |
| 268 | + | + | + | ++ | ++ | ++ | + | ++ |
| 269 | + | + | + | +++ | ++ | + | + | ++ |
| 270 | +++ | + | + | +++ | ++ | + | + | ++ |
| 271 | +++ | ++ | + | +++ | ++ | ++ | + | ++ |
| 272 | +++ | + | + | +++ | ++ | + | + | ++ |
| 273 | + | ++ | + | +++ | ++ | ++ | + | ++ |
| 274 | + | + | + | ++ | + | + | + | ++ |
| 275 | + | + | + | ++ | ++ | ++ | + | ++ |
| 276 | + | + | + | ++ | ++ | + | + | ++ |
| 277 | + | + | + | + | + | + | + | + |
| 278 | + | + | − | + | + | + | − | + |
| 279 | ++ | + | − | ++ | + | + | − | ++ |
| 280 | + | + | + | ++ | + | + | + | ++ |
| 281 | + | + | + | +++ | ++ | + | + | ++ |
| 282 | + | + | + | ++ | + | + | + | ++ |
| 283 | + | + | + | ++ | + | + | + | ++ |
| 284 | + | + | + | + | ++ | + | ++ | ++ |
| 285 | + | + | + | + | + | + | + | + |
| 286 | + | + | − | +++ | ++ | + | − | ++ |
| 287 | + | + | + | +++ | + | + | + | ++ |
| 288 | ++ | + | − | +++ | ++ | + | − | ++ |
| 289 | + | + | + | ++ | + | + | + | ++ |
| 290 | ++ | + | + | ++ | ++ | ++ | + | ++ |
| 291 | + | + | + | + | + | + | + | + |
| 292 | ++ | ++ | + | +++ | ++ | ++ | + | ++ |
| 293 | ++ | ++ | − | ++ | ++ | ++ | − | ++ |
| 294 | + | + | + | ++ | + | + | + | ++ |
| 295 | +++ | ++ | + | +++ | ++ | ++ | + | ++ |
| 296 | ++ | + | + | ++ | ++ | + | + | ++ |
| 297 | ++ | + | + | ++ | ++ | + | + | ++ |
| 298 | ++ | + | + | +++ | ++ | + | + | ++ |
| 299 | − | − | − | − | − | − | − | − |
| 300 | ++ | ++ | + | +++ | ++ | ++ | + | ++ |
| 301 | ++ | + | − | ++ | ++ | + | − | ++ |
| 302 | + | + | + | ++ | + | + | + | ++ |
| 303 | + | + | + | ++ | + | + | + | ++ |
| 304 | + | + | − | + | + | + | − | ++ |
| 305 | + | + | + | ++ | + | + | + | ++ |
| 306 | +++ | +++ | +++ | +++ | ++ | ++ | ++ | ++ |
| 307 | ++ | + | + | +++ | ++ | ++ | − | ++ |
| 308 | + | + | − | ++ | + | + | − | ++ |
| 309 | + | ++ | + | ++ | ++ | ++ | + | ++ |
| 310 | + | + | + | +++ | + | + | + | ++ |
| 311 | + | + | + | +++ | + | + | + | ++ |
| 312 | + | + | − | + | + | + | − | + |
| 313 | + | + | + | + | + | + | + | + |
| 314 | + | + | + | + | + | + | + | ++ |
| 315 | + | + | − | +++ | ++ | ++ | − | ++ |
| 316 | ++ | + | − | ++ | ++ | + | − | ++ |
| 317 | ++ | + | + | ++ | ++ | + | + | ++ |
| 318 | + | + | + | + | + | + | + | ++ |

TABLE 3-continued

Compound activities and efficacies for modulating $M_1$ and $M_4$ receptors

| Compound No. | $M_1$ Activity | $M_2$ Activity | $M_3$ Activity | $M_4$ Activity | $M_1$ Efficacy | $M_2$ Efficacy | $M_3$ Efficacy | $M_4$ Efficacy |
|---|---|---|---|---|---|---|---|---|
| 319 | + | + | − | ++ | + | + | − | ++ |
| 320 | + | + | + | ++ | + | + | + | ++ |
| 321 | + | + | + | + | + | + | + | + |
| 322 | +++ | ++ | + | +++ | ++ | + | + | ++ |
| 323 | + | + | + | ++ | + | + | + | ++ |
| 324 | + | + | + | +++ | + | + | + | ++ |
| 325 | ++ | + | + | ++ | ++ | ++ | ++ | ++ |
| 326 | + | + | + | ++ | ++ | ++ | + | ++ |
| 327 | ++ | + | + | ++ | ++ | ++ | + | ++ |
| 328 | + | + | + | ++ | + | + | + | ++ |
| 329 | + | + | + | ++ | ++ | + | − | ++ |
| 330 | +++ | +++ | + | +++ | ++ | ++ | + | ++ |
| 331 | + | + | + | +++ | ++ | + | + | ++ |
| 332 | + | + | + | + | ++ | + | + | ++ |
| 333 | + | + | + | ++ | + | + | + | ++ |
| 334 | +++ | + | + | +++ | ++ | + | + | ++ |
| 335 | ++ | + | − | ++ | ++ | + | − | ++ |
| 336 | ++ | + | + | +++ | ++ | + | + | ++ |
| 337 | ++ | + | + | +++ | ++ | + | + | ++ |
| 338 | ++ | + | − | ++ | ++ | + | − | ++ |
| 339 | + | + | + | + | ++ | + | + | ++ |
| 340 | + | + | + | +++ | ++ | ++ | + | ++ |
| 341 | + | + | + | ++ | + | + | − | ++ |
| 342 | + | + | + | ++ | ++ | + | + | ++ |
| 343 | + | + | + | +++ | ++ | + | + | ++ |
| 344 | + | + | − | ++ | + | + | − | ++ |
| 345 | ++ | + | + | +++ | ++ | + | + | ++ |
| 346 | + | + | + | + | + | + | + | + |
| 347 | + | + | + | ++ | + | + | + | ++ |
| 348 | + | + | − | ++ | ++ | + | − | ++ |
| 349 | + | + | + | +++ | ++ | + | + | ++ |
| 350 | +++ | ++ | + | +++ | ++ | + | + | ++ |
| 351 | − | − | − | − | − | − | − | − |
| 352 | + | + | + | + | ++ | + | + | ++ |
| 353 | + | + | + | ++ | + | + | + | ++ |
| 354 | +++ | ++ | + | +++ | ++ | ++ | + | ++ |
| 355 | +++ | + | + | +++ | ++ | + | + | ++ |
| 356 | + | + | + | +++ | ++ | ++ | + | ++ |
| 357 | + | + | + | + | + | + | + | + |
| 358 | ++ | + | + | ++ | ++ | ++ | + | ++ |
| 359 | ++ | ++ | − | +++ | ++ | ++ | − | ++ |
| 360 | + | + | + | ++ | + | + | + | ++ |
| 361 | + | + | + | + | ++ | + | + | ++ |
| 362 | +++ | ++ | + | +++ | ++ | ++ | + | ++ |
| 363 | +++ | +++ | + | +++ | ++ | ++ | ++ | ++ |
| 364 | +++ | + | + | +++ | ++ | + | + | ++ |
| 365 | + | + | + | + | ++ | ++ | + | ++ |
| 366 | + | + | + | + | + | + | + | ++ |
| 367 | + | + | + | + | + | + | + | + |
| 368 | ++ | ++ | + | +++ | ++ | ++ | + | ++ |
| 369 | + | + | + | ++ | ++ | + | + | ++ |
| 370 | + | + | + | ++ | + | + | + | ++ |
| 371 | ++ | ++ | + | +++ | ++ | ++ | + | ++ |
| 372 | ++ | ++ | + | +++ | ++ | ++ | + | ++ |
| 373 | + | + | + | + | + | + | + | ++ |
| 374 | + | + | + | ++ | + | + | + | ++ |
| 375 | + | + | + | + | + | + | + | ++ |
| 376 | ++ | + | + | +++ | ++ | + | + | ++ |
| 377 | + | + | + | +++ | + | + | + | ++ |
| 378 | + | + | + | +++ | ++ | + | + | ++ |
| 379 | + | + | − | + | + | + | − | + |
| 380 | + | + | − | ++ | + | + | − | ++ |
| 381 | ++ | ++ | + | +++ | ++ | ++ | + | ++ |
| 382 | + | + | + | + | + | + | + | ++ |
| 383 | + | + | + | ++ | ++ | + | + | ++ |
| 384 | + | + | + | ++ | ++ | + | + | ++ |
| 385 | ++ | + | − | +++ | ++ | + | − | ++ |
| 386 | + | + | + | + | + | + | + | ++ |
| 387 | + | + | + | ++ | ++ | + | + | ++ |
| 388 | + | + | + | +++ | + | + | + | ++ |
| 389 | + | + | + | + | + | + | + | + |
| 390 | +++ | + | + | +++ | ++ | + | + | ++ |
| 391 | + | + | + | + | + | + | + | + |

TABLE 3-continued

Compound activities and efficacies for modulating $M_1$ and $M_4$ receptors

| Compound No. | $M_1$ Activity | $M_2$ Activity | $M_3$ Activity | $M_4$ Activity | $M_1$ Efficacy | $M_2$ Efficacy | $M_3$ Efficacy | $M_4$ Efficacy |
|---|---|---|---|---|---|---|---|---|
| 392 | +++ | +++ | +++ | +++ | ++ | ++ | ++ | ++ |
| 393 | + | + | + | + | + | + | + | ++ |
| 394 | + | + | + | +++ | + | ++ | + | ++ |
| 395 | + | + | + | + | + | + | + | ++ |
| 396 | + | + | + | +++ | ++ | + | + | ++ |
| 397 | ++ | + | + | +++ | ++ | + | + | ++ |
| 398 | + | + | + | +++ | ++ | + | + | ++ |
| 399 | + | + | + | ++ | + | + | + | ++ |
| 400 | + | + | + | + | + | + | + | + |
| 401 | + | + | + | + | + | + | + | + |
| 402 | + | + | + | ++ | + | + | + | ++ |
| 403 | + | + | + | ++ | ++ | + | + | ++ |
| 404 | ++ | + | + | +++ | ++ | + | + | ++ |
| 405 | +++ | ++ | + | +++ | ++ | ++ | + | +++ |
| 406 | +++ | +++ | + | +++ | ++ | ++ | ++ | ++ |
| 407 | + | + | + | +++ | + | + | + | ++ |
| 408 | + | + | + | +++ | ++ | + | + | ++ |
| 409 | + | + | + | ++ | ++ | ++ | + | ++ |
| 410 | + | + | + | ++ | + | + | + | ++ |
| 411 | +++ | + | + | +++ | ++ | + | + | + |
| 412 | +++ | ++ | − | +++ | ++ | + | − | ++ |
| 413 | − | − | − | − | − | − | − | − |
| 414 | + | + | + | ++ | + | + | + | ++ |
| 415 | + | + | + | + | + | + | + | ++ |
| 416 | + | + | + | ++ | + | + | + | ++ |
| 417 | +++ | +++ | + | +++ | ++ | ++ | ++ | +++ |
| 418 | ++ | + | + | ++ | + | + | + | ++ |
| 419 | ++ | + | − | +++ | + | + | − | ++ |
| 420 | + | + | + | ++ | ++ | + | + | ++ |
| 421 | ++ | ++ | − | +++ | ++ | + | − | ++ |
| 422 | ++ | ++ | + | +++ | ++ | ++ | + | ++ |
| 423 | + | + | + | + | + | + | + | ++ |
| 424 | ++ | ++ | + | +++ | ++ | ++ | + | ++ |

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:
1. A compound of formula Ib:

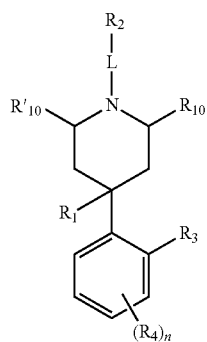

Ib or a pharmaceutically acceptable salt thereof, wherein:
$R_1$ is hydrogen, halo, cyano, hydroxy, —$OCF_3$, —COOH, —C(O)O-alkyl, or —O-alkyl;

$R_2$ is a 5-12 membered bicycloalkyl or 5-12 membered bicycloalkenyl, which is optionally substituted with 1-3 of $R_6$;

Each $R_6$ is independently —$Z^B R_7$, wherein each $Z^B$ is independently a bond;

Each $R_7$ is independently $R^B$, halo, —OH, —$NH_2$, —$NO_2$, —CN, or —$OCF_3$;

Each $R^B$ is independently hydrogen;

$R_3$ is a $C_{1-8}$alkyl or alkenyl, which is optionally substituted with 1-3 of halo, hydroxy, cyano, alkylcarbonyl, alkoxy, phenyl, or combinations thereof; or $R_3$ is a $C_{1-8}$ alkoxy optionally substituted with 1-3 of hydroxy, alkoxy, alkoxycarbonyl, phenyl, phenylcarbonyl, (alkoxyphenyl)carbonyl, (halophenyl)carbonyl, (alkylphenyl)carbonyl, or combinations thereof; or $R_3$ is phenyl which is optionally substituted with 1-3 of halo, cyano, aminocarbonyl, cyanoalkyl, alkyl, alkenyl, alkoxy, or combinations thereof;

Each $R_4$ is
 (a) hydrogen, halo, trifluoromethyl, hydroxy, cyano, methoxy;
 (b) methyl, ethyl, tert-butyl, (4-methyl)pentyne-1-yl, 2-phenylethynyl, 2-(1-hydroxycyclopentane-1-yl) ethyn-1-yl, morpholinylmethyl, cyclopropylcarbonylaminomethyl;
 (c) tert-butylcarbonyl, cyclopropylcarbonyl, isopropylcarbonyl, ethylcarbonyl, phenylcarbonyl, furanylcarbonyl, thiophenylcarbonyl;
 (d) methylcarbonylamino;

(e) benzo[d][1,3]dioxlyl, pyridyl, furanyl, thiophenyl; or
(f) phenyl optionally substituted with one of
  (i) fluoro, chloro, methyl, ethyl, methoxy, cyano, trifluoromethyl, trifluoromethoxy, cyanomethyl, (2-cyano)propane-2-yl, ethenyl, 2-(1-hydroxycyclohexane-1-yl)ethyn-1-yl,
  (ii) aminocarbonyl, ethylaminocarbonyl, (2-methoxy)ethylaminocarbonyl, diethylaminocarbonyl, methylaminocarbonyl, thiazolylaminocarbonyl, dimethylaminocarbonyl, cyclopropylaminocarbonyl,
  (iii) methylsulfonyl, N-pyrrolidinylsulfonyl, isopropylsulfonyl, ethylsulfonyl,
  (iv) methylcarbonyl, piperidinylcarbonyl, methoxycarbonyl, pyrrolidinylcarbonyl, N-morpholinocarbonyl,
  (v) methylcarbonylamino; and
  wherein the phenyl is further optionally substituted with a substituent selected from fluoro, chloro, methyl and methoxy;

L is a bond or —CH$_2$—;

R$_{10}$ and R'$_{10}$ are each independently hydrogen; and
n is 0-4.

2. The compound of claim 1, wherein R$_2$ is selected from bicyclo[2.1.1]hexyl, bicyclo[2.2.1]heptyl, bicyclo[3.1.1]heptyl, bicyclo[2.2.2]octyl, bicyclo[3.2.1]octyl, bicyclo[3.3.1]nonyl, and bicyclo[3.3.3]undecyl; each of which is optionally substituted with 1-3 of halo, hydroxy or combinations thereof.

3. The compound of claim 1 wherein R$_2$ is bicyclo[2.1.1]hexenyl, bicyclo[2.2.1]heptenyl, bicyclo[3.1.1]heptenyl, bicyclo[2.2.2]octenyl, bicyclo[3.2.1]octenyl, bicyclo[3.3.1]nonenyl, or bicyclo[3.3.3]undecenyl; each of which is optionally substituted with 1-3 of halo, hydroxy or combinations thereof.

4. The compound of claim 1, wherein -L-R$_2$ is one selected from (bicyclo[2.2.1]hept-2-ene-5-yl-)methyl; bicyclo[3.2.1]octan-3-yl, bicyclo[3.2.1]octan-2-yl; bicyclo[2.2.1]heptan-2-yl; bicyclo[2.2.1]heptan-2-ylmethyl; bicyclo[2.2.2]octan-2-ylmethyl; 7-methylbicyclo[3.3.1]nonan-3-yl and spiro[5.5]undecan-2-yl.

5. The compound of claim 1, where R$_4$ is hydrogen, halo, hydroxy, cyano, or combinations thereof.

6. A pharmaceutical composition comprising a compound according to claim 1, and a pharmaceutical carrier.

7. A compound selected from

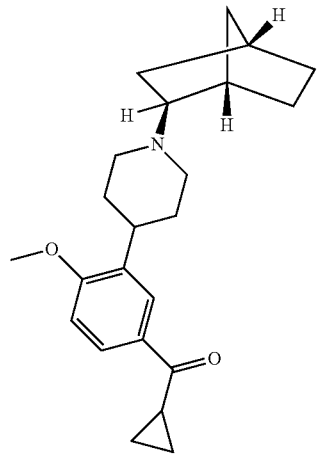

3

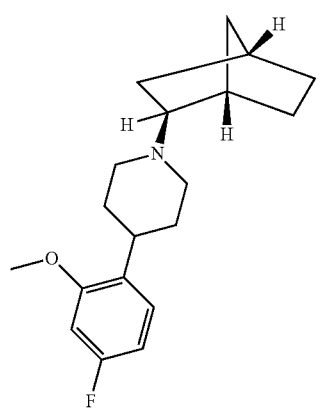

4

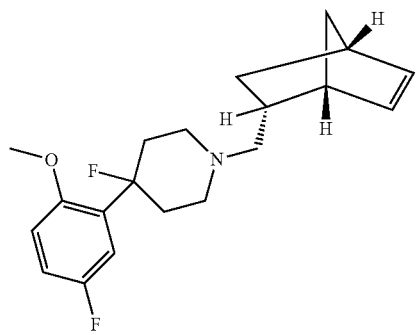

5

-continued
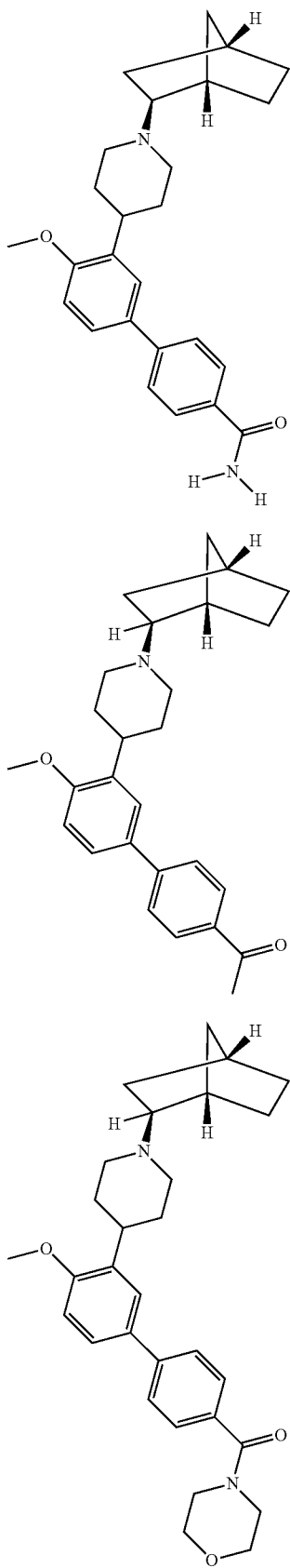
-continued
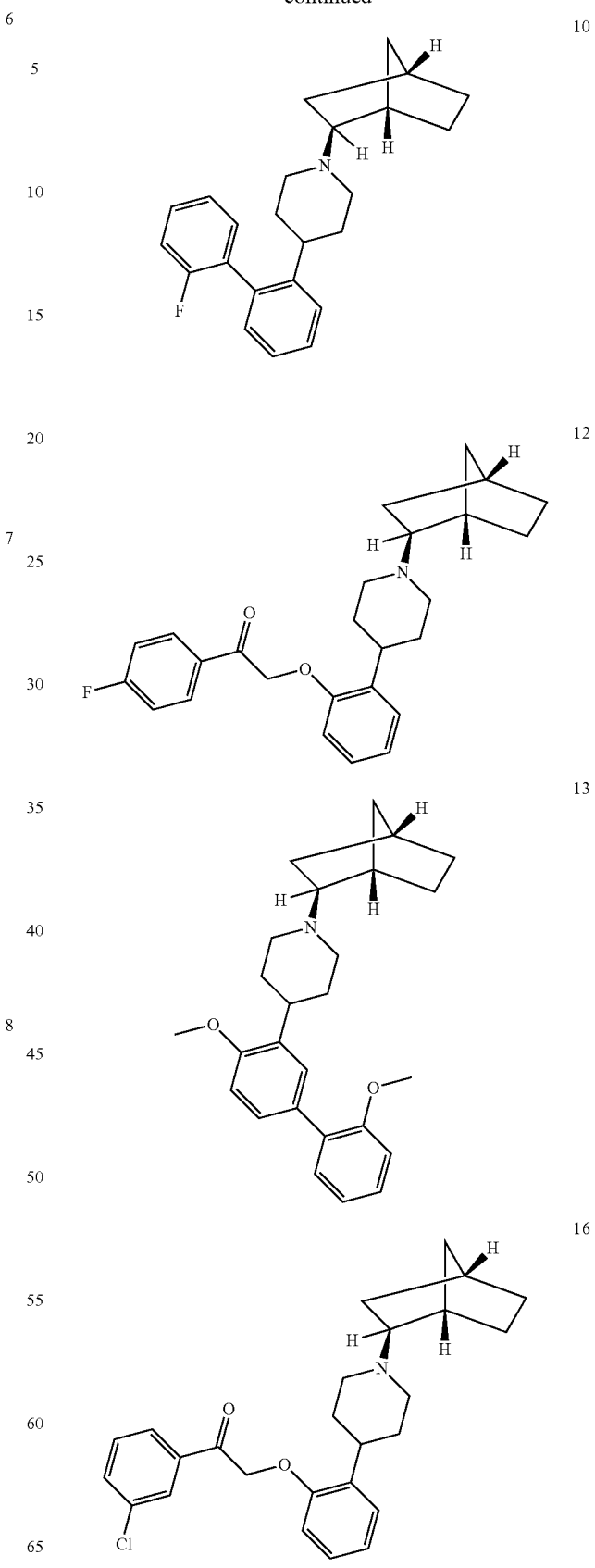

207
-continued
| | |
|---|---|
| 17 | 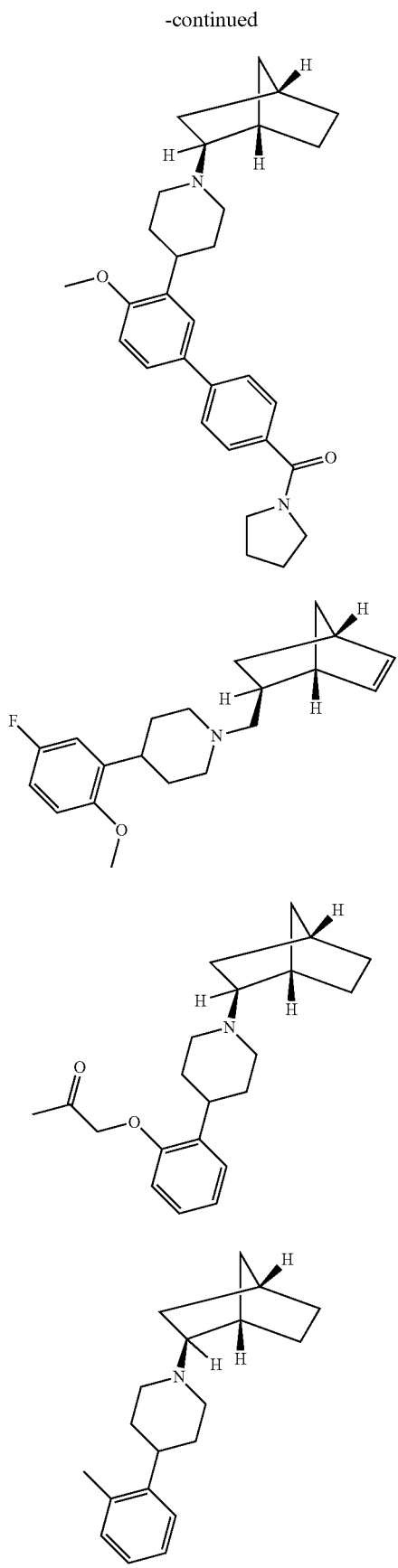 |
| 18 | |
| 19 | |
| 24 | |
208
-continued
| | |
|---|---|
| 25 | 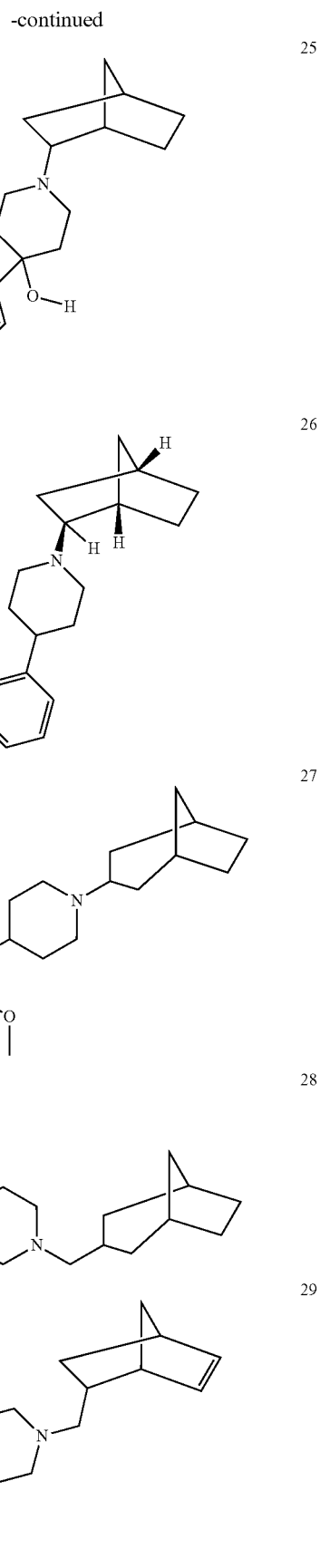 |
| 26 | |
| 27 | |
| 28 | |
| 29 | |

-continued
| | |
|---|---|
| 30 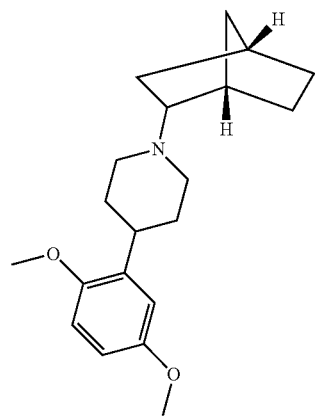 | 41 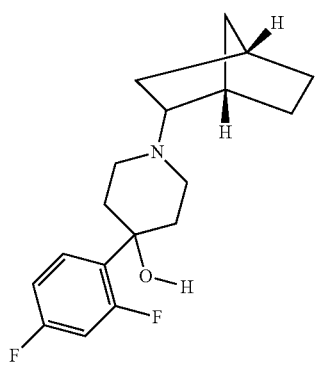 |
| 32 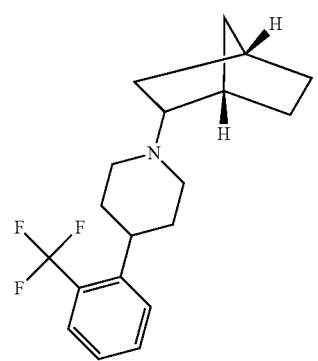 | 42 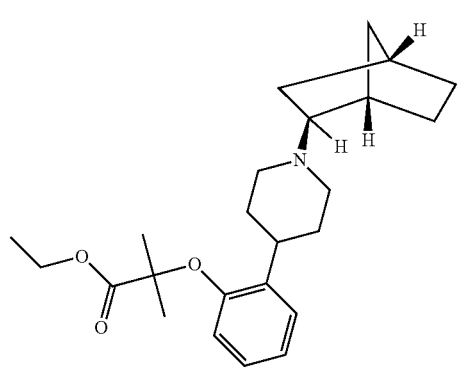 |
| 35 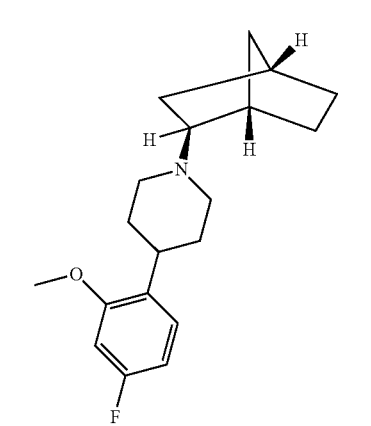 | 44 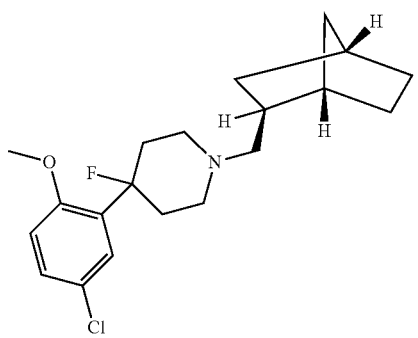 |
| 40 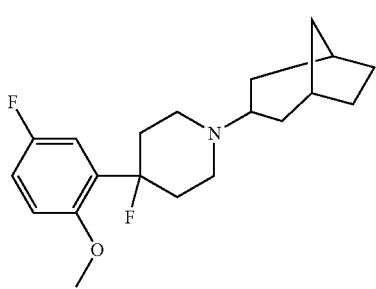 | 45 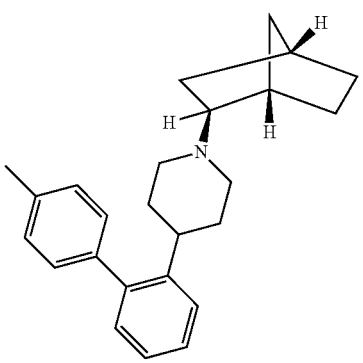 |

-continued
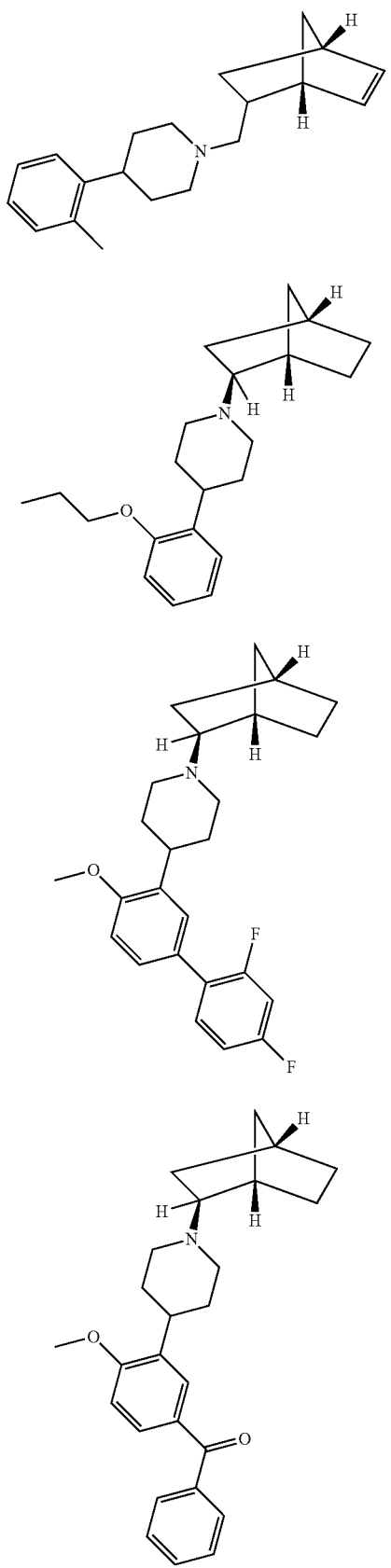
-continued
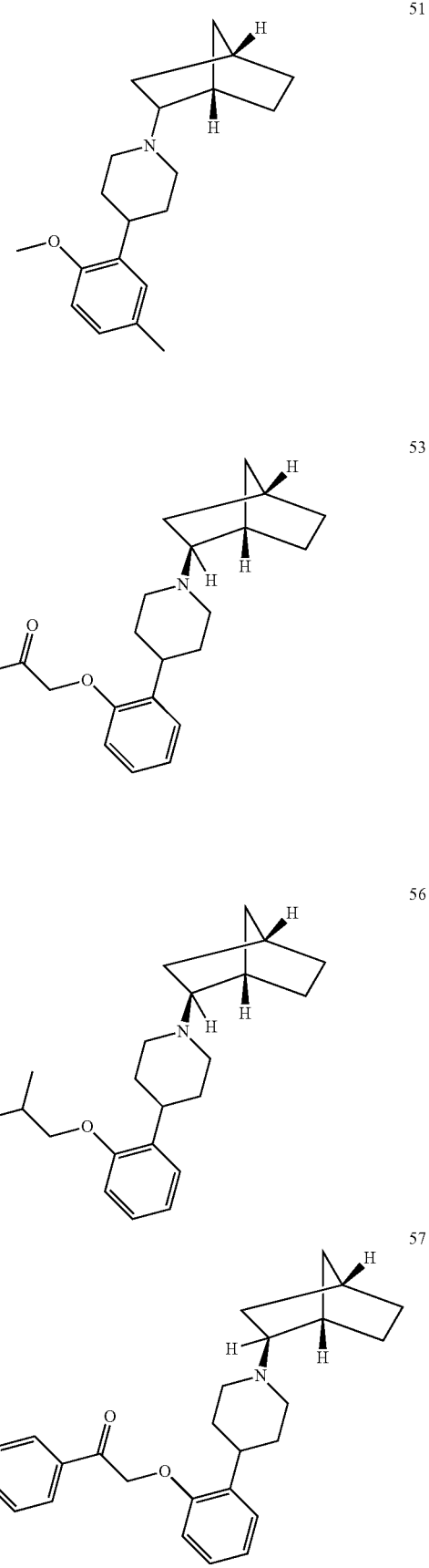

58
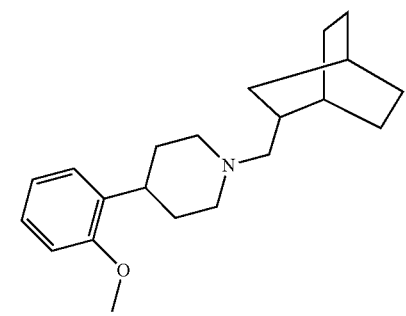
60
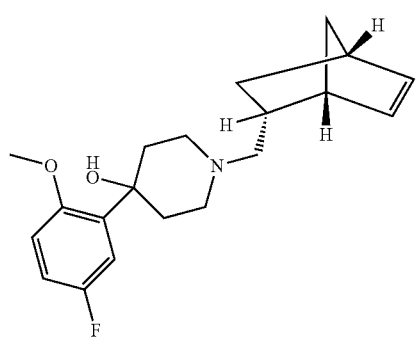
61
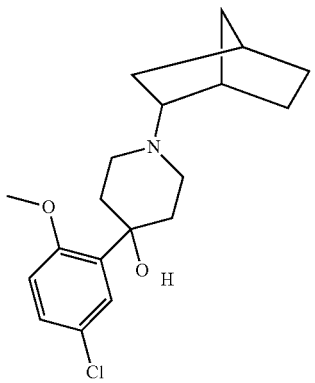
62
63
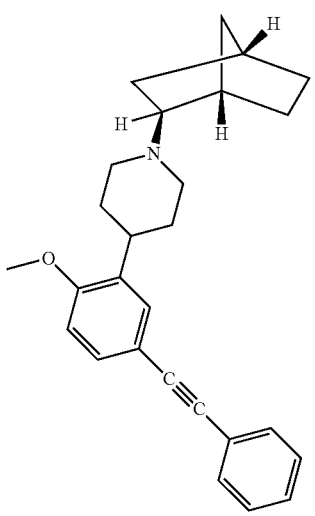
64
67
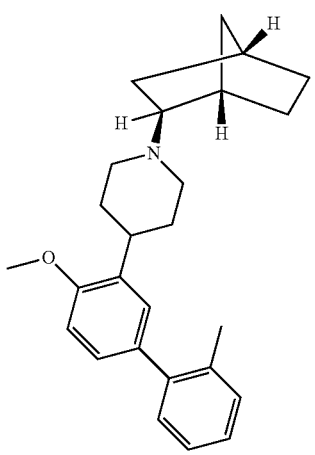

-continued
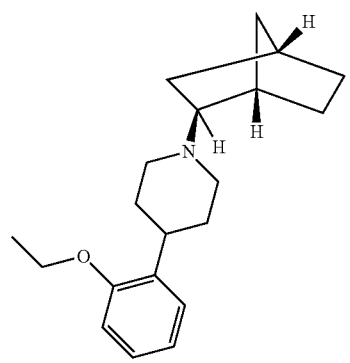
68
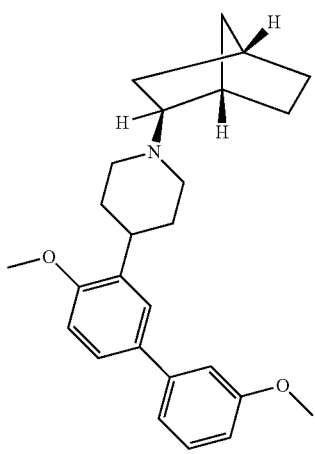
69
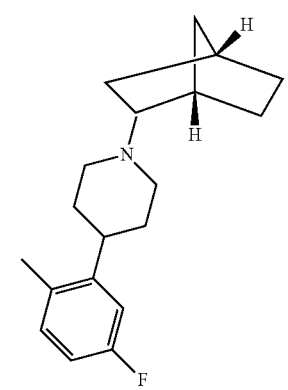
73
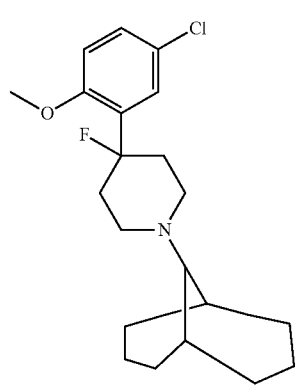
74
-continued
75
76
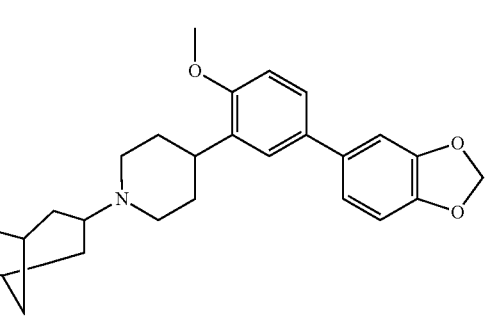
77
78

-continued
79
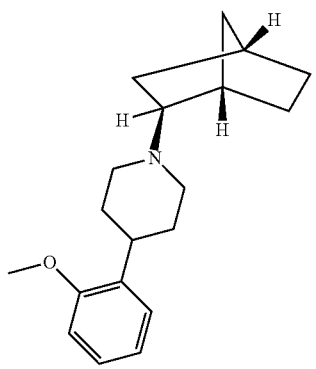
80
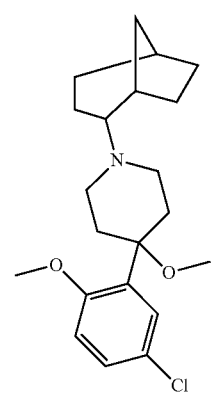
81
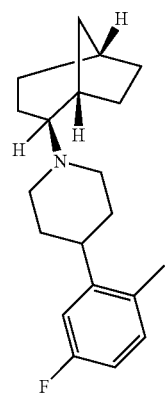
82
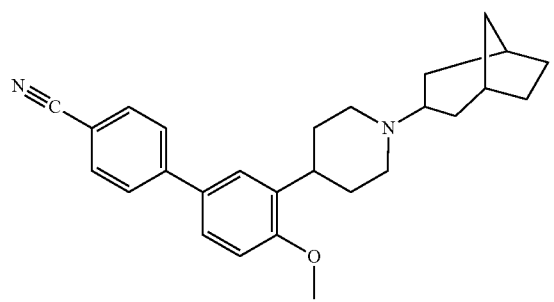
-continued
83
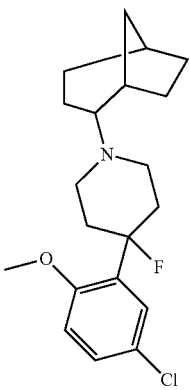
84
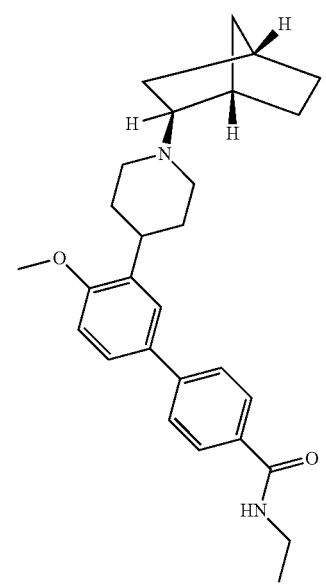
85
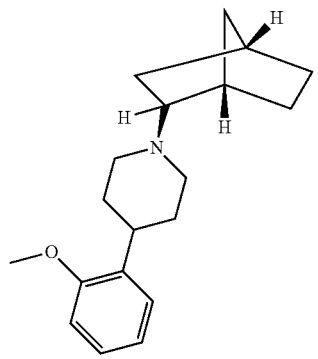
86
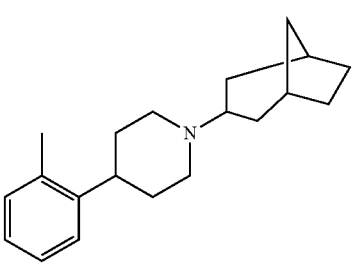

-continued
87
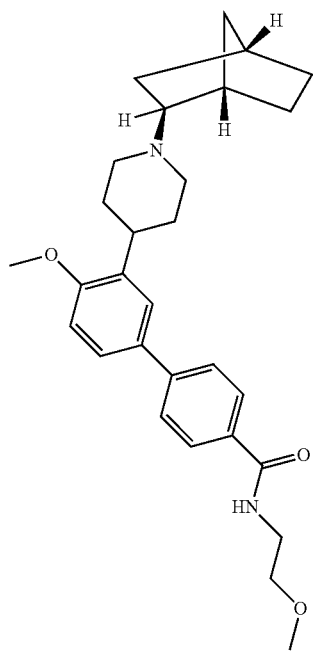
88
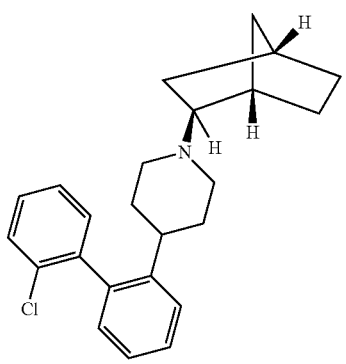
89
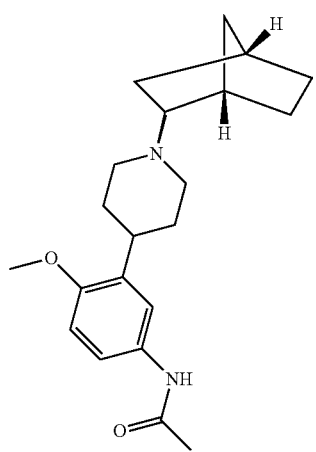
-continued
92
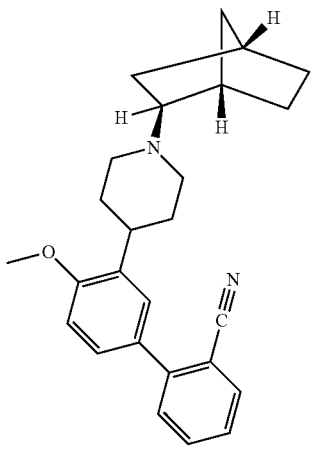
93
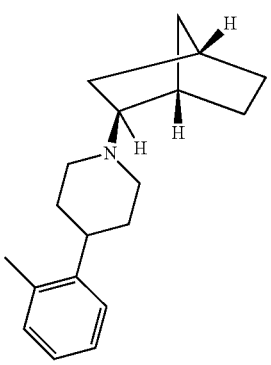
96
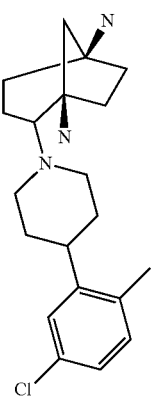

221
-continued
97
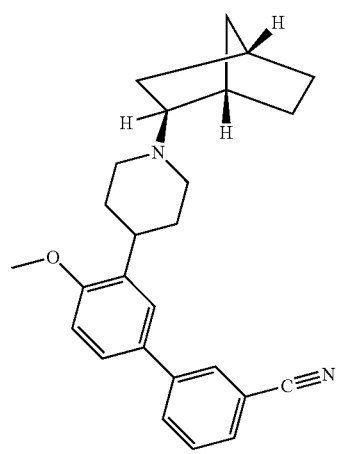
98
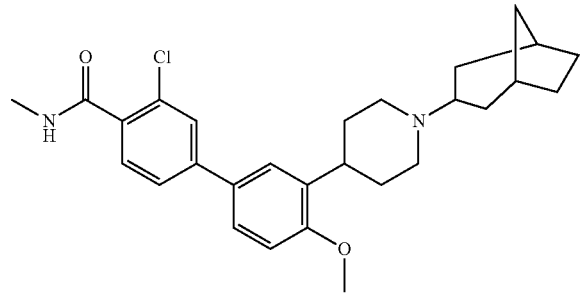
100
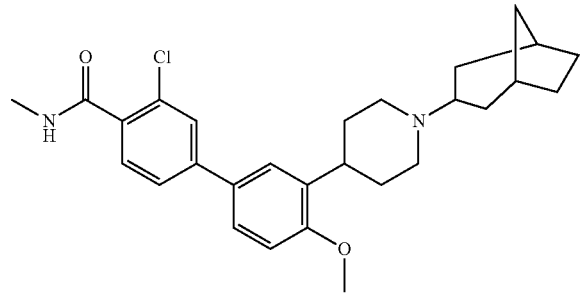
222
-continued
102
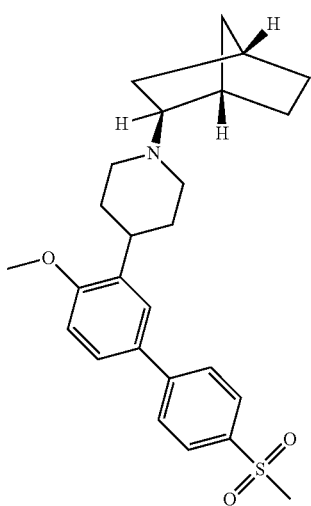
103
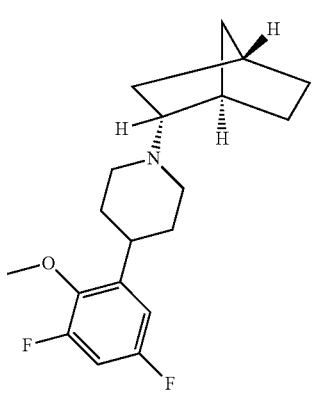
104
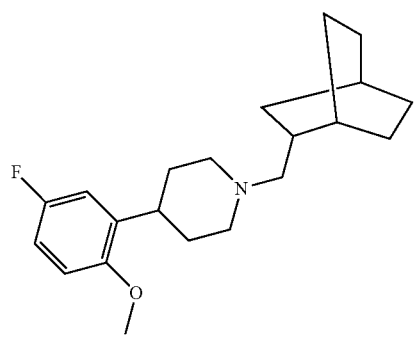
107
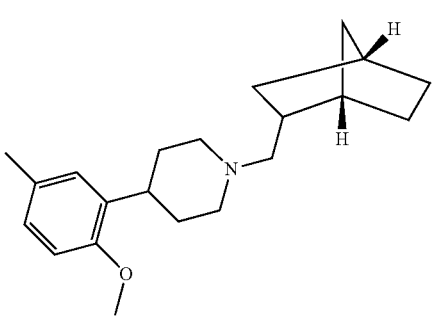

223 -continued
109
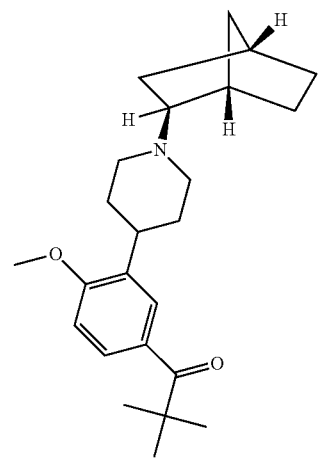
110
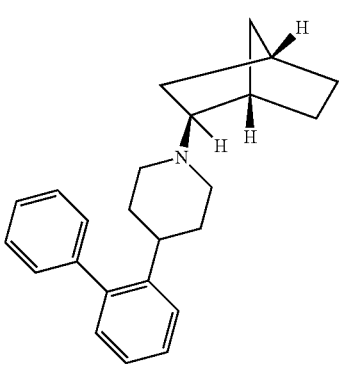
111
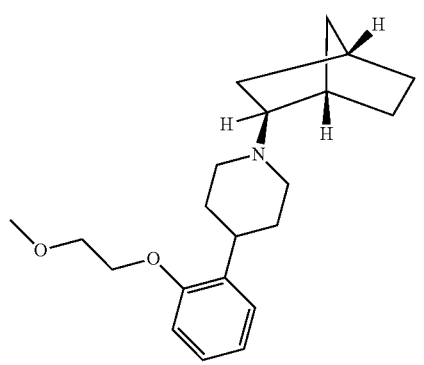
112
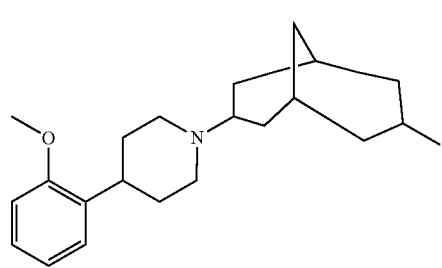
224 -continued
114
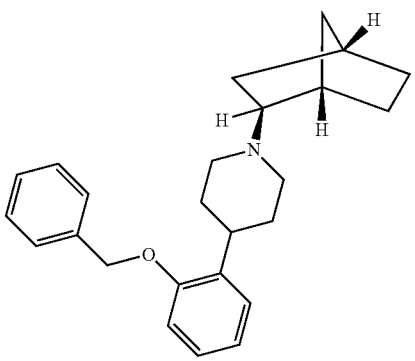
116
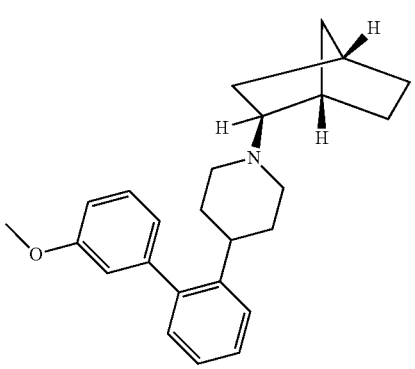
117
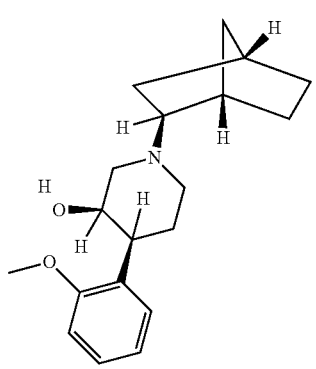
119
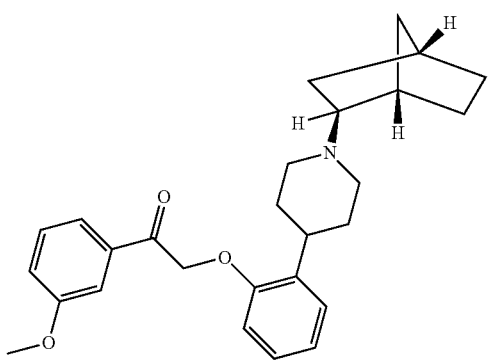

-continued
120 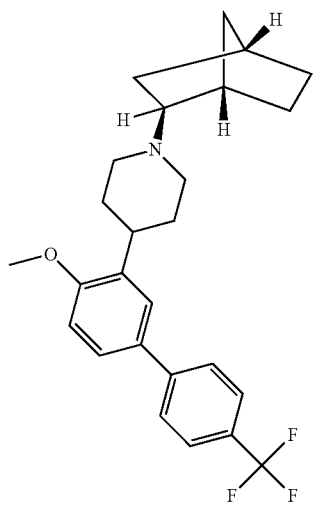
124 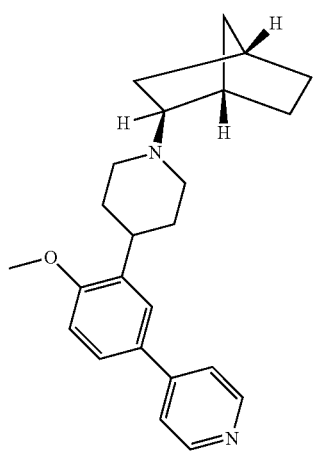
126 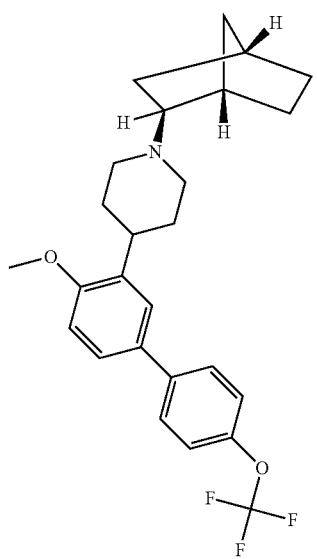
-continued
127 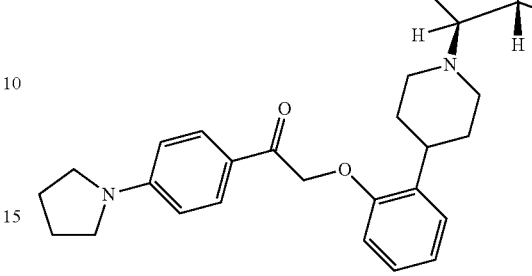
128 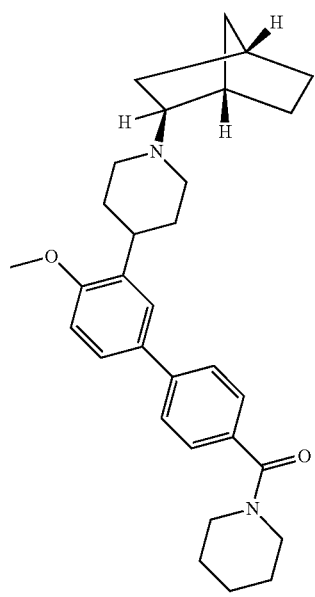
129 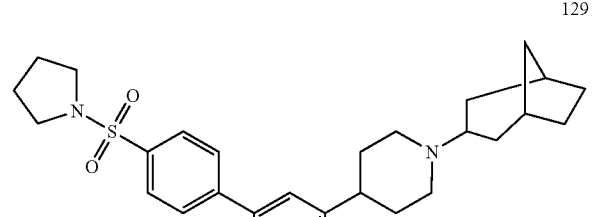
133 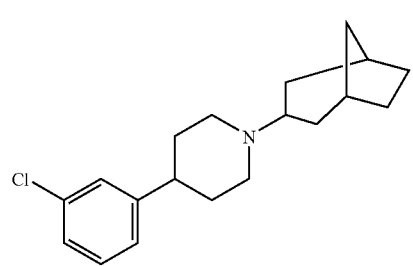

-continued
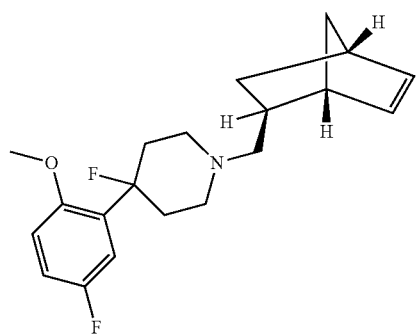
134
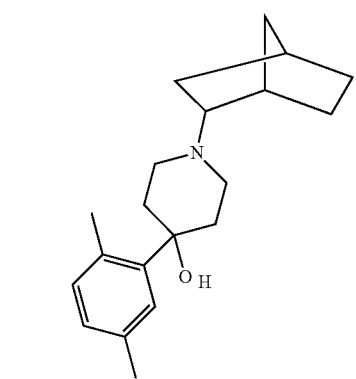
135
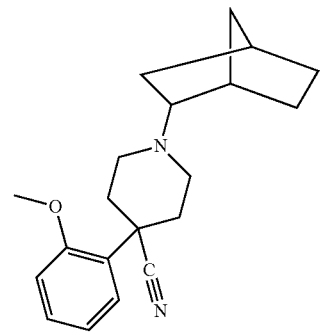
136
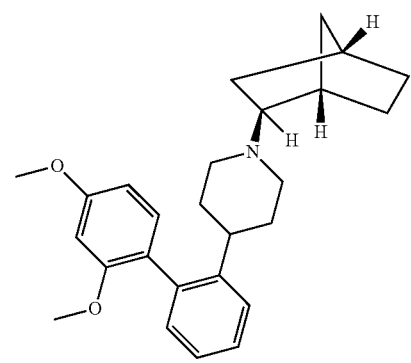
139
-continued
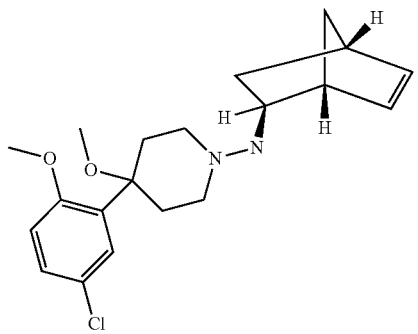
140
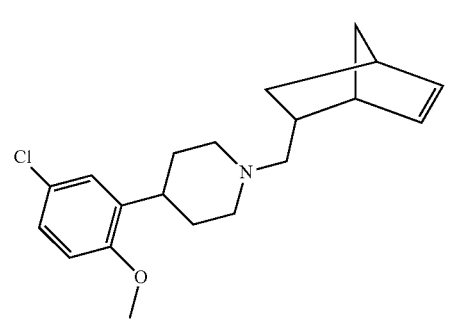
141
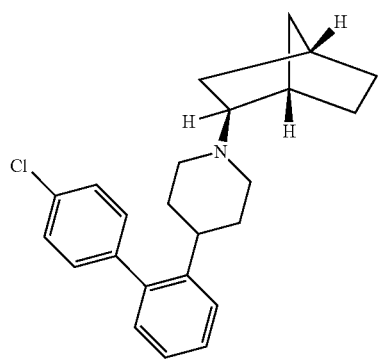
142
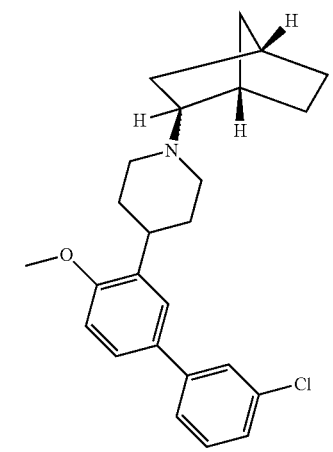
143

-continued
144
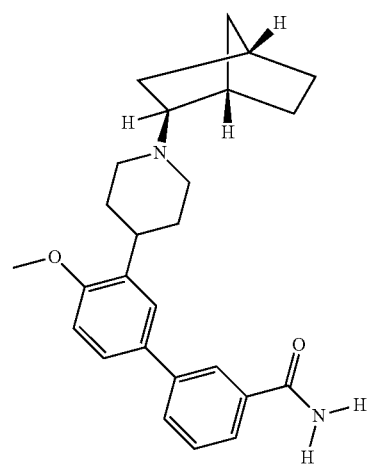
147
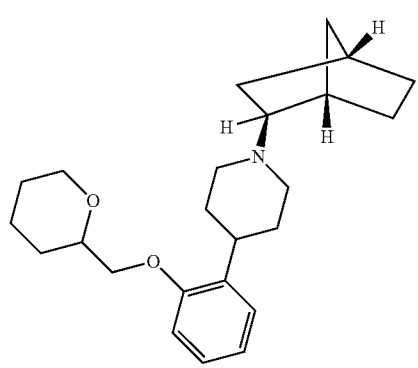
148
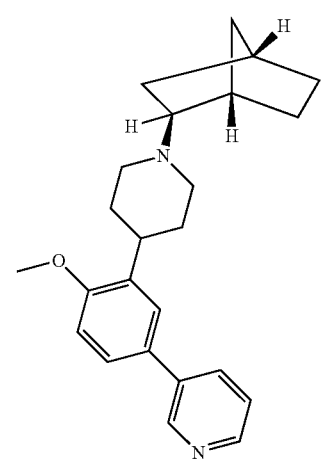
-continued
149
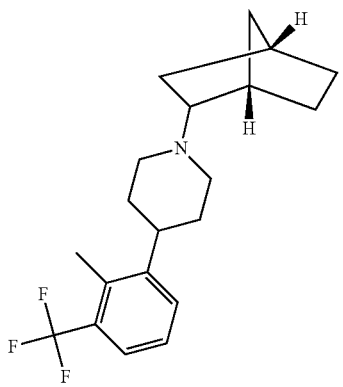
151
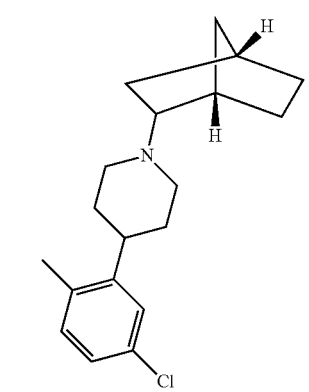
154
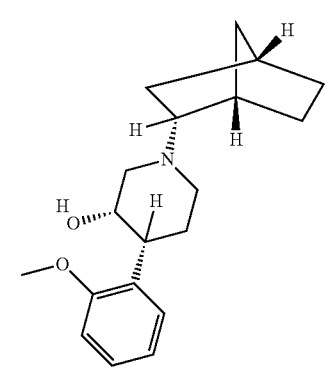
156
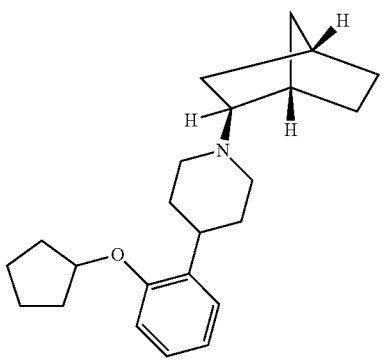

-continued
159
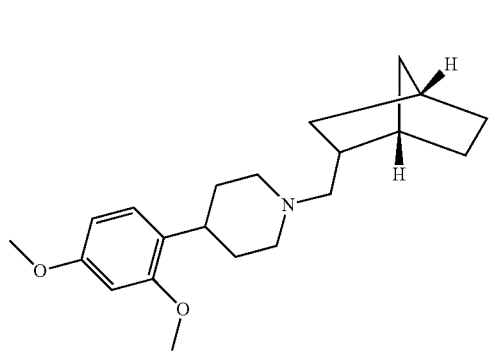
160
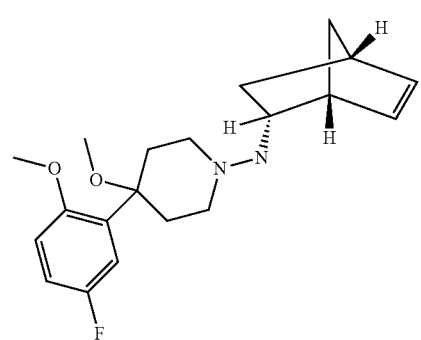
162
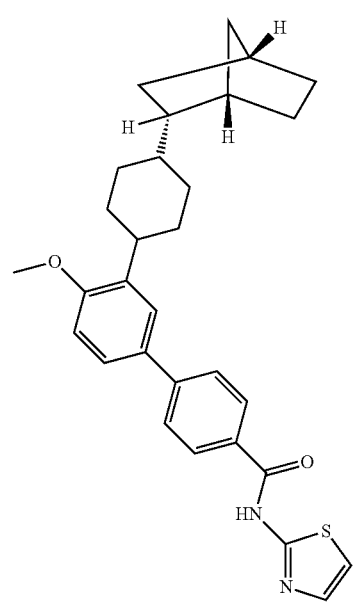
-continued
165
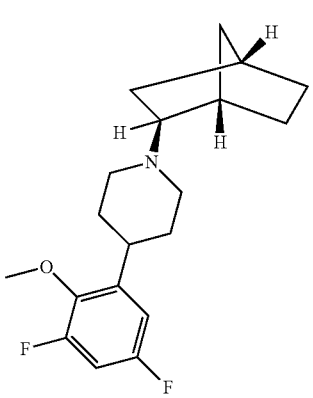
166
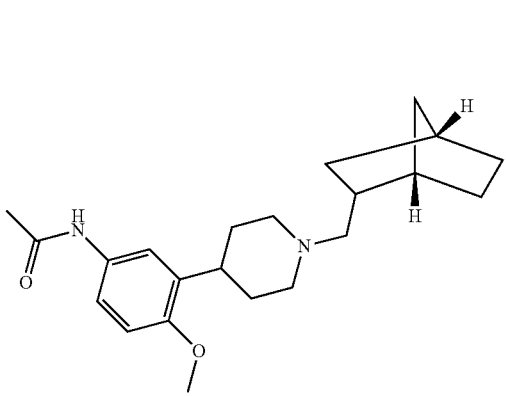
167
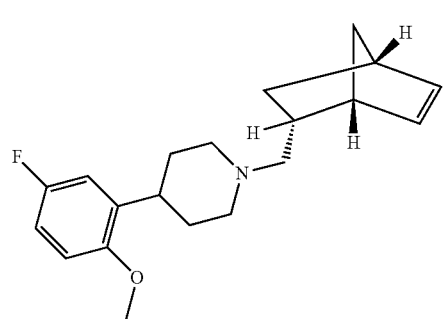
168
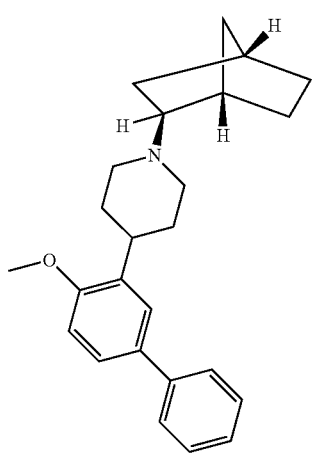

-continued
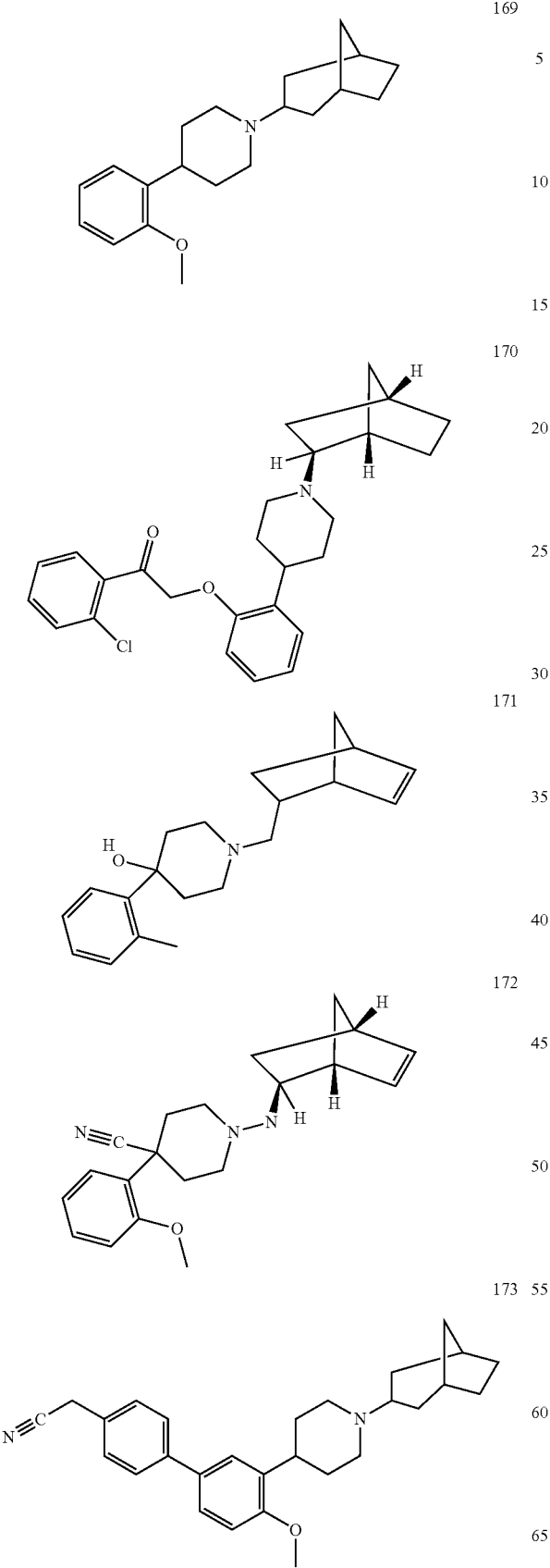
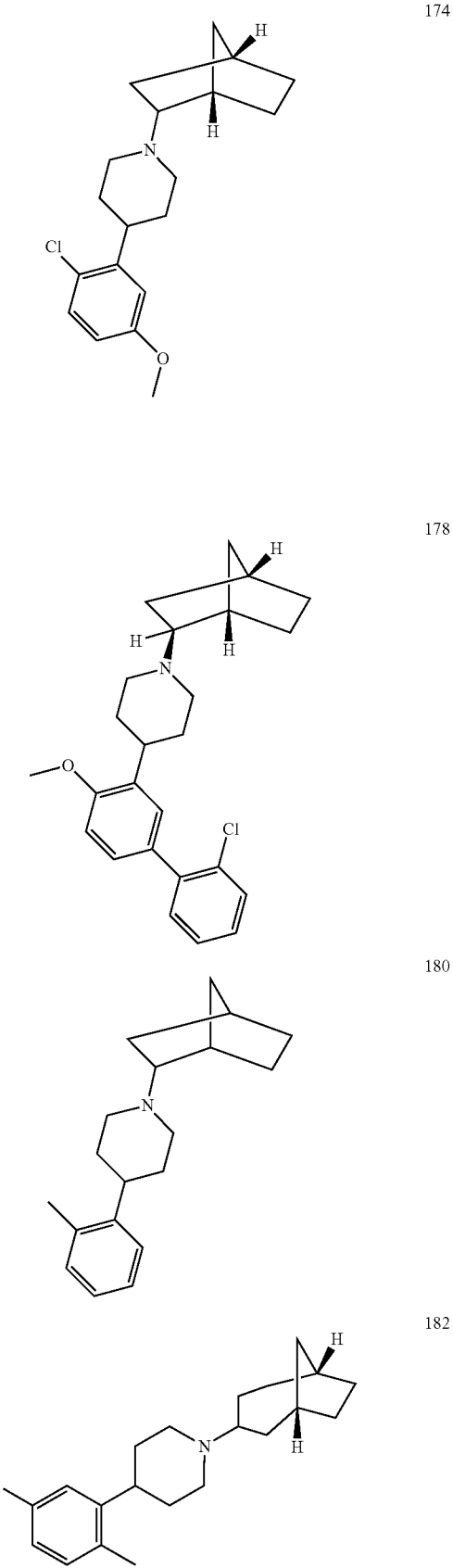

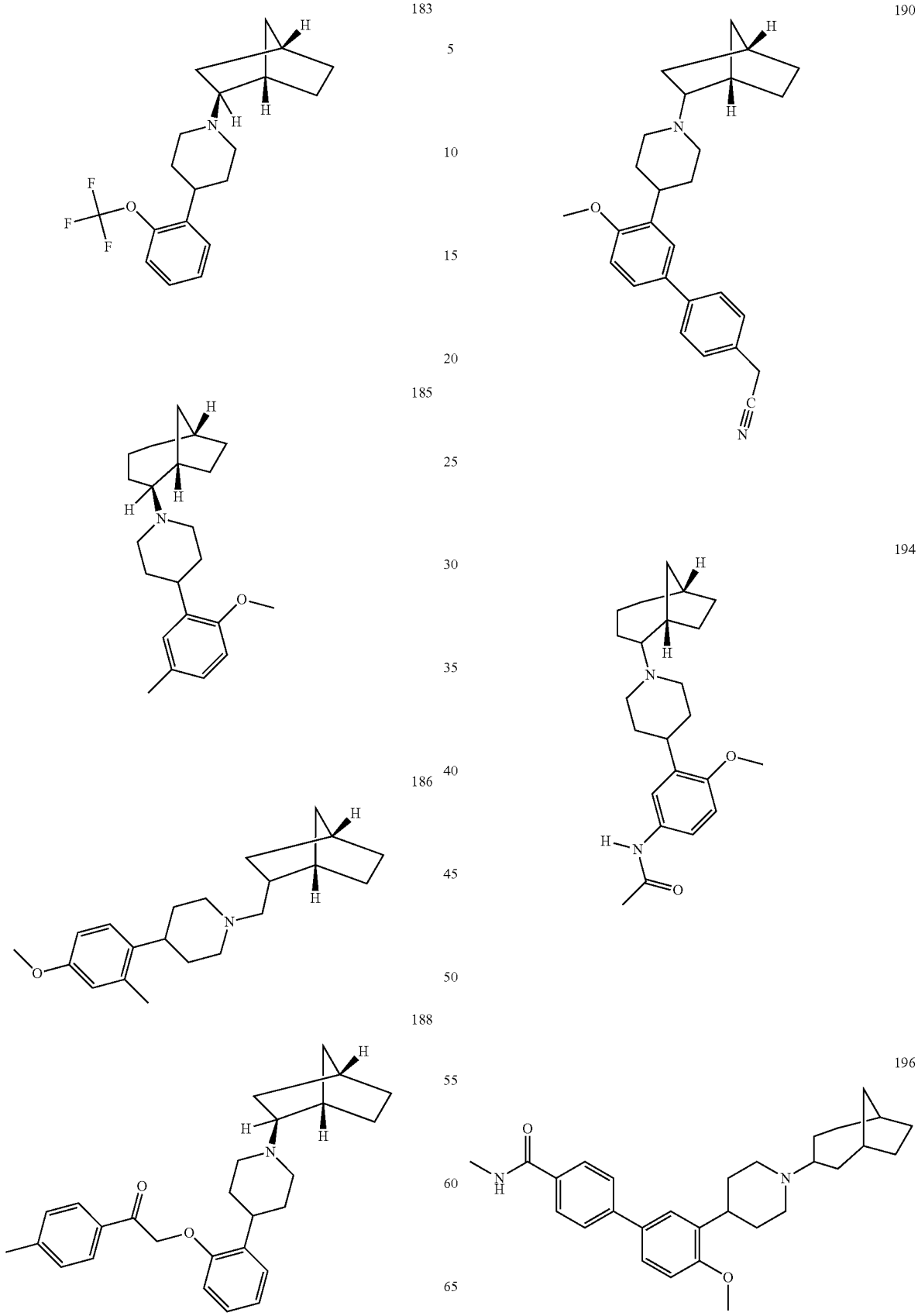

-continued
197 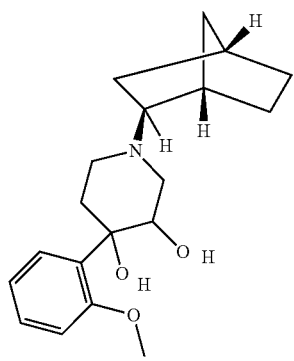
204 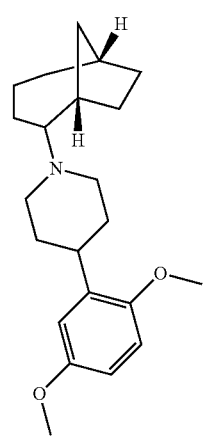
205 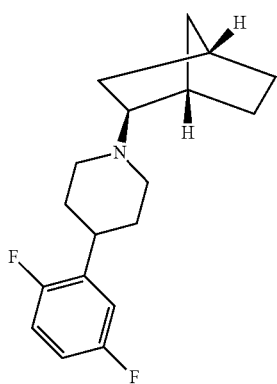
-continued
206 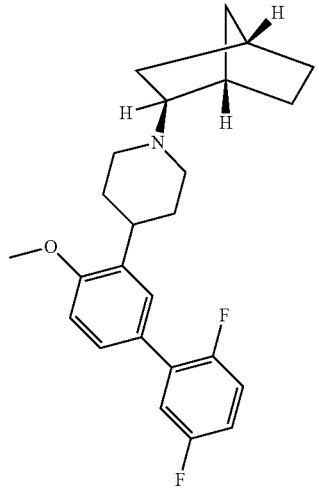
207 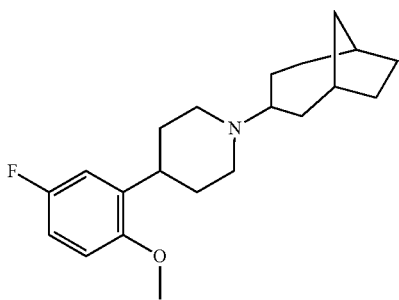
209 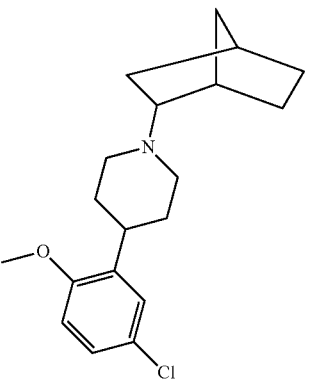
212 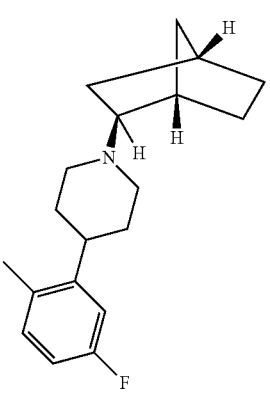

-continued
213
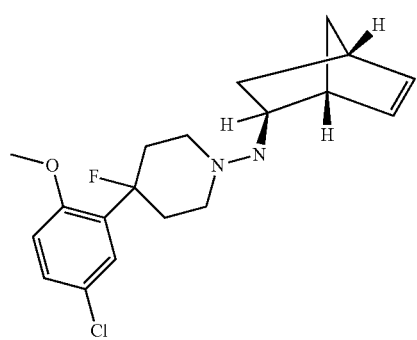
214
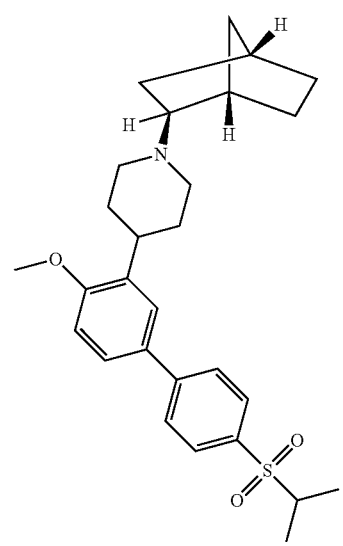
216
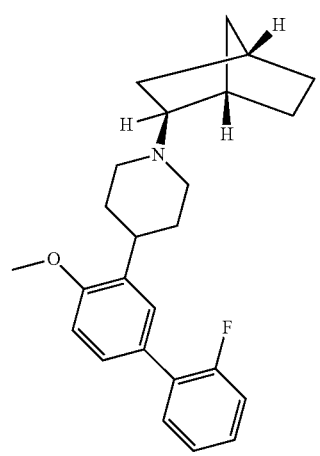
-continued
220
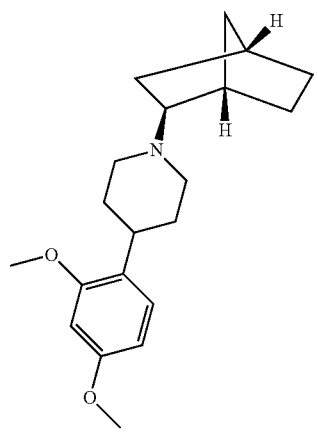
221
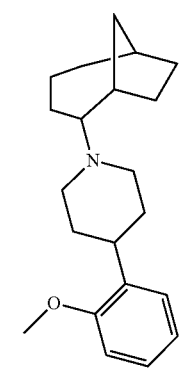
222
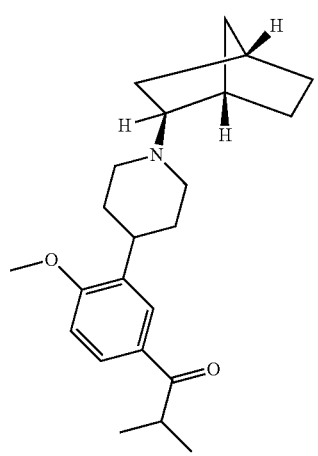

-continued
223
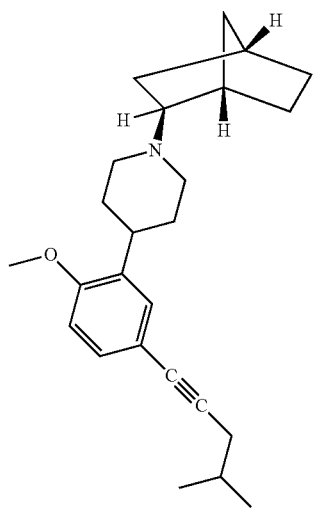
225
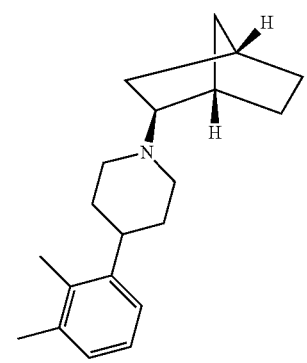
227
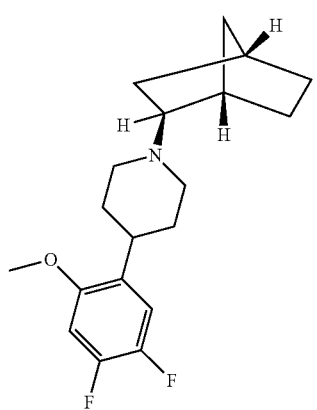
-continued
228
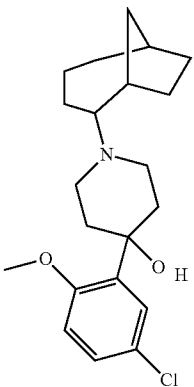
229
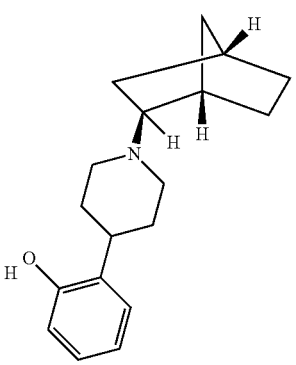
230
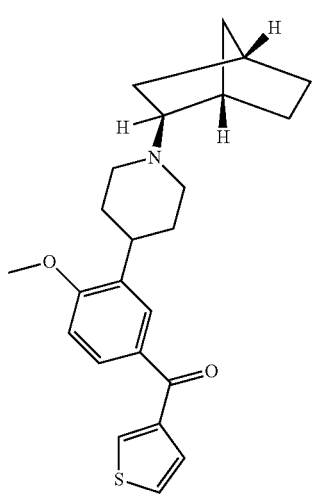

-continued
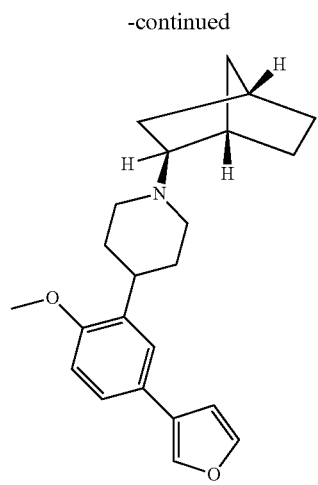

-continued
251
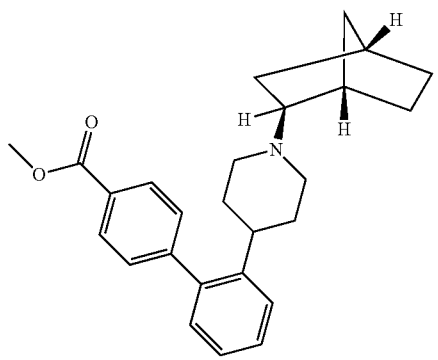
252
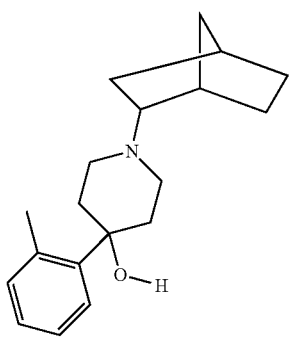
256
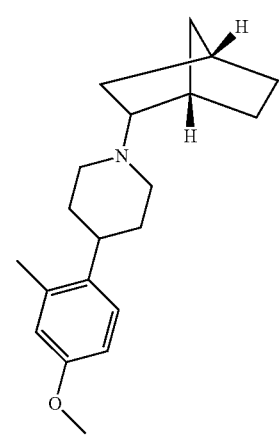
-continued
258
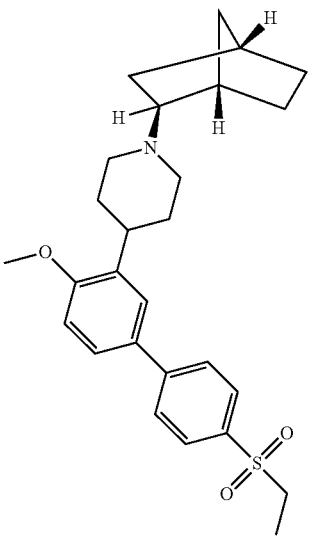
259
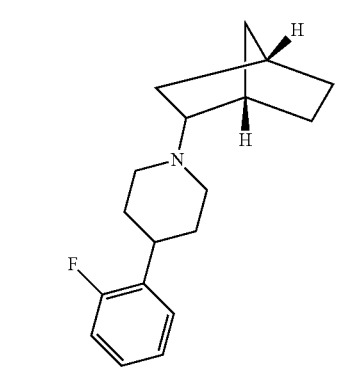
260
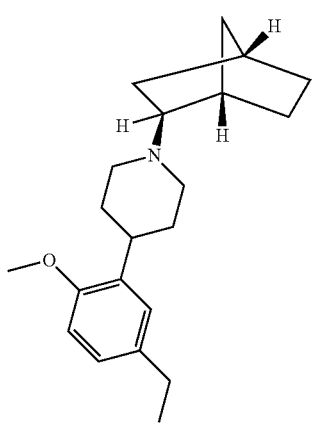

-continued
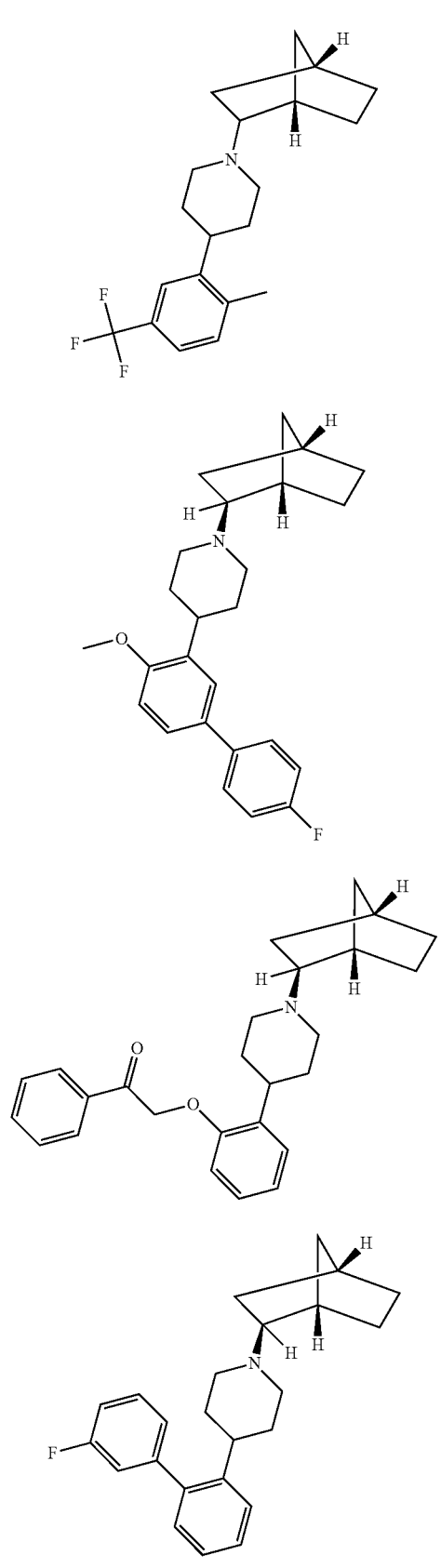
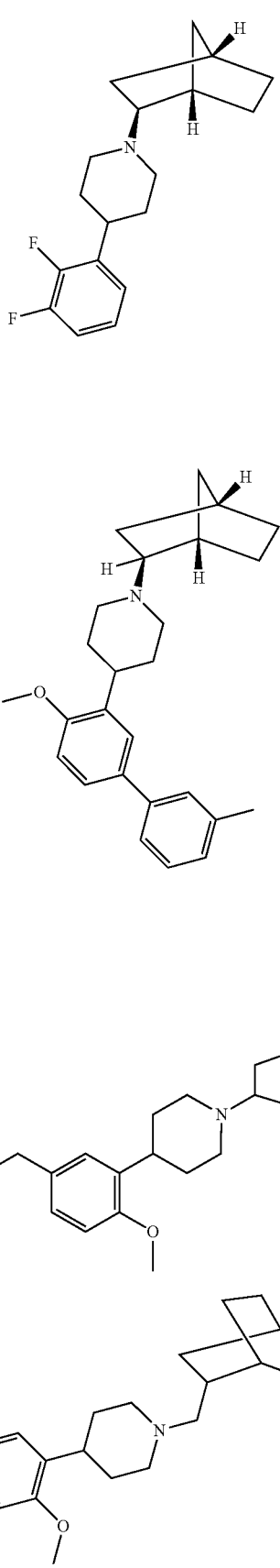

-continued
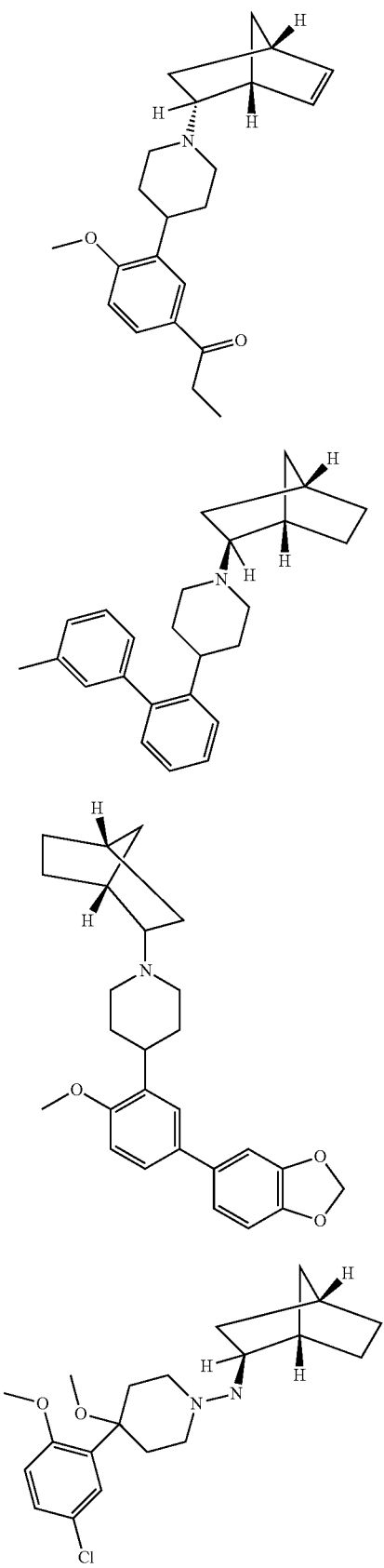
-continued
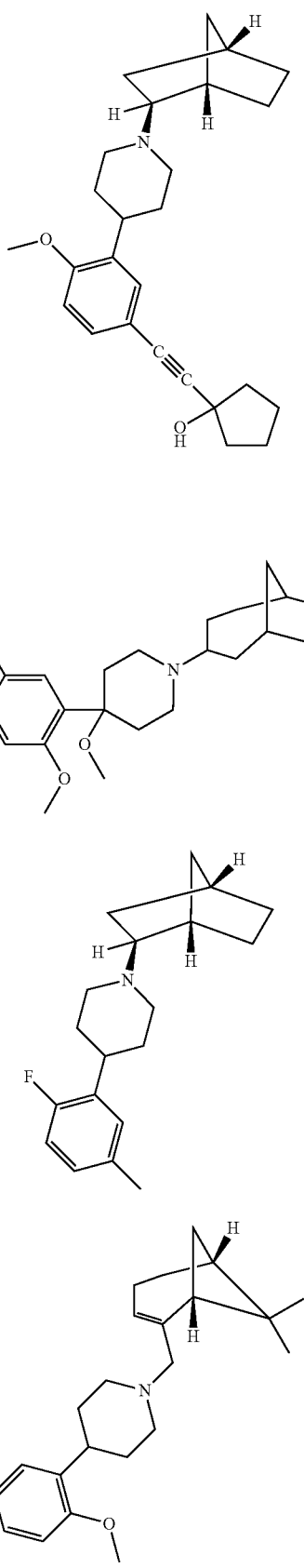

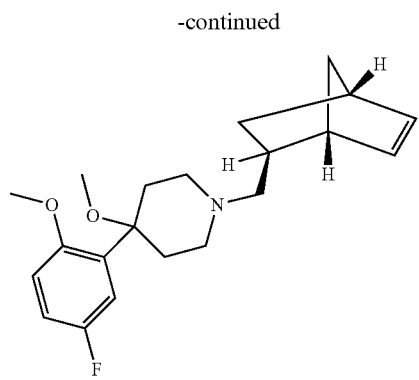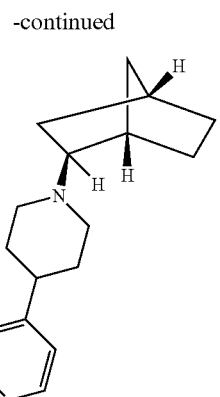

-continued
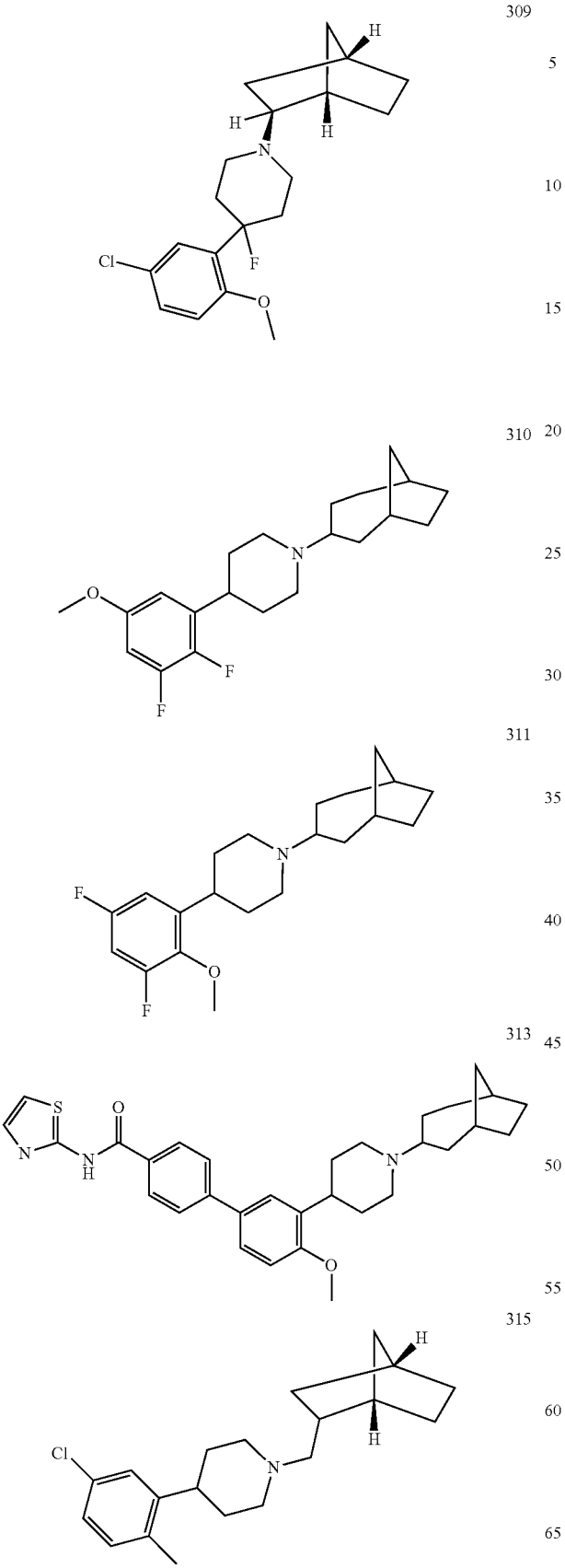
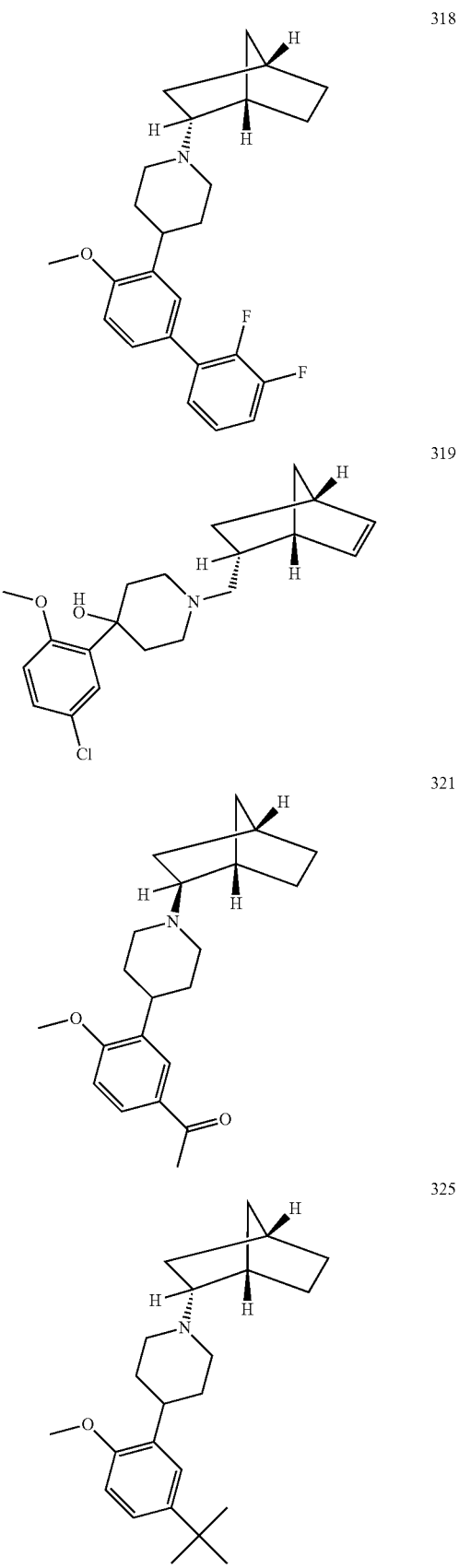

-continued
326
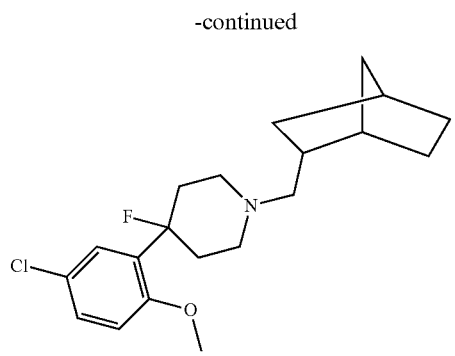
328
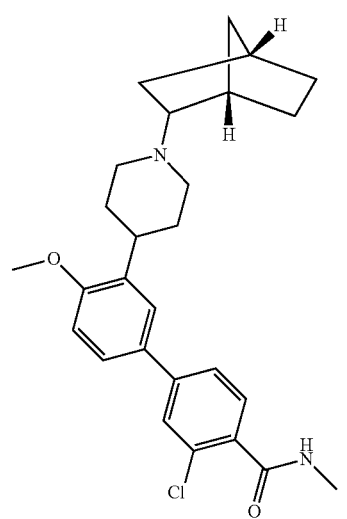
329
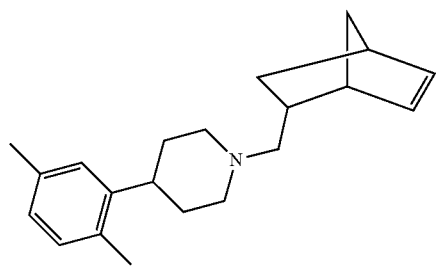
340
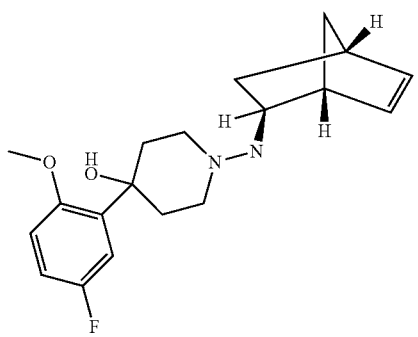
-continued
341
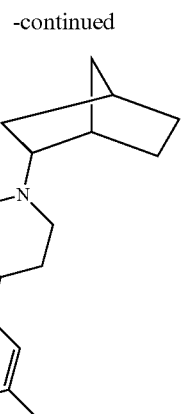
343
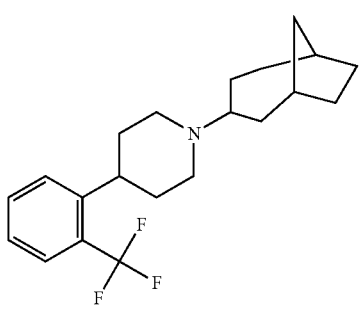
344
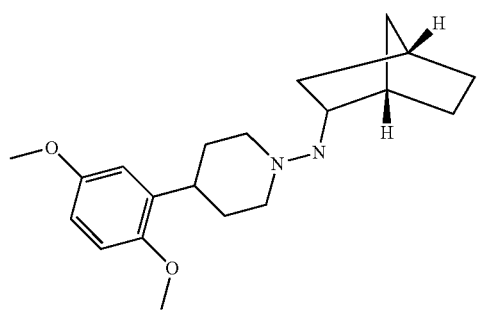
347
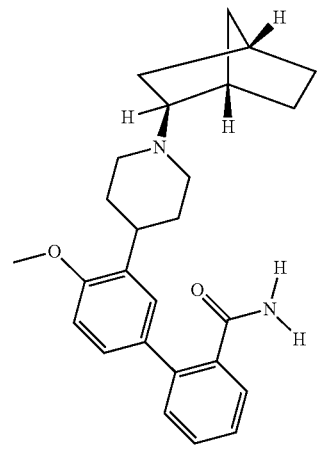

257
-continued
351
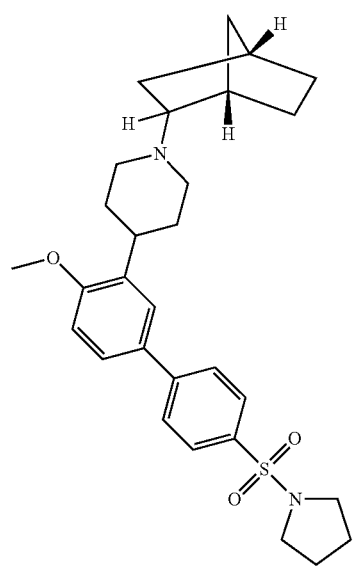
354
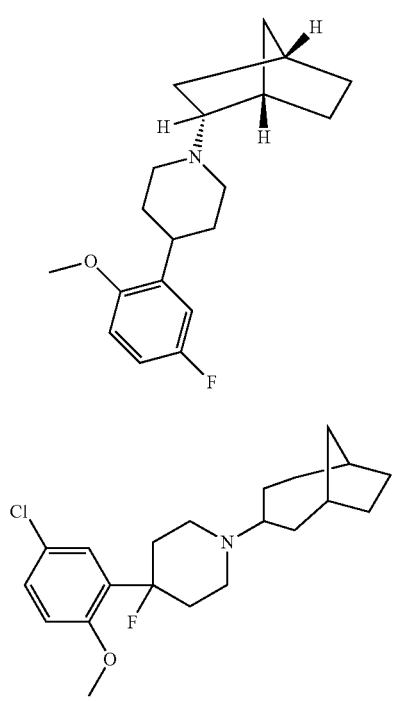
356
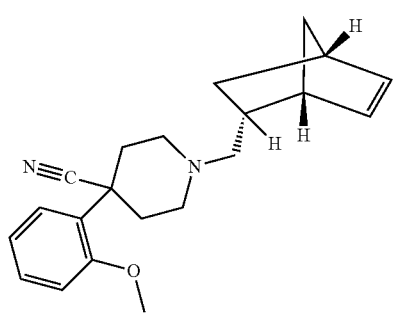
258
-continued
360
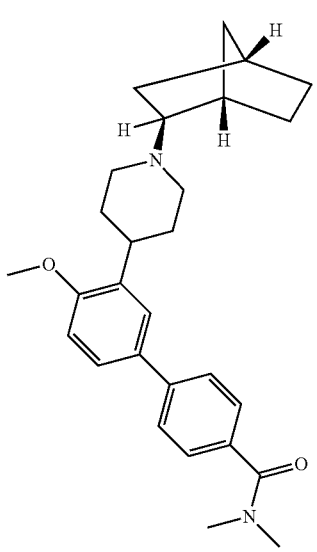
361
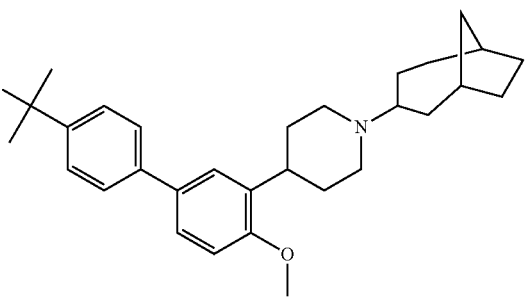
366
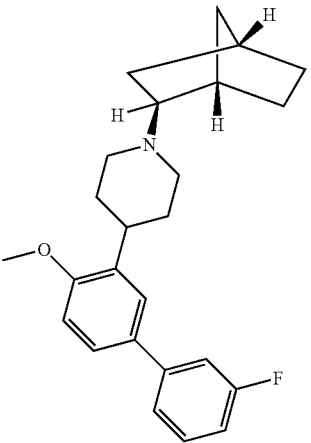

| 259 | 260 |
|---|---|
| -continued | -continued |
367 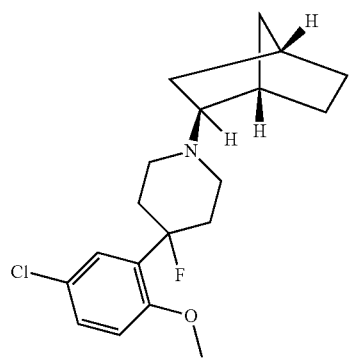
371 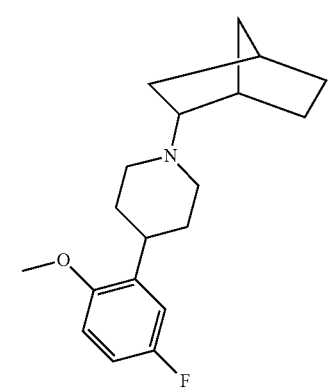
375 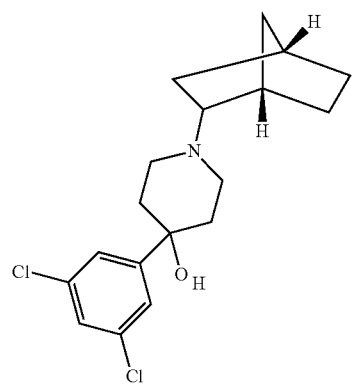
377 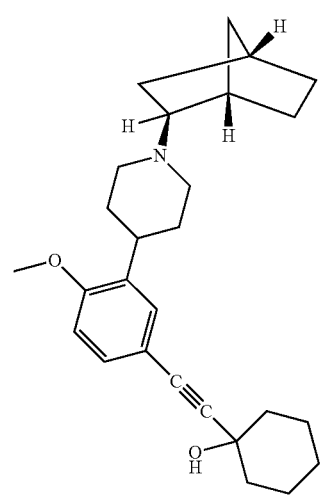
381 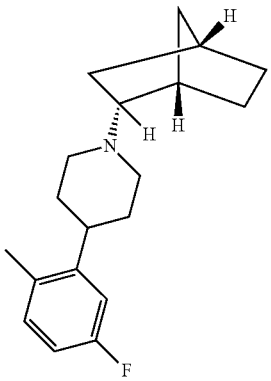
383 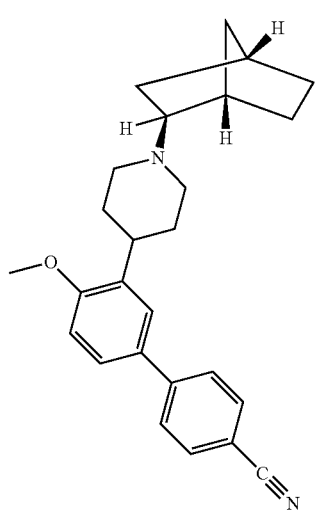
384 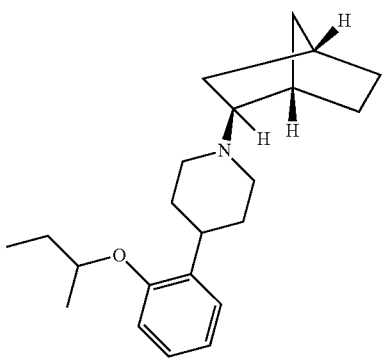
385 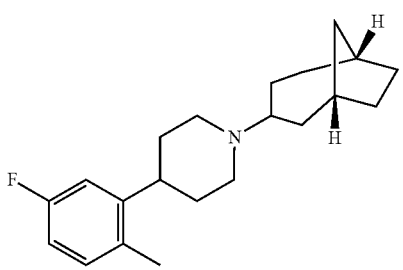

-continued
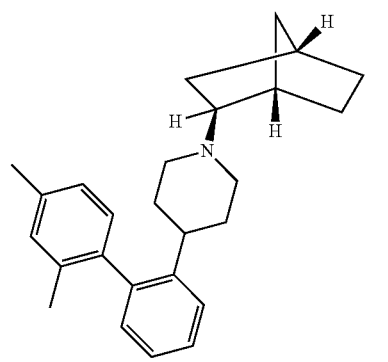
386
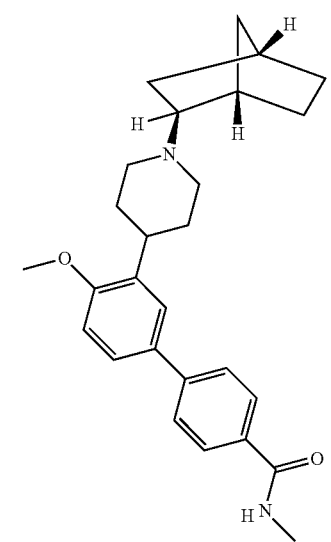
388
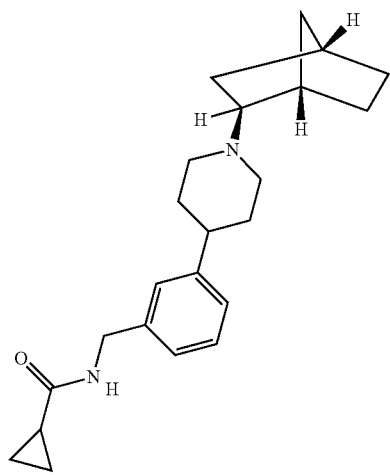
391
-continued
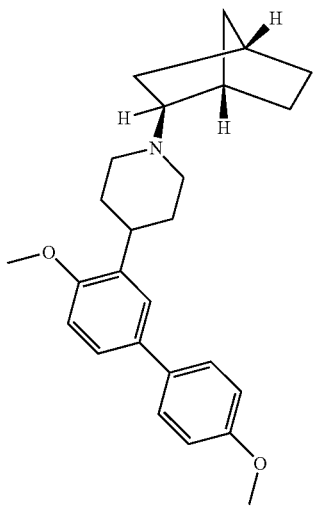
393
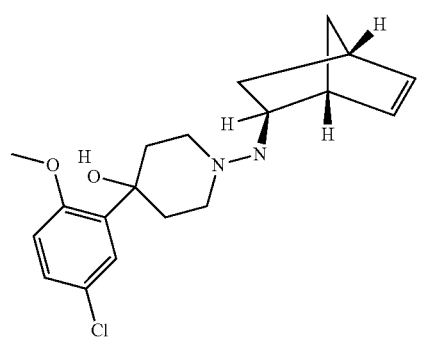
394
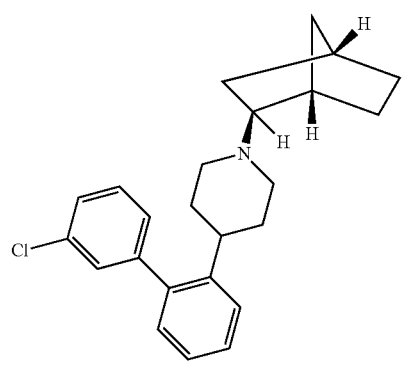
395
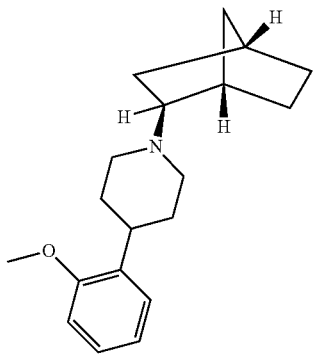
397

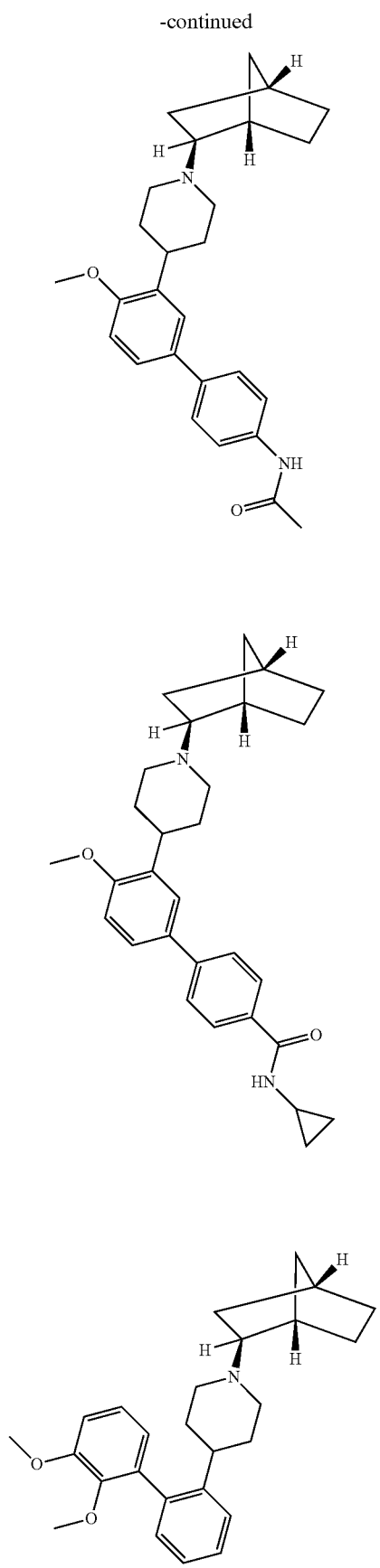
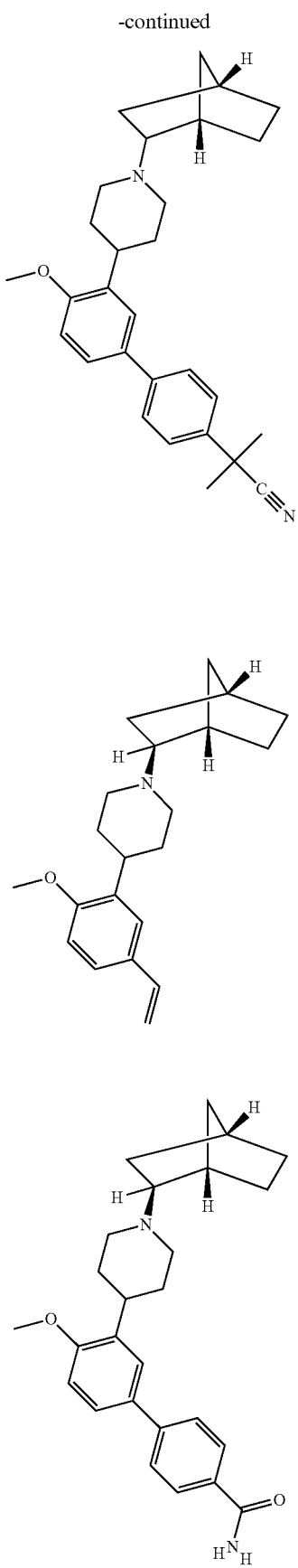

-continued
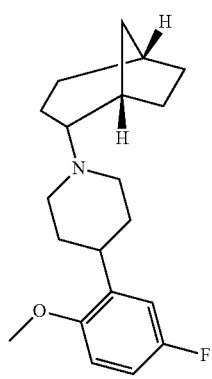
412
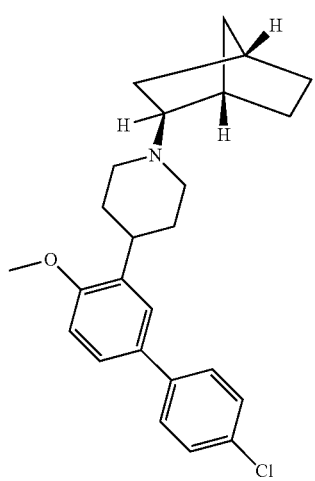
413
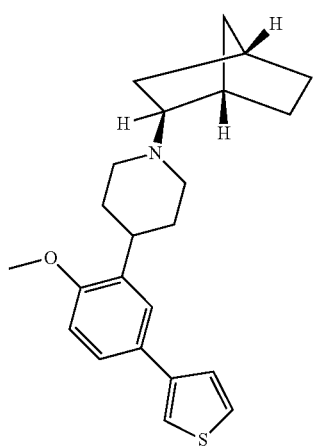
414
-continued
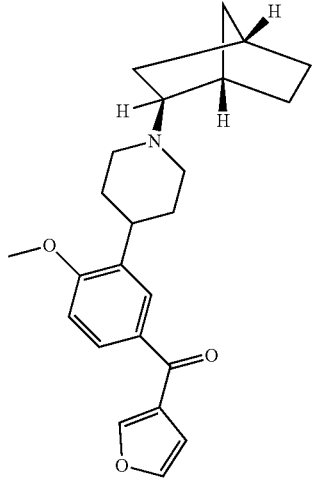
416
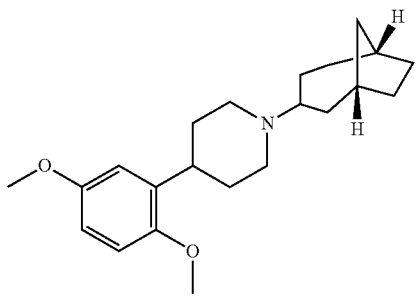
419
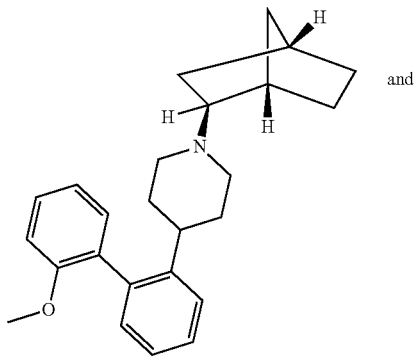
420
and -continued
421
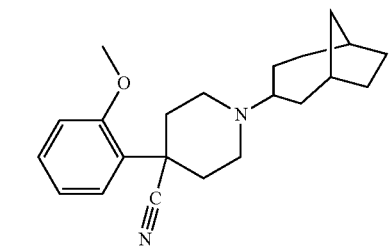
422
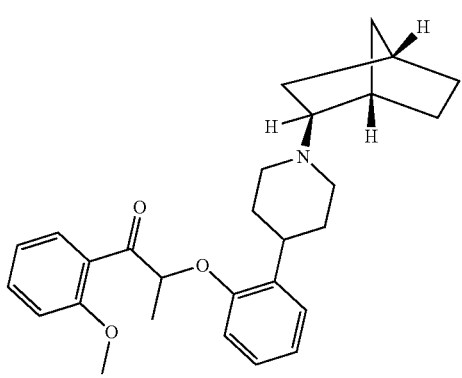
423
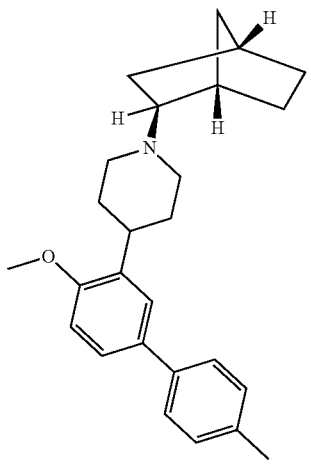
424
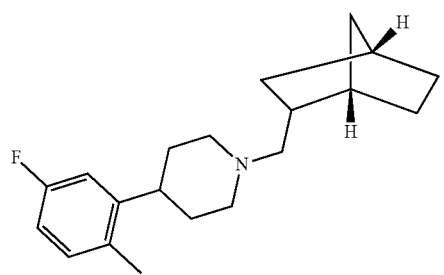
* * * * *